US009103830B2

(12) United States Patent
Yang et al.

(10) Patent No.: US 9,103,830 B2
(45) Date of Patent: Aug. 11, 2015

(54) ENZYME SENSORS, METHODS FOR PREPARING AND USING SUCH SENSORS, AND METHODS OF DETECTING PROTEASE ACTIVITY

(71) Applicant: Georgia State University Research Foundation, Inc., Atlanta, GA (US)

(72) Inventors: Jenny J. Yang, Atlanta, GA (US); Ning Chen, Atlanta, GA (US)

(73) Assignee: Georgia State University Research Foundation, Atlanta, GA (US)

(*) Notice: Subject to any disclaimer, the term of this patent is extended or adjusted under 35 U.S.C. 154(b) by 0 days.

(21) Appl. No.: 14/494,014

(22) Filed: Sep. 23, 2014

(65) Prior Publication Data

US 2015/0010920 A1    Jan. 8, 2015

Related U.S. Application Data

(63) Continuation of application No. 13/848,435, filed on Mar. 21, 2013, now Pat. No. 8,846,323, which is a continuation of application No. 12/227,404, filed as application No. PCT/US2007/017462 on Aug. 6, 2007, now Pat. No. 8,481,272.

(60) Provisional application No. 60/821,490, filed on Aug. 4, 2006.

(51) Int. Cl.
| | |
|---|---|
| *G01N 33/53* | (2006.01) |
| *G01N 33/573* | (2006.01) |
| *C12Q 1/00* | (2006.01) |
| *C12Q 1/37* | (2006.01) |
| *C07K 19/00* | (2006.01) |

(52) U.S. Cl.
CPC .............. *G01N 33/573* (2013.01); *C07K 19/00* (2013.01); *C12Q 1/00* (2013.01); *C12Q 1/37* (2013.01); *G01N 2333/9015* (2013.01); *G01N 2333/95* (2013.01); *G01N 2333/96466* (2013.01); *G01N 2333/974* (2013.01); *G01N 2333/976* (2013.01)

(58) Field of Classification Search
None
See application file for complete search history.

(56) References Cited

U.S. PATENT DOCUMENTS

| 5,679,548 A | 10/1997 | Barbas et al. |
| 5,690,903 A | 11/1997 | Hainfeld |
| 5,922,302 A | 7/1999 | Goldenberg et al. |
| 6,197,258 B1 | 3/2001 | Thompson et al. |
| 7,049,400 B1 | 5/2006 | Chang et al. |
| 2002/0015038 A1 | 2/2002 | Patel et al. |
| 2002/0136692 A1 | 9/2002 | Haroon et al. |
| 2003/0149254 A1 | 8/2003 | Anderson et al. |
| 2003/0180222 A1 | 9/2003 | Zhang et al. |
| 2004/0208827 A1 | 10/2004 | McMurry et al. |
| 2006/0029942 A1 | 2/2006 | Yang |
| 2006/0030029 A1 | 2/2006 | Yang |
| 2006/0031020 A1 | 2/2006 | Yang |

FOREIGN PATENT DOCUMENTS

| EP | 1238982 A | 9/2002 |
| WO | 0130398 A2 | 5/2001 |
| WO | 02063035 A | 8/2002 |
| WO | 03014157 A2 | 2/2003 |
| WO | 03057829 A2 | 7/2003 |
| WO | 2006080022 A2 | 8/2006 |
| WO | 2006107794 A2 | 10/2006 |
| WO | 2007009058 A2 | 1/2007 |

OTHER PUBLICATIONS

Kathy Q. Luo, Vivian C. Yu, Yongmei Pu, and Donald C. Chang, Application of the Fluorescence Resonance Energy Transfer Method for Studying the Dynamics of Caspase-3 Activation during UV-Induced Apoptosis in Living HeLa Cells, Biochemical and Biophysical Research Communications, 2001, 1054-1060, 283, Academic Press.
Hans Neurath, Proteolytic enzymes, past and future, Proc. Natl. Acad. Sci. USA, Sep. 1999, 10962-10963, 96, Colloquium Paper.
Hans Neurath, From proteases to proteomics, Protein Science, 2001, 892-904, 10, Cold Spring Harbor Laboratory Press.
Kathy Q. Luo, Vivian C. Yu, Donald C. Chang, Measuring dynamics of caspase-8 activation in a single living HeLa cell during TNF alpha-induced apoptosis, Biochemical and Biophysical Research Communications, 2003, 217-222, 304, Elsevier Science, USA.
Bin Zhang, Design of FRET-based GFP probes for detection of protease inhibitors, Biochemical and Biophysical Research Communications, 2004, 674-678, 323, Elsevier Inc.
Andreas Wunder, Ching-Hsuan Tung, Ulf Muller-Ladner, Ralph Weissleder, Umar Mahmood, In Vivo Imaging of Protease Activity in Arthritis—A Novel Approach for Monitoring Treatment Response, Arthritis and Rheumatism, 2004, 2459-2465, 50, American College of Rheumatology, USA.
Paul M. Kasili, Joon Myong Song, Tuan Vo-Dinh, Optical Sensor for the Detection of Caspase-9 Activity in a Single Cell, J. Am. Chem. Soc., 2004, 2799-2806, 126, American Chemical Society, USA.
J. Oliver McIntyre, Barbara Fingleton, K. Sam Wells, David W. Piston, Conor C. Lynch, Shiva Gautam, Lynn M. Matrisian, Development of a novel fluorogenic proteolytic beacon for in vivo detection and imaging of tumor-associated matrix metalloproteinase-7 activity, Biochemistry Journal, 2004, 617-628, 377, Biochemical Society.
Sriram Kumaraswamy, Troy Bergstedt, Xiaobo Shi, Frauke Rininsland, Stuart Kushon, Wensheng Xia, Kevin Ley, Komandoor Achyuthan, Duncan McBranch, David Whitten, Fluorescent-conjugated polymer superquenching facilitates highly sensitive detection of proteases, PNAS, May 18, 2004, 7511-7515, 101, The National Academy of Sciences of the USA, USA.

(Continued)

*Primary Examiner* — Jacob Cheu
(74) *Attorney, Agent, or Firm* — Thomas Horstemeyer, LLP

(57) ABSTRACT

Embodiments of the present disclosure provide for enzyme sensors, protease sensors, methods for producing and using the enzyme and protease sensors, methods of detecting and/or measuring protease activity, methods for characterizing protease cellular activity, fusion proteins, polynucleotides, and vectors corresponding to the enzyme and protease sensors, kits, and the like.

18 Claims, 23 Drawing Sheets

(56) References Cited

OTHER PUBLICATIONS

Kathryn E.S. Dean, Gerard Klein, Olivier Renaudet, and Jean-Lois Reymond, A Green Fluorescent Chemosensor for Amino Acids Provides a Versatile High-Throughput Screening (HTS) Assay for Proteases, Bioorganic and Medicinal Chemistry Letters, 2003, 1653-1656, 13, Elsevier Science Ltd.
Martin Funovics, Ralph Weissleder, Ching-Hsuan Tung, Protease sensors for bioimaging, Anal Bioanal Chem, 2003, 956-963, 377, Springer-Verlag.
Stephanie Cabantous, Thomas C. Terwilliger, and Geoffrey S. Waldo, Protein tagging and detection with engineered self-assembling fragments of green fluorescent protein, Nature Biotechnology, Jan. 2005, 102-107, 1, Nature Publishing Group.
Chin, et al., "Development of Protease Sensors Based on Enhanced Green Fluorescent Protein (EGFP)", Abstracts of Papers American Chemical Society, vol. 231, Mar. 2006, pp. 31-MEDI.
European Search Report dated Sep. 23, 2009.
Mesecar, et al., "Orbital Steering in the Catalytic Power of Enzymes: Small Structural Changes with Large Catalytic Consequences," Science Jul. 11, 1997:277(5323):202-6.
Smith, et al., "Entry for Quaternary Structure," Oxford Dictionary of Biochemistry and Molecular Biology, Oxford University Press, New Yoir 1997, p. 551.
Todd, et al., "Engineered Metal Binding Sites on Green Fluorescence Protein," Biochemical and Biophysical Research Communications, vol. 268, No. 2, Feb. 16, 2000, pp. 462-465.
Romoser, et al., "Detection in Living Cells of Ca-2+-dependent Changes in the Fluroescence Emission of an Indicator Composed of Two Green Fluorescent Protein Variants Linked by a Calmodulin-binding Sequence: A New Class of Fluorescent Indicators," Journal of Biological Chemistry, col. 272, No. 20, 1997, pp. 13270-13274.
Nagal, et al., "Circularly Permuted Green Fluorescent Proteins Engineered to Sense Ca2+" Proceedings of the National Academy of Sciences of USA, National Academy of Science, Washington, DC, vol. 98, No. 6, Mar. 13, 2001, pp. 3197-3202.
Wilkins, et al., "Metal-Binding Studies for a De Novo Designed Calcium-Binding Protein," Protein Engineering, vol. 15, No. 7, Jul. 2002, pp. 571-574.
Hellinga, et al., "Protein Engineering and the Development of Generic Biosensors," Trends in Biotechnology, vol. 16, No. 4, 1998, p. 183.
Supplemental European Search Report dated Aug. 25, 2009.
Elbanowski, et al., "Fluorescence of Lanthanide (III) Complexes in Aqueous Solutions: The Influence of pH and Solution Composition," Monatshfte fur Chemie, 1985, vol. 116, pp. 901-911.
Johnson, et al., "Structural Changes Required for Activation of Protein C are Induced by CA2+ Binding to a High Affinity Site that Does Not Contain g-Carboxyglutamic Acid," The Journal of Biological Chemistry, 1983, vol. 268, pp. 5554-5560.
Lewis, et al., "Fluroescence Binding Assay for a Small Peptide Based on a GFP Fusion Protein," Analytica Chimica Acta., vol. 397, 1999, pp. 279-286.
Schlyer et al., "Time-Resolved Room Temperature Protein Phosphorescence: Nonexponential Decay from Single Emitting Tryptophans," Biophysical Journal, vol. 67, 1994, pp. 1192-1202.
Yang, et al., "The Molecular Structure of Green Fluorescent Protein," Nature Biotechnology, vol. 14, 1996, pp. 1246-151.
Shelling, et al., "Protein Nuclear Magnetic Resonance Studies of the Interaction of the Lanthanide Yetterbium and Lutetium with Apo-and Calcium Saturated Porcine Intestinal Calcium Binding Protein," Biochemistry, 1985, vol. 24, pp. 2332-2338.
Yang, et al., "Rational Design of a Calcium-Binding Protein," Journal of the American Chemical Society, Apr. 2003, vol. 125, pp. 6165-6171.
Ye, et al., "A Grafting Approach to Obtain Site-Specific Metal-Binding Properties of EF-Hand Proteins," Protein Engineering, vol. 16, No. 6; pp. 429-434, 2003.
Ye, et al., "Metal Binding Affinity and Structural Properties of an Isolated EF-Loop in a Scaffold Protein," Protein Engineering, vol. 14, No. 12, pp. 1001-1013; 2001.
MacKenzie, et al., "Bifunctional Fusion Proteins Consisting of a Single-Chain Antibody and an Engineered Lanthanide=Binding Protein," Immunotechnology 1 (1995), pp. 139-150.
Lee, et al., "Isolated EF-Loop III of Calmodulin in a Scaffold Protein Remains Unpaired in Solution Using Pulsed-Field-Gradient NMR Spectroscopy," Biochimica et Biophysica Acta; 1598 (2002), pp. 80-87.
Miyawaki, et al., Fluorescent Indicators for CA2+ Based on Green Fluorescent Proteins and Calmodulin; Nature, vol. 388, Aug. 28, 1997, pp. 882887.
Prasher, et al., "Primary Structure of the Aequorea Victoria Green-Fluorescent Protein," Gene, 1992, vol. 111, 99. 229-233.
Yang et al., "Obtaining Site-Specific Calcium-Binding Affinities of Calmodulin," Protein and Peptide Letters, vol. 10, No. 4, pp. 331-345, 2003.
Kawasaki, et al., "Classification and Evolution of EF-Hand Proteins," BioMetals; 1998, vol. 11, pp. 275-295.
International Search Report and Written Opinion, dated Jul. 14, 2008.
Anton, et al., "Biotinylation of a Bombesin" 1991, Peptides, 12, pp. 375-381.
International Search Report and Written Opinion dated Nov. 28, 2007.
Cohen, et al., "Ferritin as an Endogenous MRI Reporter for Noninvasive Imaging of Gene Expression in C6 Glioma Tumors," Neoplasia, Feb. 2005, vol. 7, No. 2, pp. 109-111.
Pessl, et al., "A Designed Metal-Binding Protein with a Novel Fold," Nature, Mar. 25, 1993, 362, 367, 369 (online).

SEQUENCE LISTING

<160> NUMBER OF SEQ ID NOS: 144

<210> SEQ ID NO 1
<211> LENGTH: 270
<212> TYPE: PRT
<213> ORGANISM: Artificial Sequence
<220> FEATURE:
<223> OTHER INFORMATION: Chemically synthesized

<400> SEQUENCE: 1

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
            195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 2
<211> LENGTH: 270
<212> TYPE: PRT
<213> ORGANISM: Artificial Sequence
<220> FEATURE:
<223> OTHER INFORMATION: Chemically synthesized

<400> SEQUENCE: 2

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Gly Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 3
<211> LENGTH: 259

```
<212> TYPE: PRT
<213> ORGANISM: Artificial Sequence
<220> FEATURE:
<223> OTHER INFORMATION: Chemically synthesized

<400> SEQUENCE: 3

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 4
<211> LENGTH: 259
<212> TYPE: PRT
<213> ORGANISM: Artificial Sequence
<220> FEATURE:
<223> OTHER INFORMATION: Chemically synthesized

<400> SEQUENCE: 4

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60
```

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
            195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 5
<211> LENGTH: 262
<212> TYPE: PRT
<213> ORGANISM: Artificial Sequence
<220> FEATURE:
<223> OTHER INFORMATION: Chemically Synthesized

<400> SEQUENCE: 5

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
```

```
                165                 170                 175
Ile Arg Glu Ala Phe Arg Val Phe Asp Lys Asp Gly Asn Gly Tyr Ile
            180                 185                 190

Ser Ala Ala Glu Asp Gly Ser Val Gln Leu Ala Asp His Tyr Gln Gln
            195                 200                 205

Asn Thr Pro Ile Gly Asp Gly Pro Val Leu Leu Pro Asp Asn His Tyr
            210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
            245                 250                 255

Met Asp Glu Leu Tyr Lys
            260

<210> SEQ ID NO 6
<211> LENGTH: 262
<212> TYPE: PRT
<213> ORGANISM: Artificial Sequence
<220> FEATURE:
<223> OTHER INFORMATION: Chemically Synthesized

<400> SEQUENCE: 6

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
```

260

<210> SEQ ID NO 7
<211> LENGTH: 251
<212> TYPE: PRT
<213> ORGANISM: Artificial Sequence
<220> FEATURE:
<223> OTHER INFORMATION: Chemically synthesized

<400> SEQUENCE: 7

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250
```

<210> SEQ ID NO 8
<211> LENGTH: 251
<212> TYPE: PRT
<213> ORGANISM: Artificial Sequenceq
<220> FEATURE:
<223> OTHER INFORMATION: Chemically synthesized

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

```
Cys Thr Thr Gly Lys Leu Pro Val Pro Trp Pro Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                 100                 105                 110

Val Lys Phe Glu Gly Asp Thr Leu Val Asn Arg Ile Glu Leu Lys Gly
                 115                 120                 125

Ile Asp Phe Lys Glu Asp Gly Asn Ile Leu Gly His Lys Leu Glu Tyr
 130                 135                 140

Asn Tyr Asn Ser His Asn Val Tyr Ile Thr Ala Asp Lys Gln Lys Asn
145                  150                 155                 160

Gly Ile Lys Ala Asn Phe Lys Ile Arg His Asn Ile Glu Asp Lys Asp
                 165                 170                 175

Gly Asn Gly Tyr Ile Ser Ala Ala Glu Asp Gly Ser Val Gln Leu Ala
                 180                 185                 190

Asp His Tyr Gln Gln Asn Thr Pro Ile Gly Asp Gly Pro Val Leu Leu
                 195                 200                 205

Pro Asp Asn His Tyr Leu Ser Thr Gln Ser Ala Leu Ser Lys Asp Pro
 210                 215                 220

Asn Glu Lys Arg Asp His Ile Val Leu Leu Glu Phe Val Thr Ala Ala
 225                 230                 235                 240

Gly Ile Thr Leu Gly Met Asp Glu Leu Tyr Lys
                 245                 250

<210> SEQ ID NO 9
<211> LENGTH: 270
<212> TYPE: PRT
<213> ORGANISM: Artificial Sequence
<220> FEATURE:
<223> OTHER INFORMATION: Chemically synthesized

<400> SEQUENCE: 9

Met Val Ser Lys Gly Glu Glu Leu Phe Thr Gly Val Val Pro Ile Leu
 1               5                   10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                 100                 105                 110

Val Lys Phe Glu Gly Asp Thr Leu Val Asn Arg Ile Glu Leu Lys Gly
                 115                 120                 125

Ile Asp Phe Lys Glu Asp Gly Asn Ile Leu Gly His Lys Leu Glu Tyr
 130                 135                 140

Asn Tyr Asn Ser His Asn Val Tyr Ile Met Ala Asp Lys Gln Lys Asn
145                  150                 155                 160
```

```
Gly Ile Lys Val Asn Phe Lys Ile Arg His Asn Ile Glu Glu Glu Glu
                165                 170                 175

Ile Ala Glu Ala Phe Ala Val Phe Asp Ala Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 10
<211> LENGTH: 270
<212> TYPE: PRT
<213> ORGANISM: Artificial Sequence
<220> FEATURE:
<223> OTHER INFORMATION: Chemically synthesized

<400> SEQUENCE: 10

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255
```

Thr Ala Ala Gly Ile Thr Leu Gly Met Asp Glu Leu Tyr Lys
            260                 265                 270

<210> SEQ ID NO 11
<211> LENGTH: 270
<212> TYPE: PRT
<213> ORGANISM: Artificial Sequence
<220> FEATURE:
<223> OTHER INFORMATION: Chemically synthesized

<400> SEQUENCE: 11

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Gly Pro Arg Leu Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 12
<211> LENGTH: 270
<212> TYPE: PRT
<213> ORGANISM: Artificial Sequence
<220> FEATURE:
<223> OTHER INFORMATION: Chemically synthesized

<400> SEQUENCE: 12

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

```
Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
         50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
         115                 120                 125

Ile Asp Phe Lys Glu Asp Gly Asn Ile Leu Gly His Lys Leu Glu Tyr
     130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                 165                 170                 175

Ile Arg Glu Ala Phe Arg Val Phe Asp Lys Asp Gly Asn Gly Tyr Ile
            180                 185                 190

Ser Ala Ala Gly Pro Arg Leu Val Met Thr Asn Leu Asp Gly Ser Val
         195                 200                 205

Gln Leu Ala Asp His Tyr Gln Gln Asn Thr Pro Ile Gly Asp Gly Pro
     210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                 245                 250                 255

Thr Ala Ala Gly Ile Thr Leu Gly Met Asp Glu Leu Tyr Lys
            260                 265                 270

<210> SEQ ID NO 13
<211> LENGTH: 259
<212> TYPE: PRT
<213> ORGANISM: Artificial Sequence
<220> FEATURE:
<223> OTHER INFORMATION: Chemically synthesized

<400> SEQUENCE: 13

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
         115                 120                 125
```

```
Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Gly Pro Arg Leu Val Met Thr Asn
                180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
        210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 14
<211> LENGTH: 259
<212> TYPE: PRT
<213> ORGANISM: Artificial Sequence
<220> FEATURE:
<223> OTHER INFORMATION: Chemically synthesized

<400> SEQUENCE: 14

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Gly Pro Arg Leu Val Met Thr Asn
                180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
        210                 215                 220
```

```
Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
            245                 250                 255

Leu Tyr Lys

<210> SEQ ID NO 15
<211> LENGTH: 270
<212> TYPE: PRT
<213> ORGANISM: Artificial Sequence
<220> FEATURE:
<223> OTHER INFORMATION: Chemically synthesized

<400> SEQUENCE: 15

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Ala Glu Ala Phe Ala Val Phe Asp Ala Asp Gly Asn Gly Tyr Ile
            180                 185                 190

Ser Ala Ala Gly Pro Arg Leu Val Met Thr Asn Leu Asp Gly Ser Val
        195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 16
<211> LENGTH: 270
<212> TYPE: PRT
<213> ORGANISM: Artificial Sequence
<220> FEATURE:
<223> OTHER INFORMATION: Chemically synthesized

<400> SEQUENCE: 16
```

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Gly Glu Glu
                165                 170                 175

Ile Ala Glu Ala Phe Ala Val Phe Asp Ala Asp Gly Asn Gly Tyr Ile
            180                 185                 190

Ser Ala Ala Gly Pro Arg Leu Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 17
<211> LENGTH: 271
<212> TYPE: PRT
<213> ORGANISM: Artificial Sequence
<220> FEATURE:
<223> OTHER INFORMATION: Chemically synthesized

<400> SEQUENCE: 17

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Gly Pro Ala Arg Leu Val Met Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 18
<211> LENGTH: 271
<212> TYPE: PRT
<213> ORGANISM: Artificial Sequence
<220> FEATURE:
<223> OTHER INFORMATION: Chemically synthesized

<400> SEQUENCE: 18

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190
```

```
Ser Ala Ala Gly Pro Ala Arg Leu Val Met Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270
```

<210> SEQ ID NO 19
<211> LENGTH: 270
<212> TYPE: PRT
<213> ORGANISM: Artificial Sequence
<220> FEATURE:
<223> OTHER INFORMATION: Chemically synthesized

<400> SEQUENCE: 19

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Glu Glu
                165                 170                 175

Ile Arg Glu Ala Phe Arg Val Phe Asp Lys Asp Gly Asn Gly Tyr Ile
            180                 185                 190

Ser Ala Ala Gly Pro Arg Leu Ala Ile Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 20
<211> LENGTH: 271

```
<212> TYPE: PRT
<213> ORGANISM: Artificial Sequence
<220> FEATURE:
<223> OTHER INFORMATION: Chemically synthesized

<400> SEQUENCE: 20

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Gly Pro Ala Arg Leu Ala Ile Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 21
<211> LENGTH: 260
<212> TYPE: PRT
<213> ORGANISM: Artificial Sequence
<220> FEATURE:
<223> OTHER INFORMATION: Chemically synthesized

<400> SEQUENCE: 21

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Gly Pro Ala Arg Leu Ala Ile Thr
            180                 185                 190

Asn Leu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Ile
225                 230                 235                 240

Val Leu Leu Glu Phe Val Thr Ala Ala Gly Ile Thr Leu Gly Met Asp
                245                 250                 255

Glu Leu Tyr Lys
            260

<210> SEQ ID NO 22
<211> LENGTH: 260
<212> TYPE: PRT
<213> ORGANISM: Artificial Sequence
<220> FEATURE:
<223> OTHER INFORMATION: Chemically synthesized

<400> SEQUENCE: 22

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160
```

-continued

```
Gly Ile Lys Ala Asn Phe Lys Ile Arg His Asn Ile Glu Asp Lys Asp
                165                 170                 175

Gly Asn Gly Tyr Ile Ser Ala Ala Gly Pro Ala Arg Leu Ala Ile Thr
            180                 185                 190

Asn Leu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Ile
225                 230                 235                 240

Val Leu Leu Glu Phe Val Thr Ala Ala Gly Ile Thr Leu Gly Met Asp
                245                 250                 255

Glu Leu Tyr Lys
            260

<210> SEQ ID NO 23
<211> LENGTH: 271
<212> TYPE: PRT
<213> ORGANISM: Artificial Sequence
<220> FEATURE:
<223> OTHER INFORMATION: Chemically synthesized

<400> SEQUENCE: 23

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Ala Glu Ala Phe Ala Val Phe Asp Ala Asp Gly Asn Gly Tyr Ile
            180                 185                 190

Ser Ala Ala Gly Pro Ala Arg Leu Ala Ile Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255
```

```
Val Thr Ala Ala Gly Ile Thr Leu Gly Met Asp Glu Leu Tyr Lys
            260                 265                 270

<210> SEQ ID NO 24
<211> LENGTH: 271
<212> TYPE: PRT
<213> ORGANISM: Artificial Sequence
<220> FEATURE:
<223> OTHER INFORMATION: Chemically synthesized

<400> SEQUENCE: 24

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Ala Glu Ala Phe Ala Val Phe Asp Ala Asp Gly Asn Gly Tyr Ile
            180                 185                 190

Ser Ala Ala Gly Pro Ala Arg Leu Ala Ile Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 25
<211> LENGTH: 268
<212> TYPE: PRT
<213> ORGANISM: Artificial Sequence
<220> FEATURE:
<223> OTHER INFORMATION: Chemically synthesized

<400> SEQUENCE: 25

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
```

```
                  20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
        50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
        130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Glu Phe Lys
                165                 170                 175
Glu Ala Phe Ser Leu Phe Asp Lys Asp Gly Asp Gly Thr Ile Thr Thr
            180                 185                 190
Lys Glu Leu Gly Thr Val Met Arg Ser Leu Asp Gly Ser Val Gln Leu
        195                 200                 205
Ala Asp His Tyr Gln Gln Asn Thr Pro Ile Gly Asp Gly Pro Val Leu
        210                 215                 220
Leu Pro Asp Asn His Tyr Leu Ser Thr Gln Ser Ala Leu Ser Lys Asp
225                 230                 235                 240
Pro Asn Glu Lys Arg Asp His Ile Val Leu Leu Glu Phe Val Thr Ala
                245                 250                 255
Ala Gly Ile Thr Leu Gly Met Asp Glu Leu Tyr Lys
            260                 265

<210> SEQ ID NO 26
<211> LENGTH: 268
<212> TYPE: PRT
<213> ORGANISM: Artificial Sequence
<220> FEATURE:
<223> OTHER INFORMATION: Chemically synthesized

<400> SEQUENCE: 26

Met Val Ser Lys Gly Glu Glu Leu Phe Thr Gly Val Val Pro Ile Leu
1               5                   10                  15
Val Glu Leu Asp Gly Asp Leu Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
        50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
```

```
              115                 120                 125
Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Phe Lys
                165                 170                 175

Glu Ala Phe Ser Leu Phe Asp Lys Asp Gly Asp Gly Thr Ile Thr Thr
                180                 185                 190

Lys Glu Leu Gly Thr Val Met Arg Ser Leu Asp Gly Ser Val Gln Leu
                195                 200                 205

Ala Asp His Tyr Gln Gln Asn Thr Pro Ile Gly Asp Gly Pro Val Leu
210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
                260                 265

<210> SEQ ID NO 27
<211> LENGTH: 268
<212> TYPE: PRT
<213> ORGANISM: Artificial Sequence
<220> FEATURE:
<223> OTHER INFORMATION: Chemically synthesized

<400> SEQUENCE: 27

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
                35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Phe Lys
                165                 170                 175

Glu Ala Phe Ser Leu Phe Asp Lys Asp Gly Asp Gly Thr Ile Thr Thr
                180                 185                 190

Lys Glu Leu Gly Pro Ala Arg Leu Ala Ile Asp Gly Ser Val Gln Leu
                195                 200                 205

Ala Asp His Tyr Gln Gln Asn Thr Pro Ile Gly Asp Gly Pro Val Leu
```

```
            210                 215                 220
Leu Pro Asp Asn His Tyr Leu Ser Thr Gln Ser Ala Leu Ser Lys Asp
225                 230                 235                 240

Pro Asn Glu Lys Arg Asp His Ile Val Leu Glu Phe Val Thr Ala
                245                 250                 255

Ala Gly Ile Thr Leu Gly Met Asp Glu Leu Tyr Lys
                260                 265

<210> SEQ ID NO 28
<211> LENGTH: 268
<212> TYPE: PRT
<213> ORGANISM: Artificial Sequence
<220> FEATURE:
<223> OTHER INFORMATION: Chemically synthesized

<400> SEQUENCE: 28

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Phe Lys
                165                 170                 175

Glu Ala Phe Ser Leu Phe Asp Lys Asp Gly Asp Gly Thr Ile Thr Thr
            180                 185                 190

Lys Glu Leu Gly Pro Ala Arg Leu Ala Ile Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Glu Phe Val Thr Ala
                245                 250                 255

Ala Gly Ile Thr Leu Gly Met Asp Glu Leu Tyr Lys
                260                 265

<210> SEQ ID NO 29
<211> LENGTH: 268
<212> TYPE: PRT
<213> ORGANISM: Artificial Sequence
<220> FEATURE:
<223> OTHER INFORMATION: Chemically synthesized
```

<400> SEQUENCE: 29

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Leu Gln
                165                 170                 175

Asp Met Ile Asn Glu Val Asp Ala Asp Gly Asn Gly Thr Ile Asp Phe
            180                 185                 190

Pro Glu Phe Leu Thr Met Met Ala Arg Lys Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265
```

<210> SEQ ID NO 30
<211> LENGTH: 268
<212> TYPE: PRT
<213> ORGANISM: Artificial Sequence
<220> FEATURE:
<223> OTHER INFORMATION: Chemically synthesized

<400> SEQUENCE: 30

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80
```

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Leu Gln
                165                 170                 175

Asp Met Ile Asn Glu Val Asp Ala Asp Gly Asn Gly Thr Ile Asp Phe
            180                 185                 190

Pro Glu Phe Leu Thr Met Met Ala Arg Lys Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265

<210> SEQ ID NO 31
<211> LENGTH: 269
<212> TYPE: PRT
<213> ORGANISM: Artificial Sequence
<220> FEATURE:
<223> OTHER INFORMATION: Chemically synthesized

<400> SEQUENCE: 31

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Leu Gln
                165                 170                 175
```

```
Asp Met Ile Asn Glu Val Asp Ala Asp Gly Asn Gly Thr Ile Asp Phe
            180                 185                 190

Pro Glu Phe Leu Gly Pro Ala Arg Leu Ala Ile Asp Gly Ser Val Gln
        195                 200                 205

Leu Ala Asp His Tyr Gln Gln Asn Thr Pro Ile Gly Asp Gly Pro Val
    210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
            260                 265
```

<210> SEQ ID NO 32
<211> LENGTH: 269
<212> TYPE: PRT
<213> ORGANISM: Artificial Sequence
<220> FEATURE:
<223> OTHER INFORMATION: Chemically synthesized

<400> SEQUENCE: 32

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Leu Gln
                165                 170                 175

Asp Met Ile Asn Glu Val Asp Ala Asp Gly Asn Gly Thr Ile Asp Phe
            180                 185                 190

Pro Glu Phe Leu Gly Pro Ala Arg Leu Ala Ile Asp Gly Ser Val Gln
        195                 200                 205

Leu Ala Asp His Tyr Gln Gln Asn Thr Pro Ile Gly Asp Gly Pro Val
    210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
            260                 265
```

<210> SEQ ID NO 33
<211> LENGTH: 269
<212> TYPE: PRT
<213> ORGANISM: Artificial Sequence
<220> FEATURE:
<223> OTHER INFORMATION: Chemically synthesized

<400> SEQUENCE: 33

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Val
                165                 170                 175

Asp Glu Met Ile Arg Glu Ala Asp Ile Asp Gly Asp Gly Gln Val Asn
            180                 185                 190

Tyr Glu Glu Phe Val Gln Met Met Thr Ala Lys Asp Gly Ser Val Gln
        195                 200                 205

Leu Ala Asp His Tyr Gln Gln Asn Thr Pro Ile Gly Asp Gly Pro Val
210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
            260                 265
```

<210> SEQ ID NO 34
<211> LENGTH: 269
<212> TYPE: PRT
<213> ORGANISM: Artificial Sequence
<220> FEATURE:
<223> OTHER INFORMATION: Chemically synthesized

<400> SEQUENCE: 34

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

```
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Val
                165                 170                 175

Asp Glu Met Ile Arg Glu Ala Asp Ile Asp Gly Asp Gly Gln Val Asn
                180                 185                 190

Tyr Glu Glu Phe Val Gln Met Met Thr Ala Lys Asp Gly Ser Val Gln
            195                 200                 205

Leu Ala Asp His Tyr Gln Gln Asn Thr Pro Ile Gly Asp Gly Pro Val
            210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
                260                 265

<210> SEQ ID NO 35
<211> LENGTH: 268
<212> TYPE: PRT
<213> ORGANISM: Artificial Sequence
<220> FEATURE:
<223> OTHER INFORMATION: Chemically synthesized

<400> SEQUENCE: 35

Met Val Ser Lys Gly Glu Glu Leu Phe Thr Gly Val Val Pro Ile Leu
  1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140
```

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Val
                165                 170                 175

Gly Pro Ala Arg Leu Ala Ile Asp Ile Asp Gly Asp Gly Gln Val Asn
            180                 185                 190

Tyr Glu Glu Phe Val Gln Met Met Thr Ala Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265

<210> SEQ ID NO 36
<211> LENGTH: 268
<212> TYPE: PRT
<213> ORGANISM: Artificial Sequence
<220> FEATURE:
<223> OTHER INFORMATION: Chemically synthesized

<400> SEQUENCE: 36

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Val
                165                 170                 175

Gly Pro Ala Arg Leu Ala Ile Asp Ile Asp Gly Asp Gly Gln Val Asn
            180                 185                 190

Tyr Glu Glu Phe Val Gln Met Met Thr Ala Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240
```

```
Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265

<210> SEQ ID NO 37
<211> LENGTH: 270
<212> TYPE: PRT
<213> ORGANISM: Artificial Sequence
<220> FEATURE:
<223> OTHER INFORMATION: Chemically synthesized

<400> SEQUENCE: 37

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Gly Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Gly Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Tyr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 38
<211> LENGTH: 270
<212> TYPE: PRT
<213> ORGANISM: Artificial Sequence
<220> FEATURE:
<223> OTHER INFORMATION: Chemically synthesized

<400> SEQUENCE: 38

Met Val Ser Lys Gly Glu Glu Leu Phe Thr Gly Val Val Pro Ile Leu
```

```
            1               5              10              15
         Val Glu Leu Asp Gly Asp Leu Asn Gly His Lys Phe Ser Val Ser Gly
                        20              25              30

Glu Gly Glu Gly Asp Ala Thr Tyr Gly Lys Leu Thr Leu Lys Leu Ile
                    35              40              45

Cys Thr Thr Gly Lys Leu Pro Val Pro Trp Pro Thr Leu Val Thr Thr
                 50              55              60

Leu Gly Tyr Gly Leu Gln Cys Phe Ala Arg Tyr Pro Asp His Met Lys
         65              70              75              80

Gln His Asp Phe Phe Lys Ser Ala Met Pro Glu Gly Tyr Val Gln Glu
                        85              90              95

Arg Thr Ile Phe Phe Lys Asp Asp Gly Asn Tyr Lys Thr Arg Ala Glu
                    100             105             110

Val Lys Phe Glu Gly Asp Thr Leu Val Asn Arg Ile Glu Leu Lys Gly
                 115             120             125

Ile Asp Phe Lys Glu Asp Gly Asn Ile Leu Gly His Lys Leu Glu Tyr
             130             135             140

Asn Tyr Asn Ser His Asn Val Tyr Ile Met Ala Asp Lys Gln Lys Asn
         145             150             155             160

Gly Ile Lys Ala Asn Phe Lys Ile Arg His Asn Ile Glu Glu Glu
                        165             170             175

Ile Arg Glu Ala Phe Arg Val Phe Asp Lys Asp Gly Asn Gly Tyr Ile
                    180             185             190

Ser Ala Ala Glu Leu Arg His Val Met Thr Asn Leu Asp Gly Val
                 195             200             205

Gln Leu Ala Asp His Tyr Gln Gln Asn Thr Pro Ile Gly Asp Gly Pro
             210             215             220

Val Leu Leu Pro Asp Asn His Tyr Leu Ser Tyr Gln Ser Ala Leu Ser
         225             230             235             240

Lys Asp Pro Asn Glu Lys Arg Asp His Ile Val Leu Leu Glu Phe Val
                        245             250             255

Thr Ala Ala Gly Ile Thr Leu Gly Met Asp Glu Leu Tyr Lys
                    260             265             270

<210> SEQ ID NO 39
<211> LENGTH: 273
<212> TYPE: PRT
<213> ORGANISM: Artificial Sequence
<220> FEATURE:
<223> OTHER INFORMATION: Chemically synthesized

<400> SEQUENCE: 39

Met Val Ser Lys Gly Glu Glu Leu Phe Thr Gly Val Val Pro Ile Leu
         1               5              10              15

Val Glu Leu Asp Gly Asp Leu Asn Gly His Lys Phe Ser Val Ser Gly
                        20              25              30

Glu Gly Glu Gly Asp Ala Thr Tyr Gly Lys Leu Thr Leu Lys Phe Ile
                    35              40              45

Cys Thr Thr Gly Lys Leu Pro Val Pro Trp Pro Thr Leu Val Thr Thr
                 50              55              60

Leu Ser Trp Gly Val Gln Cys Phe Ser Arg Tyr Pro Asp His Met Lys
         65              70              75              80

Gln His Asp Phe Phe Lys Ser Ala Met Pro Glu Gly Tyr Val Gln Glu
                        85              90              95

Arg Thr Ile Phe Phe Lys Asp Asp Gly Asn Tyr Lys Thr Arg Ala Glu
```

```
                100             105             110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135             140

Ile Tyr Asn Ser His Asn Val Tyr Ile Thr Ala Asp Lys Gln Lys Asn
145                 150             155                 160

Gly Ile Lys Ala Asn Phe Lys Ile Arg His Asn Ile Glu Glu Glu
                165                 170             175

Ile Arg Glu Ala Phe Arg Val Phe Asp Lys Asp Gly Asn Gly Tyr Ile
            180                 185                 190

Ser Ala Ala Glu Val Asp Glu Val Asp Ser Val Met Thr Asn Leu Asp
            195                 200             205

Gly Ser Val Gln Leu Ala Asp His Tyr Gln Gln Asn Thr Pro Ile Gly
            210                 215             220

Asp Gly Pro Val Leu Leu Pro Asp Asn His Tyr Leu Ser Thr Gln Ser
225                 230             235                 240

Ala Leu Ser Lys Asp Pro Lys Glu Lys Arg Asp His Ile Val Leu Leu
                245                 250             255

Glu Phe Val Thr Ala Ala Gly Ile Thr Leu Gly Met Asp Glu Leu Tyr
            260                 265             270

Lys
```

<210> SEQ ID NO 40
<211> LENGTH: 270
<212> TYPE: PRT
<213> ORGANISM: Artificial Sequence
<220> FEATURE:
<223> OTHER INFORMATION: Chemically synthesized

<400> SEQUENCE: 40

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Phe
            130                 135             140

Asn Tyr Asn Ser His Asn Val Tyr Ile Met Ala Asp Lys Gln Lys Asn
145                 150             155                 160

Gly Ile Lys Val Asn Phe Lys Ile Arg His Asn Ile Glu Glu Glu
                165                 170             175

Ile Arg Glu Ala Phe Arg Val Phe Asp Lys Asp Gly Asn Gly Tyr Ile
            180                 185                 190
```

```
Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
            245                 250                 255

Thr Ala Ala Gly Ile Thr Leu Gly Met Asp Glu Leu Tyr Lys
            260                 265                 270

<210> SEQ ID NO 41
<211> LENGTH: 267
<212> TYPE: PRT
<213> ORGANISM: Artificial Sequence
<220> FEATURE:
<223> OTHER INFORMATION: Chemically synthesized

<400> SEQUENCE: 41

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Gly His
        195                 200                 205

Tyr Asp Ala Glu Val Lys Thr Thr Tyr Lys Ala Lys Lys Pro Val Gln
    210                 215                 220

Leu Pro Gly Ala Tyr Asn Val Asn Ile Lys Leu Asp Ile Thr Ser His
225                 230                 235                 240

Asn Glu Asp Tyr Thr Ile Val Glu Gln Tyr Glu Arg Ala Glu Gly Arg
                245                 250                 255

His Ser Thr Gly Gly Met Asp Glu Leu Tyr Lys
            260                 265

<210> SEQ ID NO 42
```

<211> LENGTH: 267
<212> TYPE: PRT
<213> ORGANISM: Artificial Sequence
<220> FEATURE:
<223> OTHER INFORMATION: Chemically synthesized

<400> SEQUENCE: 42

```
Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Thr Pro Asn Phe Thr Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Gly His
        195                 200                 205

Tyr Asp Ala Glu Val Lys Thr Thr Tyr Lys Ala Lys Lys Pro Val Gln
    210                 215                 220

Leu Pro Gly Ala Tyr Ile Val Gly Ile Lys Leu Asp Ile Thr Ser His
225                 230                 235                 240

Asn Glu Asp Tyr Thr Ile Val Glu Leu Tyr Glu Arg Ala Glu Gly Arg
                245                 250                 255

His Ser Thr Gly Gly Met Asp Glu Leu Tyr Lys
            260                 265
```

<210> SEQ ID NO 43
<211> LENGTH: 274
<212> TYPE: PRT
<213> ORGANISM: Artificial Sequence
<220> FEATURE:
<223> OTHER INFORMATION: Chemically synthesized

<400> SEQUENCE: 43

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
```

```
            50                  55                  60
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
                180                 185                 190

Ser Ala Ala Gly Pro Arg Leu Val Met Thr Asn Leu Asp Gly Ser Val
            195                 200                 205

Gln Leu Ala Asp His Tyr Gln Gln Asn Thr Pro Ile Gly Asp Gly Pro
            210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys Lys Asp
                260                 265                 270

Glu Leu

<210> SEQ ID NO 44
<211> LENGTH: 288
<212> TYPE: PRT
<213> ORGANISM: Artificial Sequence
<220> FEATURE:
<223> OTHER INFORMATION: Chemically synthesized

<400> SEQUENCE: 44

Met Leu Leu Ser Val Pro Leu Leu Leu Gly Leu Leu Gly Leu Ala Ala
 1               5                  10                  15

Ala Asp Met Val Ser Lys Gly Glu Glu Leu Phe Thr Gly Val Val Pro
                 20                  25                  30

Ile Leu Val Glu Leu Asp Gly Asp Val Asn Gly His Lys Phe Ser Val
             35                  40                  45

Ser Gly Glu Gly Glu Gly Asp Ala Thr Tyr Gly Lys Leu Thr Leu Lys
         50                  55                  60

Phe Ile Cys Thr Thr Gly Lys Leu Pro Val Pro Trp Pro Thr Leu Val
 65                  70                  75                  80

Thr Thr Leu Thr Tyr Gly Val Gln Cys Phe Ser Arg Tyr Pro Asp His
                 85                  90                  95

Met Lys Gln His Asp Phe Phe Lys Ser Ala Met Pro Glu Gly Tyr Val
                100                 105                 110

Gln Glu Arg Thr Ile Phe Phe Lys Asp Asp Gly Asn Tyr Lys Thr Arg
            115                 120                 125

Ala Glu Val Lys Phe Glu Gly Asp Thr Leu Val Asn Arg Ile Glu Leu
        130                 135                 140
```

```
Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Glu
            180                 185                 190

Glu Glu Ile Arg Glu Ala Phe Arg Val Phe Asp Lys Asp Gly Asn Gly
        195                 200                 205

Tyr Ile Ser Ala Ala Gly Pro Arg Leu Val Met Thr Asn Leu Asp Gly
210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

<210> SEQ ID NO 45
<211> LENGTH: 270
<212> TYPE: PRT
<213> ORGANISM: Artificial Sequence
<220> FEATURE:
<223> OTHER INFORMATION: Chemically synthesized

<400> SEQUENCE: 45

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Lys Asp Gly Arg Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
210                 215                 220
```

```
Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Glu Phe Val
            245                 250                 255

Thr Ala Ala Gly Ile Thr Leu Gly Met Asp Glu Leu Tyr Lys
            260                 265                 270

<210> SEQ ID NO 46
<211> LENGTH: 270
<212> TYPE: PRT
<213> ORGANISM: Artificial Sequence
<220> FEATURE:
<223> OTHER INFORMATION: Chemically synthesized

<400> SEQUENCE: 46

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Glu Phe Val
            245                 250                 255

Thr Ala Ala Gly Ile Thr Leu Gly Met Asp Glu Leu Tyr Lys
            260                 265                 270

<210> SEQ ID NO 47
<211> LENGTH: 259
<212> TYPE: PRT
<213> ORGANISM: Artificial Sequence
<220> FEATURE:
<223> OTHER INFORMATION: Chemically synthesized
```

<400> SEQUENCE: 47

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Arg Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 48
<211> LENGTH: 259
<212> TYPE: PRT
<213> ORGANISM: Artificial Sequence
<220> FEATURE:
<223> OTHER INFORMATION: Chemically synthesized

<400> SEQUENCE: 48

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Arg Gly Tyr Ile Ser Ala Ala Glu Leu Arg His Val Met Thr Asn
                180                 185                 190

Leu Asp Gly Ser Val Gln Leu Ala Asp His Tyr Gln Gln Asn Thr Pro
            195                 200                 205

Ile Gly Asp Gly Pro Val Leu Leu Pro Asp Asn His Tyr Leu Ser Thr
            210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 49
<211> LENGTH: 262
<212> TYPE: PRT
<213> ORGANISM: Artificial Sequence
<220> FEATURE:
<223> OTHER INFORMATION: Chemically synthesized

<400> SEQUENCE: 49

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Lys Asp Gly Arg Gly Tyr Ile
            180                 185                 190

```
Ser Ala Ala Glu Asp Gly Ser Val Gln Leu Ala Asp His Tyr Gln Gln
            195                 200                 205

Asn Thr Pro Ile Gly Asp Gly Pro Val Leu Leu Pro Asp Asn His Tyr
        210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 50
<211> LENGTH: 262
<212> TYPE: PRT
<213> ORGANISM: Artificial Sequence
<220> FEATURE:
<223> OTHER INFORMATION: Chemically synthesized

<400> SEQUENCE: 50

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Glu Glu
                165                 170                 175

Ile Arg Glu Ala Phe Arg Val Phe Asp Lys Asp Gly Arg Gly Tyr Ile
            180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 51
<211> LENGTH: 251
```

<212> TYPE: PRT
<213> ORGANISM: Artificial Sequence
<220> FEATURE:
<223> OTHER INFORMATION: Chemically synthesized

<400> SEQUENCE: 51

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Arg Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 52
<211> LENGTH: 251
<212> TYPE: PRT
<213> ORGANISM: Artificial Sequence
<220> FEATURE:
<223> OTHER INFORMATION: Chemically synthesized

<400> SEQUENCE: 52

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Arg Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 53
<211> LENGTH: 270
<212> TYPE: PRT
<213> ORGANISM: Artificial Sequence
<220> FEATURE:
<223> OTHER INFORMATION: Chemically synthesized

<400> SEQUENCE: 53

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Lys Asp Gly Arg Gly Tyr Ile
            180                 185                 190
```

```
Ser Ala Phe Asn Pro Arg Gly Phe Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 54
<211> LENGTH: 270
<212> TYPE: PRT
<213> ORGANISM: Artificial Sequence
<220> FEATURE:
<223> OTHER INFORMATION: Chemically synthesized

<400> SEQUENCE: 54

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Phe Asn Pro Arg Gly Phe Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 55
```

<211> LENGTH: 270
<212> TYPE: PRT
<213> ORGANISM: Artificial Sequence
<220> FEATURE:
<223> OTHER INFORMATION: Chemically synthesized

<400> SEQUENCE: 55

```
Met Val Ser Lys Gly Glu Glu Leu Phe Thr Gly Val Val Pro Ile Leu
1               5                   10                  15
Val Glu Leu Asp Gly Asp Leu Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Glu Glu
                165                 170                 175
Ile Arg Glu Ala Phe Arg Val Phe Asp Lys Asp Gly Arg Gly Tyr Ile
            180                 185                 190
Ser Ala Phe Asn Pro Arg Ser Phe Met Thr Asn Leu Asp Gly Ser Val
        195                 200                 205
Gln Leu Ala Asp His Tyr Gln Gln Asn Thr Pro Ile Gly Asp Gly Pro
    210                 215                 220
Val Leu Leu Pro Asp Asn His Tyr Leu Ser Thr Gln Ser Ala Leu Ser
225                 230                 235                 240
Lys Asp Pro Asn Glu Lys Arg Asp His Ile Val Leu Leu Glu Phe Val
                245                 250                 255
Thr Ala Ala Gly Ile Thr Leu Gly Met Asp Glu Leu Tyr Lys
            260                 265                 270
```

<210> SEQ ID NO 56
<211> LENGTH: 270
<212> TYPE: PRT
<213> ORGANISM: Artificial Sequence
<220> FEATURE:
<223> OTHER INFORMATION: Chemically synthesized

<400> SEQUENCE: 56

```
Met Val Ser Lys Gly Glu Glu Leu Phe Thr Gly Val Val Pro Ile Leu
1               5                   10                  15
Val Glu Leu Asp Gly Asp Leu Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
```

```
                50                  55                  60
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Phe Asn Pro Arg Gly Phe Met Thr Asn Leu Asp Gly Ser Val
            195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 57
<211> LENGTH: 270
<212> TYPE: PRT
<213> ORGANISM: Artificial Sequence
<220> FEATURE:
<223> OTHER INFORMATION: Chemically synthesized

<400> SEQUENCE: 57

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
```

```
145                 150                 155                 160
Gly Ile Lys Val Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Phe Thr Pro Arg Gly Phe Met Thr Asn Leu Asp Gly Ser Val
            195                 200                 205

Gln Leu Ala Asp His Tyr Gln Gln Asn Thr Pro Ile Gly Asp Gly Pro
            210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 58
<211> LENGTH: 270
<212> TYPE: PRT
<213> ORGANISM: Artificial Sequence
<220> FEATURE:
<223> OTHER INFORMATION: Chemically synthesized

<400> SEQUENCE: 58

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Phe Thr Pro Arg Gly Phe Met Thr Asn Leu Asp Gly Ser Val
            195                 200                 205

Gln Leu Ala Asp His Tyr Gln Gln Asn Thr Pro Ile Gly Asp Gly Pro
            210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
```

```
                         245                 250                 255

Thr Ala Ala Gly Ile Thr Leu Gly Met Asp Glu Leu Tyr Lys
            260                 265                 270

<210> SEQ ID NO 59
<211> LENGTH: 270
<212> TYPE: PRT
<213> ORGANISM: Artificial Sequence
<220> FEATURE:
<223> OTHER INFORMATION: Chemically synthesized

<400> SEQUENCE: 59

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Phe Thr Pro Arg Ser Phe Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 60
<211> LENGTH: 270
<212> TYPE: PRT
<213> ORGANISM: Artificial Sequence
<220> FEATURE:
<223> OTHER INFORMATION: Chemically synthesized

<400> SEQUENCE: 60

Met Val Ser Lys Gly Glu Glu Leu Phe Thr Gly Val Val Pro Ile Leu
1               5                   10                  15
```

```
Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Arg Gly Tyr Ile
            180                 185                 190

Ser Ala Phe Thr Pro Arg Ser Phe Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 61
<211> LENGTH: 243
<212> TYPE: PRT
<213> ORGANISM: Artificial Sequence
<220> FEATURE:
<223> OTHER INFORMATION: Chemically synthesized

<400> SEQUENCE: 61

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Glu Val
                165                 170                 175

Asp Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Ile Val
    210                 215                 220

Leu Leu Glu Phe Val Thr Ala Ala Gly Ile Thr Leu Gly Met Asp Glu
225                 230                 235                 240

Leu Tyr Lys
```

<210> SEQ ID NO 62
<211> LENGTH: 243
<212> TYPE: PRT
<213> ORGANISM: Artificial Sequence
<220> FEATURE:
<223> OTHER INFORMATION: Chemically synthesized

<400> SEQUENCE: 62

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Glu Val
                165                 170                 175

Asp Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Ile Val
    210                 215                 220

Leu Leu Glu Phe Val Thr Ala Ala Gly Ile Thr Leu Gly Met Asp Glu
```

```
            225                 230                 235                 240
Leu Tyr Lys

<210> SEQ ID NO 63
<211> LENGTH: 253
<212> TYPE: PRT
<213> ORGANISM: Artificial Sequence
<220> FEATURE:
<223> OTHER INFORMATION: Chemically synthesized

<400> SEQUENCE: 63

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Gly Gly Ser
                165                 170                 175

Gly Gly Asp Glu Val Asp Gly Ser Gly Gly Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
    210                 215                 220

Asp Pro Asn Glu Lys Arg Asp His Ile Val Leu Glu Phe Val Thr
225                 230                 235                 240

Ala Ala Gly Ile Thr Leu Gly Met Asp Glu Leu Tyr Lys
                245                 250

<210> SEQ ID NO 64
<211> LENGTH: 253
<212> TYPE: PRT
<213> ORGANISM: Artificial Sequence
<220> FEATURE:
<223> OTHER INFORMATION: Chemically synthesized

<400> SEQUENCE: 64

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
```

```
            35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Gly Gly Ser
                165                 170                 175

Gly Gly Asp Glu Val Asp Gly Gly Ser Gly Gly Asp Gly Ser Val Gln
                180                 185                 190

Leu Ala Asp His Tyr Gln Gln Asn Thr Pro Ile Gly Asp Gly Pro Val
                195                 200                 205

Leu Leu Pro Asp Asn His Tyr Leu Ser Thr Gln Ser Ala Leu Ser Lys
210                 215                 220

Asp Pro Asn Glu Lys Arg Asp His Ile Val Leu Leu Glu Phe Val Thr
225                 230                 235                 240

Ala Ala Gly Ile Thr Leu Gly Met Asp Glu Leu Tyr Lys
                245                 250

<210> SEQ ID NO 65
<211> LENGTH: 254
<212> TYPE: PRT
<213> ORGANISM: Artificial Sequence
<220> FEATURE:
<223> OTHER INFORMATION: Chemically synthesized

<400> SEQUENCE: 65

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
                35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
```

```
145                 150                 155                 160
Gly Ile Lys Val Asn Phe Lys Ile Arg His Asn Ile Glu Asp Lys Asp
                165                 170                 175
Gly Arg Gly Tyr Ile Ser Ala Ala Glu Asp Glu Val Asp Gly Ser Val
                180                 185                 190
Gln Leu Ala Asp His Tyr Gln Gln Asn Thr Pro Ile Gly Asp Gly Pro
                195                 200                 205
Val Leu Leu Pro Asp Asn His Tyr Leu Ser Thr Gln Ser Ala Leu Ser
                210                 215                 220
Lys Asp Pro Asn Glu Lys Arg Asp His Ile Val Leu Leu Glu Phe Val
225                 230                 235                 240
Thr Ala Ala Gly Ile Thr Leu Gly Met Asp Glu Leu Tyr Lys
                245                 250

<210> SEQ ID NO 66
<211> LENGTH: 254
<212> TYPE: PRT
<213> ORGANISM: Artificial Sequence
<220> FEATURE:
<223> OTHER INFORMATION: Chemically synthesized

<400> SEQUENCE: 66

Met Val Ser Lys Gly Glu Glu Leu Phe Thr Gly Val Val Pro Ile Leu
1               5                   10                  15
Val Glu Leu Asp Gly Asp Leu Asn Gly His Lys Phe Ser Val Ser Gly
                20                  25                  30
Glu Gly Glu Gly Asp Ala Thr Tyr Gly Lys Leu Thr Leu Lys Phe Ile
                35                  40                  45
Cys Thr Thr Gly Lys Leu Pro Val Pro Trp Pro Thr Leu Val Thr Thr
50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
                115                 120                 125
Ile Asp Phe Lys Glu Asp Gly Asn Ile Leu Gly His Lys Leu Glu Tyr
                130                 135                 140
Asn Tyr Asn Ser His Asn Val Tyr Ile Thr Ala Asp Lys Gln Lys Asn
145                 150                 155                 160
Gly Ile Lys Ala Asn Phe Lys Ile Arg His Asn Ile Glu Asp Lys Asp
                165                 170                 175
Gly Arg Gly Tyr Ile Ser Ala Ala Glu Asp Glu Val Asp Gly Ser Val
                180                 185                 190
Gln Leu Ala Asp His Tyr Gln Gln Asn Thr Pro Ile Gly Asp Gly Pro
                195                 200                 205
Val Leu Leu Pro Asp Asn His Tyr Leu Ser Thr Gln Ser Ala Leu Ser
                210                 215                 220
Lys Asp Pro Asn Glu Lys Arg Asp His Ile Val Leu Leu Glu Phe Val
225                 230                 235                 240
Thr Ala Ala Gly Ile Thr Leu Gly Met Asp Glu Leu Tyr Lys
                245                 250
```

-continued

```
<210> SEQ ID NO 67
<211> LENGTH: 262
<212> TYPE: PRT
<213> ORGANISM: Artificial Sequence
<220> FEATURE:
<223> OTHER INFORMATION: Chemically synthesized

<400> SEQUENCE: 67

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Gly Glu Glu
                165                 170                 175

Ile Arg Glu Ala Phe Arg Val Phe Asp Glu Val Asp Leu Arg His Val
            180                 185                 190

Met Thr Asn Leu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 68
<211> LENGTH: 262
<212> TYPE: PRT
<213> ORGANISM: Artificial Sequence
<220> FEATURE:
<223> OTHER INFORMATION: Chemically synthesized

<400> SEQUENCE: 68

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

```
Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Glu Val Asp Leu Arg His Val
            180                 185                 190

Met Thr Asn Leu Asp Gly Ser Val Gln Leu Ala Asp His Tyr Gln Gln
            195                 200                 205

Asn Thr Pro Ile Gly Asp Gly Pro Val Leu Leu Pro Asp Asn His Tyr
            210                 215                 220

Leu Ser Thr Gln Ser Ala Leu Ser Lys Asp Pro Asn Glu Lys Arg Asp
225                 230                 235                 240

His Ile Val Leu Glu Phe Val Thr Ala Ala Gly Ile Thr Leu Gly
                245                 250                 255

Met Asp Glu Leu Tyr Lys
            260

<210> SEQ ID NO 69
<211> LENGTH: 268
<212> TYPE: PRT
<213> ORGANISM: Artificial Sequence
<220> FEATURE:
<223> OTHER INFORMATION: Chemically synthesized

<400> SEQUENCE: 69

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140
```

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Glu Val Asp Gly Gly Asp Glu
            180                 185                 190

Val Asp Leu Arg His Val Met Thr Asn Leu Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265
```

```
<210> SEQ ID NO 70
<211> LENGTH: 268
<212> TYPE: PRT
<213> ORGANISM: Artificial Sequence
<220> FEATURE:
<223> OTHER INFORMATION: Chemically synthesized

<400> SEQUENCE: 70

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asp Glu Val Asp Gly Gly Asp Glu
            180                 185                 190

Val Asp Leu Arg His Val Met Thr Asn Leu Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240
```

-continued

Pro Asn Glu Lys Arg Asp His Ile Val Leu Glu Phe Val Thr Ala
            245                 250                 255

Ala Gly Ile Thr Leu Gly Met Asp Glu Leu Tyr Lys
        260                 265

<210> SEQ ID NO 71
<211> LENGTH: 273
<212> TYPE: PRT
<213> ORGANISM: Artificial Sequence
<220> FEATURE:
<223> OTHER INFORMATION: Chemically synthesized

<400> SEQUENCE: 71

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Asp Glu Val Asp Gly Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 72
<211> LENGTH: 273
<212> TYPE: PRT
<213> ORGANISM: Artificial Sequence
<220> FEATURE:
<223> OTHER INFORMATION: Chemically synthesized

<400> SEQUENCE: 72

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Asp Glu Val Asp Gly Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

```
<210> SEQ ID NO 73
<211> LENGTH: 273
<212> TYPE: PRT
<213> ORGANISM: Artificial Sequence
<220> FEATURE:
<223> OTHER INFORMATION: Chemically synthesized

<400> SEQUENCE: 73
```

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu

```
            85                  90                  95
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                    165                 170                 175

Ile Arg Glu Ala Phe Arg Val Phe Asp Lys Asp Gly Asn Gly Tyr Ile
                    180                 185                 190

Ser Ala Ala Glu Leu Asp Glu Val Asp Ser Val Met Thr Asn Leu Asp
                    195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                    245                 250                 255

Glu Phe Val Thr Ala Ala Gly Ile Thr Leu Gly Met Asp Glu Leu Tyr
                    260                 265                 270

Lys

<210> SEQ ID NO 74
<211> LENGTH: 273
<212> TYPE: PRT
<213> ORGANISM: Artificial Sequence
<220> FEATURE:
<223> OTHER INFORMATION: Chemically synthesized

<400> SEQUENCE: 74

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                    20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                    165                 170                 175
```

```
Ile Arg Glu Ala Phe Arg Val Phe Asp Lys Asp Gly Asn Gly Tyr Ile
            180                 185                 190

Ser Ala Ala Glu Leu Asp Glu Val Asp Ser Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
                260                 265                 270

Lys

<210> SEQ ID NO 75
<211> LENGTH: 273
<212> TYPE: PRT
<213> ORGANISM: Artificial Sequence
<220> FEATURE:
<223> OTHER INFORMATION: Chemically synthesized

<400> SEQUENCE: 75

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Asp Glu Val Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255
```

Glu Phe Val Thr Ala Ala Gly Ile Thr Leu Gly Met Asp Glu Leu Tyr
        260                 265                 270

Lys

<210> SEQ ID NO 76
<211> LENGTH: 273
<212> TYPE: PRT
<213> ORGANISM: Artificial Sequence
<220> FEATURE:
<223> OTHER INFORMATION: Chemically synthesized

<400> SEQUENCE: 76

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Asp Glu Val Asp Gly Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 77
<211> LENGTH: 273
<212> TYPE: PRT
<213> ORGANISM: Artificial Sequence
<220> FEATURE:
<223> OTHER INFORMATION: Chemically synthesized

<400> SEQUENCE: 77

Met Val Ser Lys Gly Glu Glu Leu Phe Thr Gly Val Val Pro Ile Leu

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
            165                 170                 175

Ile Arg Glu Ala Phe Arg Val Phe Asp Lys Asp Gly Asn Gly Tyr Ile
            180                 185                 190

Ser Ala Ala Glu Val Asp Glu Val Asp Ser Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asn His Tyr Leu Ser Thr Gln Ser
225                 230                 235                 240

Ala Leu Ser Lys Asp Pro Asn Glu Lys Arg Asp His Ile Val Leu Leu
            245                 250                 255

Glu Phe Val Thr Ala Ala Gly Ile Thr Leu Gly Met Asp Glu Leu Tyr
            260                 265                 270

Lys

<210> SEQ ID NO 78
<211> LENGTH: 273
<212> TYPE: PRT
<213> ORGANISM: Artificial Sequence
<220> FEATURE:
<223> OTHER INFORMATION: Chemically synthesized

<400> SEQUENCE: 78

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

```
Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
                180                 185                 190

Ser Ala Ala Glu Val Asp Glu Val Asp Ser Val Met Thr Asn Leu Asp
            195                 200                 205

Gly Ser Val Gln Leu Ala Asp His Tyr Gln Gln Asn Thr Pro Ile Gly
        210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
                260                 265                 270

Lys

<210> SEQ ID NO 79
<211> LENGTH: 261
<212> TYPE: PRT
<213> ORGANISM: Artificial Sequence
<220> FEATURE:
<223> OTHER INFORMATION: Chemically synthesized

<400> SEQUENCE: 79

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Glu Glu Glu
                165                 170                 175
```

Ile Arg Glu Ala Phe Arg Val Phe Val Asp Glu Val Asp Gly Leu Arg
            180                 185                 190

His Val Met Thr Asn Leu Asp Gly Gly His Tyr Asp Ala Glu Val Lys
            195                 200                 205

Thr Thr Tyr Lys Ala Lys Lys Pro Val Gln Leu Pro Gly Ala Tyr Asn
            210                 215                 220

Val Asn Ile Lys Leu Asp Ile Thr Ser His Asn Glu Asp Tyr Thr Ile
225                 230                 235                 240

Val Glu Gln Tyr Glu Arg Ala Glu Gly Arg His Ser Thr Gly Gly Met
            245                 250                 255

Asp Glu Leu Tyr Lys
            260

<210> SEQ ID NO 80
<211> LENGTH: 261
<212> TYPE: PRT
<213> ORGANISM: Artificial Sequence
<220> FEATURE:
<223> OTHER INFORMATION: Chemically synthesized

<400> SEQUENCE: 80

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
50                  55                  60

Ile Leu Thr Pro Asn Phe Thr Tyr Gly Ser Lys Ala Tyr Val Lys His
65                  70                  75                  80

Pro Ala Asp Ile Pro Asp Tyr Leu Lys Leu Ser Phe Pro Glu Gly Phe
            85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Glu Gly Glu
            165                 170                 175

Ile Arg Glu Ala Phe Arg Val Phe Val Asp Glu Val Asp Gly Leu Arg
            180                 185                 190

His Val Met Thr Asn Leu Asp Gly Gly His Tyr Asp Ala Glu Val Lys
            195                 200                 205

Thr Thr Tyr Lys Ala Lys Lys Pro Val Gln Leu Pro Gly Ala Tyr Ile
            210                 215                 220

Val Gly Ile Lys Leu Asp Ile Thr Ser His Asn Glu Asp Tyr Thr Ile
225                 230                 235                 240

Val Glu Leu Tyr Glu Arg Ala Glu Gly Arg His Ser Thr Gly Gly Met
            245                 250                 255

Asp Glu Leu Tyr Lys
            260

<210> SEQ ID NO 81
<211> LENGTH: 243
<212> TYPE: PRT
<213> ORGANISM: Artificial Sequence
<220> FEATURE:
<223> OTHER INFORMATION: Chemically synthesized

<400> SEQUENCE: 81

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Leu Glu Thr
                165                 170                 175

Asp Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Ile Val
    210                 215                 220

Leu Leu Glu Phe Val Thr Ala Ala Gly Ile Thr Leu Gly Met Asp Glu
225                 230                 235                 240

Leu Tyr Lys
```

<210> SEQ ID NO 82
<211> LENGTH: 243
<212> TYPE: PRT
<213> ORGANISM: Artificial Sequence
<220> FEATURE:
<223> OTHER INFORMATION: Chemically synthesized

<400> SEQUENCE: 82

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60
```

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Leu Glu Thr
                165                 170                 175

Asp Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Ile Val
    210                 215                 220

Leu Leu Glu Phe Val Thr Ala Ala Gly Ile Thr Leu Gly Met Asp Glu
225                 230                 235                 240

Leu Tyr Lys

<210> SEQ ID NO 83
<211> LENGTH: 253
<212> TYPE: PRT
<213> ORGANISM: Artificial Sequence
<220> FEATURE:
<223> OTHER INFORMATION: Chemically synthesized

<400> SEQUENCE: 83

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Gly Gly Ser
                165                 170                 175

Gly Gly Leu Glu Thr Asp Gly Gly Ser Gly Gly Asp Gly Ser Val Gln

```
                180               185               190
Leu Ala Asp His Tyr Gln Gln Asn Thr Pro Ile Gly Asp Gly Pro Val
        195               200               205

Leu Leu Pro Asp Asn His Tyr Leu Ser Thr Gln Ser Ala Leu Ser Lys
        210               215               220

Asp Pro Asn Glu Lys Arg Asp His Ile Val Leu Glu Phe Val Thr
225             230               235               240

Ala Ala Gly Ile Thr Leu Gly Met Asp Glu Leu Tyr Lys
                245               250
```

<210> SEQ ID NO 84
<211> LENGTH: 253
<212> TYPE: PRT
<213> ORGANISM: Artificial Sequence
<220> FEATURE:
<223> OTHER INFORMATION: Chemically synthesized

<400> SEQUENCE: 84

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Gly Gly Ser
                165                 170                 175

Gly Gly Leu Glu Thr Asp Gly Gly Ser Gly Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
        210                 215                 220

Asp Pro Asn Glu Lys Arg Asp His Ile Val Leu Glu Phe Val Thr
225             230                 235                 240

Ala Ala Gly Ile Thr Leu Gly Met Asp Glu Leu Tyr Lys
                245                 250
```

<210> SEQ ID NO 85
<211> LENGTH: 254
<212> TYPE: PRT
<213> ORGANISM: Artificial Sequence
<220> FEATURE:
<223> OTHER INFORMATION: Chemically synthesized

<400> SEQUENCE: 85

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Arg Gly Tyr Ile Ser Ala Ala Glu Leu Glu Thr Asp Gly Ser Val
            180                 185                 190

Gln Leu Ala Asp His Tyr Gln Gln Asn Thr Pro Ile Gly Asp Gly Pro
        195                 200                 205

Val Leu Leu Pro Asp Asn His Tyr Leu Ser Thr Gln Ser Ala Leu Ser
    210                 215                 220

Lys Asp Pro Asn Glu Lys Arg Asp His Ile Val Leu Leu Glu Phe Val
225                 230                 235                 240

Thr Ala Ala Gly Ile Thr Leu Gly Met Asp Glu Leu Tyr Lys
                245                 250
```

<210> SEQ ID NO 86
<211> LENGTH: 254
<212> TYPE: PRT
<213> ORGANISM: Artificial Sequence
<220> FEATURE:
<223> OTHER INFORMATION: Chemically synthesized

<400> SEQUENCE: 86

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Arg Gly Tyr Ile Ser Ala Ala Glu Leu Gly Thr Asp Gly Ser Val
            180                 185                 190

Gln Leu Ala Asp His Tyr Gln Gln Asn Thr Pro Ile Gly Asp Gly Pro
        195                 200                 205

Val Leu Leu Pro Asp Asn His Tyr Leu Ser Thr Gln Ser Ala Leu Ser
    210                 215                 220

Lys Asp Pro Asn Glu Lys Arg Asp His Ile Val Leu Leu Glu Phe Val
225                 230                 235                 240

Thr Ala Ala Gly Ile Thr Leu Gly Met Asp Glu Leu Tyr Lys
                245                 250

<210> SEQ ID NO 87
<211> LENGTH: 262
<212> TYPE: PRT
<213> ORGANISM: Artificial Sequence
<220> FEATURE:
<223> OTHER INFORMATION: Chemically synthesized

<400> SEQUENCE: 87

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Leu Glu Thr Asp Leu Arg His Val
            180                 185                 190

Met Thr Asn Leu Asp Gly Ser Val Gln Leu Ala Asp His Tyr Gln Gln
        195                 200                 205
```

```
Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 88
<211> LENGTH: 262
<212> TYPE: PRT
<213> ORGANISM: Artificial Sequence
<220> FEATURE:
<223> OTHER INFORMATION: Chemically synthesized

<400> SEQUENCE: 88

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Leu Glu Thr Asp Leu Arg His Val
            180                 185                 190

Met Thr Asn Leu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 89
<211> LENGTH: 268
<212> TYPE: PRT
<213> ORGANISM: Artificial Sequence
<220> FEATURE:
```

<223> OTHER INFORMATION: Chemically synthesized

<400> SEQUENCE: 89

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Leu Glu Thr Asp Gly Gly Leu Glu
            180                 185                 190

Thr Asp Leu Arg His Val Met Thr Asn Leu Asp Gly Ser Val Gln Leu
        195                 200                 205

Ala Asp His Tyr Gln Gln Asn Thr Pro Ile Gly Asp Gly Pro Val Leu
210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265
```

<210> SEQ ID NO 90
<211> LENGTH: 268
<212> TYPE: PRT
<213> ORGANISM: Artificial Sequence
<220> FEATURE:
<223> OTHER INFORMATION: Chemically synthesized

<400> SEQUENCE: 90

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80
```

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Leu Glu Thr Asp Gly Gly Leu Glu
            180                 185                 190

Thr Asp Leu Arg His Val Met Thr Asn Leu Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265

<210> SEQ ID NO 91
<211> LENGTH: 273
<212> TYPE: PRT
<213> ORGANISM: Artificial Sequence
<220> FEATURE:
<223> OTHER INFORMATION: Chemically synthesized

<400> SEQUENCE: 91

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175
```

```
Ile Arg Glu Ala Phe Arg Val Phe Asp Lys Asp Gly Asn Gly Tyr Ile
            180                 185                 190

Ser Ala Ala Glu Leu Leu Glu Thr Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
            245                 250                 255

Glu Phe Val Thr Ala Ala Gly Ile Thr Leu Gly Met Asp Glu Leu Tyr
            260                 265                 270

Lys

<210> SEQ ID NO 92
<211> LENGTH: 273
<212> TYPE: PRT
<213> ORGANISM: Artificial Sequence
<220> FEATURE:
<223> OTHER INFORMATION: Chemically synthesized

<400> SEQUENCE: 92

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Leu Glu Thr Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
            245                 250                 255
```

```
Glu Phe Val Thr Ala Ala Gly Ile Thr Leu Gly Met Asp Glu Leu Tyr
            260                 265                 270
Lys
```

<210> SEQ ID NO 93
<211> LENGTH: 273
<212> TYPE: PRT
<213> ORGANISM: Artificial Sequence
<220> FEATURE:
<223> OTHER INFORMATION: Chemically synthesized

<400> SEQUENCE: 93

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Leu Glu Thr Asp Ser Val Met Thr Asn Leu Asp
        195                 200                 205

Gly Ser Val Gln Leu Ala Asp His Tyr Gln Gln Asn Thr Pro Ile Gly
210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys
```

<210> SEQ ID NO 94
<211> LENGTH: 273
<212> TYPE: PRT
<213> ORGANISM: Artificial Sequence
<220> FEATURE:
<223> OTHER INFORMATION: Chemically synthesized

<400> SEQUENCE: 94

```
Met Val Ser Lys Gly Glu Glu Leu Phe Thr Gly Val Val Pro Ile Leu
```

```
                1               5                  10                 15
            Val Glu Leu Asp Gly Asp Leu Asn Gly His Lys Phe Ser Val Ser Gly
                           20                  25                 30
            Glu Gly Glu Gly Asp Ala Thr Tyr Gly Lys Leu Thr Leu Lys Phe Ile
                       35                  40                 45
            Cys Thr Thr Gly Lys Leu Pro Val Pro Trp Pro Thr Leu Val Thr Thr
             50                  55                  60
            Leu Thr Tyr Gly Val Gln Cys Phe Ser Arg Tyr Pro Asp His Met Lys
             65                  70                  75                  80
            Gln His Asp Phe Phe Lys Ser Ala Met Pro Glu Gly Tyr Val Gln Glu
                           85                  90                 95
            Arg Thr Ile Phe Phe Lys Asp Asp Gly Asn Tyr Lys Thr Arg Ala Glu
                       100                 105                110
            Val Lys Phe Glu Gly Asp Thr Leu Val Asn Arg Ile Glu Leu Lys Gly
                   115                 120                 125
            Ile Asp Phe Lys Glu Asp Gly Asn Ile Leu Gly His Lys Leu Glu Tyr
               130                 135                 140
            Asn Tyr Asn Ser His Asn Val Tyr Ile Thr Ala Asp Lys Gln Lys Asn
            145                 150                 155                 160
            Gly Ile Lys Ala Asn Phe Lys Ile Arg His Asn Ile Glu Glu Glu
                           165                 170                 175
            Ile Arg Glu Ala Phe Arg Val Phe Asp Lys Asp Gly Asn Gly Tyr Ile
                       180                 185                 190
            Ser Ala Ala Glu Leu Leu Glu Thr Asp Ser Val Met Thr Asn Leu Asp
                   195                 200                 205
            Gly Ser Val Gln Leu Ala Asp His Tyr Gln Gln Asn Thr Pro Ile Gly
               210                 215                 220
            Asp Gly Pro Val Leu Leu Pro Asn His Tyr Leu Ser Thr Gln Ser
            225                 230                 235                 240
            Ala Leu Ser Lys Asp Pro Asn Glu Lys Arg Asp His Ile Val Leu Leu
                           245                 250                 255
            Glu Phe Val Thr Ala Ala Gly Ile Thr Leu Gly Met Asp Glu Leu Tyr
                       260                 265                 270
            Lys

<210> SEQ ID NO 95
<211> LENGTH: 273
<212> TYPE: PRT
<213> ORGANISM: Artificial Sequence
<220> FEATURE:
<223> OTHER INFORMATION: Chemically synthesized

<400> SEQUENCE: 95

Met Val Ser Lys Gly Glu Glu Leu Phe Thr Gly Val Val Pro Ile Leu
             1               5                  10                 15
            Val Glu Leu Asp Gly Asp Leu Asn Gly His Lys Phe Ser Val Ser Gly
                           20                  25                 30
            Glu Gly Glu Gly Asp Ala Thr Tyr Gly Lys Leu Thr Leu Lys Phe Ile
                       35                  40                 45
            Cys Thr Thr Gly Lys Leu Pro Val Pro Trp Pro Thr Leu Val Thr Thr
             50                  55                  60
            Leu Thr Tyr Gly Val Gln Cys Phe Ser Arg Tyr Pro Asp His Met Lys
             65                  70                  75                  80
            Gln His Asp Phe Phe Lys Ser Ala Met Pro Glu Gly Tyr Val Gln Glu
                           85                  90                 95
```

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Leu Glu Thr Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 96
<211> LENGTH: 273
<212> TYPE: PRT
<213> ORGANISM: Artificial Sequence
<220> FEATURE:
<223> OTHER INFORMATION: Chemically synthesized

<400> SEQUENCE: 96

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Leu Glu Thr Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
            245                 250                 255

Glu Phe Val Thr Ala Ala Gly Ile Thr Leu Gly Met Asp Glu Leu Tyr
            260                 265                 270

Lys

<210> SEQ ID NO 97
<211> LENGTH: 273
<212> TYPE: PRT
<213> ORGANISM: Artificial Sequence
<220> FEATURE:
<223> OTHER INFORMATION: Chemically synthesized

<400> SEQUENCE: 97

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
            165                 170                 175

Ile Arg Glu Ala Phe Arg Val Phe Asp Lys Asp Gly Asn Gly Tyr Ile
            180                 185                 190

Ser Ala Ala Glu Val Leu Glu Thr Asp Ser Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
            245                 250                 255

Glu Phe Val Thr Ala Ala Gly Ile Thr Leu Gly Met Asp Glu Leu Tyr

<210> SEQ ID NO 98
<211> LENGTH: 273
<212> TYPE: PRT
<213> ORGANISM: Artificial Sequence
<220> FEATURE:
<223> OTHER INFORMATION: Chemically synthesized

<400> SEQUENCE: 98

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Leu Glu Thr Asp Ser Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys
```

<210> SEQ ID NO 99
<211> LENGTH: 261
<212> TYPE: PRT
<213> ORGANISM: Artificial Sequence
<220> FEATURE:
<223> OTHER INFORMATION: Chemically synthesized

<400> SEQUENCE: 99

```
Met Val Ser Lys Gly Glu Glu Asp Asn Met Ala Ile Ile Lys Glu Phe
1               5                   10                  15
```

```
Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Glu Glu Glu
                165                 170                 175

Ile Arg Glu Ala Phe Arg Val Phe Val Leu Glu Thr Asp Gly Leu Arg
                180                 185                 190

His Val Met Thr Asn Leu Asp Gly Gly His Tyr Asp Ala Glu Val Lys
            195                 200                 205

Thr Thr Tyr Lys Ala Lys Lys Pro Val Gln Leu Pro Gly Ala Tyr Asn
210                 215                 220

Val Asn Ile Lys Leu Asp Ile Thr Ser His Asn Glu Asp Tyr Thr Ile
225                 230                 235                 240

Val Glu Gln Tyr Glu Arg Ala Glu Gly Arg His Ser Thr Gly Gly Met
                245                 250                 255

Asp Glu Leu Tyr Lys
                260

<210> SEQ ID NO 100
<211> LENGTH: 261
<212> TYPE: PRT
<213> ORGANISM: Artificial Sequence
<220> FEATURE:
<223> OTHER INFORMATION: Chemically synthesized

<400> SEQUENCE: 100

Met Val Ser Lys Gly Glu Glu Asn Asn Met Ala Ile Ile Lys Glu Phe
 1               5                  10                  15

Met Arg Phe Lys Val Arg Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
 50                  55                  60

Ile Leu Thr Pro Asn Phe Thr Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110
```

-continued

```
Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Glu Glu Glu
                165                 170                 175

Ile Arg Glu Ala Phe Arg Val Phe Val Leu Glu Thr Asp Gly Leu Arg
            180                 185                 190

His Val Met Thr Asn Leu Asp Gly Gly His Tyr Asp Ala Glu Val Lys
        195                 200                 205

Thr Thr Tyr Lys Ala Lys Lys Pro Val Gln Leu Pro Gly Ala Tyr Ile
210                 215                 220

Val Gly Ile Lys Leu Asp Ile Thr Ser His Asn Glu Asp Tyr Thr Ile
225                 230                 235                 240

Val Glu Leu Tyr Glu Arg Ala Glu Gly Arg His Ser Thr Gly Gly Met
                245                 250                 255

Asp Glu Leu Tyr Lys
            260

<210> SEQ ID NO 101
<211> LENGTH: 243
<212> TYPE: PRT
<213> ORGANISM: Artificial Sequence
<220> FEATURE:
<223> OTHER INFORMATION: Chemically synthesized

<400> SEQUENCE: 101

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Leu Glu His
                165                 170                 175

Asp Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205
```

```
Gln Ser Ala Leu Ser Lys Asp Pro Asn Glu Lys Arg Asp His Ile Val
    210                 215                 220

Leu Leu Glu Phe Val Thr Ala Ala Gly Ile Thr Leu Gly Met Asp Glu
225                 230                 235                 240

Leu Tyr Lys

<210> SEQ ID NO 102
<211> LENGTH: 243
<212> TYPE: PRT
<213> ORGANISM: Artificial Sequence
<220> FEATURE:
<223> OTHER INFORMATION: Chemically synthesized

<400> SEQUENCE: 102

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Leu Glu His
                165                 170                 175

Asp Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Ile Val
    210                 215                 220

Leu Leu Glu Phe Val Thr Ala Ala Gly Ile Thr Leu Gly Met Asp Glu
225                 230                 235                 240

Leu Tyr Lys

<210> SEQ ID NO 103
<211> LENGTH: 253
<212> TYPE: PRT
<213> ORGANISM: Artificial Sequence
<220> FEATURE:
<223> OTHER INFORMATION: Chemically synthesized

<400> SEQUENCE: 103

Met Val Ser Lys Gly Glu Glu Leu Phe Thr Gly Val Val Pro Ile Leu
1               5                   10                  15
```

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Gly Gly Ser
                165                 170                 175

Gly Gly Leu Glu His Asp Gly Gly Ser Gly Gly Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
    210                 215                 220

Asp Pro Asn Glu Lys Arg Asp His Ile Val Leu Leu Glu Phe Val Thr
225                 230                 235                 240

Ala Ala Gly Ile Thr Leu Gly Met Asp Glu Leu Tyr Lys
                245                 250

<210> SEQ ID NO 104
<211> LENGTH: 253
<212> TYPE: PRT
<213> ORGANISM: Artificial Sequence
<220> FEATURE:
<223> OTHER INFORMATION: Chemically synthesized

<400> SEQUENCE: 104

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

```
Ile Asp Phe Lys Glu Asp Gly Asn Ile Leu Gly His Lys Leu Glu Tyr
    130                 135                 140
Asn Tyr Asn Ser His Asn Val Tyr Ile Thr Ala Asp Lys Gln Lys Asn
145                 150                 155                 160
Gly Ile Lys Ala Asn Phe Lys Ile Arg His Asn Ile Glu Gly Gly Ser
                165                 170                 175
Gly Gly Leu Glu His Asp Gly Ser Gly Gly Asp Gly Ser Val Gln
            180                 185                 190
Leu Ala Asp His Tyr Gln Gln Asn Thr Pro Ile Gly Asp Gly Pro Val
            195                 200                 205
Leu Leu Pro Asp Asn His Tyr Leu Ser Thr Gln Ser Ala Leu Ser Lys
        210                 215                 220
Asp Pro Asn Glu Lys Arg Asp His Ile Val Leu Leu Glu Phe Val Thr
225                 230                 235                 240
Ala Ala Gly Ile Thr Leu Gly Met Asp Glu Leu Tyr Lys
                245                 250
```

<210> SEQ ID NO 105
<211> LENGTH: 254
<212> TYPE: PRT
<213> ORGANISM: Artificial Sequence
<220> FEATURE:
<223> OTHER INFORMATION: Chemically synthesized

<400> SEQUENCE: 105

```
Met Val Ser Lys Gly Glu Glu Leu Phe Thr Gly Val Val Pro Ile Leu
1               5                   10                  15
Val Glu Leu Asp Gly Asp Leu Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Lys Asp
                165                 170                 175
Gly Arg Gly Tyr Ile Ser Ala Ala Glu Leu Glu His Asp Gly Ser Val
            180                 185                 190
Gln Leu Ala Asp His Tyr Gln Gln Asn Thr Pro Ile Gly Asp Gly Pro
        195                 200                 205
Val Leu Leu Pro Asp Asn His Tyr Leu Ser Thr Gln Ser Ala Leu Ser
210                 215                 220
Lys Asp Pro Asn Glu Lys Arg Asp His Ile Val Leu Leu Glu Phe Val
225                 230                 235                 240
```

Thr Ala Ala Gly Ile Thr Leu Gly Met Asp Glu Leu Tyr Lys
            245                 250

<210> SEQ ID NO 106
<211> LENGTH: 254
<212> TYPE: PRT
<213> ORGANISM: Artificial Sequence
<220> FEATURE:
<223> OTHER INFORMATION: Chemically synthesized

<400> SEQUENCE: 106

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Arg Gly Tyr Ile Ser Ala Ala Glu Leu Glu His Asp Gly Ser Val
            180                 185                 190

Gln Leu Ala Asp His Tyr Gln Gln Asn Thr Pro Ile Gly Asp Gly Pro
        195                 200                 205

Val Leu Leu Pro Asp Asn His Tyr Leu Ser Thr Gln Ser Ala Leu Ser
    210                 215                 220

Lys Asp Pro Asn Glu Lys Arg Asp His Ile Val Leu Leu Glu Phe Val
225                 230                 235                 240

Thr Ala Ala Gly Ile Thr Leu Gly Met Asp Glu Leu Tyr Lys
            245                 250

<210> SEQ ID NO 107
<211> LENGTH: 262
<212> TYPE: PRT
<213> ORGANISM: Artificial Sequence
<220> FEATURE:
<223> OTHER INFORMATION: Chemically synthesized

<400> SEQUENCE: 107

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Leu Glu His Asp Leu Arg His Val
                180                 185                 190

Met Thr Asn Leu Asp Gly Ser Val Gln Leu Ala Asp His Tyr Gln Gln
                195                 200                 205

Asn Thr Pro Ile Gly Asp Gly Pro Val Leu Leu Pro Asp Asn His Tyr
210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
                260

<210> SEQ ID NO 108
<211> LENGTH: 262
<212> TYPE: PRT
<213> ORGANISM: Artificial Sequence
<220> FEATURE:
<223> OTHER INFORMATION: Chemically synthesized

<400> SEQUENCE: 108

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

```
Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Leu Glu His Asp Leu Arg His Val
            180                 185                 190

Met Thr Asn Leu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
                260

<210> SEQ ID NO 109
<211> LENGTH: 268
<212> TYPE: PRT
<213> ORGANISM: Artificial sequence
<220> FEATURE:
<223> OTHER INFORMATION: Chemically synthesized

<400> SEQUENCE: 109

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Leu Glu Thr Asp Gly Gly Leu Glu
            180                 185                 190

His Asp Leu Arg His Val Met Thr Asn Leu Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240
```

```
Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265
```

<210> SEQ ID NO 110
<211> LENGTH: 268
<212> TYPE: PRT
<213> ORGANISM: Artificial Sequence
<220> FEATURE:
<223> OTHER INFORMATION: Chemically synthesized

<400> SEQUENCE: 110

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Gly Glu Glu
                165                 170                 175

Ile Arg Glu Ala Phe Arg Val Phe Leu Glu Thr Asp Gly Gly Leu Glu
            180                 185                 190

His Asp Leu Arg His Val Met Thr Asn Leu Asp Gly Ser Val Gln Leu
        195                 200                 205

Ala Asp His Tyr Gln Gln Asn Thr Pro Ile Gly Asp Gly Pro Val Leu
    210                 215                 220

Leu Pro Asp Asn His Tyr Leu Ser Thr Gln Ser Ala Leu Ser Lys Asp
225                 230                 235                 240

Pro Asn Glu Lys Arg Asp His Ile Val Leu Leu Glu Phe Val Thr Ala
                245                 250                 255

Ala Gly Ile Thr Leu Gly Met Asp Glu Leu Tyr Lys
            260                 265
```

<210> SEQ ID NO 111
<211> LENGTH: 273
<212> TYPE: PRT
<213> ORGANISM: Artificial Sequence
<220> FEATURE:
<223> OTHER INFORMATION: Chemically synthesized

<400> SEQUENCE: 111

```
Met Val Ser Lys Gly Glu Glu Leu Phe Thr Gly Val Val Pro Ile Leu
```

```
            1               5                  10                 15
Val Glu Leu Asp Gly Asp Leu Asn Gly His Lys Phe Ser Val Ser Gly
                20                  25                 30
Glu Gly Glu Gly Asp Ala Thr Tyr Gly Lys Leu Thr Leu Lys Phe Ile
                35                  40                 45
Cys Thr Thr Gly Lys Leu Pro Val Pro Trp Pro Thr Leu Val Thr Thr
                50                  55                 60
Leu Thr Tyr Gly Val Gln Cys Phe Ser Arg Tyr Pro Asp His Met Lys
 65                  70                 75                     80
Gln His Asp Phe Phe Lys Ser Ala Met Pro Glu Gly Tyr Val Gln Glu
                 85                 90                  95
Arg Thr Ile Phe Phe Lys Asp Asp Gly Asn Tyr Lys Thr Arg Ala Glu
                100                 105                110
Val Lys Phe Glu Gly Asp Thr Leu Val Asn Arg Ile Glu Leu Lys Gly
                115                 120                125
Ile Asp Phe Lys Glu Asp Gly Asn Ile Leu Gly His Lys Leu Glu Tyr
                130                 135                140
Asn Tyr Asn Ser His Asn Val Tyr Ile Met Ala Asp Lys Gln Lys Asn
145                 150                 155                160
Gly Ile Lys Val Asn Phe Lys Ile Arg His Asn Ile Glu Glu Glu
                165                 170                175
Ile Arg Glu Ala Phe Arg Val Phe Asp Lys Asp Gly Asn Gly Tyr Ile
                180                 185                190
Ser Ala Ala Glu Leu Leu Glu His Asp Gly Val Met Thr Asn Leu Asp
                195                 200                205
Gly Ser Val Gln Leu Ala Asp His Tyr Gln Gln Asn Thr Pro Ile Gly
                210                 215                220
Asp Gly Pro Val Leu Leu Pro Asp Asn His Tyr Leu Ser Thr Gln Ser
225                 230                 235                240
Ala Leu Ser Lys Asp Pro Asn Glu Lys Arg Asp His Ile Val Leu Leu
                245                 250                255
Glu Phe Val Thr Ala Ala Gly Ile Thr Leu Gly Met Asp Glu Leu Tyr
                260                 265                270
Lys

<210> SEQ ID NO 112
<211> LENGTH: 273
<212> TYPE: PRT
<213> ORGANISM: Artificial Sequence
<220> FEATURE:
<223> OTHER INFORMATION: Chemically synthesized

<400> SEQUENCE: 112

Met Val Ser Lys Gly Glu Glu Leu Phe Thr Gly Val Val Pro Ile Leu
 1               5                  10                 15
Val Glu Leu Asp Gly Asp Leu Asn Gly His Lys Phe Ser Val Ser Gly
                20                  25                 30
Glu Gly Glu Gly Asp Ala Thr Tyr Gly Lys Leu Thr Leu Lys Phe Ile
                35                  40                 45
Cys Thr Thr Gly Lys Leu Pro Val Pro Trp Pro Thr Leu Val Thr Thr
                50                  55                 60
Leu Thr Tyr Gly Val Gln Cys Phe Ser Arg Tyr Pro Asp His Met Lys
 65                  70                 75                     80
Gln His Asp Phe Phe Lys Ser Ala Met Pro Glu Gly Tyr Val Gln Glu
                 85                 90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Leu Glu His Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 113
<211> LENGTH: 273
<212> TYPE: PRT
<213> ORGANISM: Artificial Sequence
<220> FEATURE:
<223> OTHER INFORMATION: Chemically synthesized

<400> SEQUENCE: 113

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175
```

```
Ile Arg Glu Ala Phe Arg Val Phe Asp Lys Asp Gly Asn Gly Tyr Ile
            180                 185                 190

Ser Ala Ala Glu Leu Leu Glu His Asp Ser Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 114
<211> LENGTH: 273
<212> TYPE: PRT
<213> ORGANISM: Artificial Sequence
<220> FEATURE:
<223> OTHER INFORMATION: Chemically synthesized

<400> SEQUENCE: 114

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Leu Glu His Asp Ser Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
```

-continued

```
                260                 265                 270
Lys

<210> SEQ ID NO 115
<211> LENGTH: 273
<212> TYPE: PRT
<213> ORGANISM: Artificial Sequence
<220> FEATURE:
<223> OTHER INFORMATION: Chemically synthesized

<400> SEQUENCE: 115

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Leu Glu His Asp Gly Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 116
<211> LENGTH: 273
<212> TYPE: PRT
<213> ORGANISM: Artificial Sequence
<220> FEATURE:
<223> OTHER INFORMATION: Chemically synthesized

<400> SEQUENCE: 116

Met Val Ser Lys Gly Glu Glu Leu Phe Thr Gly Val Val Pro Ile Leu
1               5                   10                  15
```

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
            165                 170                 175

Ile Arg Glu Ala Phe Arg Val Phe Asp Lys Asp Gly Asn Gly Tyr Ile
            180                 185                 190

Ser Ala Ala Glu Val Leu Glu His Asp Gly Val Met Thr Asn Leu Asp
            195                 200                 205

Gly Ser Val Gln Leu Ala Asp His Tyr Gln Gln Asn Thr Pro Ile Gly
            210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 117
<211> LENGTH: 273
<212> TYPE: PRT
<213> ORGANISM: Artificial Sequence
<220> FEATURE:
<223> OTHER INFORMATION: Chemically synthesized

<400> SEQUENCE: 117

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Val Leu Glu His Asp Ser Val Met Thr Asn Leu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 118
<211> LENGTH: 273
<212> TYPE: PRT
<213> ORGANISM: Artificial Sequence
<220> FEATURE:
<223> OTHER INFORMATION: Chemically synthesized

<400> SEQUENCE: 118

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile

```
                180                 185                 190
Ser Ala Glu Val Leu Glu His Asp Ser Val Met Thr Asn Leu Asp
            195                 200                 205

Gly Ser Val Gln Leu Ala Asp His Tyr Gln Gln Asn Thr Pro Ile Gly
        210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
            245                 250                 255

Glu Phe Val Thr Ala Ala Gly Ile Thr Leu Gly Met Asp Glu Leu Tyr
            260                 265                 270

Lys

<210> SEQ ID NO 119
<211> LENGTH: 239
<212> TYPE: PRT
<213> ORGANISM: Artificial Sequence
<220> FEATURE:
<223> OTHER INFORMATION: Chemically synthesized

<400> SEQUENCE: 119

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 120
<211> LENGTH: 239
<212> TYPE: PRT
<213> ORGANISM: Artificial Sequence
```

<220> FEATURE:
<223> OTHER INFORMATION: Chemically synthesized

<400> SEQUENCE: 120

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 121
<211> LENGTH: 239
<212> TYPE: PRT
<213> ORGANISM: Artificial Sequence
<220> FEATURE:
<223> OTHER INFORMATION: Chemically synthesized

<400> SEQUENCE: 121

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu

```
                100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 122
<211> LENGTH: 239
<212> TYPE: PRT
<213> ORGANISM: Artificial Sequence
<220> FEATURE:
<223> OTHER INFORMATION: Chemically synthesized

<400> SEQUENCE: 122

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Ile Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Lys Glu Lys Arg Asp His Ile Val Leu Leu Glu Phe
    210                 215                 220

Val Thr Ala Ala Gly Ile Thr Leu Gly Met Asp Glu Leu Tyr Lys
```

```
225                 230                 235

<210> SEQ ID NO 123
<211> LENGTH: 239
<212> TYPE: PRT
<213> ORGANISM: Artificial Sequence
<220> FEATURE:
<223> OTHER INFORMATION: Chemically synthesized

<400> SEQUENCE: 123

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Phe
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 124
<211> LENGTH: 236
<212> TYPE: PRT
<213> ORGANISM: Artificial Sequence
<220> FEATURE:
<223> OTHER INFORMATION: Chemically synthesized

<400> SEQUENCE: 124

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60
```

```
Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 125
<211> LENGTH: 236
<212> TYPE: PRT
<213> ORGANISM: Artificial Sequence
<220> FEATURE:
<223> OTHER INFORMATION: Chemically synthesized

<400> SEQUENCE: 125

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Thr Pro Asn Phe Thr Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
            180                 185                 190
```

Gln Leu Pro Gly Ala Tyr Ile Val Gly Ile Lys Leu Asp Ile Thr Ser
            195                 200                 205

His Asn Glu Asp Tyr Thr Ile Val Glu Leu Tyr Glu Arg Ala Glu Gly
        210                 215                 220

Arg His Ser Thr Gly Gly Met Asp Glu Leu Tyr Lys
225                 230                 235

<210> SEQ ID NO 126
<211> LENGTH: 31
<212> TYPE: PRT
<213> ORGANISM: Artificial Sequence
<220> FEATURE:
<223> OTHER INFORMATION: Chemically synthesized

<400> SEQUENCE: 126

Glu Glu Glu Ile Arg Glu Ala Phe Arg Val Phe Asp Lys Asp Gly Asn
1               5                   10                  15

Gly Tyr Ile Ser Ala Ala Glu Leu Arg His Val Met Thr Asn Leu
            20                  25                  30

<210> SEQ ID NO 127
<211> LENGTH: 23
<212> TYPE: PRT
<213> ORGANISM: Artificial Sequence
<220> FEATURE:
<223> OTHER INFORMATION: Chemically synthesized

<400> SEQUENCE: 127

Glu Glu Glu Ile Arg Glu Ala Phe Arg Val Phe Asp Lys Asp Gly Asn
1               5                   10                  15

Gly Tyr Ile Ser Ala Ala Glu
            20

<210> SEQ ID NO 128
<211> LENGTH: 20
<212> TYPE: PRT
<213> ORGANISM: Artificial Sequence
<220> FEATURE:
<223> OTHER INFORMATION: Chemically synthesized

<400> SEQUENCE: 128

Asp Lys Asp Gly Asn Gly Tyr Ile Ser Ala Ala Glu Leu Arg His Val
1               5                   10                  15

Met Thr Asn Leu
            20

<210> SEQ ID NO 129
<211> LENGTH: 31
<212> TYPE: PRT
<213> ORGANISM: Artificial Sequence
<220> FEATURE:
<223> OTHER INFORMATION: Chemically synthesized

<400> SEQUENCE: 129

Glu Glu Glu Ile Ala Glu Ala Phe Ala Val Phe Asp Ala Asp Gly Asn
1               5                   10                  15

Gly Tyr Ile Ser Ala Ala Glu Leu Arg His Val Met Thr Asn Leu
            20                  25                  30

<210> SEQ ID NO 130
<211> LENGTH: 12
<212> TYPE: PRT
<213> ORGANISM: Artificial Sequence
<220> FEATURE:

<223> OTHER INFORMATION: Chemically synthesized

<400> SEQUENCE: 130

Asp Lys Asp Gly Asn Gly Tyr Ile Ser Ala Ala Glu
1               5                   10

<210> SEQ ID NO 131
<211> LENGTH: 31
<212> TYPE: PRT
<213> ORGANISM: Artificial Sequence
<220> FEATURE:
<223> OTHER INFORMATION: Chemically synthesized

<400> SEQUENCE: 131

Glu Glu Glu Ile Arg Glu Ala Phe Arg Val Phe Asp Lys Asp Gly Asn
1               5                   10                  15

Gly Tyr Ile Ser Ala Ala Gly Pro Arg Leu Val Met Thr Asn Leu
            20                  25                  30

<210> SEQ ID NO 132
<211> LENGTH: 20
<212> TYPE: PRT
<213> ORGANISM: Artificial Sequence
<220> FEATURE:
<223> OTHER INFORMATION: Chemically synthesized

<400> SEQUENCE: 132

Asp Lys Asp Gly Asn Gly Tyr Ile Ser Ala Ala Gly Pro Arg Leu Val
1               5                   10                  15

Met Thr Asn Leu
            20

<210> SEQ ID NO 133
<211> LENGTH: 31
<212> TYPE: PRT
<213> ORGANISM: Artificial Sequence
<220> FEATURE:
<223> OTHER INFORMATION: Chemically synthesized

<400> SEQUENCE: 133

Glu Glu Glu Ile Ala Glu Ala Phe Ala Val Phe Asp Ala Asp Gly Asn
1               5                   10                  15

Gly Tyr Ile Ser Ala Ala Gly Pro Arg Leu Val Met Thr Asn Leu
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Chemically synthesized

<400> SEQUENCE: 134

Glu Glu Glu Ile Arg Glu Ala Phe Arg Val Phe Asp Lys Asp Gly Asn
1               5                   10                  15

Gly Tyr Ile Ser Ala Ala Gly Pro Ala Arg Leu Val Met Thr Asn Leu
            20                  25                  30

<210> SEQ ID NO 135
<211> LENGTH: 21
<212> TYPE: PRT
<213> ORGANISM: Artificial Sequence
<220> FEATURE:
<223> OTHER INFORMATION: Chemically synthesized

```
<400> SEQUENCE: 135

Asp Lys Asp Gly Asn Gly Tyr Ile Ser Ala Ala Gly Pro Ala Arg Leu
1               5                   10                  15

Val Met Thr Asn Leu
            20

<210> SEQ ID NO 136
<211> LENGTH: 32
<212> TYPE: PRT
<213> ORGANISM: Artificial Sequence
<220> FEATURE:
<223> OTHER INFORMATION: Chemically synthesized

<400> SEQUENCE: 136

Glu Glu Glu Ile Ala Glu Ala Phe Ala Val Phe Asp Ala Asp Gly Asn
1               5                   10                  15

Gly Tyr Ile Ser Ala Ala Gly Pro Ala Arg Leu Val Met Thr Asn Leu
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Chemically synthesized

<400> SEQUENCE: 137

Glu Glu Glu Ile Arg Glu Ala Phe Arg Val Phe Asp Lys Asp Gly Asn
1               5                   10                  15

Gly Tyr Ile Ser Ala Ala Gly Pro Ala Arg Leu Ala Ile Thr Asn Leu
            20                  25                  30

<210> SEQ ID NO 138
<211> LENGTH: 21
<212> TYPE: PRT
<213> ORGANISM: Artificial Sequence
<220> FEATURE:
<223> OTHER INFORMATION: Chemically synthesized

<400> SEQUENCE: 138

Asp Lys Asp Gly Asn Gly Tyr Ile Ser Ala Ala Gly Pro Ala Arg Leu
1               5                   10                  15

Ala Ile Thr Asn Leu
            20

<210> SEQ ID NO 139
<211> LENGTH: 32
<212> TYPE: PRT
<213> ORGANISM: Artificial Sequence
<220> FEATURE:
<223> OTHER INFORMATION: Chemically synthesized

<400> SEQUENCE: 139

Glu Glu Glu Ile Ala Glu Ala Phe Ala Val Phe Asp Ala Asp Gly Asn
1               5                   10                  15

Gly Tyr Ile Ser Ala Ala Gly Pro Ala Arg Leu Ala Ile Thr Asn Leu
            20                  25                  30

<210> SEQ ID NO 140
<211> LENGTH: 31
<212> TYPE: PRT
<213> ORGANISM: Artificial Sequence
<220> FEATURE:
<223> OTHER INFORMATION: Chemically synthesized
```

<400> SEQUENCE: 140

Glu Glu Glu Ile Arg Glu Ala Phe Arg Val Phe Asp Lys Asp Gly Arg
1               5                   10                  15

Gly Tyr Ile Ser Ala Ala Glu Leu Arg His Val Met Thr Asn Leu
            20                  25                  30

<210> SEQ ID NO 141
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 141

Glu Glu Glu Ile Arg Glu Ala Phe Arg Val Phe Asp Lys Asp Gly Asn
1               5                   10                  15

Gly Tyr Ile Ser Ala Phe Asn Pro Arg Gly Phe Met Thr Asn Leu
            20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Chemically synthesized

<400> SEQUENCE: 142

Glu Glu Glu Ile Arg Glu Ala Phe Arg Val Phe Asp Lys Asp Gly Asn
1               5                   10                  15

Gly Tyr Ile Ser Ala Phe Asn Pro Arg Ser Phe Met Thr Asn Leu
            20                  25                  30

<210> SEQ ID NO 143
<211> LENGTH: 31
<212> TYPE: PRT
<213> ORGANISM: Artificial Sequence
<220> FEATURE:
<223> OTHER INFORMATION: Chemically synthesized

<400> SEQUENCE: 143

Glu Glu Glu Ile Arg Glu Ala Phe Arg Val Phe Asp Lys Asp Gly Asn
1               5                   10                  15

Gly Tyr Ile Ser Ala Phe Thr Pro Arg Gly Phe Met Thr Asn Leu
            20                  25                  30

<210> SEQ ID NO 144
<211> LENGTH: 31
<212> TYPE: PRT
<213> ORGANISM: Artificial Sequence
<220> FEATURE:
<223> OTHER INFORMATION: Chemically synthesized

<400> SEQUENCE: 144

Glu Glu Glu Ile Arg Glu Ala Phe Arg Val Phe Asp Lys Asp Gly Asn
1               5                   10                  15

Gly Tyr Ile Ser Ala Phe Thr Pro Arg Ser Phe Met Thr Asn Leu
            20                  25                  30

ENZYME SENSORS, METHODS FOR PREPARING AND USING SUCH SENSORS, AND METHODS OF DETECTING PROTEASE ACTIVITY

CROSS-REFERENCE TO RELATED APPLICATION

This application is a continuation of Ser. No. 13/848,435, filed Mar. 21, 2013, entitled "ENZYME SENSORS, METHODS FOR PREPARING AND USING SUCH SENSORS, AND METHODS OF DETECTING PROTEASE ACTIVITY," which is a continuation of Ser. No. 12/227,404, filed on Nov. 20, 2009, entitled "ENZYME SENSORS, METHODS FOR PREPARING AND USING SUCH SENSORS, AND METHODS OF DETECTING PROTEASE ACTIVITY", which claims priority to the PCT APPLICATION ENTITLED "ENZYME SENSORS, METHODS FOR PREPARING AND USING SUCH SENSORS, AND METHODS OF DETECTING PROTEASE ACTIVITY," HAVING SERIAL NUMBER PCT/US2007/017462, FILED ON Aug. 6, 2007, which claims priority to U.S. provisional applications entitled, "Protease Sensors, Methods for Preparing and using such sensors," having Ser. No. 60/821,490, filed on Aug. 4, 2006, which is entirely incorporated herein by reference.

SEQUENCE LISTING

This application contains a sequence listing filed in electronic form as an ASCII.txt file entitled 02084232.txt, created on Mar. 21, 2013, and having a size of 302,497 bytes. The content of the sequence listing is incorporated herein in its entirety.

BACKGROUND

Proteases, including proteinases peptidases and proteolytic enzymes, are enzymes that catalyze the cleavage of peptide bonds. The process is called proteolytic cleavage, a common mechanism of activation or inactivation of enzymes especially involved in blood coagulation or digestion. Proteases use a molecule of water for this catalysis and are thus classified as hydrolases. For example, peptidases can break either specific peptide bonds (limited proteolysis), depending on the amino acid sequence of a protein, or break down a complete peptide to amino acids (unlimited proteolysis). The activity can be a destructive change abolishing a protein's function or digesting it into its principal components, which can activate or be a signal in a signalling pathway.

Proteases have important roles in many physiological regulations including blood coagulation, fibrinolysis, complement cascading, hormone maturation, protein degradation, and apoptosis. These enzymes are involved in a multitude of physiological reactions from simple digestion of food proteins to highly regulated cascades (e.g. the blood clotting cascade, the complement system, apoptosis pathways, and the invertebrate prophenoloxidase activating cascade). Importantly, malfunctions of proteases are often involved with or are indications of diseases.

To detect and to characterize photolytic activity, the prior art discloses methods using FRET and green fluorescent proteins (GFPs) to detect proteolysis and denaturation. More particularly, such examples include monitoring protease activity by altering the FRET between a specific GFP and another fluorescent protein, such as yellow fluorescent proteins. These protease sensors have limitations for accurate quantitative measurement of enzymatic activity especially for in vivo application, which is partly attributable to problems associated with photon bleaching/activation and small signal change as well as problems for the orientation change in the living cells Accordingly, there is a need for improved protease sensors and methods for measuring and detecting protease activity. Such protease sensors can be applied both in vivo and in vitro systems. Such protease sensors should be able to detect protease activity in microenvironments so as to be useful as probes of cellular events involving changes in such microenvironments in real time. It is to these needs among others that the present invention is directed.

SUMMARY

Embodiments of the present disclosure provide for enzyme sensors, protease sensors, methods for producing and using the enzyme and protease sensors, methods of detecting and/or measuring protease activity, methods for characterizing protease cellular activity, fusion proteins, polynucleotides, and vectors corresponding to the enzyme and protease sensors, kits, and the like.

One exemplary enzyme sensor, among others, includes: a molecular recognition motif that binds an analyte; and an optically-active fluorescent host protein in which the molecular recognition motif is operatively linked to or integrated therein, and wherein the interaction of the analyte to the molecular recognition motif produces a detectable change.

One exemplary protease sensor, among others, includes: a molecular recognition motif that binds an analyte; and an optically-active fluorescent host protein in which the molecular recognition motif is operatively linked to or integrated therein, and wherein the interaction of the analyte to the molecular recognition motif produces a detectable change.

One exemplary method for constructing an enzyme sensor, among others, includes: operatively inserting or integrating a molecular recognition motif that binds an analyte into an optically-active fluorescent host protein.

One exemplary method of detecting protease activity, among others, includes: providing a protease sensor comprising: a molecular recognition motif that binds an analyte; and an optically-active fluorescent host protein in which the molecular recognition motif is operatively linked to or integrated therein, and wherein the interaction of the analyte to the molecular recognition motif produces a detectable change; introducing the protease sensor to a host; measuring a signal produced from the protease sensor; and comparing the signal to a standard signal from the protease sensor prior to interaction with an analyte, wherein a ratiometric change in the signal corresponds to the detection of the analyte interacting with the protease sensor.

One exemplary fusion protein, among others, includes: an optically-active fluorescent host protein in which a molecular recognition motif is operatively linked to or integrated therein that has an amino acid sequence selected from: SEQ ID NO: 1-118.

One exemplary isolated nucleotide encoding a fusion protein, among others, includes: a nucleotide sequence encoding a fusion protein includes an optically-active fluorescent host protein in which a molecular recognition motif is operatively linked to or integrated therein that has an amino acid sequence selected from: SEQ ID NO: 1-118.

One exemplary kit for detecting protease activity, among others, includes: a protease sensor, related agents that can facilitate the delivery of the protein to its desired destination, and directions, wherein the protease sensor includes: a molecular recognition motif that binds an analyte; and an optically-active fluorescent host protein in which the molecular recognition motif is operatively linked to or integrated therein, and wherein the interaction of the analyte to the molecular recognition motif produces a detectable change.

One exemplary method for quantifying an analyte, among others, includes: introducing a polynucleotide sequence encoding protein for a protease sensor to a host, wherein the protease sensor includes: a molecular recognition motif that binds an analyte; and an optically-active fluorescent host protein in which the molecular recognition motif is operatively linked to or integrated therein, and wherein the interaction of the analyte to the molecular recognition motif produces a detectable change; measuring a signal produced from the protease sensor; and comparing the signal to a standard signal from the protease sensor prior to interaction with an analyte, wherein a ratiometric change in the signal corresponds to the detection of the analyte interacting with the protease sensor.

One exemplary method for characterizing protease cellular activity, among others, includes: expressing a protease sensor in a cell, wherein the protease sensor includes: a molecular recognition motif that binds an analyte; and an optically-active fluorescent host protein in which the molecular recognition motif is operatively linked to or integrated therein, and wherein the interaction of the analyte to the molecular recognition motif produces a detectable change; measuring a signal produced from the protease sensor; and comparing the signal to a standard signal from the protease sensor prior to interaction with an analyte, wherein a ratiometric change in the signal corresponds to the detection of the analyte interacting with the protease sensor.

One exemplary vector encoding a fusion protein, among others, includes: a vector encoding a fusion protein that includes an optically-active fluorescent host protein in which a molecular recognition motif is operatively linked to or integrated therein that has an amino acid sequence selected from: SEQ ID NO: 1-118.

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6A shows a graph that illustrates the effect of trypsin inhibitor, leupeptin with various concentrations on the cleavage of EGFP-T/C1 trypsin digestion. EGFP-T1 containing leupeptin with 0 nM (circle), 12.5 nM (square), 25 nM (triangle), 50 nM (up side down triangle), 100 nM (square with x). Samples were digested by 0.005 µM trypsin in 10 mM Tris, 20 mM CaCl2 at pH 7.4. EGFP-T/C1 with trypsin inhibitor, leupeptin with 0 nM (circle), 12.5 nM (square), 25 nM (triangle), 50 nM (up side down triangle), 100 nM (square with x). Kinetic studies (FIG. 6B) reveal the competitive inhibition to trypsin, with Ki value of $31.1 \pm 2.3$ nM.

DETAILED DESCRIPTION

Figure 1:
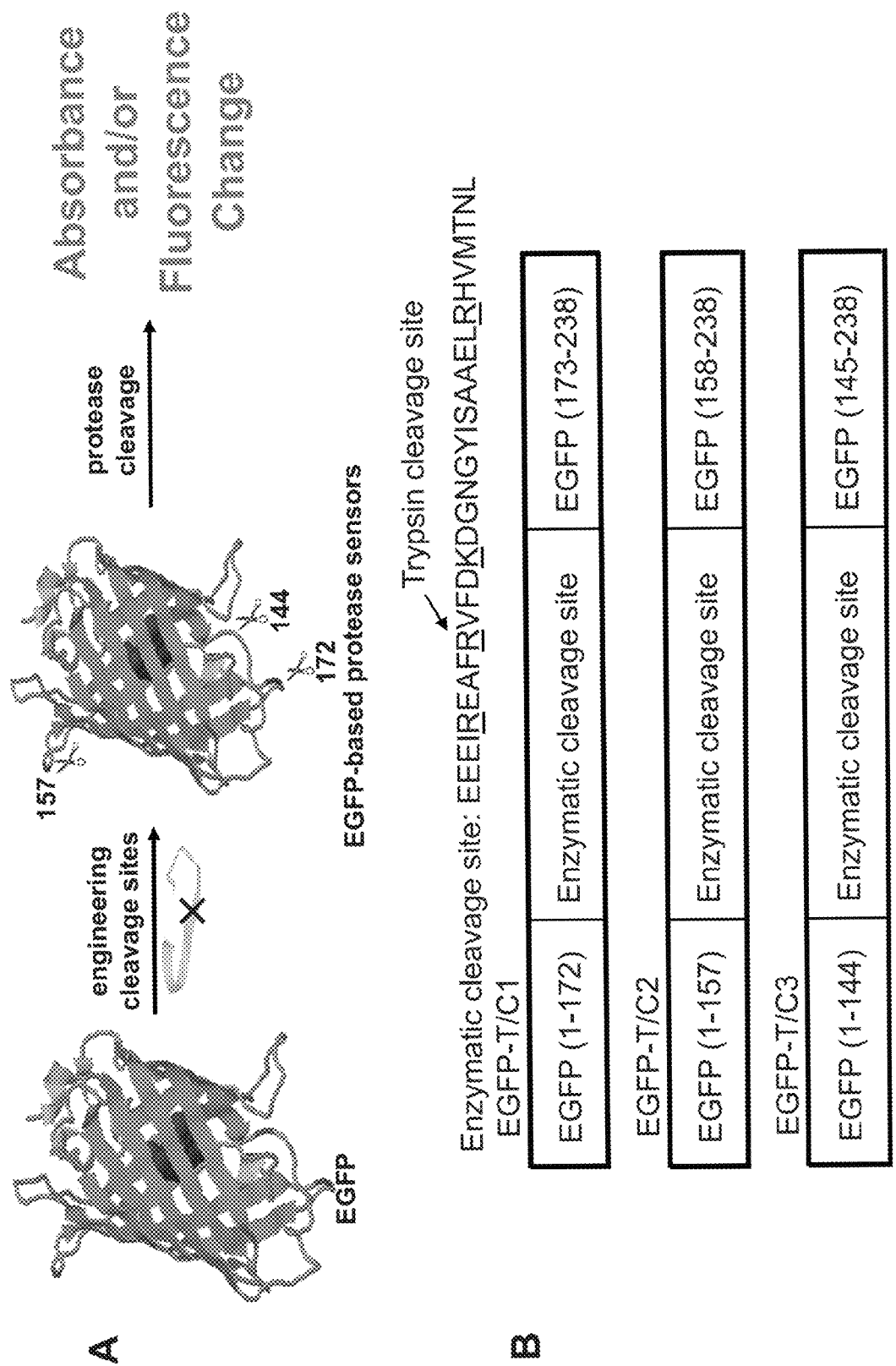
FIG. 1 illustrates a diagram of three trypsin sensors (A) based on EGFP with grafting of a trypsin-cleavable linker at position 144, 157 and 172, and the enzymatic cleavage sites in the linker (B).

Embodiments of the present disclosure will employ, unless otherwise indicated, techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.*, 113: 2722, 1991; Ellman, et al., *Methods Enzymol.*, 202: 301, 1991; Chung, et al., *Science,* 259: 806-9, 1993; and Chung, et al., *Proc. Natl. Acad. Sci. USA,* 90: 10145-9, 1993). In a second method, translation is carried out in *Xenopus* oocytes by microinjection of mutated mRNA and chemically aminoacylated suppressor tRNAs (Turcatti, et al., *J. Biol. Chem.,* 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.,* 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.,* 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

As used herein, DNA may obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

The DNA encoding the protein disclosed herein can be prepared by the usual methods: cloning cDNA from mRNA encoding the protein, isolating genomic DNA and splicing it, chemical synthesis, and so on.

cDNA can be cloned from mRNA encoding the protein by, for example, the method described below:

First, the mRNA encoding the protein is prepared from the above-mentioned tissues or cells expressing and producing the protein. mRNA can be prepared by isolating total RNA by a known method such as guanidine-thiocyanate method (Chirgwin et al., Biochemistry, 18:5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase, such as the method of Okayama et al (Mol. Cell. Biol. 2:161 (1982); Mol. Cell. Biol. 3:280 (1983)) or the method of Hoffman et al. (Gene 25:263 (1983)), and converted into double-stranded cDNA. A cDNA library is prepared by transforming *E. coli* with plasmid vectors, phage vectors, or cosmid vectors having this cDNA or by transfecting *E. coli* after in vitro packaging.

The plasmid vectors used herein are not limited as long as they are replicated and maintained in hosts. Any phage vector that can be replicated in hosts can also be used. Examples of usually used cloning vectors are pUC19, .lambda.gt10, .lambda.gt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p. 1.53, 1989). cDNA can be inserted into a phage vector by, for example, the method of Hyunh et al. (DNA cloning, a practical approach, 1, p. 49 (1985)). These methods can be simply performed by using a commercially available cloning kit (for example, a product from Takara Shuzo). The recombinant plasmid or phage vector thus obtained is introduced into an appropriate host cell such as a prokaryote (for example, *E. coli*: HB101, DH5a, MC1061/P3, etc).

Examples of a method for introducing a plasmid into a host are, calcium chloride method, calcium chloride/rubidium chloride method and electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The identification of cDNA encoding protein, its expression being augmented depending on the stimulation of cytokines like AID protein disclosed herein, can be carried out by for example suppression subtract hybridization (SSH)(Proc. Natl. Acad. Sci. USA, 93:6025-6030, 1996; Anal. Biochem., 240:90-97, 1996) taking advantage of suppressive PCR effect (Nucleic Acids Res., 23:1087-1088, 1995), using two cDNA libraries, namely, cDNA library constructed from mRNA derived from stimulated cells (tester cDNA library) and that constructed from mRNA derived from unstimulated cells (driver cDNA library).

Embodiments of the present disclosure relate to a recombinant vector comprising the DNA encoding the protein used herein. As a recombinant vector disclosed herein, any vector can be used as long as it is capable of retaining replication or self-multiplication in each host cell of prokaryotic and/or eukaryotic cells, including plasmid vectors and phage vectors. The recombinant vector can easily be prepared by ligating the DNA encoding protein with a vector for recombination available in the art (plasmid DNA and bacteriophage DNA) by the usual method.

Specific examples of the vectors for recombination used are *E. coli*-derived plasmids such as pBR322, pBR325, pUC12, pUC13, and pUC19, yeast-derived plasmids such as pSH19 and pSH15, and *Bacillus subtilis*-derived plasmids such as pUB110, pTP5, and pC194. Examples of phages are a bacteriophage such as lambda phage, and an animal or insect virus (pVL1393, Invitrogen) such as a retrovirus, vaccinia virus, and nuclear polyhedrosis virus.

An "expression vector" is useful for expressing the DNA encoding the protein used herein and for producing the protein. The expression vector is not limited as long as it expresses the gene encoding the protein in various prokaryotic and/or eukaryotic host cells and produces this protein. Examples thereof are pMAL C2, pEF-BOS (Nucleic Acids Res. 18:5322 (1990) and so on), pME18S (Experimental Medicine: SUPPLEMENT, "Handbook of Genetic Engineering" (1992)), etc.

When bacteria, particularly *E. coli* are used as host cells, an expression vector generally comprises, at least, a promoter/operator region, an initiation codon, the DNA encoding the protein termination codon, terminator region, and replicon.

When yeast, animal cells, or insect cells are used as hosts, an expression vector is preferably comprising, at least, a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used.

A promoter/operator region to express the protein in bacteria comprises a promoter, an operator, and a Shine-Dalgarno (SD) sequence (for example, AAGG). For example, when the host is *Escherichia*, it preferably comprises Trp promoter, lac promoter, recA promoter, lambda.PL promoter, b 1pp promoter, tac promoter, or the like. Examples of a promoter to express the protein in yeast are PH05 promoter, PGK promoter, GAP promoter, ADH promoter, and so on. When the host is *Bacillus*, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon. Usually, used natural or synthetic terminators are used as a terminator region.

A "replicon" means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 with appropriate restriction enzymes) for *E. coli*, yeast 2.mu. plasmid or yeast chromosomal DNA for yeast, and pRSVneo ATCC 37198, pSV2dhfr ATCC 37145, pdBPV-MMTneo ATCC 37224, pSV2neo ATCC 37149, and such for mammalian cells.

An enhancer sequence, polyadenylation site, and splicing junction that are usually used in the art, such as those derived from SV40 can also be used.

A selectable marker usually employed can be used according to the usual method. Examples thereof are resistance genes for antibiotics, such as tetracycline, ampicillin, or kanamycin.

Examples of genes for gene amplification are dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, aspartate transcarbamylase gene, etc.

The expression vector used herein can be prepared by continuously and circularly linking at least the above-mentioned promoter, initiation codon, DNA encoding the protein, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

As used herein, "Transformants" can be prepared by introducing the expression vector mentioned above into host cells.

As used herein, "host" cells are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces*, *Pichia*, and such), animal cells, or insect cells).

*E. coli* or animal cells are preferably used. Specific examples are *E. coli* (DH5 alpha, TB1, HB101, and such), mouse-derived cells (COP, L, C127, Sp2/0, NS-1, NIH 3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such).

An expression vector can be introduced (transformed (transfected)) into host cells by known methods.

Transformation can be performed, for example, according to the method of Cohen et al. (Proc. Natl. Acad. Sci. USA, 69:2110 (1972)), protoplast method (Mol, Gen. Genet., 168: 111 (1979)), or competent method (J. Mol. Biol., 56:209 (1971)) when the hosts are bacteria (*E. coli, Bacillus subtilis*, and such), the method of Hinnen et al. (Proc. Natl. Acad. Sci. USA, 75:1927 (1978)), or lithium method (J. Bacteriol., 153: 163 (1983)) when the host is *Saccharomyces cerevisiae*, the method of Graham (Virology, 52:456 (1973)) when the hosts are animal cells, and the method of Summers et al. (Mol. Cell. Biol., 3:2156-2165 (1983)) when the hosts are insect cells.

The protein disclosed herein, can be produced by cultivating transformants (in the following, this term includes transfectants) comprising an expression vector prepared as mentioned above in nutrient media.

The nutrient media preferably comprise carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

Cultivation of cell lines is performed by a method known in the art. Cultivation conditions such as temperature, pH of the media, and cultivation time are selected appropriately so that the protein is produced in large quantities.

Examples of the isolation and purification method are a method utilizing solubility, such as salting out and solvent precipitation method; a method utilizing the difference in molecular weight, such as dialysis, ultrafiltration, gel filtration, and sodium dodecyl sulfate-polyacrylamide gel electrophoresis; a method utilizing charges, such as ion exchange chromatography and hydroxylapatite chromatography; a method utilizing specific affinity, such as affinity column chromatography; a method utilizing the difference in hydrophobicity, such as reverse phase high performance liquid chromatography; and a method utilizing the difference in isoelectric point, such as isoelectric focusing.

Furthermore, unless the context demands otherwise, the term peptide, polypeptide and protein are used interchangeably to refer to amino acids in which the amino acid residues are linked by covalent peptide bonds or alternatively (where post-translational processing has removed an internal segment) by covalent di-sulphide bonds, etc. The amino acid chains can be of any length and comprise at least two amino acids, they can include domains of proteins or full-length proteins. Unless otherwise stated the terms, peptide, polypeptide and protein also encompass various modified forms thereof, including but not limited to glycosylated forms, phosphorylated forms etc.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genome or plasmid DNA, animal virus genome, or viral DNA, or may contain elements of both.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating transcription of a downstream (3' direction) coding sequence. The promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The terms "chimeric", "fusion" and "composite" are used to denote a protein, peptide domain or nucleotide sequence or molecule containing at least two component portions that are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences that encode them, are recombinant in the sense that they contain at least two constituent portions that are not otherwise found directly linked (covalently) together in nature.

The term "domain" in this context is not intended to be limited to a single discrete folding domain.

A "reporter polynucleotide" includes any gene that expresses a detectable gene product, which may be RNA or a reporter polypeptide. Reporter genes include coding sequences for which the transcriptional and/or translational products are readily detectable or selectable.

An "insertion" or "addition", as used herein, refers to a change in an amino acid or nucleotide sequence resulting in the addition or insertion of one or more amino acid or nucleotide residues, respectively, as compared to the corresponding naturally occurring molecule.

A "deletion" or "subtraction", as used herein, refers to a change in an amino acid or nucleotide sequence resulting in the deletion or subtraction of one or more amino acid or nucleotide residues, respectively, as compared to the corresponding naturally occurring molecule.

A "substitution", as used herein, refers to the replacement of one or more amino acids or nucleotides by different amino acids or nucleotides, respectively.

A "mutation" is a heritable change in a DNA sequence relative to a reference "wild-type" DNA sequence. Mutations can occur as a result of a single base change, multiple base changes, or the addition or deletion of more than one nucleotide to a DNA sequence.

The term "genotoxicity" is used to broadly refer to any deleterious change in the genetic material of a cell, regardless of the mechanism by which the change is induced.

As used herein the term mutagenicity and genotoxic activity are used to refer to the ability of an agent (e.g., a chemical compound or a drug candidate) to cause a permanent change in the structure of the genetic material of a cell which causes a heritable change in the effected cell. Contemplated changes include alterations in the sequences of the bases in the nucleic acid (gene mutation), structural changes to chromosomes (clastogenicity) and/or changes to the number of chromosomes present.

A "mutagen" or a "genotoxic agent" is an agent that creates or causes mutations. It is well-established that chemical mutagens vary in their modes of action. However, in general terms, a chemical mutagen changes a nucleic acid or nucleoside relative to the nucleotide sequence of a reference or "wild-type" genome. Generally speaking a mutagen or genotoxic agent increases the frequency of reversion or forward mutation.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

A "gene mutation" refers to a mutation that occurs entirely within one gene, or its upstream regulatory sequences and can comprise either a point mutation or other disruption of normal chromosomal structure that occurs entirely within one gene.

A "reversion assay" is an assay of genotoxic activity that detects a reverse mutation which confers normal function to a mutant gene thereby causing a gain of function. Typically, the genotoxic activity of compounds are evaluated using a bacterial reverse mutation assay that utilizes an amino acid-requiring (i.e., auxotrophic) tester strains of *Salmonella typhimurium* (*S. typhimurium*) or *Escherichia coli* (*E. coli*) to evaluate the genotoxic activity of a compound. Generally speaking, reversion assays are capable of detecting point mutations, such as a substitution, an addition or a deletion of one or more DNA bases, which are introduced into the genome of an affected tester strain.

A "forward mutation assay" is an assay of genotoxic activity which detects "forward" mutations that alter a functional gene in a way that causes a loss, rather than a gain, of function.

A "wild-type" strain is capable of a full range of metabolic activities. For example, wild-type strains of *Salmonella* can synthesize all 20 amino acids from a single carbon source.

A "mutant" strain is not capable of all of the activities of the wild-type strain from which it is derived. For example, a mutant bacterial strain that is defective in its ability to synthesize the amino acid histidine (his strain) requires the presence of exogenous histidine in order to grow.

A "point mutation" is a change in one, or a small number of base pairs, in a DNA sequence. Point mutations may result from base pair substitutions or from small insertions or deletions.

A "transition" is a point mutation in which a purine is replaced with a purine or a pyrimidine is replaced with a pyrimidine.

A "transversion" is a point mutation in which a purine is replaced with a pyrimidine or a pyrimidine with a purine. Generally speaking, transitions are more common than transversions because the former are not detected by the proofreading enzymes.

Alternatively, point mutation can also cause a nonsense mutation resulting from the insertion of a stop codon (amber, ochre, opal). Base pair mutations that generate a translation stop codon causes premature termination of translation of the coded protein.

A "frameshift mutation" results from the insertion or deletion of one or more nucleotides within a gene. The "reading frame" of a gene refers to the order of the bases with respect to the starting point for translation of the mRNA. Deletion of a single base pair results in moving ahead one base in all of the codons, and is often referred to as a positive frameshift. Addition of one base pair (or loss of two base pairs) shifts the reading frame behind by one base, and is often referred to as a negative frameshift.

As used herein the term "DNA Repair Mechanism" refers to any one of the potential repair mechanisms that exist in both prokaryotes and eukaryotes. For example: postreplication; mismatch repair; nucleotide excision-repair and photoreactivation or light-dependent repair (not found in mammals).

A "base pair substitution mutagen" is an agent that causes a base (i.e., nucleotide) change in DNA. In the context of a reversion test this change may occur at the site of the original mutation, or at a second site in the bacterial genome.

A "frameshift mutagen" is an agent that causes the addition or deletion of one or more base pairs in the DNA, thus changing the reading frame in the RNA.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used. In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

As used herein the term "isolated" is meant to describe a polynucleotide, a polypeptide, an antibody, or a host cell that is in an environment different from that in which the polynucleotide, the polypeptide, the antibody, or the host cell naturally occurs.

"Fluorescent protein" refers to any protein capable of emitting light when excited with appropriate electromagnetic radiation. Fluorescent proteins include proteins having amino acid sequences that are either natural or engineered, such as the fluorescent proteins derived from *Aequorea*-related fluorescent proteins.

A "fluorescent protein" as used herein is an *Aequorea victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed). The term "GFP-like fluorescent protein" is used to refer to members of the Anthozoa fluorescent proteins sharing the 11-beta strand "barrel" structure of GFP, as well as structural, folding and spectral variants thereof. The terms "GFP-like non-fluorescent protein" and "GFP-like chromophoric protein" (or, simply, "chromophoric protein" or "chromoprotein") are used to refer to the Anthozoa and Hydrozoa chromophoric proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A variety of fluorescent proteins may be used in the present disclosure, including proteins that fluoresce due intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium*. See, Ward, W. W., et al., Photochem. Photobiol., 35:803-808 (1982); and Levine, L. D., et al., Comp. Biochem. Physiol., 72B:77-85 (1982).

A variety of *Aequorea*-related GFPs having useful excitation and emission spectra have been engineered by modifying the amino acid sequence of a naturally occurring GFP from *Aequorea victoria*. See, Prasher, D. C., et. al., Gene, 111:229-233 (1992); Heim, R., et al., Proc. Natl. Acad. Sci., USA, 91:12501-04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions often are fluorescent and retain the biochemical features of the partner proteins. See, Cubitt, A. B., et al., Trends Biochem. Sci. 20:448-455 (1995). Mutagenesis studies have produced GFP mutants with shifted wavelengths of excitation or emission. See, Heim, R. & Tsien, R. Y. Current Biol. 6:178-182 (1996). Suitable pairs, for example a blue-shifted GFP mutant P4-3 (Y66HN145F) and an improved green mutant S65T can respectively serve as a donor and an acceptor for fluorescence resonance energy transfer (FRET). See, Tsien, R. Y., et al., Trends Cell Biol. 3:242-245 (1993). A fluorescent protein is an *Aequorea*-related fluorescent protein if any contiguous sequence of 150 amino acids of the fluorescent protein has at least 85% sequence identity with an amino acid sequence, either contiguous or non-contiguous, from the wild type *Aequorea* green fluorescent protein. More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein. Similarly, the fluorescent protein can be related to *Renilla* or *Phialidium* wild-type fluorescent proteins using the same standards.

A variant of GFP with two mutations at F64L and S65 used in embodiments of the present disclosure includes enhanced green fluorescent protein (EGFP) (SEQ ID NO: 119). Its chromophore has an excitation maximum at 488 nm and erosion maxima at 510 nm. Its fluorescent signal is significantly greater than that of w.t. GFP without these two mutations.

Another variant of GFP is called Cycle 3 (Patternson et al., 19967; Ward, 1997, which is included herein by reference). This GFP variant with mutations at F99S, M153T and V163A at w.t. GFP has an improved folding and chromophore formation at 37° C. or above.

Other fluorescent proteins can be used in the fluorescent indicators, such as, for example, yellow fluorescent protein from *Vibrio fischeri* strain Y-1, Peridinin-chlorophyll a binding protein from the dinoflagellate *Symbiodinium* sp. *phycobiliproteins* from marine cyanobacteria such as *Synechococcus*, e.g., phycoerythrin and phycocyanin, or oat phytochromes from oat reconstructed with phycoerythrobilin. These fluorescent proteins have been described in Baldwin, T. O., et al., Biochemistry 29:5509-5515 (1990), Morris, B. J., et al., Plant Molecular Biology, 24:673-677 (1994), and Wilbanks, S. M., et al., J. Biol. Chem. 268:1226-1235 (1993), and Li et al., Biochemistry 34:7923-7930 (1995).

The term "link" as used herein refers to a physical linkage as well as linkage that occurs by virtue of co-existence within a biological particle, e.g., phage, bacteria, yeast or other eukaryotic cell.

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods that are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Transformation of a host cell with recombinant DNA may be carried out by conventional techniques as are well known to those skilled in the art. Where the host is prokaryotic, such as *E. coli*, competent cells that are capable of DNA uptake can be prepared from cells harvested after exponential growth phase and subsequently treated by the CaCl method by procedures well known in the art. Alternatively, MgCl or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the calcium sensing system of the present disclosure, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the embodiments of the present disclosure may be by any conventional means such as, for example, preparative chromatographic separations and immunological separations such as those involving the use of monoclonal or polyclonal antibodies or antigen.

A variety of host-expression vector systems may be utilized to express the bioluminescent indicator coding sequence. These include, but are not limited to, microorganisms such as bacteria transformed with recombinant bacteriophage DNA, plasmid DNA or cosmid DNA expression vectors containing the calcium sensing system sequences; yeast transformed with recombinant yeast expression vectors containing the calcium sensing system sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid vectors containing the calcium sensing system sequences; insect cell systems infected with recombinant virus expression vectors (e.g., baculovirus) vectors containing the calcium sensing system sequences; or animal cell systems infected with recombinant virus expression vectors (e.g., retroviruses, adenovirus, vaccinia virus vectors containing the calcium sensing system sequences, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (See, e.g., Bitter, et al., Methods in Enzymology 153:516-544, 1987). For example, when cloning in bacterial systems, inducible promoters such as pL of bacteriophage lamda, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for calcium sensing system.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516-544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673-684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the mutation assay system may be driven by any of a number of promoters. For example, viral promoters such as the 35S RNA and 19S RNA promoters of CaMV (Brisson, et al., Nature 310:511-514, 1984), or the coat protein promoter to TMV (Takamatsu, et al., EMBO J. 6:307-311, 1987) may be used; alternatively, plant promoters such as the small subunit of RUBISCO (Coruzzi, et al., 1984, EMBO J. 3:1671-1680; Broglie, et al., Science 224:838-843, 1984); or heat shock promoters, e.g., soybean hsp17.5-E or hsp17.3-B (Gurley, et al., Mol. Cell. Biol. 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, N.Y., Section VIII, pp. 421-463, 1988; and Grierson & Corey, Plant Molecular Biology, 2d Ed., Blackie, London, Ch. 7-9, 1988.

An alternative expression system, which could be used to express mutation assay system, is an insect system. In one such system, *Autographa californica* nuclear polyhedrosis virus (AcNPV) is used as a vector to express foreign genes. The virus grows in *Spodoptera frugiperda* cells. The calcium sensing system sequences may be cloned into non-essential regions (for example, the polyhedrin gene) of the virus and placed under control of an AcNPV promoter (for example the polyhedrin promoter). Successful insertion of the calcium sensing system sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

DNA sequences encoding the mutation assay system of the present disclosure can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as a fluorescent binding ligand and a display protein or nucleic acid, and serves to place the two molecules in a preferred configuration.

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes used herein include DNA sequences that encode the fluorescent indicator that may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. As used herein, the term "transgenic" includes any transgenic technology familiar to those in the art which can produce an organism carrying an introduced transgene or one in which an endogenous gene has been rendered non-functional or "knocked out."

A "zymogen" or "proenzyme" is an inactive enzyme precursor. A zymogen requires a biochemical change (e.g., such as a hydrolysis reaction revealing the active site, or changing the configuration to reveal the active site) for it to become an active enzyme. In an embodiment, the biochemical change usually occurs in a lysosome where a specific part of the precursor enzyme is cleaved in order to activate it. The amino acid chain that is released upon activation is called the activation peptide.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

Discussion

Enzyme sensors, protease sensors, methods for producing and using enzyme and protease sensors, and methods of detecting and/or measure analyte (protease) activity, are disclosed. Embodiments of the enzyme and protease sensors can provide an accurate and convenient method for characterizing proteolytic activity in both in vivo and in vitro environments, in particular in living cell imaging.

Embodiments of the enzyme and protease sensors include an optically-active fluorescent host protein and a molecular recognition motif that interacts with an analyte (a protease or a flux of protease in its microenvironment). Upon interaction of an analyte (protease) with the molecular recognition motif, the protease sensor generates an optically-detectable signal which is produced during exposure to an analyte. The molecular recognition motif is integrated or operatively linked into (within the amino acid sequence) an optically-active fluorescent host protein. The interaction of the analyte with the molecular recognition motif produces a detectable change in fluorescence properties (e.g., change of the intensity, or maxima wavelength or the imaging of the absorption, transmitted light, fluorescent excitation or emission change, light scattering, and/or energy transfer of the chromophore and the protein) of the protease sensor based on the quantity of the analyte.

Using relevant molecular recognition motifs, the protease sensor can be used to investigate the mechanisms of diseases, track the process of diseases and diagnose some diseases related to analytes (proteases) activity in vitro, in living cells and in vivo. In addition, a specific signal peptide is also useful for investigating mechanisms such as their activation or inhibition of diseases related to proteases activities in various cellular compartments in real time and in situ, which is useful in biotechnology, cell biology and medicinal chemistry, disease diagnosis and prognosis, protease inhibitor screening and drug development. Embodiments of the present disclosure can also be used to develop a strategy for preventive medicine based on the understanding of protease activation and inhibition in programmed cell death, thrombosis, pancreatis, and neurodegenerative diseases.

Embodiments of the enzyme and protease sensors include an optically-active fluorescent host protein (hereinafter "fluorescent host protein") and a molecular recognition motif that includes an analyte binding site. The native signal of the fluorescent protein is altered by the inclusion of the analyte binding site within the amino acid sequence of the fluorescent host protein. In particular, embodiments of the present disclosure provide for specific insertion positions of the analyte binding site so that the protease sensor produces emissions at two or more wavelengths. In this regard, the relative three dimensional position of the chromophore within the fluorescent host protein is altered by the inclusion of the analyte binding site, where such alteration generates the altered signal.

Upon interaction of the analyte (e.g., protease) with the analyte binding site, the protease sensor produces an altered signal relative to the protease sensor prior to interaction. In this regard, the relative three dimensional position of the chromophore within the fluorescent host protein is altered upon interaction of the analyte with the analyte binding site, where such alteration generates the altered signal.

In other words, the enzyme and protease sensors have a folding arrangement in a three-dimensional space that produces a specific signal. The protease sensor can undergo a local conformational change into another folding arrangement with an alteration of the chromophore microenvironment under the inducement of an analyte (e.g., trypsin or zymogens thereof, chymotrypsin or zymogens thereof, thrombin or zymogens thereof, caspases (e.g., caspase-3, -5, -7, -8, or -9), or matrix metalloproteinases) with the analyte binding site. The conformational change can be detected and measured and compared to the signal generated by the protease sensor prior to interaction with the analyte.

The advantages of embodiments of the present disclosure can include one or more of the following. First, embodiments of the present disclosure are capable of monitoring numerous cellular events in living cells or organisms via live cell imaging [16-23]. Embodiments of the present disclosure can provide continuous and dynamic movie of the cellular event and their responses by the stimuli or drugs. Embodiments of the present disclosure largely overcome the limitations of currently commercial available small molecule dyes, peptide/mimics probes with one snap shot of the enzyme action. Second, embodiments of the present disclosure include single fluorescent proteins that are easier and better translocated under cellular environment to probe enzymatic reaction in situ than FRET pairs that used two fluorescent proteins. With the addition of signal peptides, these portease sensors can be specifically expressed/placed at the cellular environments such as ER, mitchnodral, Gogi or nuclei to monitor cellular event with spational resolution in addition to temporal resolution. Currently available detection methods simply rely on passive diffusion of the probe through the membrane, and permits only short snapshots of enzymatic actions without the capability of detecting reactions at targeted cellular locations. These probes do not provide continuous dynamic imaging of enzyme actions due to limited cellular lifetime and specificity.

Third, embodiments of the present disclosure include single fluorescent protein units that overcome the limitations observed with FRET-based sensors that are prone to fluorescence photobleaching, poor orientation and translocation in the cellular compartments due to their large size [33]. Fourth, the ratiometric signal change of embodiments of the present disclosure with absorption or excitations at 397 and 491 nm permits quantitative and accurate measurement of the enzymatic action by normalizing the concentration change of the sensors and cellular and instrumental interference of the fluorescence signal (Pazzan, current opinion of cell biology). The majority current available sensors such as linking GFP with ubiquitin or proteasome cleavage peptide for protein degradation or using bacterial protease sequences such as PEST and N-terminal rules [24-26] only have signal changes at one wavelength which can on provide on and off protease activity, our developed enzyme sensor. Fifth, embodiments of the present disclosure exhibit a large dynamic range for protease activity determination and presents high sensitivity. Sixth, the structural motifs used in embodiments of the present disclosure allow the maximal optical responses as well the optimal molecular recognition required for chemical reactions such as protease cleavage and enzyme specificity.

Embodiments of the present disclosure can produce a difference in the protease signal prior to and after interaction with the analyte. The difference is a measurable and a statistically-significant difference. A statistically-significant difference is indicated by a difference sufficient to distinguish between these two states, such as about 0.1%, 1%, 3%, 5%, 10%, 15%, 20%, 25%, 30%, or 40% or more difference between the amount of energy emitted in each state, where the statistically significant difference is determined, at least in part, by the components of the protease sensors or systems as well as the detection system.

Thus, the systems, sensors, and methods of the present disclosure can be used to detect, measure, quantitate, and image interactions between the analytes with the analyte binding site, in vitro and in vivo. In particular, embodiments of the present disclosure can be used to detect (and visualize) and/or quantitate protease interactions or events in in vitro as well as in in vivo.

In another embodiment, the enzyme and protease sensors include a fluorescent host protein and a molecular recognition motif. The molecular recognition motif includes an analyte binding site and a full or partial structural motif (e.g., a primary structure motif, a secondary structure motif, a tertiary structure motif, and/or a quaternary structure motif, such as a, loop, loop-helix, helix-loop, helix-loop-helix motif (including EF-hand motif)), beta-loop-helix, beta-loop-beta and other structural motifs. The structural motifs can be a small domain or fragments and their peptide mimics. The structural motifs provide good accessibility of the analyte bility sites, as well as local perturbation of the environment of the chromophore. The native signal of the fluorescent protein is altered by the inclusion of the analyte binding site within the amino acid sequence of the fluorescent host protein and the structural motif. In particular, embodiments of the present disclosure provide for insertion positions of the analyte binding site so that the protease sensor produces emissions at two or more wavelengths. In this regard, the relative three dimensional position of the chromophore within the fluorescent host protein is altered by the inclusion of the analyte binding site and the structural motif, where such alteration generates the altered signal.

Upon interaction of the analyte (e.g., protease) with the analyte binding site, the protease sensor produces an altered signal relative to the protease sensor prior to interaction. In this regard, the relative three dimensional position of the chromophore within the fluorescent host protein is altered upon interaction of the analyte with the analyte binding site, where such alteration generates the altered signal. The ratiometric change of the signal (chromophore signal) after the interaction allows an accurate measurement of the analyte activity (e.g., in vitro and in vivo with normalized sensor concentration). The inclusion of the structure motif allows optimal molecular recognition by incorporating essential structural and chemical properties required for a specifical type of any analyte. For example, a good solvent accessibility for the easy access of enzymes, a good flexibility required for the recognition, a special geometric pocket for the interaction, a hydrophilic surface or charged environments to facilitate the binding process and a required environment for the fast kinetic rates such as good off rate required for the real time measurement.

In a particular embodiment, the protease sensor can have a molecular recognition motif that includes an analyte binding site that is a cleavage site for a protease. In this regard, the cleavage site can be specific for trypsin-like proteases or their zymogens, chymotrypsin-like proteases or their zymogens, thrombin-like proteases or their zymogens, and caspase-like proteases or their zymogens. In particular, the cleavage site can be specific for trypsin or zymogens thereof, chymotrypsin or zymogens thereof, thrombin or zymogens thereof, caspases (e.g., caspase-3, -5, -7, -8, or -9), or matrix metalloproteinases. In an embodiment, the cleavage site may be specific for two proteases (e.g, trypsin and chymotrypsin). Using relevant cleavage sites, the protease sensor can be used to investigate the mechanisms of diseases, track the process of diseases and diagnose some diseases related to proteases activity in vitro and in vivo. In addition, a specific signal peptide is also useful for investigating mechanisms of diseases related to proteases activities in various cell compartments in vivo, which is useful in biotechnology, cell biology, disease diagnosis, drug development and protease inhibitor screening.

In one illustrative embodiment, the protease sensor includes a fluorescent host protein having at least one operatively incorporated cleavage site. The cleavage site can be cleaved or digested by a protease of interest, and upon cleavage or digestion, the protease sensor can exhibit altered fluorescent properties, which can include ratiometric alterations in the excitation and/or emission spectra of the protease sensor. As the change in fluorescence or absorbance of the protease sensor is a proxy for the activity of the protease of interest, the protease sensor allows for studying and quantitative evaluating protease activity.

Briefly described, embodiments of this disclosure, among others, include protease sensors and systems, fusion proteins including the protease sensor, vectors and other encoding schemes for encoding the protease sensor and system, and methods of using the protease sensors and systems, fusion proteins, vectors, and the like. Note that for each of the protease sensors and systems, proteins, fusion proteins, protein fragments, and nucleotides, one skilled in the art would be able to determine the corresponding nucleotide sequence or protein sequence, respectively, and be able to introduce each into a system of interest.

Fluorescent Host Proteins

As mentioned above, the protease sensor includes a fluorescent host protein. The native signal of the fluorescent protein is altered by the inclusion of the analyte binding site within the amino acid sequence of the fluorescent host protein. Embodiments of the present disclosure provide for specific insertion positions (described in more detail below) of the analyte binding site within the fluorescent host protein so that the protease sensor produces an emission that is altered upon interaction of the analyte with the analyte binding site. In this regard, the relative three dimensional position of the chromophore within the fluorescent host protein is altered by the inclusion of the analyte binding site, where such alteration generates the altered signal. In an embodiment, the protease sensors can emit at two or more wavelengths.

One group of fluorescent host proteins includes the Green Fluorescent Protein isolated from *Aequorea Victoria* (GFP), as well as a number of GFP variants, such as enhanced fluorescent proteins (EGFP), cyan fluorescent protein (CFP), blue fluorescent protein (BFP), yellow fluorescent protein (YFP), etc. (Zimmer, 2002, Chem. Rev. 102: 759-781; Zhang et al., 2002, Nature Reviews 3: 906-918, both of which are incorporated herein by reference). These color-shift GFP mutants have emission colors blue to yellow-green, increased brightness, and photostability (Tsien, 1998, Annual Review of Biochemistry 67: 509-544, which is incorporated herein by reference). One such GFP mutant, termed the Enhanced Yellow Fluorescent Protein (EYFP), displays an emission maximum at 529 nm. Another recently described mutant, a gold variant, was generated by incorporating a non-natural variant of tryptophan into the cyan variant, and is characterized by a significantly red-shifted emission maximum of 574 nm (Bae et al., 2003, J. Mol. Biol. 328: 1071-1081, which is incorporated herein by reference).

In particular, *Aequorea* green fluorescent proteins (GFPs) and its enhanced fluorescent proteins have 238 amino acid residues (SEQ ID NO: 119) in a single polypeptide chain. The native molecule has been shown to regenerate its intrinsic fluorescence from the totally denatured state. GFPs display a strong visible absorbance and fluorescence that is thought to be generated by the autocyclization and oxidation of the chromophore having a tripeptide Ser-Tyr-Gly sequence at positions 65 to 67. Mutations to GFPs have resulted in various shifts in absorbance and fluorescence. The usefulness of GFPs stems from the fact that fluorescence from GFP requires no additional co-factors; the fluorophore is self-assembling via a cyclization reaction of the peptide backbone.

The chromophore of GFP is formed by the cyclization of the tripeptide Ser65-Tyr66-Gly67. This chromophore is located inside of the β-barrel that is composed of 11 antiparallel strands and a single central α-helix. There are short helices capping the ends of the β-barrel. The chromophore has extensive hydrogen bonding with the protein frame and can be affected by water molecules under the different folding states. The chromophore in a tightly constructed β-barrel that exhibits absorption peaks at 400 and 480 nm and an emission peak at 510 nm with a quantum yield of about 0.72 when excited at 470 nm. The chromophore in enhanced green fluorescent protein (EGFP), which is GFP with a mutation S65T, has an improved fluorescence intensity and thermo-sensitivity.

Two (M153T, V163A) or three additional mutations (F99S, M153T, V163A) were added to EGFP to increase the protein expression, stability, chromophore formation at 37° C. or above.

Yellow fluorescent protein (YFP: S65G, V68L, S72A, T203Y) (SEQ ID. NO. 120 or an embodiment as shown in SEQ ID. NO. 37), cyanide fluorescent protein (CFP: Y66W, N1461, M153T, V163A, N212K) (SEQ ID. NO. 122 or an embodiment as shown in ID. NO. 39), and blue fluorescent protein (BFP: Y66H, Y145F), (SEQ ID. NO. 123 or an embodiment as shown in SEQ ID. NO. 40) are variants of GFP that differ in emission spectra and emission. Further, additional GFP variants, such as Venus (F46L, F64L, S65G, V68L, S72A, V163A, S175G, T203Y) (SEQ ID. NO. 121 or an embodiment as shown in ID. NO. 38), also exhibit been constructed to have accelerated maturation and brightness through two residues mutation (M153T and V163A).

Additional GFP-based variants having modified excitation and emission spectra (Tsien et al., U.S. Patent Appn. 20020123113A1, which is incorporated herein by reference), enhanced fluorescence intensity and thermal tolerance (Thastrup et al., U.S. Patent Appn. 20020107362A1; Bjorn et al., U.S. Patent Appn. 20020177189A1, which are incorporated herein by reference), and chromophore formation under reduced oxygen levels (Fisher, U.S. Pat. No. 6,414,119, which is incorporated herein by reference) have also been described. GFPs from the Anthozoans *Renilla reniformis* and *Renilla kollikeri* have also been described (Ward et al., U.S. Patent Appn. 20030013849, which is incorporated herein by reference).

Moreover, over 100 GFP-like fluorescent proteins and non-fluorescent chromoproteins from the class Anthozoa have now been identified (for review, see Verkusha et al., 2003, GFP-like fluorescent proteins and chromoproteins of the class Anthozoa, In: Protein Structures: Kaleidoscope of Structural Properties and Functions, pp. 405-439, Ed. V. Uversky. Research Signpost Press, Kereala, India, which is incorporated herein by reference). This group of Anthozoa proteins includes the red fluorescent protein isolated from *Discosoma* species of coral, DsRed (Matz et al., 1999, Nat. Biotechnol. 17:969-973, which is incorporated herein by reference), and various DsRed variants (e.g., DsRed1, DsRed2). DsRed and the other Anthozoa fluorescent proteins share only about 26-30% amino acid sequence identity to the wild-type GFP from *Aequorea victoria*, yet all the crucial motifs are conserved, indicating the formation of the 11-stranded beta-barrel structure characteristic of GFP. The crystal structure of DsRed has also been solved, and shows conservation of the 11-stranded beta-barrel structure of GFP MMDB Id: 5742.

A number of mutants of the longer wavelength red fluorescent protein DsRed have also been described. For example, recently described DsRed mutants with emission spectra shifted further to the red may be employed in the practice of the invention (Wiehler et al., 2001, FEBS Letters 487: 384-389; Terskikh et al., 2000, Science 290: 1585-1588; Baird et al., 2000, Proc. Natl. Acad. Sci. USA 97: 11984-11989, which are incorporated herein by reference). Recently, a monomeric variant of DsRed was described (Campell et al., 2002, Proc. Natl. Acad. Sci USA 99: 7877-7882, which is incorporated herein by reference). This variant, termed "mRFP1", matures quickly (in comparison to wild type DsRed, which matures over a period of 30 hours), has no residual green fluorescence, and has excitation and emission wavelengths of about 25 nm longer than other DsRed variants. Several versions of monomeric red fluorescent protein (mRFP) such as mcherry (SEQ ID NO: 124), mFruit and mStrawberry (SEQ ID NO: 125) and the like, are produced by modifying DsRed with better cellular and optical properties (Shu X, Shaner N C, Yarbrough C A, Tsien R Y, Remington S J). Novel chromophores and buried charges control color in mFruits (Biochemistry. 2006 Aug. 15; 45(32):9639-47; Campbell R E, Tour O, Palmer A E, Steinbach P A, Baird G S, Zacharias D A, Tsien R Y). A monomeric red fluorescent protein (Proc Natl Acad Sci USA. 2002 Jun. 11; 99(12):7877-82).

Furthermore, an increasingly large number of other fluorescent host proteins from a number of ocean life forms have recently been described, and the Protein Data Bank currently lists a number of GFP and GFP mutant crystal structures, as well as the crystal structures of various GFP analogs. Related fluorescent host proteins with structures inferred to be similar to GFP from corals, sea pens, sea squirts, and sea anemones have been described, and may be used in embodiments of this disclosure (for reviews, see Zimmer, 2002, Chem. Rev. 102: 759-781; Zhang et al., 2002, Nature Reviews 3: 906-918, which are incorporated herein by reference).

Additionally, fluorescent host proteins from *Anemonia majano, Zoanthus* sp., *Discosoma striata, Discosoma* sp. and *Clavularia* sp. have also been reported (Matz et al., supra). A fluorescent host protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656, which is incorporated herein by reference). Recently described fluorescent proteins from sea anemones include green and orange fluorescent proteins cloned from *Anemonia sulcata* (Wiedenmann et al., 2000, Proc. Natl. Acad. Sci. USA 97: 14091-14096, which is incorporated herein by reference), a naturally enhanced green fluorescent protein cloned from the tentacles of *Heteractis magnifica* (Hongbin et al., 2003, Biochem. Biophys. Res. Commun. 301: 879-885, which is incorporated herein by reference), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882, which is incorporated herein by reference).

A recently described red fluorescent protein isolated from the sea anenome Entacmaea quadricolor, EqFP611, is a far-red, highly fluorescent protein with a unique co-planar and trans chromophore (Wiedenmann et al., 2002, Proc. Natl. Acad. Sci USA 99: 11646-11651, which is incorporated herein by reference). The crystal structure of EqFP611 has been solved, and shows conservation of the 11-stranded beta-barrel structure of GFP MMDB Id: 5742 (Petersen et al., 2003, J. Biol. Chem, Aug. 8, 2003; M307896200, which is incorporated herein by reference).

Additionally, further classes of GFP-like proteins having chromophoric and fluorescent properties have been described. One such group of coral-derived proteins, the pocilloporins, exhibits a broad range of spectral and fluorescent characteristics (Dove and Hoegh-Guldberg, 1999, PCT application WO 00/46233; Dove et al., 2001, Coral Reefs 19: 197-204, which are incorporated herein by reference). Recently, the purification and crystallization of the pocilloporin Rtms5 from the reef-building coral Montipora efflorescens has been described (Beddoe et al., 2003, Acta Cryst. D59: 597-599, which is incorporated herein by reference). Rtms5 is deep blue in color, yet is weakly fluorescent. However, it has been reported that Rtms5, as well as other chromoproteins with sequence homology to Rtms5, can be inter-converted to a far-red fluorescent protein via single amino acid substitutions (Beddoe et al., 2003, supra; Bulina et al., 2002, BMC Biochem. 3: 7; Lukyanov et al., 2000, supra).

Various other coral-derived chromoproteins closely related to the pocilloporins are also known (see, for example, Lukyanov et al. 2000, J. Biol. Chem. 275: 25879-82; Gurskaya et al., 2001, FEBS Letters 507: 16-20, which are incorporated herein by reference). To the extent that these chromoproteins contain the conserved 11-stranded beta barrel structure of GFP and other fluorescent proteins, they may be split into self-complementing fragments and used in the assay systems as described herein.

Fluorescent host proteins that have a structure with a root mean square deviation of less than 5 angstroms, often less than 3, or 4 angstroms, and preferably less than 2 angstroms from the 11-stranded beta-barrel structure of MMDB Id:5742 may be used in the development of self-complementing fragments. In some cases, fluorescent host proteins exist in multimeric form. For example, DsRed is tetrameric (Cotlet et al., 2001, Proc. Natl. Acad. Sci. USA 98: 14398014403) which is incorporated herein by reference). As will be appreciated by those skilled in the art, structural deviation between such multimeric fluorescent proteins and GFP (a monomer) is evaluated on the basis of the monomeric unit of the structure of the fluorescent protein.

In particular, the fluorescent host protein can include, but is not limited to, green fluorescent protein variants, yellow fluorescent protein variants, cyan fluorescent protein variants, blue fluorescent protein variants and red fluorescent protein variants. The cleavage linker containing specific protease binding sites are grafted between the position 172 and 173, all of sequence are shown in SEQ ID from NO. 1 to NO. 118.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

The fluorescent protein or the split fluorescent protein can include conservatively modified variants as long as the conservatively modified variant retains certain characteristics (e.g., the ability to fluoresce upon complementation) of the protease sensor. It should be noted that polynucleotides encoding the conservatively modified variants are intended to be disclosed by and included in this disclosure.

The protease sensor can be expressed in a system (e.g., a cell) using a vector, for example by methods described herein or by methods known to those of skill in the art.

Analyte Binding Site

As described above, the protease sensor can have a molecular recognition motif that includes an analyte binding site. The native signal of the fluorescent protein is altered by the inclusion of the analyte binding site within the amino acid sequence of the fluorescent host protein. In this regard, the relative three dimensional position of the chromophore within the fluorescent host protein is altered by the inclusion of the analyte binding site, where such alteration generates the altered signal. This signal change in majority of our sensors results in a ratiometric change i.e. changes at two wavelengths for both absorption and fluorescence excitation.

The analyte binding site functions by interacting with an analyte, where such interaction causes the protease sensor to produce an altered signal relative to the protease sensor prior to interaction. In this regard, the relative three dimensional position of the chromophore within the fluorescent host protein is altered upon interaction of the analyte with the analyte binding site, where such alteration generates the altered signal.

The analyte binding site can include, but is not limited to, a cleavage site, a binding site where the analyte binds to the protease sensor, an enzyme reaction site, ligation reaction (opposite of cleavage), and/or required metal binding site. The cleavage site functions by allowing the analyte to cleave the polypeptide sequence of the biosensor upon analyte binding to the biosensor. The cleavage results in an alteration of the protease sensor signal that can be detected. The binding site is the location that the analyte/enzyme molecules bind to the protease sensor/substrate. Usually specific types of amino acids in specific arrangements in sequence and in three dimensions are used for a specific type of enzyme. Depending the reaction and the nature of the binding and relative alteration of the chromophore, the binding of the analyte may or may not alter the protease sensor signal. However, the cleavage reaction will cause large change of the sensor signal. This can be due to the alteration of the local environment of the three dimensional position of the chromophore within the fluorescent host protein which results in alteration of the signal. Such alteration could be due to the perturbation of the hydrogen network, the dynamic properties, the solvent accessibility or chemical properties such as hydrophilic and electrostatic interaction. The enzyme reaction site is the local of the chemical reaction occurs such as the cleavage of peptide bonds by proteases or the joint of the peptide bonds by ligase. In principle, the protease sensors can also function as ligase sensors by monitoring the reversed ratiometric change of the signal. In an embodiment where the analyte binding site is a cleavage site, the cleavage site is specific for a protease. In this reard, the cleavage site can be specific for trypsin-like proteases or their zymogens, chymotrypsin-like proteases or their zymogens, thrombin-like proteases or their zymogens, and caspase-like proteases or their zymogens. In particular, the cleavage site can be specific for trypsin or zymogens thereof, chymotrypsin or zymogens thereof, Granzyme, serpin, SRP-3, neutralizes chymotrypsin-like serine peptidases, thrombin or zymogens thereof, caspases (e.g., caspase-3, -5, -7, -8, or -9), or matrix metalloproteinases. In an embodiment, the cleavage site may be specific for two proteases (e.g, trypsin and chymotrypsin).

The cleavage site (analyte binding site) for trypsin in some illustrative embodiments can have one of the following sequences, SEQ ID NO. 1 to NO. 44.

The cleavage site (analyte binding site) for chymotrypsin in some illustrative embodiments can have one of the following sequences: SEQ ID from NO. 1 to NO. 44. It should be noted that these embodiments could be used for Granzyme as well.

The cleavage site (analyte binding site) for thrombin in some illustrative embodiments can have one of the following sequences: SEQ ID NO. 45 to NO. 60.

The cleavage site (analyte binding site) for caspase in some illustrative embodiments can have one of the following sequences: SEQ ID NO. 61 to NO. 118. In particular, the cleavage site for caspase-3 and caspase-7 can be SEQ ID. NO. 61 to NO. 80; the cleavage site for caspase-8 can be SEQ ID. NO. 81 to NO. 100 and the cleavage site for caspase-9 can be SEQ ID. NO. 101 to NO. 118.

The site within the fluorescent host protein for inserting the analyte binding site cleavage site can be selected so that the location is accessible by the analyte (protease). In addition, the location within the fluorescent host protein can be selected so that the location does not substantially reduce the fluorescence from the fluorescent host protein and so that the locations do not substantially denature or alter the protein folding of the fluorescent host protein or chromophore. Furthermore, the site within the fluorescent host protein for inserting the analyte binding site cleavage site can be selected based on one or more of the following criteria: maximization of solvent accessibility to allow efficient enzymatic action, maximization of fluorescent/optical signals once the analyte biding site is operatively incorporated into the fluorescent host protein; minimization of the disruption to the chromophore environment after interaction of the analyte binding site with the analyte; minimize the affect on the protein folding and packing of the fluorescent host protein; and maximization of the ratiometric change of chromophore signal due to interaction of the analyte binding site with the analyte so to allow an accurate measurement of the analyte activity in vitro or in vivo.

It should be noted that the analyte binding site can be include within or between motifs of the fluorescent host protein, such as within or between a secondary structure motif, a tertiary structure motif, or a quaternary structure motif. In particular, the analyte binding site can be inserted in the loop of the β-barrel, and between loops.

In one embodiment, the analyte binding site is a cleavage site. The site for inserting the cleave site within the fluorescent host protein (GFP) can be selected based on the following criteria: maximization of solvent accessibility to allow efficient enzymatic action, maximization of fluorescent/optical once the enzyme cleavage site(s) was operatively incorporated into the GFP; minimization of the disruption to the chromophore environment after protein cleavage; minimization of the affect on the protein folding and packing of the GFP; and maximization of the ratiometric change of chromophore signal due after the protease cleavage so to allow an accurate measurement of the protease activity in vivo with normalized sensor concentration.

Structure Motifs

The inclusion of the structure motif allows optimal molecular recognition by incorporating essential structural and chemical properties required for a specifical type of any analyte. For example, a good solvent accessibility for the easy access of enzymes, a good flexibility required for the recognition, a special geometric pocket for the interaction, a hydrophilic surface or charged environments to facilitate the binding process and a required environment for the fast kinetic rates such as good off rate required for the real time measurement. Any exposed motifs with a good solvent accessibility and flexibility such as helix-loop-helix or partial motif is a good selection. These helix-loop-helix can be from EF-hand motifs from calcium binding proteins such as calmodulin or trponic c, S100, or from nuclei binding motifs. All of the sequences from SEQ ID NO. 1 to NO. 118 are composed of fluorescent host protein and cleavage linker with partial or whole helix-loop-helix motifs.

In an embodiment, the structural motifs can include the calcium binding motif with helix-loop-helix from one site of calmodulin. In addition, other structural motifs from calmodulin (total 4) and other EF-hand proteins with EF-hand motifs (>1000) can be incorporated as well as long as they contain the analyte binding/cleavage sequence in the motif by modification. In addition, helix-loop-helix motifs that do not have calcium or metal binding capability as long as they have the cleavage/binding sequences incorporated can be used as a structural motif in embodiments of the present disclosure.

In addition, other structural motifs such as beta-loop-beta or beta-loop-helix, or coiled structures or domains and fragments that contain the cleavage sequence and located at the sensitive location of chromophore with the capability to alter the chromophore environment can be used in embodiments of the present disclosure.

Methods of Use

In general, protease sensors or systems can be used in vivo and/or in vitro. In an embodiment, the protease sensors or systems can be introduced into a system (e.g., inside a cell or outside a cell and/or to a host), the protease sensors or systems can be expressed (e.g., using a vector or other appropriate expression system) in the system, and/or the protease folding sensors or systems can be included in a transgenic animal or plant. In an embodiment, the protease sensors or systems can be introduced into a cell, host, or organism in vivo. In another embodiment, the protease sensor can include a specific signal peptide for the delivery of protease sensor to different subcellular compartments (e.g., cytosol, nucleus, mitochondrial matrix, edoplasmic reticulum, golgi and peroxisome, and the like).

Embodiments of the present disclosure provide for methods of detecting and measuring analyte (protease) activity or proteolytic activity. In an embodiment, the methods can include: introducing a protease sensor into a system; allowing the protease sensor to interact with the analyte (protease) of interest, which can interact (e.g., cleave) with the analyte binding site (e.g., cleavage site) of the protease sensor; and detecting or measuring the fluorescent properties or changes. The protease sensor can include any of the protease sensors described herein. As the change in fluorescent activity of the protease sensor is a proxy for the activity of the analyte of interest, this method provides a means for studying and evaluating analyte activity.

In another embodiment, the methods can include: introducing a plasmid containing a protease sensor into a host cell by standard gene transfer methods; expressing the protease sensor in the host cell; allowing the protease sensor to interact with the protease of interest, which can interact (e.g., cleave) the analyte binding site (e.g., cleavage site) of the protease sensor; and detecting or measuring the fluorescent properties or changes. The protease sensor can include any of the protease sensors described herein. As the change in fluorescent activity of the protease sensor is a proxy for the activity of the analyte of interest, this method provides a means for studying and evaluating analyte activity.

Samples useful with this invention include biological samples, environmental samples, or any other samples for which it is desired to determine whether a particular molecule is present therein. With some embodiments, the sample can include a living cell or a cell extract, which may be obtained from an animal (e.g, mammal or humans) or a plant. Alternatively, the cells can originate from or be derived from bacterial cells. Further, the cells may be obtained from a culture of such cells, for example, a cell line, or can be isolated from an organism. Where the method is performed using an intact living cell or a freshly isolated tissue or organ sample, the presence of a molecule of interest in living cells can be identified, thus providing a means to determine, for example, the intracellular compartmentalization of the molecule in real time. One of ordinary skill in the art may select a suitable sample without undue experimentation.

Methods for detecting with the protease sensor or of a cell expressing containing an optical sensor may comprise, for example, illuminating the protease sensor or cell expressing the protease sensor with an illumination source such that the protease sensor or cell expressing the protease sensor emits radiation. Such detection methods may use an illumination source such as an incandescent light source, a fluorescent light source, a halogen light source, sunlight, and other equivalent sources. When illuminated by such an illumination source, the protease sensor will emit fluorescent light that may be detected by unaided optical observation or by other qualitative or quantitative methods. Suitable methods for measuring fluorescence of samples are known and understood by those with ordinary skill in the art.

Based on the fluorescence properties of the protease sensor, a DNA construct of the protease sensor may be inserted into a recombinant vector or any suitable vectors that may conveniently be subjected to recombinant DNA procedures. The specific vector can depend on the type of host cells. For example, recombinant DNA plasmid vectors, which can exist as an extrachromosomal entity, may be a suitable vector. Alternatively, the vector may be one that, when introduced into a host cell, is integrated into the host cell genome and replicated together with the chromosome(s) into which it has been integrated. Once the protease sensor has been constructed, vectors comprising the fluorescent nucleic acid molecules may be formulated into a variety of compositions, such as solutions (for example, buffer solutions) to be used in transfecting host cells.

A fluorescent host protein variant can be linked to the molecule directly or indirectly, using any linkage that is stable under the conditions to which the protein-molecule complex is to be exposed. Thus, the fluorescent host protein and molecule can be linked via a chemical reaction between reactive groups present on the protein and molecule, or the linkage can be mediated by a linker moiety, which contains reactive groups specific for the fluorescent host protein and the molecule. It will be recognized that the appropriate conditions for linking the fluorescent host protein variant and the molecule are selected depending, for example, on the chemical nature of the molecule and the type of linkage desired. Where the molecule of interest is a polypeptide, a convenient means for linking a fluorescent host protein variant and the molecule is by expressing them as a fusion protein from a recombinant nucleic acid molecule, which includes a polynucleotide encoding, for example, a fluorescent host protein operatively linked to a polynucleotide encoding the polypeptide molecule.

The protease sensor may be produced as chimeric proteins by recombinant DNA technology. Recombinant production of proteins including fluorescent host proteins involves expressing nucleic acids having sequences that encode the proteins. Nucleic acids encoding fluorescent host proteins can be obtained by methods known in the art. For example, a nucleic acid encoding the protein can be isolated by a polymerase chain reaction of DNA from *A. victoria* using primers based on the DNA sequence of *A. victoria* GFP. Mutant versions of fluorescent host proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

One advantage of the protease sensor is that it can be a relatively small. As a small protein sensor, it may be applied to measure proteolytic activity or metabolism in living cells. Further, the protease sensor can emit a strong and stable fluorescence, event with the inserted a cleavage linker for specific proteases at its sensitive spots to obtain the protease sensors and high selectivity and high sensitivity. The smaller size can allow expression in various organisms due to characteristics of fluorescent host protein expression which does not require of cofactors. The protease sensor also can easily targeted to different subcellular compartments with the help of signal peptides, which offers significant benefits for monitoring the protease activity in various cellular compartments in real time in vivo. As such, the protease sensor can be small, sensitive and quantitative.

It is contemplated that this invention can be used to measure and characterize protease activity associated with various diseases and disorders. For example, acute or chronic pancreatitis is related to trypsin-like activity including trypsin, chymotrypsin and elastase and trypsin from pancreatic sources. Further, some cardiovascular diseases are related to the abnormality of thrombin. Alzheimer's disease, Parkinson's disease and cancers also are related to the activity of caspase family. Moreover, the selective cleavage at the insertion location can also be exploited to develop various protease sensors for detecting diseases associated with thrombin, caspases and metalloproteinases.

Additional Methods of Use

In another embodiment, the protease sensors and methods described herein can be used to monitor and assess biological interactions by modifying vector constructs (e.g., protease activity, and the like) in a transgenic animal.

In another embodiment, a cell line or transgenic animal is marked with vector sets described herein that are developed utilizing coding regions for the two proteins of interest, for example, followed by optical imaging to quantify protein-protein interaction in the presence and absence of pharmaceuticals designed to modulate the interaction. As will be appreciated by the skilled practitioner, this technique will significantly accelerate drug validation by allowing testing in vivo.

In this regard, the present disclosure also includes transgenic animals comprising exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are mammals, most typically mice.

The exogenous nucleic acid sequence may be present as an extrachromosomal element or stably integrated in all or a portion of the animal's cells, especially in germ cells.

Unless otherwise indicated, a transgenic animal includes stable changes to the GERMLINE sequence. During the initial construction of the animal, chimeric animals (chimeras) are generated, in which only a subset of cells have the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions.

For example, an introduced transgene may include genes corresponding to protease sensors, which may become functional when exposed to appropriate test proteins or, alternatively, which may become non-functional when exposed to a particular test protein that blocks complementation or reconstitution. Such a transgene, when introduced into a transgenic animal or cells in culture, is useful for testing potential therapeutic agents known or believed to interact with a particular target protein implicated in a disease or disorder. Where the introduced gene is a coding sequence, it is usually operably linked to a promoter, which may be constitutive or inducible, and other regulatory sequences required for expression in the host animal.

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known and others will likely be developed. See, e.g., U.S. Pat. Nos. 6,252,131, 6,455,757, 6,028,245, and 5,766,879, all incorporated herein by reference. Any method that produces a transgenic animal expressing a reporter gene following complementation or reconstitution is suitable for use in the practice of the present invention. The microinjection technique is particularly useful for incorporating transgenes into the genome without the accompanying removal of other genes.

Kits

This disclosure encompasses kits that include, but are not limited to, protease sensor (e.g., proteins or polynucleotides), related agents that can facilitate the delivery of the protein to its desired destination and directions (written instructions for their use). The components listed above can be tailored to the particular biological event (e.g., a particular protease) to be monitored as described herein. A kit for use in transfecting host cells may be assembled using the nucleic acid molecules encoding the protease sensor, or for labeling target polypeptides with the protease sensor. Host cell transfection kits may include at least one container containing one or more of the nucleic acid molecules encoding a protease sensor (or a composition including one or more of the nucleic acid molecules or plasmids described above), which nucleic acid molecule preferably includes plasmid. The kit can further include appropriate buffers and reagents known in the art for administering various combinations of the components listed above to the host cell or host organism. The components of the present disclosure and carrier may be provided in solution or in lyophilized form. When the components of the kit are in lyophilized form, the kit may optionally contain a sterile and physiologically acceptable reconstitution medium such as water, saline, buffered saline, and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include $\pm 1\%$, $\pm 2\%$, $\pm 3\%$, $\pm 4\%$, $\pm 5\%$, $\pm 6\%$, $\pm 7\%$, $\pm 8\%$, $\pm 9\%$, or $\pm 10\%$, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

EXAMPLES

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Proteases are essential for regulating a wide range of physiological and pathological processes and for regulating quality control of life cycles. Currently there is a strong need to develop protease sensors that are capable of quantitatively measuring protease activity in real time and monitoring activation and inhibition of enzymatic activity in various cellular compartments to facilitate disease diagnosis and screen protease inhibitors with therapeutic effects. Here we report a novel strategy to create protease sensors by grafting an enzymatic cleavage site into a chromophore-sensitive location of the enhanced green fluorescent protein (EGFP). Our designed trypsin sensor exhibits a large ratiometric optical signal change as a response to the action of proteases. They exhibit high enzymatic selectivity and rapid kinetic responses for enzyme activation and inhibition. Our developed trypsin sensor provides for the first real-time monitoring of cellular activation of trypsinogen and the effects of inhibitors in living pancreatic cells.

Introduction

Normally, digestive proteases are produced as inactive proenzymes inside the membrane-bound zymogen gradules [1]. The proenzyme becomes active after physiological stimulation during exocytosis. Usually a large amount of protease inhibitors coexist with the proteases to inhibit autodigestion [2]. Fatal human diseases such as acute pancreatitis result from autodegradation of trypsin, chymotrypsin and elastase derived from pancreatic tissues. Trypsin is one of the major digestive enzymes responsible for regulating protein degradation [2]. Misbalanced trypsinogen secretion, activation, inhibition, and turnover can result in acute and chronic pancreatic diseases [3, 4]. Approximately 35,000 new cases of pancreatic cancer related to serine proteases, including trypsin, are reported annually, which ranks as the fourth leading cause of cancer deaths in the United State [5]. Because the overall survival rate for pancreatic cancer patients is less than 4%, diagnosis at an early stage may significantly improve these odds [6]. Clearly, finding an effective way to improve early diagnosis of pancreatic cancer and improve or develop new treatments would have significant medical value.

The study of protease actions in living systems is frequently hindered by the lack of tools or probes capable of monitoring dynamic protease processes in various cellular locations. Although elevated expression of proteases and protease inhibitors can be monitored by PCR and Western blotting, to date, the assessment of enzymatic the functional roles of proteases by quantitatively measuring protease activity and its inhibition in the cell and in real-time is largely unavailable. Currently, the actions of most proteases are mainly measured in cell lysates using: chromophores conjugated to short peptides; peptide mimics encompassing enzymatic cleavage sites, or fluorescence antibody detection of the cleaved product monitored by fixed cell imaging [14, 15]. The most common chromophores linked to short peptide fragments of 3-6 amino acids mimic the sequence encompassing the P1 to Pn cleavage sites (usually up to P3) are p-nitroaniline, 7-amino-4-methylcoumarin or fluorescein isothiocyanate-labeled casein. Currently available detection methods simply rely on passive diffusion of the probe through the membrane, and permits only short snapshots of enzymatic actions without the capability of detecting reactions at targeted cellular locations. These probes do not provide continuous dynamic imaging of enzyme actions due to limited cellular lifetime and specificity. The diagnosis of chronic pancreatic diseases are largely restricted to later stages of the illness due to limitations inherent in the currently available peptide kits designed for the detection of trypsin activity in cell lysate[7, 8].

To design functional protease probes capable of monitoring dynamic enzymatic action in living cells, several factors must be considered. First, the sensor must be able to monitor the dynamics of enzymatic activity over the entire natural course of activation or inhibition in intact living cells, in real time. They should be easily translocated under cellular environment to probe enzymatic reaction in situ. Second, protease sensors should have high sensitivity and exhibit a large dynamic change. Ideally, the enzyme-induced change of fluorescence emission or excitation signals should be ratiometric to permit precise quantitative measurement of enzymatic activity with the capability to normalize variations in sensor concentrations, fluorescence signal variations caused by different cellular conditions and instrumentation. A large dynamic change of the signal upon enzymatic cleavage allows for the early detection of enzyme activation and for the sensitive screening of therapeutic inhibitors as drugs. Third, the optical signal change must rapidly respond to the catalytic cleavage with an optimal kinetic activity and the designed protease sensor must have a good selectivity for the enzymatic action of interest.

Example 1

Introduction

Design and Engineering of Protease Sensors

A specific cleavable linker for proteases was selected as the cleavage sequence for trypsin, chymotrypsin, thrombin, caspase-3, caspase-8 and caspase-9. These sequences have specific recognition sites for these proteases in loop region or flanking helices located in a solvent accessible area. After selecting a cleavage site suitable with a protease of interest, the cleavage site was inserted at position within various GFPs to:

a) maximize solvent accessibility, maximize fluorescence, maximize fluorescent/optical signal change following the cleavage of the enzyme cleavage site (s)

b) minimize the disruption to the chromophore environment after either insertion of the cleavage linker or protein cleavage;

c) minimize the effects on the protein folding and packing of the GFP; and d) maximize the ratiometric optical signal change of the chromophore due to the protease cleavage which allows for an accurate measurement of the protease activity in vivo with normalized sensor concentration.

The accessible surface areas of EGFP-T/C1 were calculated with the software of Analytical Surface Calculation (ASC). The results revealed that residue 157 and 172 are 156.0 KDa and 118.6 KDa, respectively. Proteases sensors being characteristic of these criteria are shown in Sequence ID. Nos. 1-118.

Plasmid Construction of Protease Sensors

Pet28a plasmid encoding EGFP was subjected to insertion of nucleotide sequences encoding a cleavable linker (EEEIR-EAFRVFDKDGNGYISAAELRHVMTNL) for trypsin at three locations (Glu172, Gln157 and Asn144) of EGFP using polymerase chain reaction (PCR) technique. The resulting variants of trypsin sensors were labeled EGFP-T/C1, EGFP-T/C2 and EGFP-T/C3, respectively. The newly-synthesized plasmid DNA was ligated with T4 DNA ligase, transformed into DH5α competent cells grown in Luria-Bertani (LB) media containing kanamycin, and then purified with a QIAprep Miniprep Kit (Qiagen, Valencia, USA). The constructed plasmid DNA was verified through automated DNA sequencing.

Expression and Purification Protease Sensors

The protease sensor was expressed in various cells and tissues. For example, to express protease sensors, a single colony was inoculated into 20 ml of LB media with 30 μg/ml kanamycin at 37° C. with agitation at 200 rpm overnight and then transferred to 1 L of LB media with 30 μg/mL fresh kanamycin. The cell culture was induced with 0.2 mM isopropyl-β-D-thiogalactopyranoside (IPTG) when $O.D._{600\ nm}$ reached 0.6 and allowed to grow at 30° C. for another 16 to 20 h. The cells were harvested by centrifugation at 7000×g for 20 min.

The protease sensors were extracted from cell pellets by resuspension in 10 ml of lysis buffer (20 mM Tris, 10 mM NaCl, 0.1% Triton X-100, pH 8.8) and sonicated to disrupt the cell membrane. The solution was centrifuged at 20000×g for 20 min, and the supernatant was filtered and injected into a nickel-chelating column connected on FPLC loaded with 0.1 M nickel sulfate solution. After washing with buffer A (50 mM phosphate, 250 mM NaCl, pH 7.4), the bond protein was eluted with a gradient of imidazole from 0 to 0.5 M in phosphate buffer. The purity of the fractions was monitored by SDS-PAGE. The protein collected from FPLC was dialyzed into 10 mM Tris buffer with 1 mM DTT at pH 7.4 to remove imidazole.

The concentration of purified protein was determined by a UV-visible spectrometer at 280 nm with an extinction coefficient of $21,890\ M^{-1}\ cm^{-1}$.

Spectral Properties of EGFP-Based Protease Sensors

In order to determine the spectral properties of EGFP-based protease sensors, the UV-visible spectra were monitored by a UV-1601 spectrophotometer (Shimdzu Scientific Instruments Inc.) with scanning from 600 nm to 200 nm and their fluorescence spectra were measured in the emission region of 410 nm to 600 nm with an excitation wavelength at 398 nm by a fluorescence spectrophotometer.

Spectral Properties Protease Sensors after Protease Digestion

Trypsin digestion of 15 μM EGFP-T/C1 and EGFP-T/C2 was performed by adding stock trypsin from bovine pancreas (Sigma, St. Louis) up to a final concentration of 0.02 μM in trypsin digestion buffer (10 mM Tris, 20 mM $CaCl_2$, pH 7.4). The UV-visible spectra after trypsin digestion were measured in a 1 cm pathway cuvette at different time intervals (0, 1, 3, 5, 10, 20, 30, 60, 90 and 120 min). In order to measure fluorescence spectra of EGFP-T/C1 and EGFP-T/C2 following trypsin digestion, 0.02 μM trypsin were added to 1 μM EGFP-T/C1 and EGFP-T/C2 samples in trypsin digestion buffer (10 mM Tris, 20 mM $CaCl_2$, pH 7.4), respectively. Fluorescence emission of trypsin sensors at 508 nm with excitation at 398 and 490 nm was recorded at different time intervals (0, 1, 3, 5, 10, 20, 30, 60, 90 and 120 min). Similarly, EGFP-wt was subjected to trypsin digestion under the same conditions, as the experimental control.

Verification of Cleavage Status of Protease Sensors

To examine the cleavage status of the protease sensors (EGFP-T/C1, and EGFP-wt) at different time points, 20 μl of reaction mixtures of 15 μM EGFP variants during trypsin digestion were removed and immediately added SDS sample buffer and boiled to stop the reaction for monitoring by SDS-PAGE at different digestion time intervals (0 min, 5 min, 10 min, 30 min, 60 min, 2 h, 6 h, and 24 h). The samples were loaded on 15% SDS-PAGE to examine the cleavage status of three EGFP variants.

Similarly, after digestion with trypsin, the cleavage status was confirmed using matrix assisted laser desorption/ionization-mass spectrometry (MALDI-MS).

The two assays demonstrated that the protease sensors were being cleaved by the proteases of interest.

Kinetic Studies on the Protease Sensors

Initial rates of trypsin digestion reaction for EGFP-T/C1 with various concentrations were measured using a time-course model to monitor the change of absorbance at 490 nm for 10 min on a UV-1700 spectrometer (Shimadzu, Japan), where the initial rate was equivalent to the resulting slope of absorbance increase. These data were then used to calculate the steady-state kinetic parameters, Michaelis constants ($K_m$), turnover number ($k_{cat}$) and specificity constants ($k_{cat}/K_m$) for hydrolysis of EGFP-T/C1 upon the action of trypsin through the fitting with Michaelis-Menten equation by nonlinear regression using KaleidaGraph 3.5 software (Synergy software) to obtain $k_{cat}$, $K_m$, and $k_{cat}/K_m$ values.

In order to investigate the kinetic change and to determine the steady-state kinetic parameters $k_{cat}$, $K_m$, and $k_{cat}/K_m$ for hydrolysis of EGFP-based trypsin sensors upon the action of trypsin, initial rates were measured at various EGFP-based trypsin sensor concentrations. The change of absorbance was monitored at 490 nm for 10 min using UV-1700 spectrometer (Shimadzu, Japan) in time-course model and the slope of absorbance increase was determined as the initial rate data. The data were fitted to the Michaelis-Menten equation by nonlinear regression using KaleidaGraph 3.5 software (Synergy software) to obtain the Michaelis constants ($K_m$), turnover numbers ($k_{cat}$) and specificity constants ($k_{cat}/K_m$).

Inhibition of the Protease Sensor

In order to examine inhibition effect of leupeptin (Sigma, St. Louis), a trypsin inhibitor, leupeptin at various concentrations (0, 12.5, 25, 50 and 100 nM) was mixed with EGFP-T/C1 and subsequently digested by trypsin at a final concentration of 0.005 µM. The kinetic studies of EGFP-T/C1 with various concentrations were performed at each inhibitor concentration level and the absorbance change at 490 nm was mintored using a time course model. The double reciprocal of initial rates and trypsin sensor concentrations was performed to obtain the plot for confirming inhibition type and calculation of $K_i$ value.

Cleavage Specificity of Protease Sensors

In order to examine cleavage specificity of EGFP-T/C1 to different proteases, thrombin (GE healthcare, USA) and protease type X (Sigma, St. Louis) were used to digest trypsin sensor, EGFP-T/C1. Thrombin or protease type X were added to 15 µM EGFP-T/C1, buffered in 20 mM Tris, 150 mM NaCl, 2.5 mM $CaCl_2$, pH 8.0, to a final concentration of 0.02 µM. A time-course model with a 4-second interval was used to monitor absorbance signal change at 397 nm.

Dynamic Range Calculation for Optical Change.

In order to evaluate designed trypsin sensors, the dynamic range calculation for optical signal change in absorbance or fluorescence upon trypsin digestion is determined by equation 1:

$$D = (A_{490a}/A_{398a})/(A_{490b}/A_{398b}) \quad \text{Eq. 1}$$

or $$D = (F_{490a}/F_{398a})/(F_{490b}/F_{398b})$$

where $A_{490a}$ and $A_{398a}$ are absorbances at 490 nm and 398 nm following trypsin cleavage; $A_{490b}$ and $A_{398b}$ are absorbances at 490 nm and 398 nm before trypsin cleavage; $F_{490a}$ and $F_{398a}$ are fluorescence intensities at 490 nm and 398 nm excitation following trypsin cleavage; and $A_{490b}$ and $A_{398b}$ are fluorescence intensities at 490 nm and 398 nm excitation before trypsin cleavage, respectively.

In order to evaluate designed trypsin sensors, the dynamic range calculation for absorbance change upon trypsin digestion is determined through the following equation:

$$R_D = \frac{\frac{A_{490a}}{A_{398a}}}{\frac{A_{490b}}{A_{398b}}}$$

Where $A_{490a}$ and $A_{398a}$ are the absorbances at 490 nm and 398 nm after cleavage, respectively; $A_{490b}$ and $A_{398b}$ are the absorbances at 490 nm and 398 nm before cleavage, respectively.

Extinction Coefficient Constants of Trypsin Sensors

In order to determine the concentration of the product after trypsin digestion, 5 µl of 40 µM trypsin were added to the trypsin sensor samples after 10 min time course for overnight digestion to completely cleave trypsin sensors. The absorbance at 490 nm of trypsin sensors was measured and then extinction coefficient constants were calculated using the Beer-Lambert law. Based on the calculated extinction coefficient constants and absorbance change, the product concentration can be determined for initial rate calculation.

Cell Culture and Transfection.

MIA PaCa-2 cells were grown on glass coverslips (0.5-1.0×10$^6$ cells/dish) in 35 mm culture dishes in Dulbecco's Modified Eagles Medium (DMEM) (Sigma Chemical Co., St. Louis, Mo.) with 44 mM $NaHCO_3$, pH 7.2, and supplemented with 10% (v/v) fetal bovine serum (FBS), 100 U/ml penicillin and 0.1 mg/ml streptomycin (Pen/Strep) at 37° C. with 5% CO2 in a humidified incubation chamber. After the cells were seeded and grown overnight, EGFP-T/C1 was transfected into MIA PaCa-2 cells with lipofectamine-2000 (Invitrogen Life Technologies) and serum-free Opti-MEM (Gibco Invitrogen Corporation) according to the manufacturer's instructions. For transfection, 2 µg of EGFP-T/C1 DNA was added at a 1:1 (µg/µl) ratio of DNA to lipofectamine-2000. Following overnight incubation at 37° C., the medium containing the DNA and lipofectamine complex was removed, and replaced by DMEM enriched with FBS and Pen/Strep. The cells were then grown 24 to 48 hours in a humidified chamber with 5% CO2 at 30° C. before fluorescence microscope imaging. EGFP-wt was used as the control.

Fluorescence Microscope Imaging.

MIA PaCa-2 cells with transfected EGFP-T/C1 were imaged following trypsin sensor expression for 24 or 48 hours. Cell imaging was performed using a 40× oil objective lens on a Zeiss Axiovert 200 Inverted Microscope connected to a CCD camera (AxioCam HRc). Excitation from a light source (FluoArc, Zeiss) was passed though a FITC filter set (excitation wavelength: 480±20 nm; emission wavelength: 510±20 nm) or 398 nm filter set (excitation wavelength: 400±20 nm; emission wavelength: 510±20 nm). Axiovision software was used for image acquisition with the time course model. During image acquisition, caerulein was added to the cell plate to a final concentration of 10 nM for trypsin activation. The ratiometric change between fluorescence emission for excitation at 398 nm and 488 nm was used to detect trypsin activity at different time intervals in the living cells. Fluorescence for both excitation wavelengths is expected to decrease at 398 nm and produce a corresponding increase at 488 nm during the course of reaction. The fluorescence intensity of the cells was normalized with equation 2:

$$NF = \frac{F_t}{F_0} \quad \text{Eq. 2}$$

where $F_t$ and $F_0$ are the fluorescence intensities of various time points and initial time point at both excitation wavelengths.

The fluorescence ratiometric change (R) is expressed by equation 3:

$$R_{488/398} = \frac{NF_{t\text{-}488}}{NF_{t\text{-}398}} \quad \text{Eq. 3}$$

where $NF_{t-488}$ is the normalization fluorescence intensity of various time points at 488 nm of excitation; $NF_{t-398}$ is the normalization fluorescence intensity of various time points at 398 nm of excitation.

Statistical Analysis

The data for normalization fluorescence intensity and fluorescence ratio change of living cells transfected EGFP-T/C1 and EGFP-wt are represented as means±SD with at least 6 living cells. Student's t-test analysis was performed to determine statistical significance between EGFP-T/C1 and EGFP-wt.

Results

FIG. 1 shows our design of trypsin sensors by grafting an enzymatic cleavage sequence onto enhanced fluorescent green protein (EGFP). We hypothesize that grafting the enzyme cleavage sequence at sensitive locations near the chromophore should enable an efficient change by the proteolytic cleavage to transfer from the cleavage site to the fluorescence chromophore. Three grafting sites on the EGFP scaffold were selected to confer these essential sensor properties, which are immediately following Glu172 within loop-9, Gln157 within loop-8, and Asn144 within loop-7 and the resulted sensors are named as EGFP-T/C1, EGFP-T/C2 and EGFP-T/C3, respectively. Since trypsin demonstrates a strong preference to cleave the peptide bond immediately following an Arg or Lys residue in a solvent-accessible region, we selected a trypsin cleavage sequence derived from EF-hand motif loop III of calmodulin as the basic graft structure as it contains three Arg and one Lys residues in the loop and flanking helices, and has good solvent accessibility.

EGFP-based protease sensors (EGFP-T/C1) were engineered and successfully expressed in *E. coli* BL21 (DE3) strains. EGFP-T/C2 and EGFP-T/C1 were prepared by grafting a trypsin cleavage site. Each sensor maintained a strong green fluorescence both in bacteria and as a purified protein.

Figure 2:
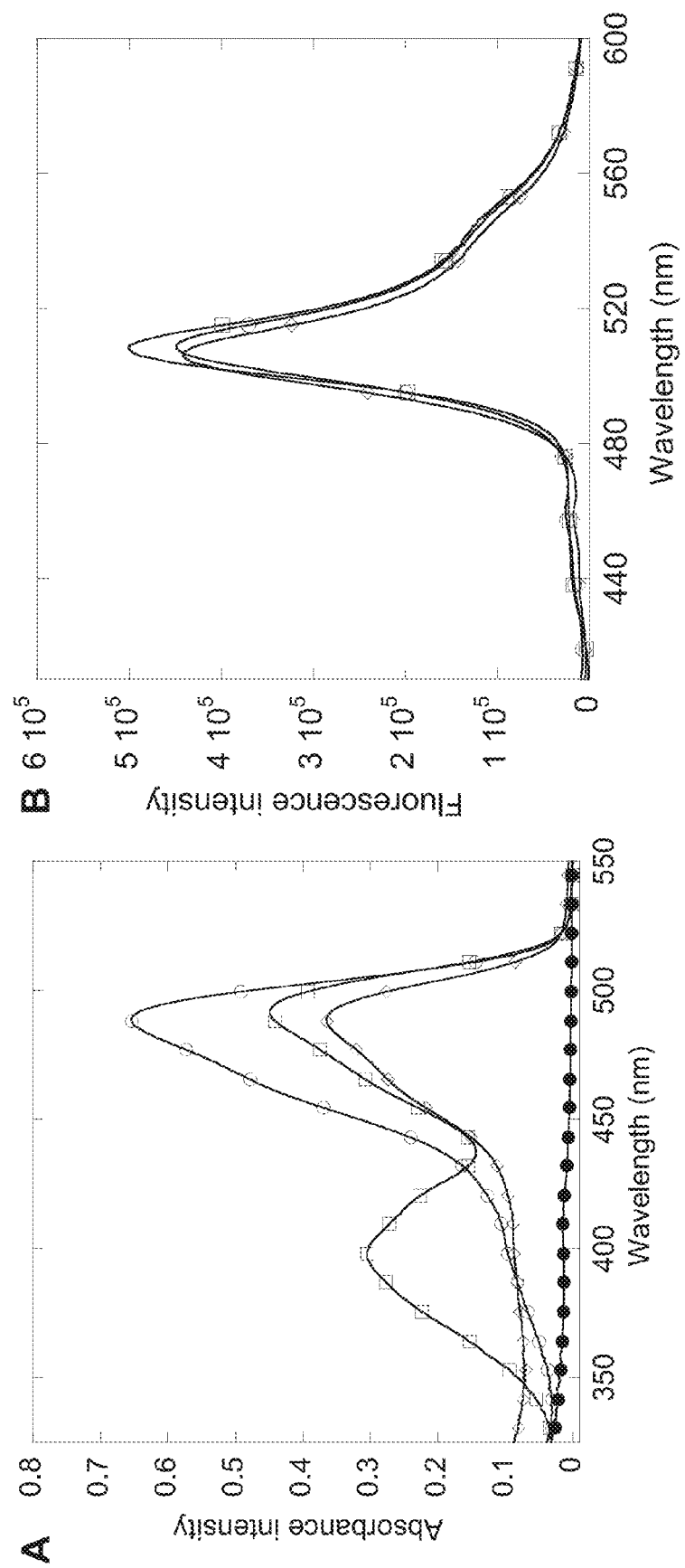
FIG. 2 are graphs that illustrate the visible absorbance (A) and fluorescence (B) spectra of EGFP-wt (circle), EGFP-T/C1 (square), EGFP-T/C2 (diamond) and EGFP-T/C3 (filled in circle) were measured in 10 mM Tris, 1 mM DTT, at pH 7.4.

FIG. 2A shows the UV-visible absorption spectra of purified EGFP-wt, EGFP-T/C1 in 10 mM Tris buffer containing 1 mM DTT at pH 7.4. EGFP-T/C2 has a maximum absorption wavelength similar to that of EGFP-wt at 489 nm. This absorption peak mainly reflects a deprotonated form of the chromophore. In contrast, EGFP-T/C1 has two strong absorption peaks at 491 and 397 nm, respectively. The appearance of an absorption peak at 397 nm corresponds to a protonated form of the chromophore. Therefore, the insertion of the EF-loop at position 172 in EGFP increases the relative population of the protonated form of the chromophore at 397 nm and decreases the deprotonated form of the chromophore at 491 nm.

FIG. 2B shows that the fluorescence emission spectra of EGFP-wt, EGFP-T/C1 and EGFP-T/C2 ranged from 410 to 600 nm when the excitation was at 398 nm. The fluorescence emission results indicate that the maximum emission wavelength of EGFP-wt, EGFP-T/C1 and EGFP-T/C2 are 508, 508 and 506 nm, respectively. While excited at 398 and 491 nm, EGFP-T1/C1 presents its maximum emission peak at 508 nm at both excitation wavelengths. According to the absorbance and fluorescence properties, EGFP-T/C2 has optical properties similar to that of EGFP-wt with more population of protonated chromophore, whereas the insertion of a cleavage linker for trypsin at position 172 results in a population reduction of the deprotonated chromophore and a population increase of the protonated chromophore.

This result demonstrates that position 172 in EGFP is a sensitive location. Further this result demonstrates that the cleavage sequence can be introduced into a GFP without negating its fluorescent properties.

Example 2

In order to verify the cleavage status of EGFP-based trypsin sensors, the samples during trypsin digestion at various digestion time intervals were examined with 15% SDS-PAGE and MALDI mass spectrometry.

Figure 3:
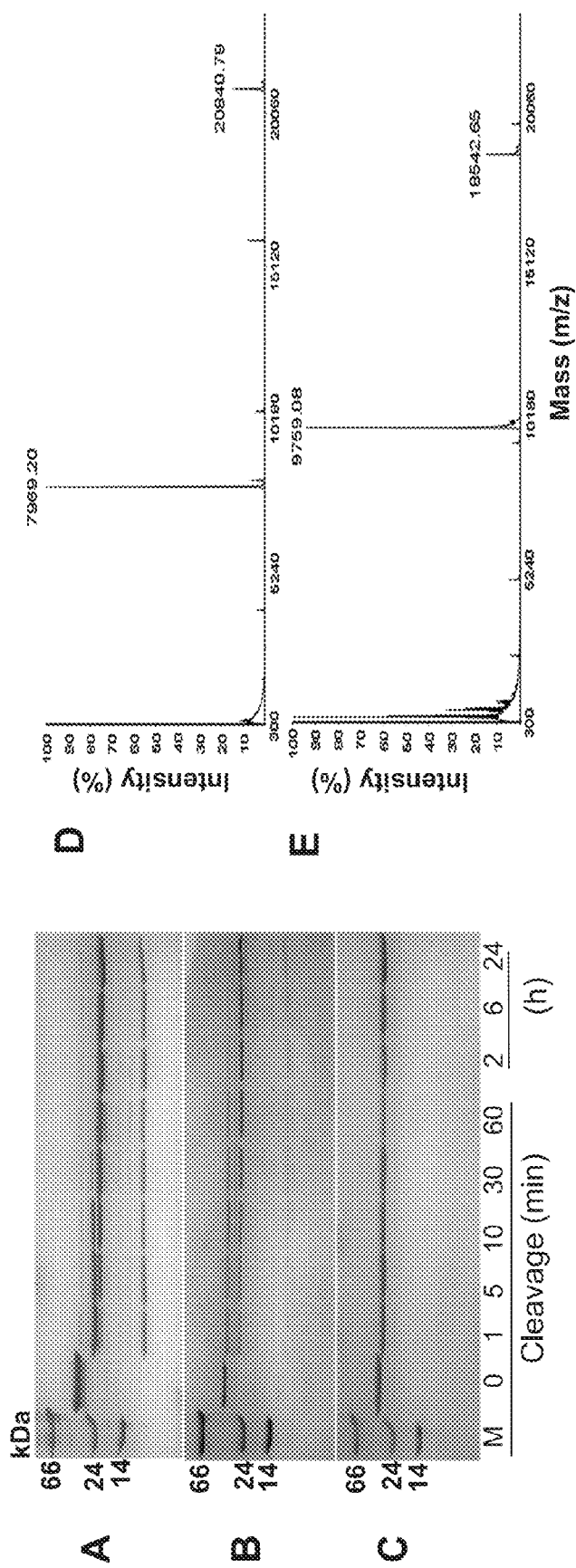
FIG. 3 illustrates SDS-PAGE of EGFP-T/C1 (A), EGFP-T/C2 (B), EGFP-wt (C) and MALDI-mass spectroscopy of EGFP-T/C1 (D) and EGFP-T/C2 (E) cleaved by trypsin at different digestion time intervals. M is a protein marker. Lane 1, 2, 3, 4, 5, 6, 7, 8 and 9 are the samples after trypsin digestion for 0 min, 1 min, 5 min, 10 min, 30 min, 60 min, 2 h, 6 h, and 24 h at room temperature, respectively.

As shown in FIGS. 3A and 3B, both EGFP-T/C1 and EGFP-T/C2 are specifically cleaved into two major fragments by trypsin. EGFP-T/C1 is cleaved into two fragments at approximately 20 kDa and 8 kDa. Even in the presence of respective enzymes, the two major fragments remain unchanged up to 40 hours later.

In contrast, as shown in FIG. 3C, EGFP-wt remains intact upon incubation with trypsin up to 40 hours. MALDI mass spectrometry spectra shows that the large fragments produced from EGFP-T/C1 (FIG. 3D) and EGFP-T/C2 (FIG. 3E) have molecular masses of 20 and 18 kDa and the small fragments have molecular masses of 8 and 10 kDa, respectively, which corresponds to the cleavage site in the insertion location. The observed molecular masses of two stable cleaved fragments from EGFP-T/C1 and EGFP-T/C2 are consistent with the calculated mass. Accordingly, this example demonstrates that EGFP-T/C1 and EGFP-T/C2 can be specifically cleaved by trypsin at the grafted cleavage site.

Example 3

The optical properties of the protease sensor were altered by the digestion of the protease sensor by the protease.

Figure 4:
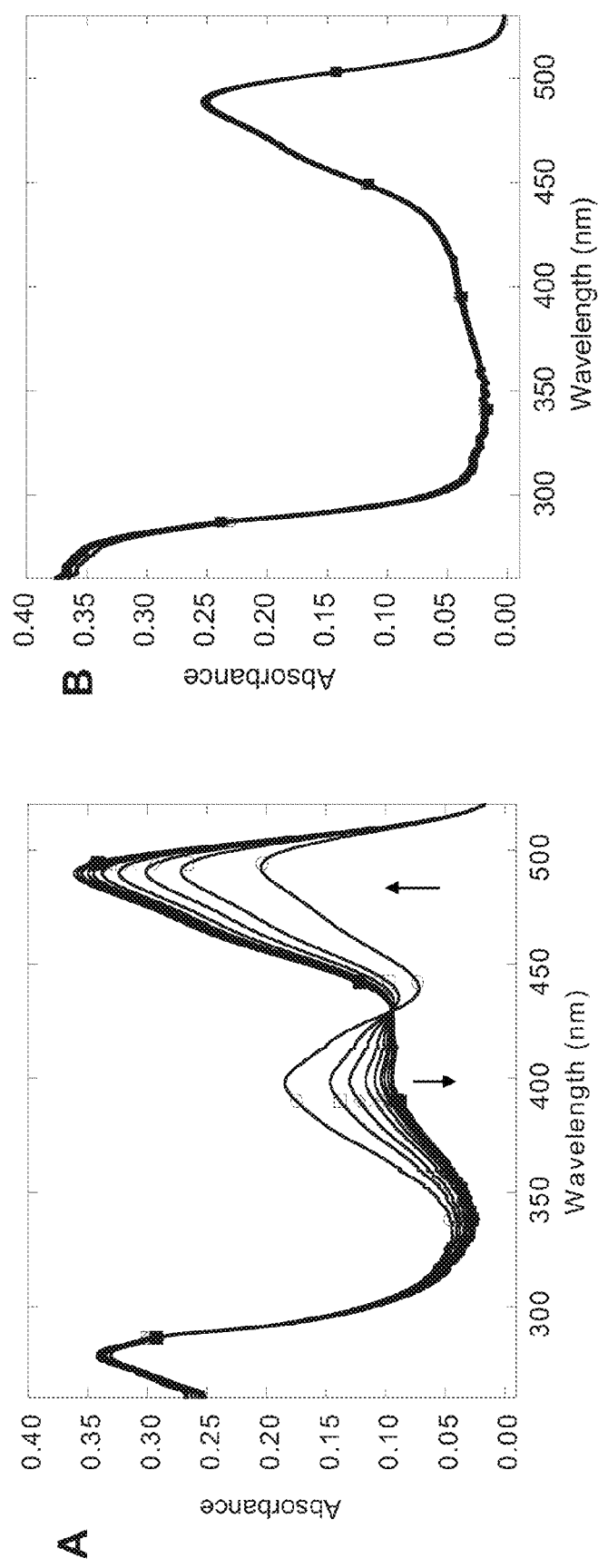
FIG. 4 illustrates the absorption spectra of EGFP-T/C1 (A) and EGFP-T/C2 (B) after trypsin digestion at 0 min (circle), 1 min (square), 3 min (diamond), 5 min (x), 10 min (+), 20 min (triangle), 30 min (filled in circle), 60 min (filled in square), 90 min (filled in diamond) and 120 min (filled in triangle) in 10 mM Tris, 20 mM CaCl2, at pH 7.4, respectively. The absorbance of EGFP-T1 decreases at 397 nm and increases at 491 nm after trypsin digestion at different digestion time intervals, respectively. Fluorescence spectra of EGFP-T1 with excitation at 397 nm (C) and with excitation at 491 nm (D) after trypsin digestion at 0 min (circle), 1 min (square), 3 min (diamond), 5 min (x), 10 min (+), 20 min (triangle), 30 min (filled in circle), 60 min (filled in square), 90 min (filled in diamond) and 120 min (filled in triangle) in 10 mM Tris, 20 mM CaCl2, at pH 7.4, respectively. The fluorescence of EGFP-T1 decreases when excited at 397 nm and increases when excited at 491 nm after trypsin digestion at different digestion time intervals.
Figure 4:
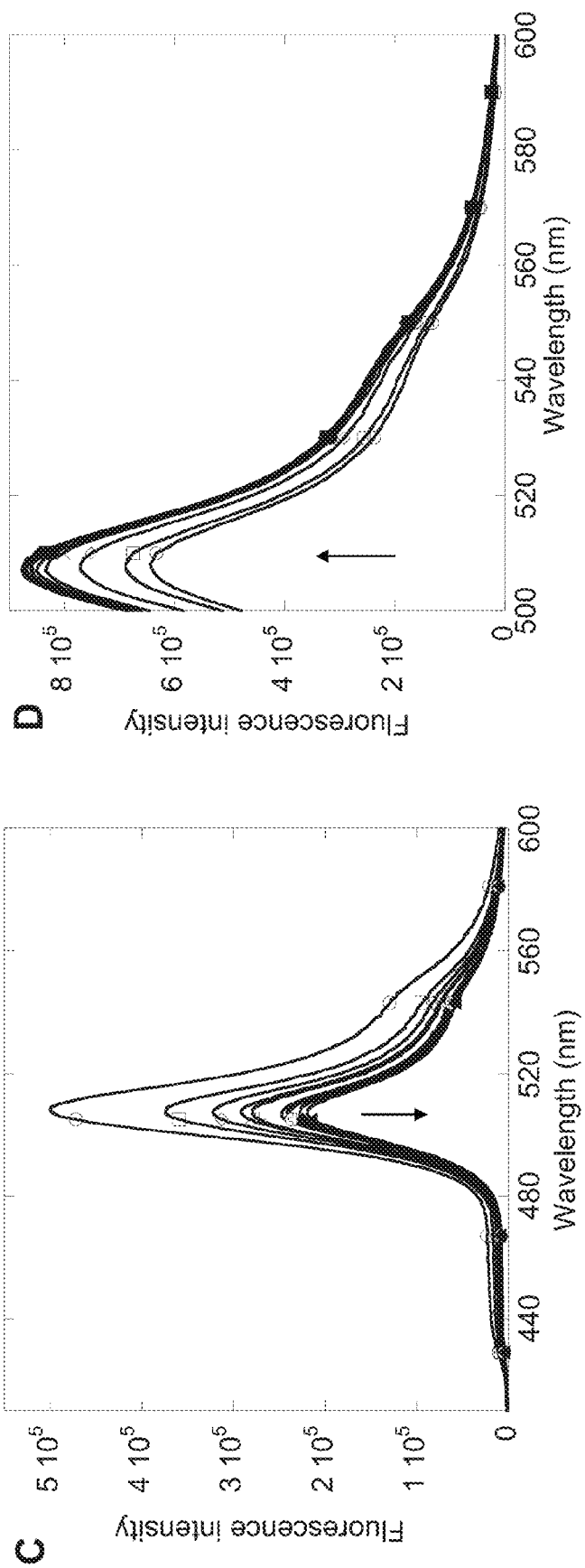

FIG. 4A shows the absorption spectra of EGFP-T/C1 before and after trypsin cleavage. The maximum absorption of EGFP-T/C1 at 491 nm significantly increased and the maximum absorption at 397 nm concurrently decreased when EGFP-T/C1 was proteolytic cleaved by trypsin. Similarly, the maximum fluorescence emission intensity of EGFP-T/C1 at 508 nm also significantly decreases with excitation wavelength of 398 nm, whereas the emission signal at 508 nm slightly increases with the excitation wavelength of 491 nm, shown in FIGS. 4C and 4D. The significant change in the maximum absorption and fluorescence emission intensity was due to the switch between the two chromophore forms in EGFP-T/C1 subsequent to the action of trypsin. However, the maximum absorption of EGFP-T/C2 at 397 and 491 nm does not have any signal change upon the action of trypsin (FIG. 4B). The main reason for absence of signal change in absorbance and fluorescence of EGFP-wt and EGFP-T/C2 is possibly due to the fact that they have only one deprotonated chromophore inside and have no population switch between deprotonated chromophore and protonated chromophore form. These results demonstrate that the insertion of a cleavage site at position 172 results in an optically sensitive chromophore.

Example 4

Figure 5:
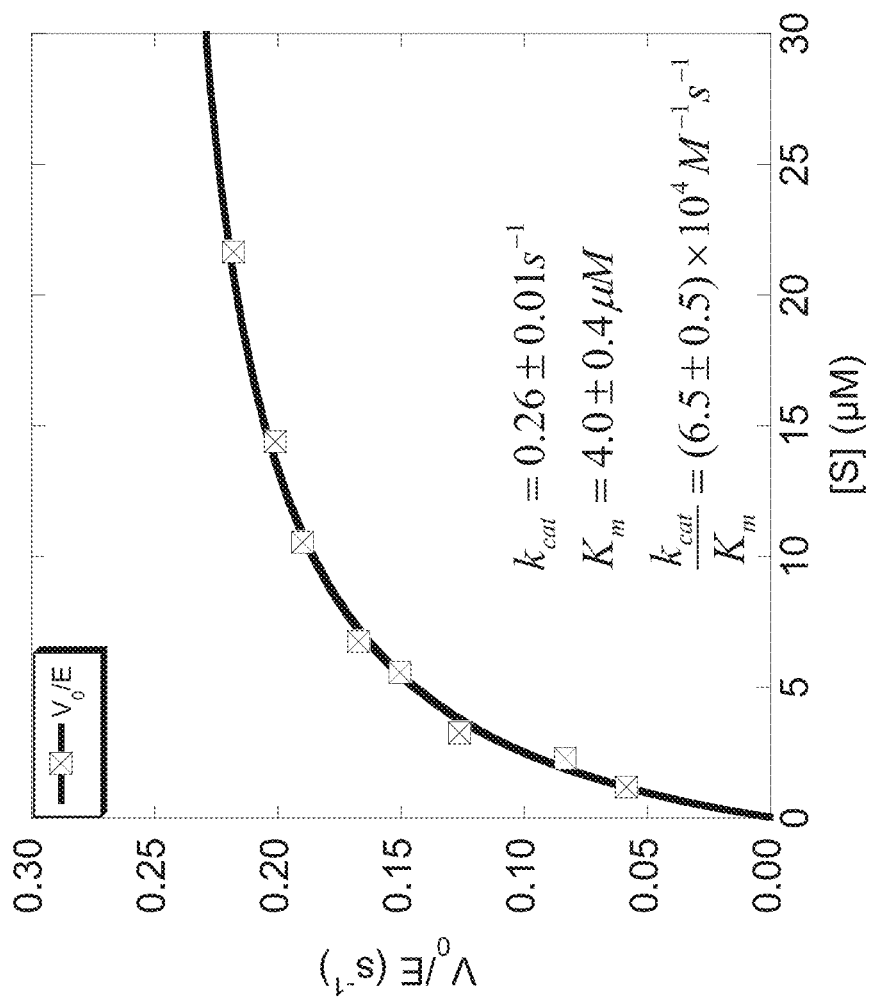
FIG. 5 is a graph that illustrates the kinetic studies of EGFP-T/C1 in trypsin digestion buffer (10 mM Tris, 20 mM CaCl2, pH 8.0). The kinetic parameters, kcat, Km and kcat/Km, are $0.26 \pm 0.01$ s-1, $4.0 \pm 0.4$ µM, and $(6.5 \pm 0.5) \times 10^4$ M-1s-1 through Michaelis-Menten equation fitting (E), respectively.

Next we conducted kinetic studies of the EGFP-T/C1 trypsin sensor compared with a commercially-available trypsin kit, benzoyl-DL-arginine-4-nitroanilide hydrochloride (Bz-DL-Arg-pNA or BAPNA) under identical buffering conditions. As shown in FIG. 5, the kinetic parameters $k_{cat}$, $K_m$ and $k_{cat}/K_m$ calculated through fitting with the Michaelis-Menten equation are 0.26±0.01 $s^{-1}$, 4.0±0.38 µM, and (6.5±0.45)×$10^4$ $M^{-1}s^{-1}$, respectively for EGFP-T/C1 trypsin sensor, and 1.3±0.2 $s^{-1}$, 3.0±0.5 mM, and (4.4±0.4)×$10^2$ $M^{-1}s^{-1}$, respectively for Bz-DL-Arg-pNA. Our designed sensor exhibits a 750-fold increase in $K_m$ and a 150-fold increase in $K_{CAt}/K_m$ compared to the BAPNA colorimetric kit. Although the $K_{at}$ value of our protein-based trypsin sensor is lower, a higher substrate specificity constant ($k_{cat}/K_m$) is observed, which may be due to the more defined structure, as compared to the unstructured small peptides.

Example 5

Figure 6:
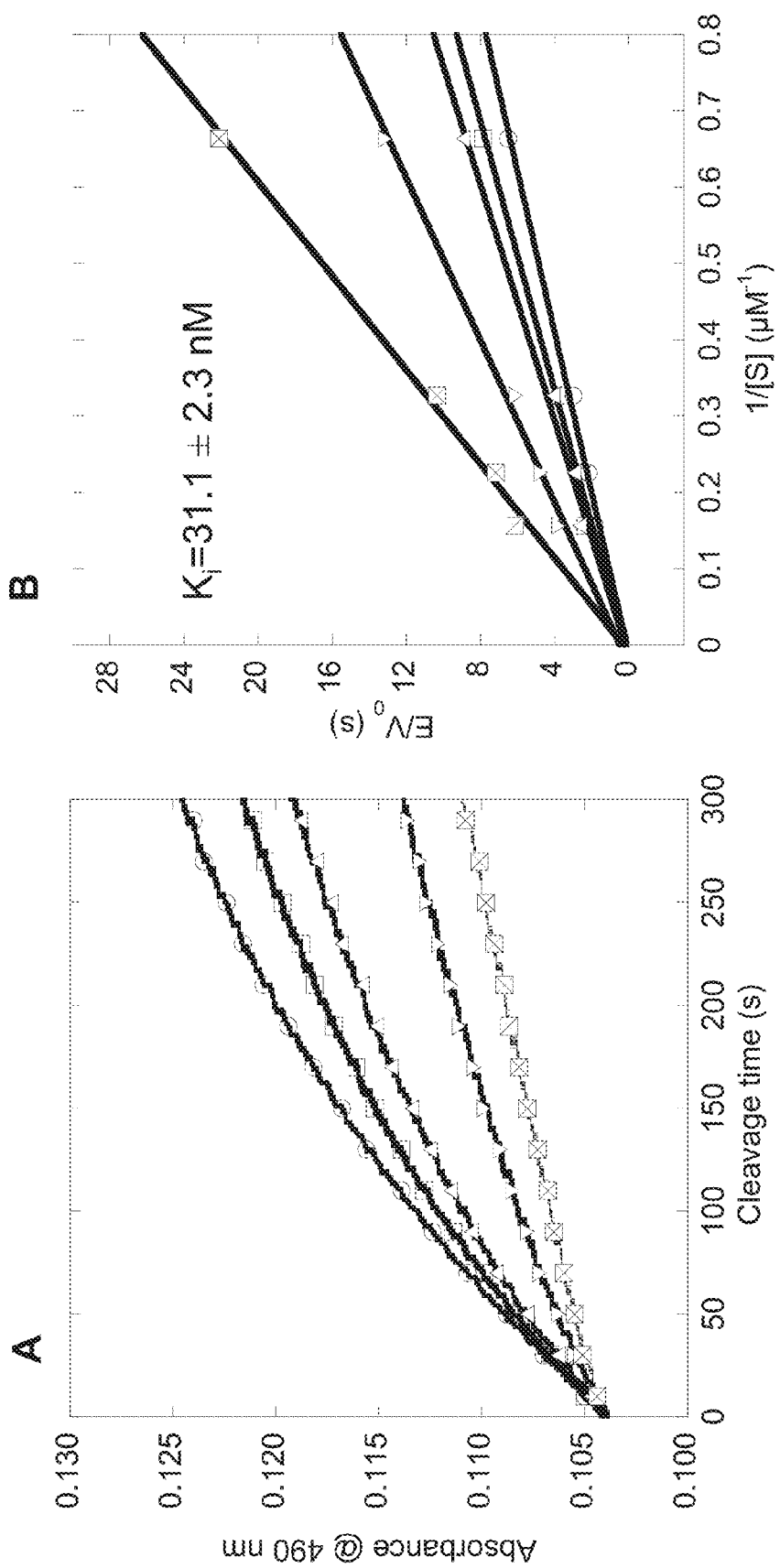
FIGS. 6A-B shows graphs that illustrate the effects of trypsin inhibitors on cleavage of EGFP-TC1 trypsin digestion (FIG. 6A) and kinetic evaluation of the same (FIG. 6B).

In order to ensure that our developed sensor is able to directly monitor the catalytic step of the enzymatic reaction, we then examined the inhibition effect of leupeptin on trypsin during the digestion of EGFP-T/C1 with various leupeptin concentrations. The rate of the signal change due to cleavage decreases with increasing leupeptin concentrations (FIG. 6A). The double reciprocal plot of EGFP-T/C1 with various concentrations at each fixed inhibitor concentration condition was revealed to be a competitive inhibition (FIG. 6B). The kinetic studies of EGFP-T/C1 with various concentrations at each fixed inhibitor concentration condition were fitted with Enzfitter (Bio-soft, Cambridge) and the result is also indicated to be a competitive inhibition with Ki value of 31.1±2.3 nM. Therefore, the result clearly demonstrates that the optical signal change of this sensor, EGFP-T/C1, is directly related to the enzymatic cleavage action rather than the binding process and can be applied to monitor inhibition processes for drug screening.

Example 6

Figure 7:
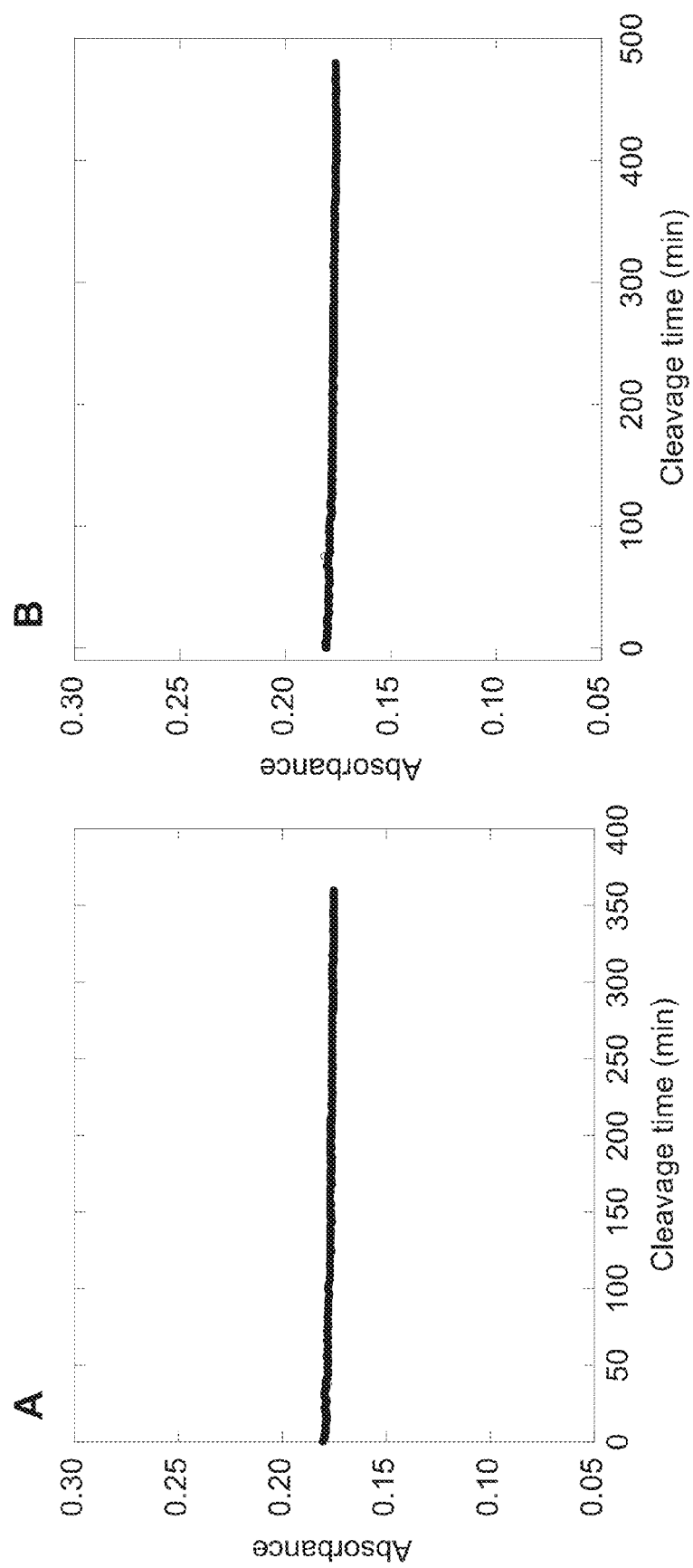
FIG. 7 are graphs that illustrates the absorbance time-based change of EGFP-T/C1 after digestion with 0.02 µM thrombin (A) and protease type X (B) monitored at 397 nm, respectively.

FIGS. 7A and 7B shows that there is no optical change of the sensor, EGFP-T/C1, when exposed to thrombin and protease type X, respectively. This is evidence of the specificity of the sensor, as this sensor was not cleaved by thrombin and protease type X as expected due to lack of substrate cleavage sites at the grafted location. This observation was confirmed by SDS-PAGE and MALDI-MS (data not shown). The absorbance signal change is significant upon the addition of chymotrypsin due to a cleavage site (Phe residue) existed within the grafted sequence. These results suggest that the designed protease sensor with specific cleavage linker has a strong specificity for monitoring proteolytic cleavage and determining protease activity.

Example 7

Figure 8:
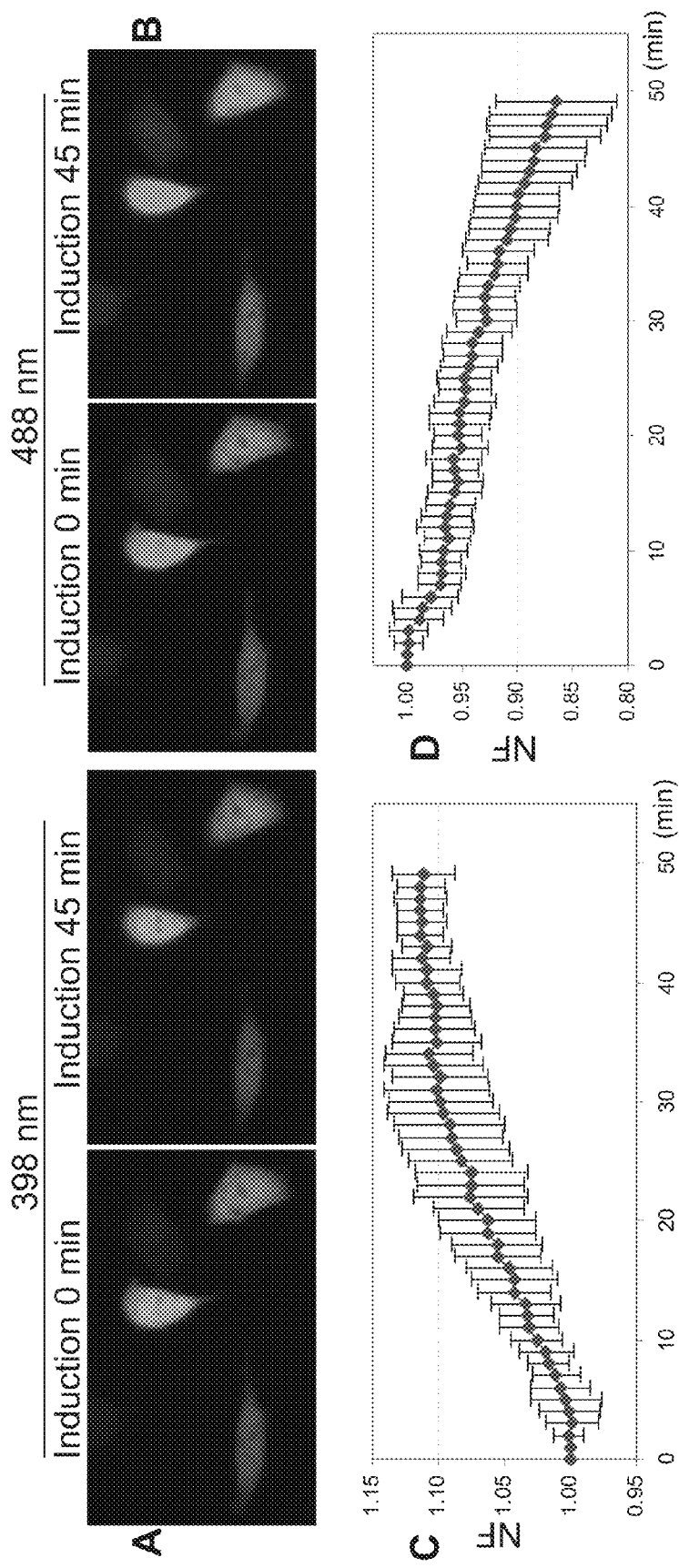
FIG. 8 illustrates the fluorescence images of MIA PaCa-2 cells transfected with EGFP-T/C1. Emission at 510 nm with excitation of 398 nm (A) and 488 nm (B) before and after incubation with 10 nM caerulein. Relative fluorescence change at 510 nm with excitation at 398 nm (C) and 488 nm (D) 488 nm upon activation by caerulein induction at different times. The relative fluorescence change ratio (E) of EGFP-T/C1 and control, EGFP-wt at 510 nm with excitation of 488/398 nm of MIA PaCa-2 cells transfected with trypsin sensor (solid circle) and EGFP-wt (solid square). After induction with 10 nm for 45 min, ratio change in fluorescence intensity of EGFP-T/C1 is significantly different than that of the control, EGFP-wt, *P<0.05.
Figure 8:
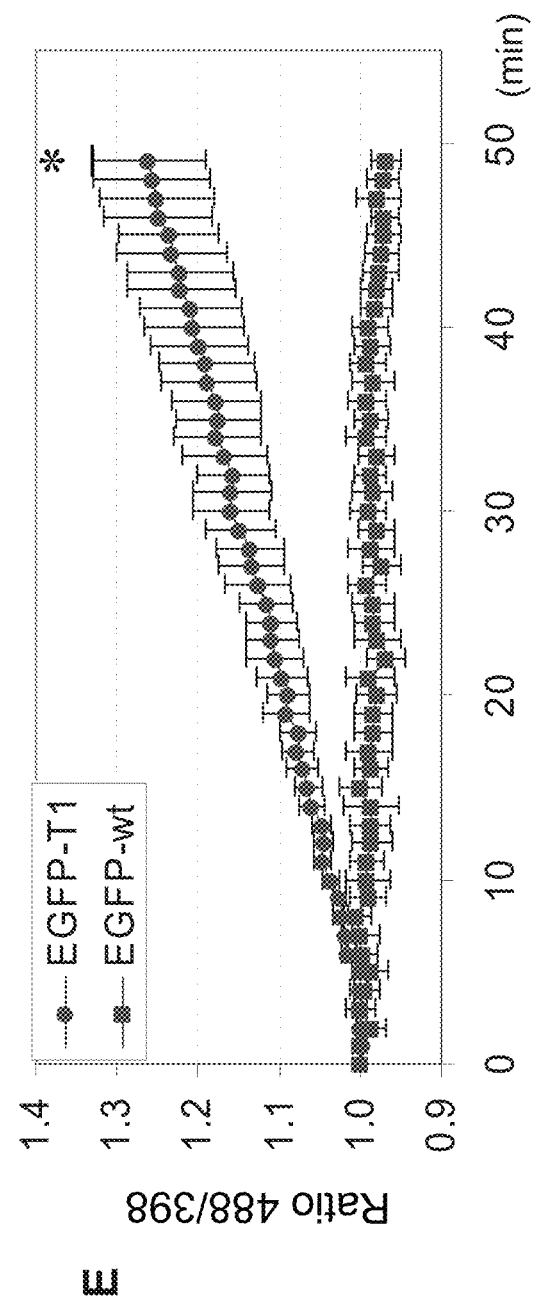

Although the activation of trypsinogen by caerulein was previously reported in pancreatic cells, MIA PaCa-2 via PAR1 and the PAR receptor pathway using cell lysate assays [9-13], the detection of zymogen activity was never achieved in live cells in real time. To address this, next we have applied our sensor to detect trypsin activity in pancreatic cancer cells. After transfection into MIA PaCa-2 pancreatic cancer cells, EGFP-T/C1 and the control (EGFP-wt) begin to exhibit strong fluorescence intensity after 16 to 48 hours. Upon zymogen activation by 10 nM caerulein, the fluorescence emission signal at 510 nm of the trypsin sensor gradually decreased at the 398 nm excitation wavelength (FIG. 8) while concurrently increasing at 488 nm resulting in a ratiometric emission change of greater than 35%. In contrast, the fluorescence emission ratio of EGFP-wt remained unchanged. The ratiometric fluorescence change after trypsin activation in living cells (n=30) starting from 15 min has significant difference (*$P<0.05$). This activation process has a half time of 20 mins and is largely dependent on the activator concentration. These results clearly demonstrate the capability of our trypsin sensor, EGFP-T/C1, to monitor enzymatic activation in living MIA PaCa-2 cells, producing data, which are in excellent agreement with the results of our in vitro trypsin digestion studies. This class of developed proteinase sensor can be specific targeted to ER and mitochondria by adding the calriticulin signal peptide sequence MLLSV-PLLLGLLGLAAAD and KDEL, respectively.

In summary, we have reported a strategy to develop protease sensors by grafting an enzymatic cleavage linker on an EGFP scaffold at various locations hypothesized to be sensitive to the proteins chromophore. Of the three cleavage linker insertion sites evaluated (144, 157, 172) for EGFP, the insertion site between residues 172-173 was found to result in the most dynamic changes in optical properties upon trypsin action. This novel trypsin sensor, EGFP-T/C1 has demonstrated high sensitivity and specificity to trypsin compared to the current, widely-used trypsin kit, BAPNA. The ratiometric signal change of the EGFP-T/C1 sensor at 397 and 491 nm also provides a large dynamic range for protease activity determination and presents high sensitivity. While several elegant studies reported the on and off measurement of protease activity by linking GFP with ubiquitin or proteasome cleavage peptide for protein degradation or by using bacterial protease sequences such as PEST and N-terminal rules [24-26], our developed enzyme sensor exhibits a large ratiometric change which allows quantitative measurement of the enzymatic action. Since it is based on a single EGFP unit which overcomes the limitations observed with FRET-based sensors that are prone to fluorescence photobleaching, poor orientation and translocation in the cellular compartments due to their large size [33]. We have successfully applied this sensor to investigate the dynamic progress of trypsin activation in living cells and monitor trypsin activity in pancreatic diseases in various cellular compartments with the help of signal peptides in real time in vivo [34]. Therefore, this class of protease sensors presents a novel method for tracking protease activity in real time and investigating mechanisms of the early stages of these deadly diseases. Utilizing this same method, it should be possible to develop similar sensors for thrombin, caspases and metalloproteinases, which will open a new area in biotechnology, cell biology, disease diagnosis, drug development and protease inhibitor screening.

REFERENCES FOR EXAMPLES 1-7, EACH OF WHICH ARE INCORPORATED BY REFERENCE

1. Thrower, E. C., Diaz de Villalvilla, A. P., Kolodecik, T. R. & Gorelick, F. S. Zymogen activation in a reconstituted pancreatic acinar cell system. *American journal of physiology* 290, G894-902 (2006).
2. Hirota, M., Ohmuraya, M. & Baba, H. The role of trypsin, trypsin inhibitor, and trypsin receptor in the onset and aggravation of pancreatitis. *Journal of gastroenterology* 41, 832-836 (2006).
3. Teich, N., Rosendahl, J., Toth, M., Mossner, J. & Sahin-Toth, M. Mutations of human cationic trypsinogen (PRSS1) and chronic pancreatitis. *Hum Mutat* (2006).
4. Goldberg, D. M. Proteases in the evaluation of pancreatic function and pancreatic disease. *Clin Chim Acta* 291, 201-221 (2000).
5. Sarkar, F. H., Banerjee, S. & Li, Y. Pancreatic cancer: Pathogenesis, prevention and treatment. *Toxicol Appl Pharmacol* (2006).
6. Shaib, Y. H., Davila, J. A. & EL-Serag, H. B. The epidemiology of pancreatic cancer in the United States: changes below the surface. *Alimentary pharmacology & therapeutics* 24, 87-94 (2006).

7. DiMagno, E. P. Early diagnosis of chronic pancreatitis and pancreatic cancer. *Med Clin North Am* 72, 979-992 (1988).
8. Lemaitre, V. & D'Armiento, J. Matrix metalloproteinases in development and disease. *Birth Defects Res C Embryo Today* 78, 1-10 (2006).
9. Yamasaki, M., Takeyama, Y., Shinkai, M. & Ohyanagi, H. Pancreatic and bile duct obstruction exacerbates rat caerulein-induced pancreatitis: a new experimental model of acute hemorrhagic pancreatitis. *J Gastroenterol* 41, 352-360 (2006).
10. Namkung, W. et al. Protease-activated receptor 2 exerts local protection and mediates some systemic complications in acute pancreatitis. *Gastroenterology* 126, 1844-1859 (2004).
11. Halangk, W., Sturzebecher, J., Matthias, R., Schulz, H. U. & Lippert, H. Trypsinogen activation in rat pancreatic acinar cells hyperstimulated by caerulein. *Biochim Biophys Acta* 1362, 243-251 (1997).
12. Yamaguchi, H., Kimura, T., Mimura, K. & Nawata, H. Activation of proteases in cerulein-induced pancreatitis. *Pancreas* 4, 565-571 (1989).
13. Kruger, B., Lerch, M. M. & Tessenow, W. Direct detection of premature protease activation in living pancreatic acinar cells. *Lab Invest* 78, 763-764 (1998).
14. Thornberry, N. A. et al. A combinatorial approach defines specificities of members of the caspase family and granzyme B. Functional relationships established for key mediators of apoptosis. *J Biol Chem* 272, 17907-17911 (1997).
15. Talanian, R. V. et al. Substrate specificities of caspase family proteases. *J Biol Chem* 272, 9677-9682 (1997).
16. Akemann, W., Raj, C. D. & Knopfel, T. Functional characterization of permuted enhanced green fluorescent proteins comprising varying linker peptides. *Photochem Photobiol* 74, 356-363 (2001).
17. Shimomura, O., Johnson, F. H. & Saiga, Y. Extraction, purification and properties of aequorin, a bioluminescent protein from the luminous hydromedusan, *Aequorea. J. Cell. Comp. Physiol.* 59, 223-240 (1962).
18. Shimomura, 0. The discovery of aequorin and green fluorescent protein. *J Microsc* 217, 3-15 (2005).
19. Tsien, R. Y. The green fluorescent protein. *Annu Rev Biochem* 67, 509-544 (1998).
20. Inouye, S. & Tsuji, F. I. *Aequorea* green fluorescent protein. Expression of the gene and fluorescence characteristics of the recombinant protein. *FEBS Lett* 341, 277-280 (1994).
21. Wang, S. & Hazelrigg, T. Implications for bcd mRNA localization from spatial distribution of exu protein in *Drosophila* oogenesis. *Nature* 369, 400-403 (1994).
22. Chalfie, M., Tu, Y., Euskirchen, G., Ward, W. W. & Prasher, D. C. Green fluorescent protein as a marker for gene expression. *Science* 263, 802-805 (1994).
23. Chalfie, M. Green fluorescent protein. *Photochem Photobiol* 62, 651-656 (1995).
24. Dantuma, N. P., Lindsten, K., Glas, R., Jellne, M. & Masucci, M. G. Short-lived green fluorescent proteins for quantifying ubiquitin/proteasome-dependent proteolysis in living cells. *Nat Biotechnol* 18, 538-543 (2000).
25. Spencer, M. L., Theodosiou, M. & Noonan, D. J. NPDC-1, a novel regulator of neuronal proliferation, is degraded by the ubiquitin/proteasome system through a PEST degradation motif. *J Biol Chem* 279, 37069-37078 (2004).
26. Lee, P., Beem, E. & Segal, M. S. Marker for real-time analysis of caspase activity in intact cells. *Biotechniques* 33, 1284-1287, 1289-1291 (2002).
27. Harpur, A. G., Wouters, F. S. & Bastiaens, P. I. Imaging FRET between spectrally similar GFP molecules in single cells. *Nat Biotechnol* 19, 167-169 (2001).
28. He, L. et al. Monitoring caspase activity in living cells using fluorescent proteins and flow cytometry. *Am J Pathol* 164, 1901-1913 (2004).
29. Jones, J., Heim, R., Hare, E., Stack, J. & Pollok, B. A. Development and application of a GFP-FRET intracellular caspase assay for drug screening. *J Biomol Screen* 5, 307-318 (2000).
30. Karasawa, S., Araki, T., Nagai, T., Mizuno, H. & Miyawaki, A. Cyan-emitting and orange-emitting fluorescent proteins as a donor/acceptor pair for fluorescence resonance energy transfer. *Biochem J* 381, 307-312 (2004).
31. Kawai, H. et al. Simultaneous real-time detection of initiator- and effector-caspase activation by double fluorescence resonance energy transfer analysis. *J Pharmacol Sci* 97, 361-368 (2005).
32. Kohl, T., Heinze, K. G., Kuhlemann, R., Koltermann, A. & Schwille, P. A protease assay for two-photon crosscorrelation and FRET analysis based solely on fluorescent proteins. *Proc Natl Acad Sci USA* 99, 12161-12166 (2002).
33. Hauser, C. T. & Tsien, R. Y. A hexahistidine-Zn2+-dye label reveals STIM1 surface exposure. *Proc Natl Acad Sci USA* 104, 3693-3697 (2007).
34. Zou, J. et al. Expression and optical properties of green fluorescent protein expressed in different cellular environments. *Journal of biotechnology* 119, 368-378 (2005).

Example 8

Figure 9:
FIG. 9 illustrates the structure of trypsin (1 EB2 [PDB]) with trypsin inhibitor (BPO, 3-[(z)-amino(imino)methyl]-N-[2-(4-benzoyl-1-piperidinyl)-2-oxo-1-phenylethyl]benzamide) binding. The His57, Asp102 and Ser195 labeled in the structure are the residues of the catalytic triad. The Asp189 labeled is the residue at the base of the catalytic binding pocket.

Trypsin, a member of a large and diverse family of classic serine proteases, is a proteolytic enzyme for the digestion of protein and plays critical roles in the activation of precursor proteins. In humans, trypsin is synthesized in its inactive form, trypsinogen, within the pancreas. Active trypsin is produced only after trypsinogen reaches the small intestine through the common bile duct and is cleaved by enterokinase. Structurally, trypsin is characterized by two perpendicular β-barrel domains with six antiparallel β-strands in each domain, and an α-helix in the C-terminal. In trypsin, a bridge connecting two β-barrel domains is also constructed in the form of an α-helix. The catalytic and substrate-binding sites are located in the cleft between the β-barrels, as shown in FIG. 9, The functional residues are organized mostly in the loops connecting the β-strands (Matthews, Sigler et al. 1967).

The main function of trypsin is protein degradation; therefore, trypsin also has the capability of digesting itself in a process termed autolysis. Autolysis is one of the most important mechanisms for regulating trypsin levels in living organisms. In healthy organisms, autolysis is regularly controlled and normally does not cause problems. However, the inability of trypsin to self-regulate or self-degrade is closely linked to acute or chronic pancreatitis. This deadly disease is believed to occur due to inappropriate activation and inhibition of trypsin within the pancreas and the autodigestion of pancreatic tissue. A mutant form of trypsin with autolysis sites removed could help investigators understand the mechanisms of hereditary pancreatitis and could also be useful for researching catalytic mechanisms of active trypsin. Many of these enzymes are of medical importance, and are potential drug targets that originate from the human genome or from the genome of the disease-causing organism (Presnell, Patil et al. 1998).

Due to the historical importance of trypsin for studies on enzyme catalysis and extensive medical interest related to their activation and inhibition, the catalytic mechanism and features of trypsin have attracted attention in the biological and medical fields as potential drug targets for human diseases (Polgar 2005). In order to study trypsin activation and inhibition or its mechanisms, trypsin activity determination in vitro and in vivo is a critical step. Currently, the detection of trypsin activity usually utilizes peptide substrates containing chromogenic or fluorescent leaving groups such as 4-nitroaniline or 7-amino-4-methylcoumarin, which can be quantified spectrophotometrically or fluorometrically. The first efficient chromogenic substrate of bovine β-trypsin, named benzoyl-D,L-arginine-p-nitroaniline (BAPNA).

Figure 10:
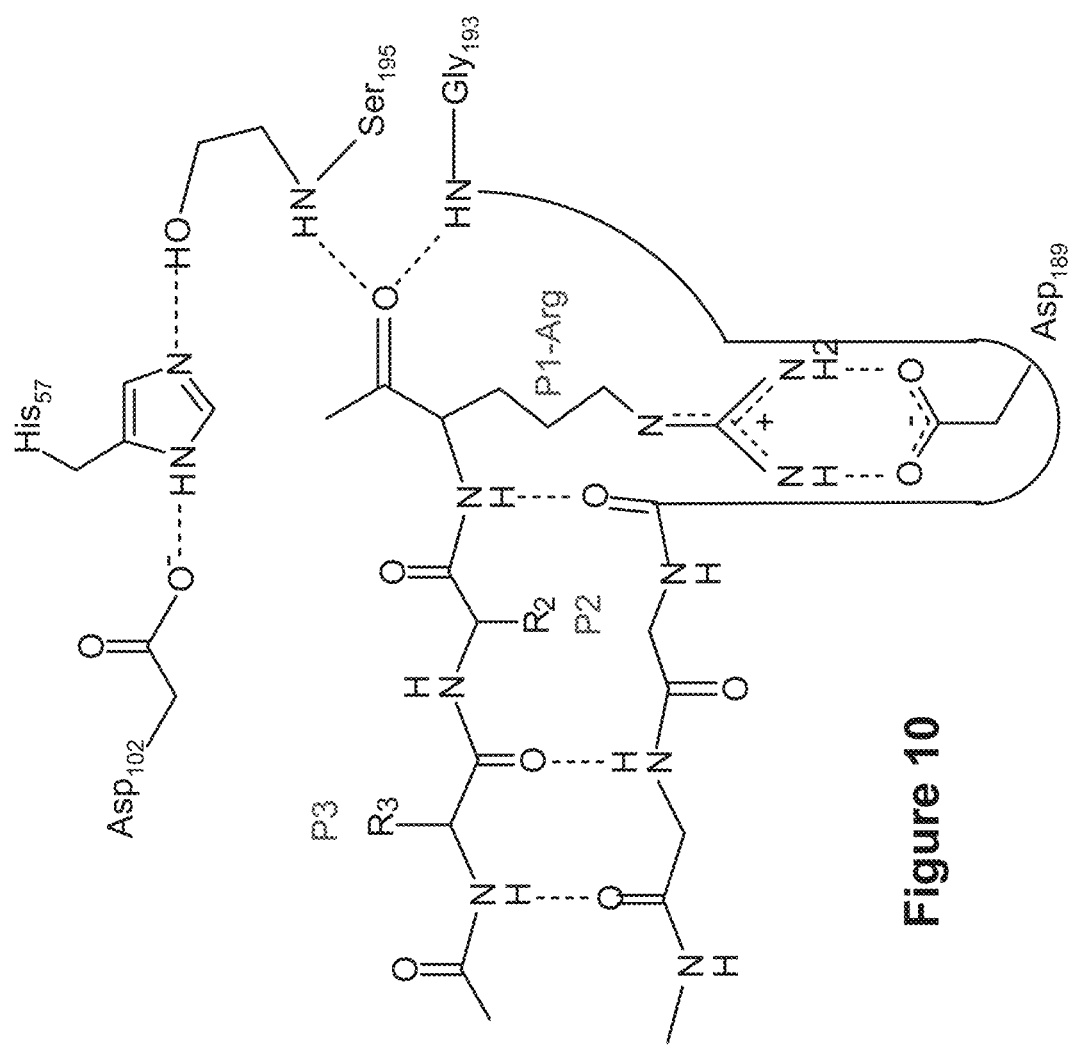
FIG. 10 illustrates the cyclic network of hydrogen bonds between the guanidinium group of P1 Arg substrate and Asp189 at the catalytic binding pocket in trypsin (Perona & Craik, 1997).

Trypsin is a proteolytic enzyme showing substrate specificity of Arg or Lys and displays an approximately $10^5$-fold preference for Arg or Lys over other residues (Graf, Jancso et al. 1988; Evnin, Vasquez et al. 1990). According to the available crystal structures for trypsin complexes, Asp189, positioned at the base of the pocket, always forms a cyclic network of hydrogen bonds with the guanidinium group of Arg at P1 position (Perona and Craik 1997), as shown in FIG. 10. The S' specificity of trypsin is very broad with little substrate discrimination. In the S' subsites, S1' and S2' subsite of trypsin prefers large hydrophobic residues and positively charged residues or aliphatic residues. However, the specificity of substrate for trypsin has the higher requirements to interact with S-subsites of trypsin (Grahn, Ullmann et al. 1998; Polticelli, Ascenzi et al. 1999; Lesner, Brzozowski et al. 2000).

To evaluate our designed trypsin sensors, kinetic parameters of our trypsin sensor variants with trypsin were systematically determined for optimization of trypsin sensor development in living cells in real time. Based on the sequence of bovine pancreatic trypsin inhibitor (BPTI) (Lesner, Kupryszewski et al. 2001), we modified the cleavage linker of EGFP-III-F-172 and mutated the cleavage linker in P1-P4 positions and P1' to P3' to obtain optimal cleavage linkers. The specificity constants of the mutated EGFP-III-F-172 trypsin sensors are significantly increased. The substrate P1 residue should be in agreement with the known primary specificity of trypsin for basic residues and P1 position always prefers to positive charged residues Arg or Lys. The specificity constant for the hydrolysis of the Arg-containing substrates is significantly higher than that for the Lys-containing substrates.

Optimization of EGFP-Based Trypsin Sensors

In order to develop sensitive trypsin sensors with optimal cleavage linkers for trypsin digestion for living cell imaging, various specific cleavage linkers for trypsin were designed and inserted in position 172 in EGFP to obtain different variants of trypsin sensors. Different trypsin sensors and their cleavage linkers for trypsin are shown in Table 1:

TABLE 1

Tryp-designed trypsin sensors and their cleavage linkers

| Trypsin sensor name | The cleavage linker sequences (Seq ID NO: 126-139) |
|---|---|
| EGFP-E-III-F-172 | EEEI<u>REA</u>F<u>R</u>VF<u>DK</u>DGNGYISAAE<u>LR</u>HVMTNL |
| EGFP-E-III-172 | EEEI<u>REA</u>F<u>R</u>VF<u>DK</u>DGNGYISAAE |
| EGFP-III-F-172 | D<u>K</u>DGNGYISAAE<u>LR</u>HVMTNL |
| EGFP-E-III-F-R197 | EEEI<u>AEA</u>F<u>A</u>VF<u>DA</u>DGNGYISAAE<u>LR</u>HVMTNL |
| EGFP-III-172 | D<u>K</u>DGNGYISAAE |

TABLE 1-continued

Tryp-designed trypsin sensors and their cleavage linkers

| Trypsin sensor name | The cleavage linker sequences (Seq ID NO: 126-139) |
|---|---|
| EGFP-E-III-F-172-GPRL | EEEI<u>REA</u>F<u>R</u>VF<u>DK</u>DGNGYISAAG<u>PRL</u>VMTNL |
| EGFP-III-F-172-GPRL | D<u>K</u>DGNGYISAAG<u>PRL</u>VMTNL |
| EGFP-E-III-F-R197-GPRL | EEEI<u>AEA</u>F<u>A</u>VF<u>DA</u>DGNGYISAAG<u>PRL</u>VMTNL |
| EGFP-E-III-F-172-GPARL | EEEI<u>REA</u>F<u>R</u>VF<u>DK</u>DGNGYISAAG<u>PARL</u>VMTNL |
| EGFP-III-F-172-GPARL | D<u>K</u>DGNGYISAAG<u>PARL</u>VMTNL |
| EGFP-E-III-F-R197-GPARL | EEEI<u>AEA</u>F<u>A</u>VF<u>DA</u>DGNGYISAAG<u>PARL</u>VMTNL |
| EGFP-E-III-F-172-GPALRAI | EEEI<u>REA</u>F<u>R</u>VF<u>DK</u>DGNGYISAAG<u>PARL</u>AITNL |
| EGFP-III-F-172-GPALRAI | D<u>K</u>DGNGYISAAG<u>PARL</u>AITNL |
| EGFP-E-III-F-R197-GPALRAI | EEEI<u>AEA</u>F<u>A</u>VF<u>DA</u>DGNGYISAAG<u>PARL</u>AITNL |

Expression and Purification of EGFP-Based Trypsin Sensors

Figure 11:
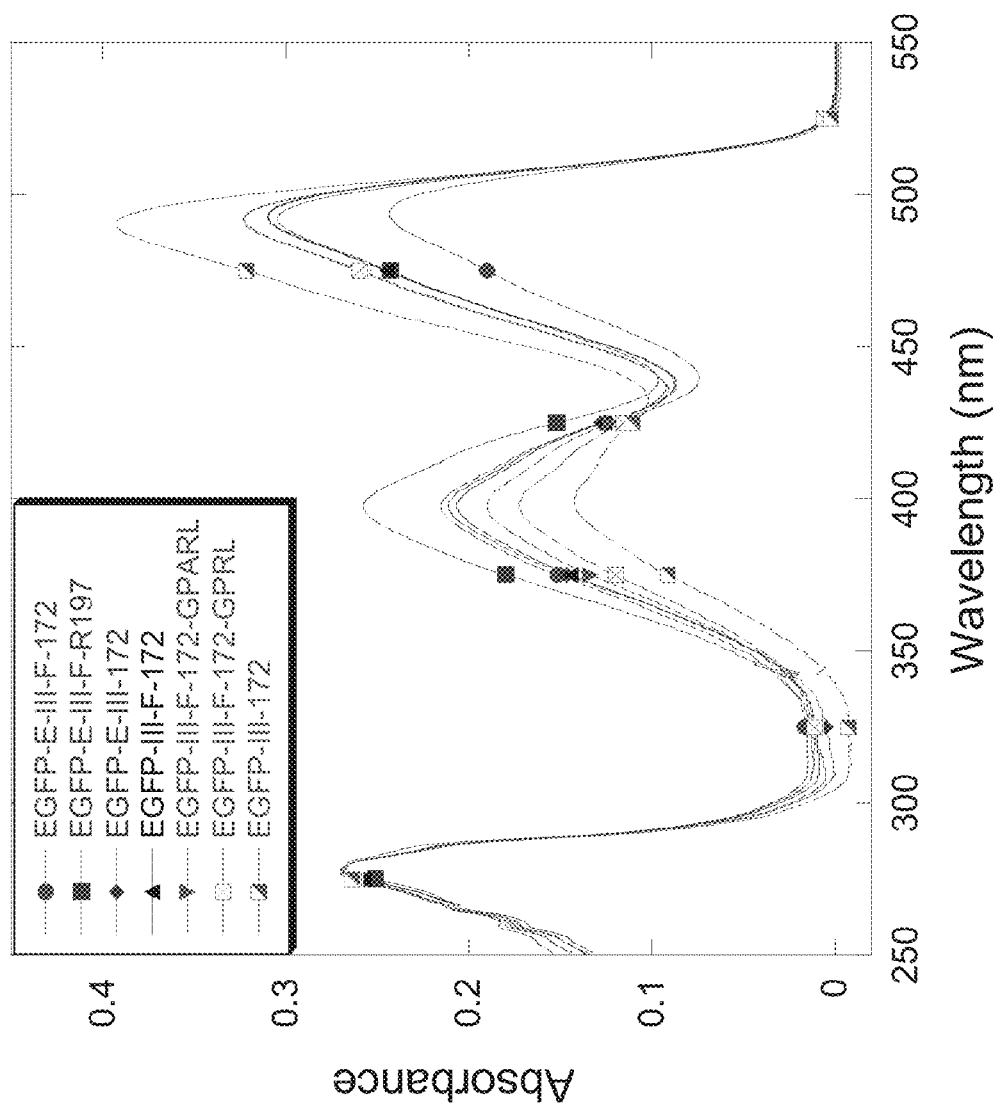
FIG. 11 is a graph that illustrates the absorption spectra of EGFP-based trypsin sensor variants. All of these trypsin sensor variants have two maximum absorption peaks at 398 nm and 490 nm respectively. The order of the ratio (A490/A397) of both maximum absorptions from large to small is EGFP-III-172, EGFP-III-F172-GPRL, EGFP-III-F-172-GPARL, EGFP-III-F-172, EGFP-E-III-172, EGFP-E-III-F-R197 and EGFP-E-III-F-172.

All variants of our designed EGFP-based trypsin sensors can be expressed in E. coli and exhibit strong fluorescence. Through nickel affinity column purification, all variants exhibit two strong absorption peaks, which are at 397 nm and 490 nm, as shown in FIG. 11. Two absorption peaks are resulted from both states of the chromophore, an ionic form and neutral form. However, different variants of these EGFP-based trypsin sensors have various components of both the ionic from and neutral forms of the chromophore due to insertion of various cleavage linkers for trypsin. Similar components of both forms of the chromophore are exhibited in EGFP-E-III-F-172 based on both maximum absorptions; however, the more neutral form of the chromophore and the less ionic form of the chromophore are shown in EGFP-III-172. The order of the ratio (A490/A397) of both maximum absorptions from large to small is EGFP-III-172, EGFP-III-F-172-GPRL, EGFP-III-F-172-GPARL, EGFP-III-F-172, EGFP-E-III-172, EGFP-E-III-F-R197 and EGFP-E-III-F-172.

Kinetic Studies of EGFP-Based Trypsin Sensors Upon Trypsin Digestion

Figure 12:
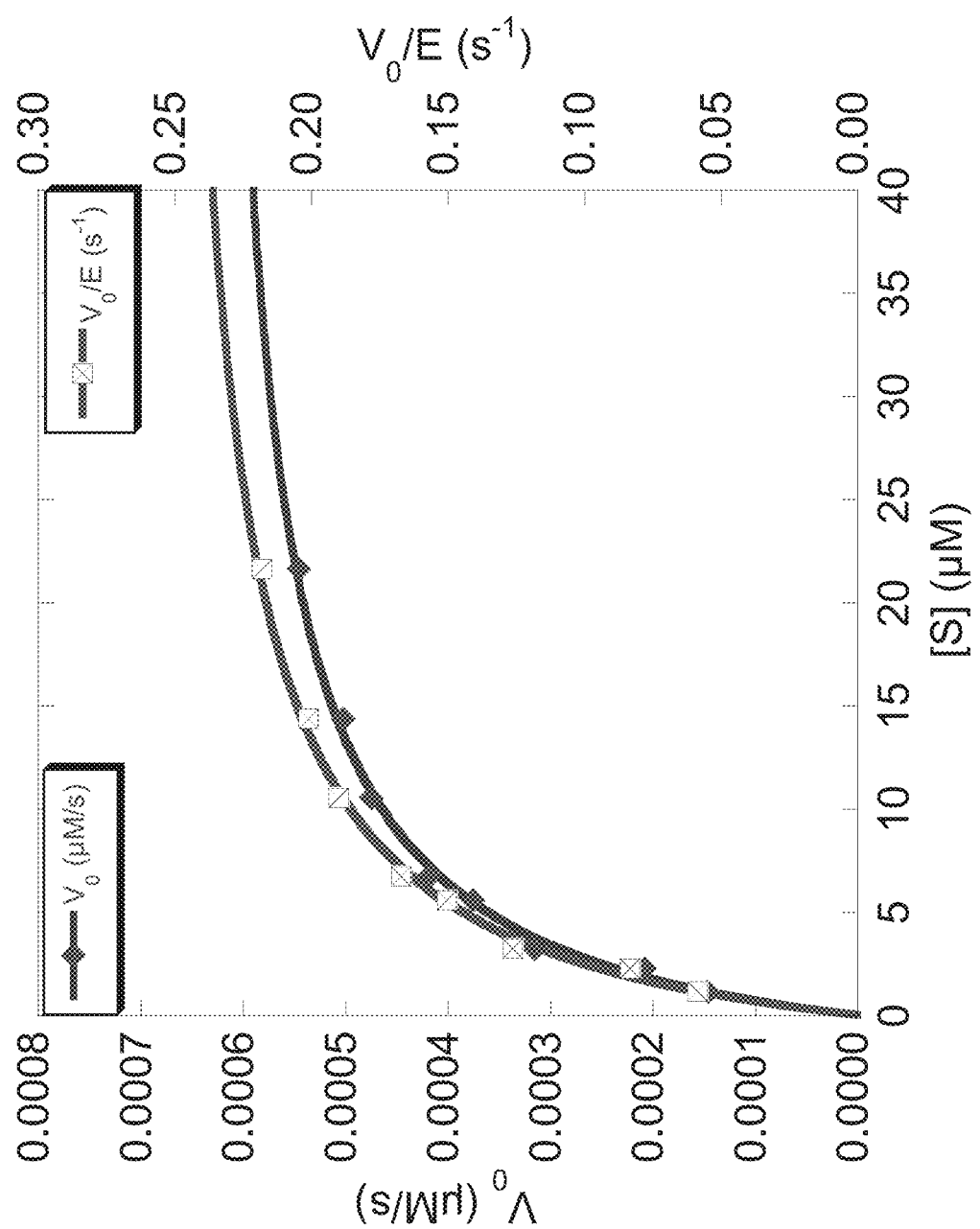
FIG. 12 illustrates a graph of the steady-state kinetic parameters of EGFP-E-III-F-172 were fitted using the Michaelis-Menten equation. The kcat, Km and kcat/Km of EGFP-E-III-F-172 to trypsin are $0.18\pm0.007$ s-1, $3.76\pm0.43$ μM, and $(4.66\pm0.38)\times10^4$ M-1s-1, respectively.

In order to investigate the optimal cleavage linkers for trypsin and to determine the steady-state kinetic parameters $k_{cat}$, $K_m$, and $k_{cat}/K_m$ for hydrolysis of EGFP-based trypsin sensors upon the action of trypsin, initial rates were measured at various EGFP-based trypsin sensor concentrations in trypsin digestion buffer (10 mM Tris, 20 mM CaCl$_2$, pH7.4). The kinetic parameters of EGFP-E-III-F-172 were fitted through the Michaelis-Menten equation, as shown in FIG. 12. Compared to the kinetic parameters of the commercially-available trypsin kit, Nα-Benzoyl-DL-Arginine-p-Nitroanilide (BAPNA), the $K_m$ value of our EGFP-E-III-F-172 is smaller than that of the trypsin kit (nearly 1000 folds), and the specificity constant is increased more than 100 folds. The trypsin sensor, EGFP-III-F-172-GPARL with improved cleavage linker at P2, P3 and P4 positions, can provide a faster cleavage rate than BAPNA. Its binding affinity and specificity are also increased nearly 400 and 500 folds, respectively. Similarly, our other EGFP-based trypsin sensor variants also exhibit great higher binding affinity to trypsin and significant increase in specificity to trypsin. The catalytic kinetic parameters of our EGFP-based trypsin sensor variants are shown in Table 2.

TABLE 2

Tryp-catalytic parameters for trypsin in 10 mM Tris, 20 mM CaCl2, pH 7.4

| Sensor name | $k_{cat}$ (s$^{-1}$) | $K_m$ (µM) | $k_{cat}/K_m$ (M$^{-1}$ s$^{-1}$) | $R^2$ |
|---|---|---|---|---|
| BAPNA | 1.33 ± 0.17 | (3.00 ± 0.50) × 10$^3$ | (4.44 ± 0.41) × 10$^2$ | 0.98169 |
| EGFP-E-III-F-172 | 0.18 ± 0.007 | 3.76 ± 0.43 | (4.66 ± 0.38) × 10$^4$ | 0.99284 |
| EGFP-E-III-172 | 0.70 ± 0.05 | 5.90 ± 1.31 | (11.12 ± 2.09) × 10$^4$ | 0.97046 |
| EGFP-III-F-172 | 0.82 ± 0.12 | 11.80 ± 1.91 | (5.18 ± 0.98) × 10$^4$ | 0.97603 |
| EGFP-E-III-F-R197 | 0.092 ± 0.006 | 2.22 ± 0.06 | (4.28 ± 0.08) × 10$^4$ | 0.9996 |
| EGFP-III-172 | | | No cleavage | |

In order to examine buffer pH effect on trypsin cleavage, kinetic parameters of our designed trypsin sensors were evaluated during trypsin digestion in PIPES buffer (20 mM PIPES, 20 mM CaCl$_2$, pH 6.7) and Tris buffer (10 mM Tris, 20 mM CaCl$_2$, pH 7.4 and pH 8.0), respectively. The kinetic parameters of EGFP-based trypsin sensor variants (EGFP-E-III-F-172 and EGFP-III-F-172) in three pH buffer conditions are shown in Table 3. The results indicate that $K_m$ value in different pH condition do not exhibit any changes, and $k_{cat}$ and $k_{cat}/K_m$ exhibit only a slight increase with the pH increase. These results strongly suggest that the cleavage of EGFP-based trypsin sensors for trypsin is pH independent.

TABLE 3 catalytic parameters for trypsin in various pH conditions

| Trypsin sensors | pH | $k_{cat}$ (s$^{-1}$) | $K_m$ (µM) | $k_{cat}/K_m$ (M$^{-1}$ s$^{-1}$) | $R^2$ |
|---|---|---|---|---|---|
| EGFP-E-III-F-172 | 6.7 | 0.14 ± 0.004 | 3.55 ± 0.25 | (4.16 ± 0.21) × 10$^4$ | 0.99523 |
| | 7.4 | 0.18 ± 0.007 | 3.76 ± 0.43 | (4.66 ± 0.38) × 10$^4$ | 0.99284 |
| | 8.0 | 0.26 ± 0.009 | 3.98 ± 0.74 | (6.52 ± 0.45) × 10$^4$ | 0.98906 |
| EGFP-III-F-172 | 6.7 | 0.50 ± 0.02 | 6.22 ± 0.69 | (7.95 ± 0.67) × 10$^4$ | 0.98795 |
| | 7.4 | 0.82 ± 0.12 | 11.80 ± 1.91 | (5.18 ± 0.98) × 10$^4$ | 0.97603 |
| | 8.0 | 0.87 ± 0.12 | 6.03 ± 1.98 | (14.46 ± 1.51) × 10$^4$ | 0.98148 |

Optimal Linker for Trypsin Cleavage

In order to investigate the optimal cleavage linker for trypsin and study trypsin specificity of EGFP-based trypsin sensors, the P region (P1, P2, P3 and P4 positions) and P' region (P1', P2' and P3' positions) in trypsin sensors were systematically studied. Based on the bovine trypsin inhibitor, the recognition sites in specific cleavage linkers (Leu-Arg, Gly-Pro-Arg-Leu, Gly-Pro-Ala-Arg-Leu and Gly-Pro-Ala-Arg-Leu-Ala-Ile) for trypsin were designed to obtain three different trypsin sensors variants, as shown in above Table 1. Studies on the kinetic parameters of these trypsin sensors were performed in Tris buffer (10 mM Tris, 20 mM CaCl$_2$, pH 7.4). The linker of Gly-Pro-Ala-Arg-Leu exhibited the fastest cleavage rate, and the linker of Leu-Arg showed the slowest cleavage. Similarly, the specificity constants ($k_{cat}/K_m$) of trypsin sensors with recognition sites (Gly-Pro-Ala-Arg-Leu) had the largest value among these variants. The kinetic parameters of trypsin sensors with different cleavage linkers were shown in Table 4. The results clearly expressed that P2, P3 and P4 positions with Ala, Pro and Gly and P1' position with Leu can provide strong binding affinity, a fast cleavage rate and better cleavage specificity for trypsin. Although P2' and P3' positions were designed to have Ala and Ile, $k_{cat}/K_m$ of these trypsin sensor variants did not differ significantly from that of trypsin sensor variants with cleavage linker, Gly-Pro-Ala-Arg-Leu.

TABLE 4 catalytic parameters of trypsin sensors upon trypsin cleavage

| Sensors | pH | $k_{cat}$ (s$^{-1}$) | $K_m$ (µM) | $k_{cat}/K_m$ (M$^{-1}$ s$^{-1}$) | $R^2$ |
|---|---|---|---|---|---|
| EGFP-III-F-172-GPARLAI | 7.4 | 1.30 ± 0.08 | 6.16 ± 0.94 | (21.18 ± 2.07) × 10$^4$ | 0.98175 |
| EGFP-III-F-172-GPARL | 7.4 | 1.80 ± 0.08 | 8.16 ± 0.87 | (22.05 ± 1.42) × 10$^4$ | 0.99401 |
| EGFP-III-F-172-GPRL | 7.4 | 1.03 ± 0.04 | 9.17 ± 0.95 | (11.21 ± 0.76) × 10$^4$ | 0.99185 |
| EGFP-III-F-172 | 7.4 | 0.82 ± 0.12 | 11.80 ± 1.91 | (5.18 ± 0.98) × 10$^4$ | 0.97603 |
| EGFP-E-III-F-172-GPARLAI | 7.4 | 0.87 ± 0.03 | 3.94 ± 0.35 | (21.99 ± 1.26) × 10$^4$ | 0.99344 |
| EGFP-E-III-F-172-GPARL | 7.4 | 0.98 ± 0.04 | 4.12 ± 0.45 | (23.80 ± 1.72) × 10$^4$ | 0.98969 |
| EGFP-E-III-F-172 | 7.4 | 0.18 ± 0.007 | 3.76 ± 0.43 | (4.66 ± 0.38) × 10$^4$ | 0.99284 |
| EGFP-E-III-F-R197-GPARL | 7.4 | 0.85 ± 0.06 | 4.21 ± 0.71 | (20.13 ± 2.14) × 10$^4$ | 0.98771 |
| EGFP-E-III-F-R197 | 7.4 | 0.092 ± 0.006 | 2.22 ± 0.06 | (4.18 ± 0.08) × 10$^4$ | 0.9996 |

Extinction Coefficient Constants of Products after Trypsin Cleavage

After trypsin sensor samples were cleaved completely through trypsin overnight digestion, the absorbance of the products at 490 nm was measured, and the extinction coefficient constants calculated through Beer-Lambert law. The extinction coefficient constants of our trypsin variants were slightly different due to the various cleavage linkers. The extinction coefficient constants of products from EGFP-III-F-172, EGFP-III-F-172-GPRL, EGFP-III-F-172-GPARL and EGFP-III-F-172-GPARLAI after cleavage are very close to each other, indicating that they have similar behavior with respect to trypsin cleavage. Extinction coefficient constants of these cleavage products are shown in Table 5.

TABLE 5 extinction coefficient constants of cleavage products from trypsin sensors

| Trypsin sensor | Extinction coefficient constants ($\epsilon$) ($\mu M^{-1} cm^{-1}$) |
| --- | --- |
| EGFP-E-III-F-172 | 0.0383 ± 0.0015 |
| EGFP-E-III-172 | 0.0332 ± 0.0042 |
| EGFP-III-F-172 | 0.0369 ± 0.0026 |
| EGFP-E-III-F-R197 | 0.0314 ± 0.0049 |
| EGFP-III-F-172-GPRL | 0.0368 ± 0.0048 |
| EGFP-III-F-172-GPARL | 0.0365 ± 0.0033 |
| EGFP-III-F-172-GPARLAI | 0.0373 ± 0.0038 |
| EGFP-E-III-F-172-GPARL | 0.0378 ± 0.0018 |
| EGFP-E-III-F-172-GPARLAI | 0.0418 ± 0.0021 |
| EGFP-E-III-F-R197-GPARL | 0.0231 ± 0.0015 |

Calculation of Dynamic Range of Trypsin Sensors

In order to evaluate the response of trypsin sensors to trypsin, the absorbance change before trypsin cleavage and after trypsin cleavage (dynamic range) was measured. Because both wavelengths (397 nm and 490 nm) of EGFP-E-III-F-172 have similar levels of absorbance, EGFP-E-III-F-172 exhibits a wider dynamic range between the decrease at 397 nm and the increase at 490 nm. However, the neutral chromophore component is higher, and the ionic chromophore component is reduced in other trypsin sensor variants, which limits the dynamic range, therefore, revealing a smaller dynamic range than that of EGFP-E-III-F-172. The dynamic range of trypsin sensor variants is shown in Table 6.

TABLE 6 the dynamic range of trypsin sensor variants

| Trypsin sensor | Dynamic range ($D_R$) |
| --- | --- |
| EGFP-E-III-F-172 | 3.7622 ± 0.2241 |
| EGFP-E-III-F-172-GPARL | 3.5692 ± 0.3608 |
| EGFP-E-III-F-172-GPARLAI | 3.4682 ± 0.2531 |
| EGFP-E-III-172 | 2.1216 ± 0.1724 |
| EGFP-III-F-172 | 2.1663 ± 0.1863 |
| EGFP-III-F-172-GPRL | 1.9971 ± 0.0498 |
| EGFP-III-F-172-GPARL | 2.0620 ± 0.0760 |
| EGFP-III-F-172-GPARLAI | 2.0863 ± 0.0724 |
| EGFP-E-III-F-R197 | 2.0468 ± 0.0505 |
| EGFP-E-III-F-R197-GPARL | 1.8034 ± 0.2855 |

EGFP-based calcium sensors were successfully designed and developed through the insertion of a calcium binding motif, EF-hand, from calmodulin, which can be expressed in mammalian cells and can be used for tracking calcium signaling in vitro and in living cell studies. According to this grafting strategy, the specific cleavable linker for trypsin can be inserted in EGFP to develop sensitive trypsin sensors. On the other hand, EGFP can be easily expressed in bacteria and mammalian cells, which offers EGFP-based trypsin sensors for exploiting trypsin activity in vitro and investigating real-time trypsin activation or trypsin inhibition in living cells. In addition, EGFP-based trypsin sensors are characterized by two inversely-correlated wavelength change for absorbance and excitation, which also provides a ratiometric measurement to determine trypsin activity.

Previous research has established that loop-III of calmodulin has strong binding affinity for calcium, and the associated flanking helices connected to loop-III can improve the flexibility of the EF-hand binding site. Cleavage sites for trypsin are located in the modified EF-hand motif, which was grafted into EGFP to develop the sensitive trypsin sensors. According to our kinetic studies of trypsin sensors, the cleavage site (residue K) in loop-III can not be cleaved by trypsin, possibly due to the reduced accessibility to trypsin at this site. With the addition of flexible helices on both sides of the loop-III, the accessibility to trypsin and the cleavage rate are significantly increased. Meanwhile, cleavage by trypsin was found to occur within the helices (E helix or F-helix). The cleavage rates on both the E-III motif and the III-F motif by trypsin are similar, but the E-helix exhibits greater binding affinity to trypsin than the F-helix, resulting in higher cleavage specificity (larger $k_{cat}/K_m$ value). Although there is slower cleavage rate of the trypsin sensor grafted with the intact EF-hand, multiple cleavage sites in the whole EF-hand motif can provide a large dynamic range and stronger binding affinity to trypsin. Due to the difference in components between the ionic and neutral chromophore forms following insertion of various cleavage linkers, the range of absorbance changes at 397 nm and 490 nm was also altered, resulting in differences between the various trypsin sensor variants. The ratio (A490 nm/A397 nm) for the trypsin sensor variants, in descending order, followed the trend EGFP-III-F-172-GPRL>EGFP-III-F-172-GPARL>EGFP-III-F-172>EGFP-E-III-172>EGFP-E-III-F-R197>EGFP-E-III-F-172. The order of dynamic range for these trypsin sensor variants exhibited the same trend.

Our designed EGFP-based trypsin sensor variants appear to have great potential to determine trypsin activity or trypsin activation in living cells in real time. Meanwhile, compared to the kinetic parameters of commercially-available trypsin kits, the binding affinity and specificity of our EGFP-based trypsin sensor variants to trypsin exhibit a significant improvement.

In summary, we have successfully developed EGFP-based trypsin sensors with optimal cleavage linkers, which exhibit fast response, high sensitivity and specificity, and large dynamic range with trypsin cleavage. Our trypsin sensor variants can be easily expressed in living cells for tracking trypsin activation and inhibition processes in real time and they exhibit ratiometric optical signal changes during analysis which eliminates effects from background, expression level or orientation limitation. These trypsin sensors will be highly-beneficial for probing physiological processes and pathological mechanisms of diseases corresponding to the imbalance of trypsin activation and inhibition. Moreover, this method for protease sensor development will likely be applicable to the investigation of other diseases related to protease activity.

REFERENCES FOR EXAMPLE 8, EACH OF WHICH ARE INCORPORATED BY REFERENCE

Evnin, L. B., Vasquez, J. R., et al. (1990). "Substrate specificity of trypsin investigated by using a genetic selection." Proc Natl Acad Sci USA 87(17): 6659-63.

Graf, L., Jancso, A., et al. (1988). "Electrostatic complementarity within the substrate-binding pocket of trypsin." Proc Natl Acad Sci USA 85(14): 4961-5.

Grahn, S., Ullmann, D., et al. (1998). "Design and synthesis of fluorogenic trypsin peptide substrates based on resonance energy transfer." Anal Biochem 265(2): 225-31.

Lesner, A., Brzozowski, K., et al. (2000). "Design, chemical synthesis and kinetic studies of trypsin chromogenic substrates based on the proteinase binding loop of Cucurbita maxima trypsin inhibitor (CMTI-III)." Biochem Biophys Res Commun 269(1): 81-4.

Lesner, A., Kupryszewski, G., et al. (2001). "Chromogenic substrates of bovine beta-trypsin: the influence of an amino acid residue in P1 position on their interaction with the enzyme." Biochem Biophys Res Commun 285(5): 1350-3.

Matthews, B. W., Sigler, P. B., et al. (1967). "Three-dimensional structure of tosyl-alpha-chymotrypsin." Nature 214 (5089): 652-6.
Perona, J. J. and Craik, C. S. (1997). "Evolutionary divergence of substrate specificity within the chymotrypsin-like serine protease fold." J Biol Chem 272(48): 29987-90.
Polgar, L. (2005). "The catalytic triad of serine peptidases." Cell Mol Life Sci 62(19-20): 2161-72.
Polticelli, F., Ascenzi, P., et al. (1999). "Structural determinants of trypsin affinity and specificity for cationic inhibitors." Protein Sci 8(12): 2621-9.
Presnell, S. R., Patil, G. S., et al. (1998). "Oxyanion-mediated inhibition of serine proteases." Biochemistry 37(48): 17068-81.
Ye, Y., Lee, H. W., et al. (2005). "Probing site-specific calmodulin calcium and lanthanide affinity by grafting." J Am Chem Soc 127(11): 3743-50.
Ye, Y., Shealy, S., et al. (2003). "A grafting approach to obtain site-specific metal-binding properties of EF-hand proteins." Protein Eng 16(6): 429-34.
Zou, J., Ye, Y., et al. (2005). "Expression and optical properties of green fluorescent protein expressed in different cellular environments." J Biotechnol 119(4): 368-78.

Example 9

As shown in this example, Applicant's invention can be used to develop caspase-3 sensors for detecting caspase-3 activity in living cells or in vivo in real time. In one example, an EGFP-based caspase-3 sensor, EGFP-cas3-1 (also called EGFP-EF172cas) was produced through a grafting approach, to exploit the significant optical property changes observed following addition of active caspase-3 in vitro or the activation of caspase-3 in living cells. The fluorescence signal change of the caspase-3 sensor is sensitive in live Hela cells and MIA PaCa-2 cells after being induced by apotosis reagents, which can be useful for probing the mechanisms of apoptosis, diseases and for tracking the pathological processes of some diseases, e.g., those related to caspase-3 activity.

We first reported a sensitive EGFP-based caspase-3 sensor was developed with a grafting approach and applied it to monitor the activation and inhibition of caspase-3 in living cells in real time. Results indicated that the fluorescence intensity of Hela cells with transfected caspase-3 sensor was exhibited both a significant increase at 398 nm and a decrease at 488 nm in real time after addition of staurosporine (STS), which provides high sensitivity for caspase-3 determination in living cells in real time due to a wide ratiometric change between the two wavelengths. On the other hand, the activity of caspase-3 in living cells can be monitored at early stage in real time. Hence, this EGFP-based ratiometric caspase-3 sensor can be useful for disease diagnosis, pathological process tracking and protease inhibitor screening related to caspase-3 activity in living cells or in vivo.

Apoptosis, Caspase Actions and Tumors

Apoptosis, or programmed cell death, is an essential physiological process that plays a critical role in tissue development and homeostasis. Many human diseases can be attributed directly or indirectly to a derangement of apoptosis, resulting in either cell accumulation, cell eradication or cell turnover impairment, cell loss, the apoptotic program inadvertently triggered (Fadeel and Orrenius 2005). It is increasingly clear that apoptosis plays a central role in the pathogenesis of several human diseases. The progress of apoptosis is regulated by a series of activations of multiple caspases in a stringently temporal order under certain circumstances. Caspases, closely associated with apoptosis, are aspartate-specific cysteine proteases and members of the interleukin-1β-converting enzyme family. The activation and function of caspases, involved in the delicate caspase-cascade system, are regulated by various kinds of molecules, such as the inhibitor of apoptosis protein, Bcl-2 family proteins, calpain, and calcium ions (Zhang, Haskins et al. 2004; Fan, Han et al. 2005). Therefore, the caspase-cascade system plays vital roles in the induction, transduction and amplification of intracellular apoptotic signals. For example, an increase in apoptosis leads to cell loss accompanied by neurodegenerative diseases (Alenzi 2005). Although the relationship between apoptosis and the caspase family has been demonstrated to some extent for certain diseases, their mechanisms by which caspase activity mediates apoptosis are not fully understood. One of the challenges in monitoring the apoptosis pathway is the involvement of a series of caspases and their activation or inhibition mechanisms. Initiator caspases (caspase 8, 9 and 10) and effector caspases (caspase 3 and 7) which have different pathways and also share substrate specificity to some extent. On the other hand, the progress in this area has been limited due to the lack of a convenient and reliable system to quantify these protease activities and quantitatively detect caspase activity in real time in living cells or in vivo (Gurtu, Kain et al. 1997). Therefore, there is a strong need to develop specific caspase sensor for monitoring activation and inhibition in living cells or in vivo in real-time determination mode.

Current Methods for Detection of Caspase Activity and their Limitations

Most caspase actions are mainly monitored either indirectly or in a semi-quantified manner. Antibody detection against caspases by western blotting is a common method with high sensitivity, which provides a qualitative assay rather than quantitative assay for caspases during the apoptosis process in apoptotic cells, tissues or organs. Caspase inhibitors or affinity labels to monitor caspase actions are limited by their relatively low specificity for each individual caspase and toxic effects especially during long-time in vivo exposure (Lee, Long et al. 2000; Tawa, Tam et al. 2001; Kohler, Orrenius et al. 2002). Current caspase-3 sensors or probes for monitoring caspase actions can be summarized within the following major classes. The first class that is commercially available involves chemical, synthetic substrates linked to chromophores, which utilizes a synthetic tetrapeptide, Asp-Glu-Val-Asp (DEVD), labeled with a fluorescent molecule, 7-amino-4-trifluoromethyl coumarin (AFC), or a colorimetric molecule, p-nitroanilide (pNA) as substrates. DEVD-dependent protease activity is assessed by detection of the free AFC or pNA cleaved from the substrates for rapid quantification of caspase-3 activity in the onset of apoptosis (Gurtu, Kain et al. 1997). To analyze caspase activity with this method, apoptotic cells were lysed and subjected to enzymatic action. Although some caspase peptide probes can be diffused into living cells, caspase activity cannot be well quantified due to difficulties in delivery, especially at the desired sub-cellular compartments such as mitochondria and ER. Quantification of caspase activity in living cells is also affected by the background interference. In addition, specificity of these commercial substrates to caspases is poor due to lack of defined structure (Liu, Bhalgat et al. 1999; Kohler, Orrenius et al. 2002; Kawai, Suzuki et al. 2004; Kawai, Suzuki et al. 2005). Another class of fluorescence probes with a fluorophore and a quencher being introduced was developed and applied to on-chip detection of caspase-3 activity. This probe is non-fluorescent in the absence of caspase-3. However, when it is treated with active caspase-3, the fluorescence intensity increases dependent on the caspase-3 activity due to the cleavage of the quencher-containing moiety on a glass slide (Han, Sonoda et al. 2006).

Due to limitations of the above methods for caspase-3 activity assay in living cells and the unique ability of GFP is to be expressed in many organisms without cofactors, GFP offered novel and effective methods for determining activity of caspase-3 in vitro and in vivo in real time. The amino acid peptide linker containing caspase-3 recognition sequence (DEVD) for linking fluorescence protein pairs, such as GFP and BFP, ECFP and EYFP, was used for monitoring the apoptosis process by FRET assay (Luo, Yu et al. 2001) (Zhang, Haskins et al. 2004). Dual color fluorescence cross-correlation spectroscopy (FCCS) was also used to directly detect the caspase-3 activation in single live cells through fusion protein between enhanced green fluorescent protein (EGFP) and monomeric red fluorescent protein (mRFP). Many reports were also presented the fluorescence energy transfer resulting in the fusion fluorescence protein pairs for monitoring with flow cytometry, fluorescence microplate reader in apoptotic cells. A method allowing for real-time observation of caspase-3 activation in situ in live cells based on FRET measurement using the prism and reflector imaging spectroscopy system (PARISS) was reported. However, current FRET techniques are limited due to lack of specificity, poor orientation, translocation and quantitative analysis in living cells or in vivo in real time.

Our research results described above indicated that the insertion of a calcium-binding motifs at position 172 is sensitive to proteases, such as trypsin and chymotrypsin. According to these results, we hypothesized that EGFP can be applied to design the protease-susceptible molecules for monitoring specific proteolytic activities in vitro and in vivo and to understand mechanisms of protease-related diseases. Our strategy to develop caspase-3 sensors involves grafting caspase-3-specific cleavage linkers at specific locations that are sensitive to the chromophore in a single EGFP. Because EGFP has high resistance to various proteases and presents the possibility of cleavage when constructed with an added, cleavable linker for proteases at the loop region of EGFP, we performed the insertion of caspase-3-specific cleavable linkers in EGFP to develop the sensor for detecting caspase-3 activation and inhibition in living cells in real time. Meanwhile, the fluorescence ratiometric change of caspase-3 sensor at 397 and 491 nm for excitation also provides large dynamic range for caspase-3 activity determination and presents high sensitivity, which avoids the limitations of poor specificity, interference from orientation change and translocation problems. Moreover, this strategy can also be specifically targeted to desired cellular compartments with the aid of specific signal peptides.

Materials and Methods
Design of Caspase-3 Sensor

The pet28a plasmid encoding EGFP was subjected to insertion of a specific cleavable linker (EEEIREAFRVFGG DEVDGGLRHVMTNL) for caspase-3 at identified loop region using polymerase chain reaction (PCR) to obtain desired caspase-3 sensor plasmid. The newly-synthesized plasmid DNA was ligated with T4 DNA ligase, transformed into DH5α competent cells grown in Luria-Bertani (LB) media containing kanamycin, and then purified with a QIAprep Miniprep Kit (Qiagen, Valencia, USA). After caspase-3 sensor plasmid was created in pet28a for bacterial expression, EGFP-based caspase-3 sensor was also sub-cloned into pcDNA 3.1 for mammalian cell expression and used to perform caspase-3 activation imaging in living cells in real time studies. The constructed plasmid DNA was verified through automated DNA sequencing.

Expression in E. coli and Purification of Caspase-3 Sensor

The EGFP-based caspase-3 sensor was transformed into E. coli BL21 (DE3) competent cells and plated on LB agarose plates containing 30 µg/ml kanamycin. A single colony was inoculated into 20 ml of LB media with 30 µg/ml kanamycin at 37° C. The cell culture was then agitated at 200 rpm overnight and transferred to 1 L of LB media with 30 µg/ml fresh kanamycin. The cell culture was further induced with 0.2 mM isopropyl-β-D-thiogalactopyranoside (IPTG) after the optical density (OD) at 600 nm reached 0.6, and allowed to grow at 30° C. for another 16 to 20 h. The cells were harvested by centrifugation at 7000×g for 20 min. The cell pellets were then resuspended in 10 ml of lysis buffer (20 mM Tris, 10 mM NaCl, 0.1% Triton X-100, pH 8.8) and sonicated to disrupt cell membrane. The solution was centrifuged at 20000×g for 20 min. The resulting supernatant was filtered and injected into an Aktaprime FPLC equipped with a nickel-chelating column loaded with 0.1 M nickel sulfate solution. After washing with buffer A (50 mM phosphate, 250 mM NaCl, pH 7.4), the bound protein was eluted with a gradient of imidazole from 0 to 0.5 M in phosphate buffer. The eluted protein was dialyzed in 10 mM Tris buffer with 1 mM DTT at pH 7.4 to remove imidazole. The concentration of the collected fractions was determined based on the absorbance at 280 nm measured using a UV-1601 spectrophotometer (Shimadzu Scientific Instruments Inc.), and then calculated using an extinction coefficient constant of 21,890 $M^{-1}cm^{-1}$ for EGFP. The purity of collected fractions was monitored using SDS-PAGE.

Kinetic Studies on EGFP-EF172cas Cleaved by Active Caspase-3

In order to understand the effect on fluorescence or spectral characters of EGFP-based caspase-3 sensor, 1 ml of 10 µM EGFP-EF172cas3 was digested by adding 0.0016 units of active caspase-3 in commonly-used caspase-3 buffer (10 mM Tris, 10% glycerol, 100 mM NaCl, 1 mM EDTA, 1 mM DTT, 0.1% CHAPS, pH 7.4) The absorption kinetics of the caspase-3 sensor was monitored at 397 nm with a 4-second time interval during digestion. In addition, the absorption spectra before and after digestion were recorded from 600 to 200 nm for comparing the spectral characteristic change. The absorbance kinetic change of the caspase-3 sensor was fitted by double exponential decay with KaleidaGraph 3.5 software to obtain the observed rate constant.

Fluorescence Imaging of Caspase-3 Sensor in HeLa Cells
Cell Culture and Transfection Hela cells were grown on glass coverslips (0.5-1.0×10⁶ cells/dish) in 35 mm culture dishes in Dulbecco's Modified Eagles Medium (DMEM) (Sigma Chemical Co., St. Louis, Mo.) with 44 mM $NaHCO_3$, pH 7.2, and supplemented with 10% (v/v) fetal calf serum (FCS), 100 U/ml penicillin and 0.1 mg/ml streptomycin (Pen/Strep) at 37° C. with 5% $CO_2$ in a humidified incubation chamber. After the cells were seeded and grown overnight, the EGFP-based caspase-3 sensor plasmid was transfected into Hela cells with lipofectamine-2000 (Invitrogen Life Technologies) and serum-free Opti-MEM (Gibco Invitrogen Corporation) according to the manufacturer's instructions. For transfection, 2 µg of caspase-3 sensor DNA was added at a 1:1 (µg/µl) ratio of DNA to lipofectamine-2000. Following overnight incubation at 37° C., the medium containing the DNA and lipofectamine complex was removed, and replaced by DMEM enriched with FBS and Pen/Strep. The cells were then grown 24 to 48 hours in a humidified chamber with 5% $CO_2$ at 30° C. before fluorescence microscope imaging. EGFP-wt was used as the control.

Apoptosis Induction and Fluorescence Imaging of HeLa Cells

Hela cells with transfected EGFP-based caspase-3 sensor were imaged following its expression for 24 or 48 hours. Cell imaging was performed using a 40× oil objective lens on a Zeiss Axiovert 200 Inverted Microscope connected to a CCD camera (AxioCam HRc). Excitation from a light source (FluoArc, Zeiss) was passed though a FITC filter set (excitation wavelength: 480±20 nm; emission wavelength: 510±20 nm) or 398 nm filter set (excitation wavelength: 400±20 nm; emission wavelength: 510±20 nm). Axiovision software was used for image acquisition with the time course model. During the imaging acquisition, a time course model with 2-min interval for each imaging was performed. The first 4 or 5 imagines represent the blank analyte. To the Hela cells with DNA transfection of caspase-3 sensor were added 2 μl of 1 mM stock staurosporine (STS) to 1 μg/ml of final concentration for caspase-3 activation. Fluorescence imaging of Hela cells with EGFP-wt transfection was used as the control.

The ratiometric change between fluorescence emission for excitation at 398 nm and 488 nm was used to detect caspase-3 activation and inhibition at different time intervals in living cells. Fluorescence for both excitation wavelengths is expected to decrease at 398 nm and produce a corresponding increase at 488 nm during the course of the reaction. The fluorescence intensity of the cells was normalized with equation 2:

$$NF = \frac{F_t}{F_0} \qquad \text{Eq. 4}$$

where $F_t$ and $F_0$ are the fluorescence intensities of various time points and initial time point at both excitation wavelengths.

The fluorescence ratiometric change (R) is expressed by equation 3:

$$R_{488/298} = \frac{NF_{t\text{-}488}}{NF_{t\text{-}398}} \qquad \text{Eq. 5}$$

where $NF_{t\text{-}488}$ is the normalization fluorescence intensity of various time points at 488 nm of excitation; $NF_{t\text{-}398}$ is the normalization fluorescence intensity of various time points at 398 nm of excitation.

Statistical Analysis

The data for normalization fluorescence intensity and fluorescence ratio change of living cells transfected EGFP-based caspase-3 and EGFP-wt are represented as means±SD with at least 6 living cells. A student's t-test analysis was performed to determine the statistical significance between EGFP-based caspase-3 and EGFP-wt.

Results

Design of Caspase-3 Sensors

To develop caspase-3 sensor based on EGFP, the caspase-3 recognition sequence (DEVD) together with associated flanking E- and F-helices was grafted into the location 172 of EGFP to obtain a caspase-3 sensor, called EGFP-cas3-1 or EGFP-EF172cas. Due to the resistance of EGFP to proteases, the cleavage site for caspase-3 was extended with the E- and F-helices to improve the solvent exposure or flexibility of the cleavage site, thus increasing the accessibility to proteases. Meanwhile, in order to improve the potential exposure of the caspase-3 cleavage site and then compare the cleavage efficiency of caspase-3 sensors containing one cleavage site and two cleavage sites, another cleavage site of caspase-3 (DEVD) was grafted into EGFP-EF172cas to obtain a caspase-3 sensor with double cleavage sites, called EGFP-cas3-1e or EGFP-E-DEVD-GG-DEVD-F-172. Both cleavage sites for caspase-3 were linked through a short glycine linker (GG). Both caspase-3 sensors were successfully designed and amplified with PCR in pcDNA and pet28a vectors, for mammalian cell expression and bacterial expression system, respectively.

Expression and Purification of Caspase-3 Sensors

Figure 13:
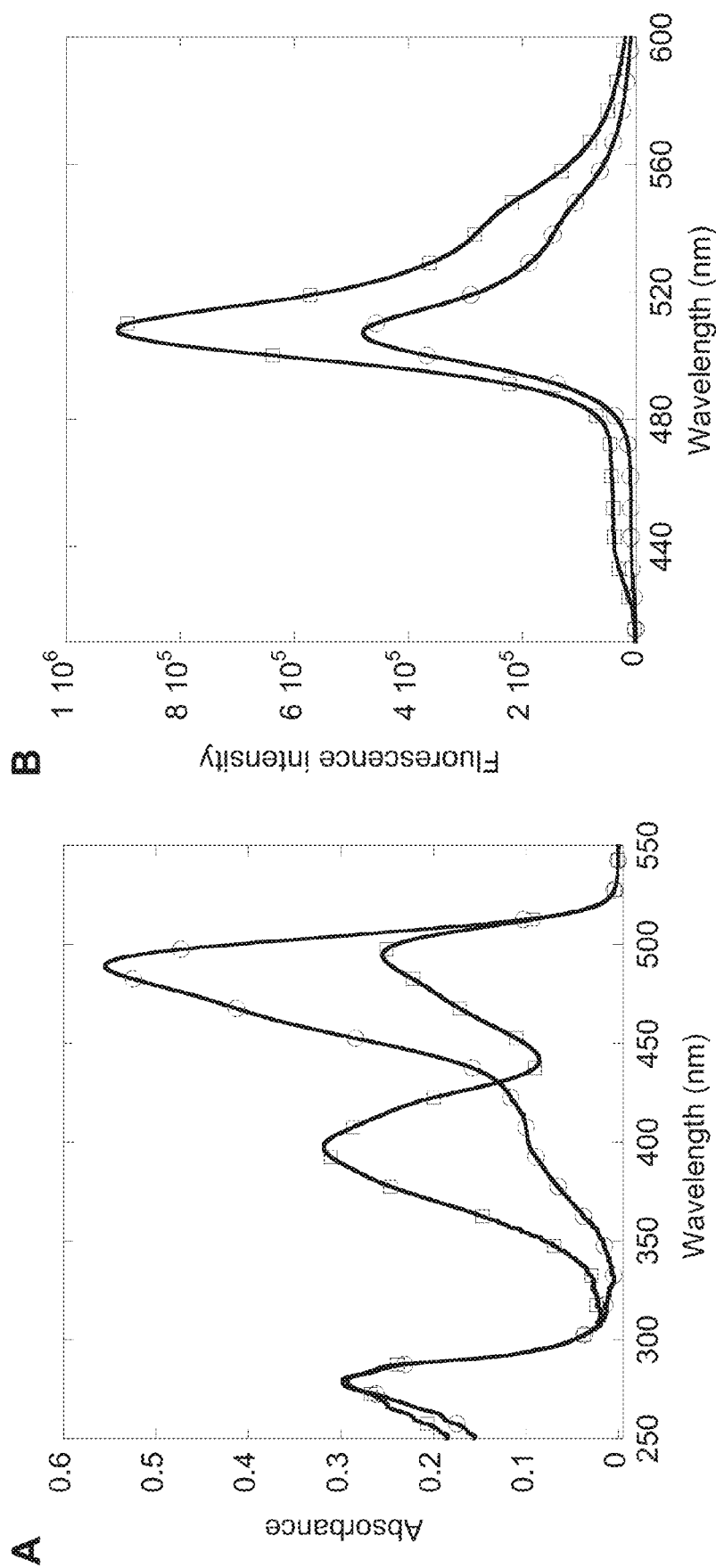
FIG. 13 are graphs that illustrates the visible absorbance (A) and fluorescence (B) spectra of EGFP-wt (circle) and EGFP-EF172cas (square).

In order to obtain sensors used for determining caspase-3 sensitivity for in vitro studies, designated caspase-3 sensors were expressed with E. coli BL21 (DE3) in LB media containing kanamycin under overnight induction of IPTG. EGFP-cas3-1 and EGFP-cas3-1e were successfully expressed in E. coli and may emit brighter fluorescence. As for sensors in mammalian cell expression system, caspase-3 sensors encoded pcDNA3.1 were transfected into HeLa cells according to above methods of cell culture. The cells were allowed to express at 30° C. for 48-72 hours. All of our designed caspase-3 sensors have strong green fluorescence under 398 or 488 nm of excitation through fluorescence microscope examination. These results indicated that cleavage sites for caspase-3 grafted into loop regions of EGFP didn't eliminate its fluorescence. After inclusion of the cleavage linkers, purified caspase-3 sensors exhibited strong absorption at 398 nm and a slight decrease in absorption at 490 nm compared to EGFP-wt (FIG. 13A). Both caspase-3 sensors show their maximal emission at 508 nm (FIG. 13B). Therefore, the insertion of the cleavage linker for caspase-3 at position 172 in EGFP can result in changes of the chromophore conformation or environments, which produces the co-existence of a protonated and deprotonated chromophore.

Kinetic Studies of Caspase-3 Sensors

In order to understand effects on the spectral characteristics of green fluorescent protein with a cleavable linker for caspase-3, kinetic studies of EGFP-cas3-1 for caspase-cas3-1e digestion were preformed to monitor the absorbance change at 397 nm in various buffers as specified in Materials and methods. The absorbance change of EGFP-cas3-1 at 397 nm was monitored and the absorbance change of EGFP-cas3-1 before digestion and after digestion were conducted using a time course model.

Figure 14:
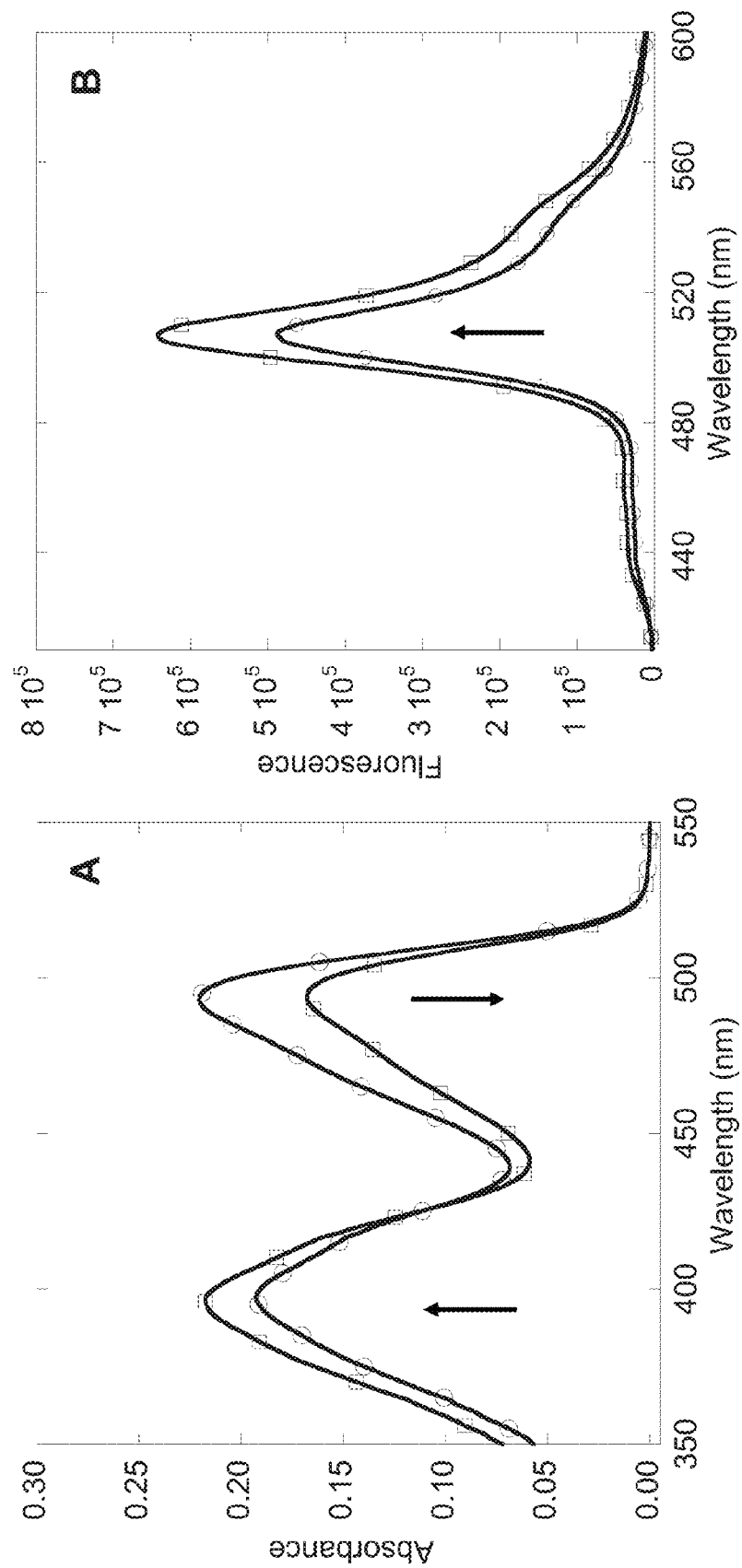
FIG. 14 are graphs that illustrate the absorbance (A) and fluorescence (B) change of EGFP-EF172cas sensor before (circle) and after caspase-3 digestion (square). The measurement was performed in 10 mM Tris, 10% glycerol, 100 mM NaCl, 1 mM EDTA, 1 mM DTT, 0.1% CHAPS, pH 7.4, monitored at 397 nm with the time-course model.
Figure 15:
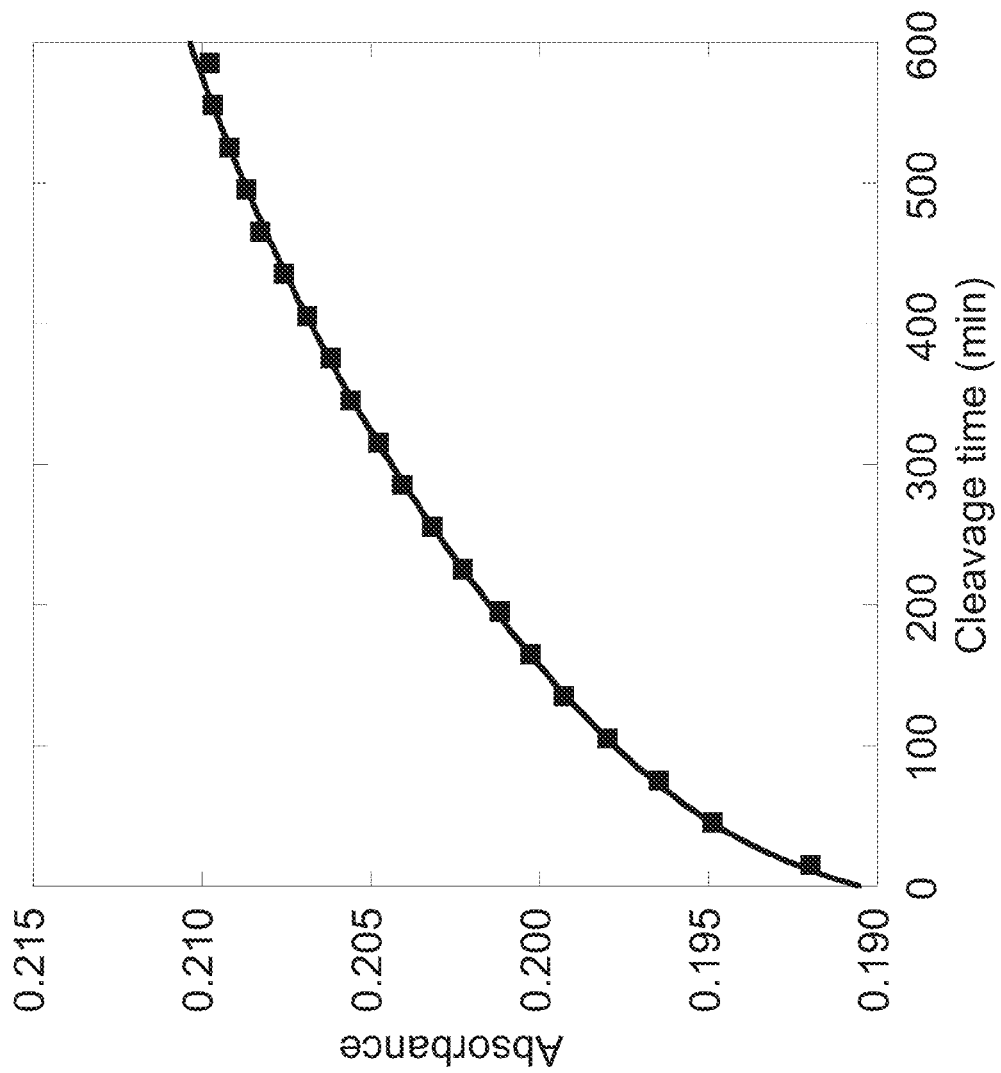
FIG. 15 is a graph that illustrates the kinetic absorbance change of EGFP-EF172cas sensor after caspase-3 digestion. The observed rate constant kobs=$0.024\pm0.003$ min-1.

When 10 μM EGFP-cas3-1 was digestion in 10 mM Tris, 10% glycerol, 100 mM NaCl, 1 mM EDTA, and 10 mM DTT, at pH 7.4 by adding 5 μl of 0.000032 unit/μl caspase-3 at room temperature, both chromophore forms exhibited only minor changes, with a slight increase at 398 nm and a decrease at 490 nm (FIG. 14A). The fluorescence intensity after caspase-3 digestion increases when excited at 398 nm (FIG. 14B). The absorbance kinetic changes were monitored with a time course model at 398 nm, and the observed rate constant based on the absorbance change was fitted by double exponential decay with KaleidaGraph 3.5 software, producing an observed rate constant of $0.024\pm0.0003$ min$^{-1}$ (FIG. 15). Similarly, the caspase-3 digestion of EGFP-cas3-1 was conducted in 50 mM HEPES, 10% glycerol, 100 mM NaCl, 1 mM EDTA, and 10 mM DTT, at pH 7.4 by adding 5 μl of 0.000032 unit/μl caspase-3 at room temperature. The cleavage of EGFP-EF172cas resulted in an observed rate constant of $0.031\pm0.00034$ min$^{-1}$ (data not shown). Due to the addition of 10% glycerol, the cleavage site of EGFP-cas3-1 and the active site of the caspase-3 were more exposed, thus improving the effect of catalysis. The 10% glycerol also can result in improved activity due to the combination of two subunits of caspase-3.

Fluorescence Imaging of Caspase-3 Sensors in HeLa Cells

Figure 16:
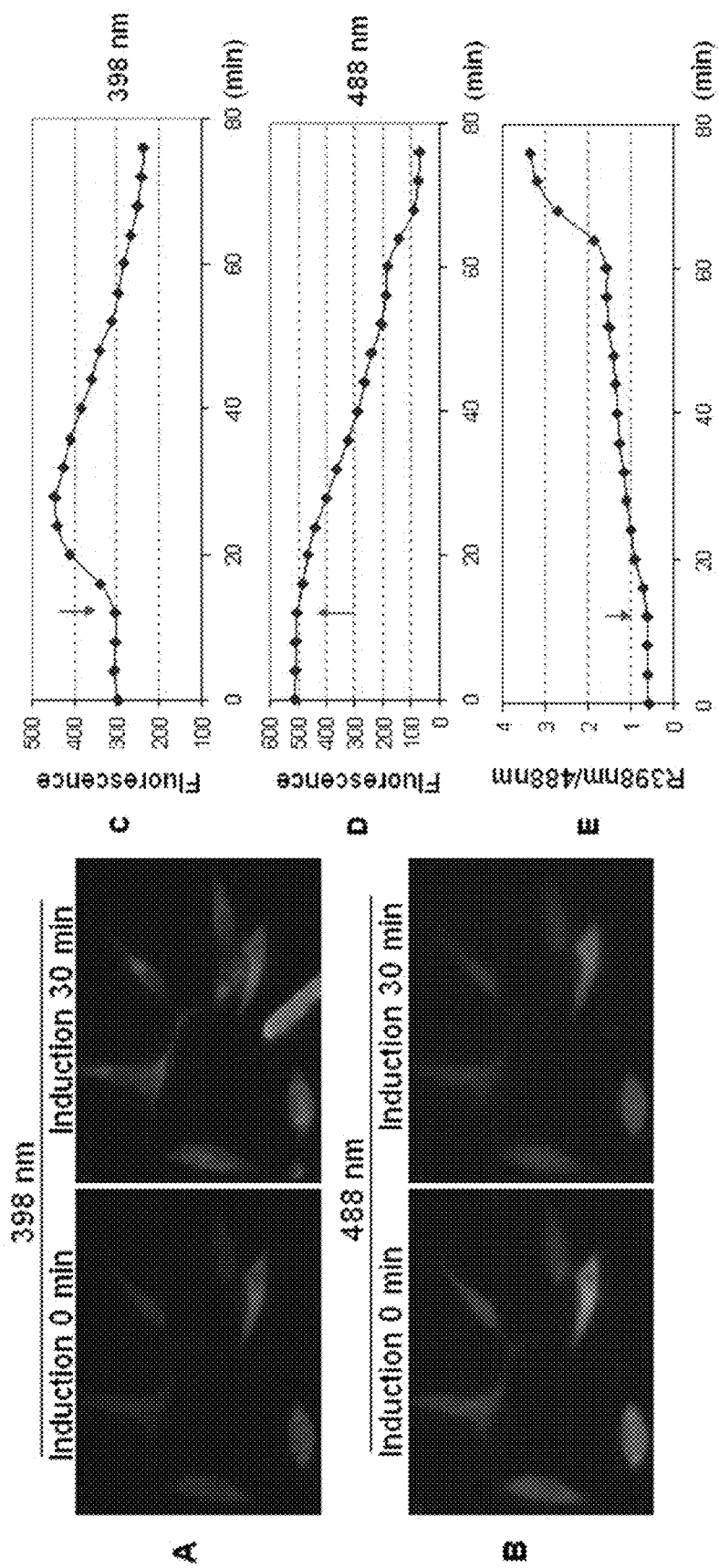
FIG. 16: Fluorescence images of Hela cells with caspase-3 sensor transfection emitted at 510 nm with excitation of 398 nm (A) and 488 nm (B) before and after incubation with 1 μM staurosporine (STS). Fluorescence emission intensity at 510 nm was determined with excitation at 398 nm (C) and 488 nm (D) upon activation using STS induction at different time points. Emission ratio (E) at 510 nm with excitation of 398/488 nm of Hela cells transfected with caspase-3 sensor exhibits significant increase following STS induction.
Figure 17:
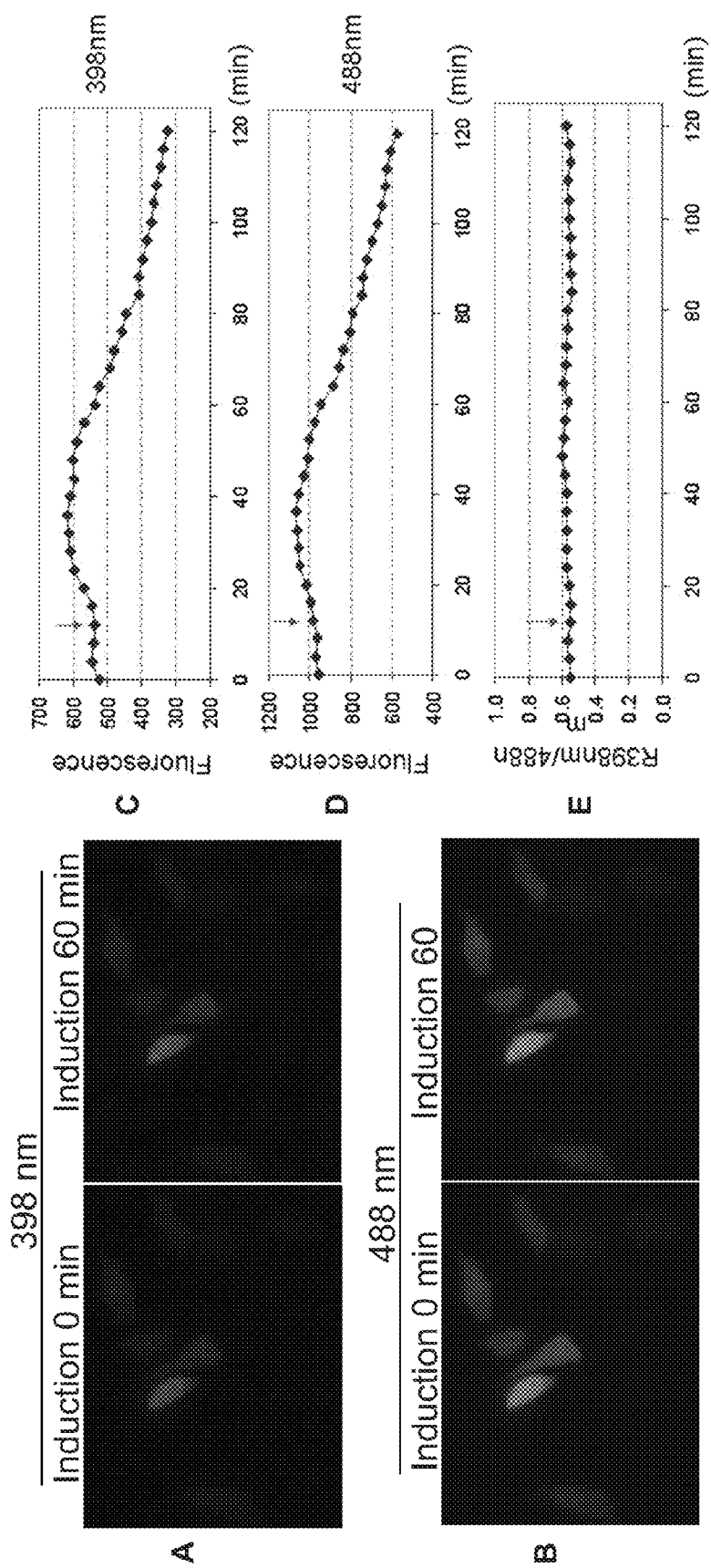
FIG. 17 illustrates fluorescence images of Hela cells with EGFP-wt transfection emitted at 510 nm with excitation of 398 nm (A) and 488 nm (B) before and after incubation with 1 μM staurosporine (STS). Fluorescence emission intensity at 510 nm was determined with excitation at 398 nm (C) and 488 nm (D) upon activation using STS induction at different time points. Emission ratio (E) at 510 nm with excitation of 398/488 nm of Hela cells transfected with EGFP-wt exhibited no change following STS induction.
Figure 18:
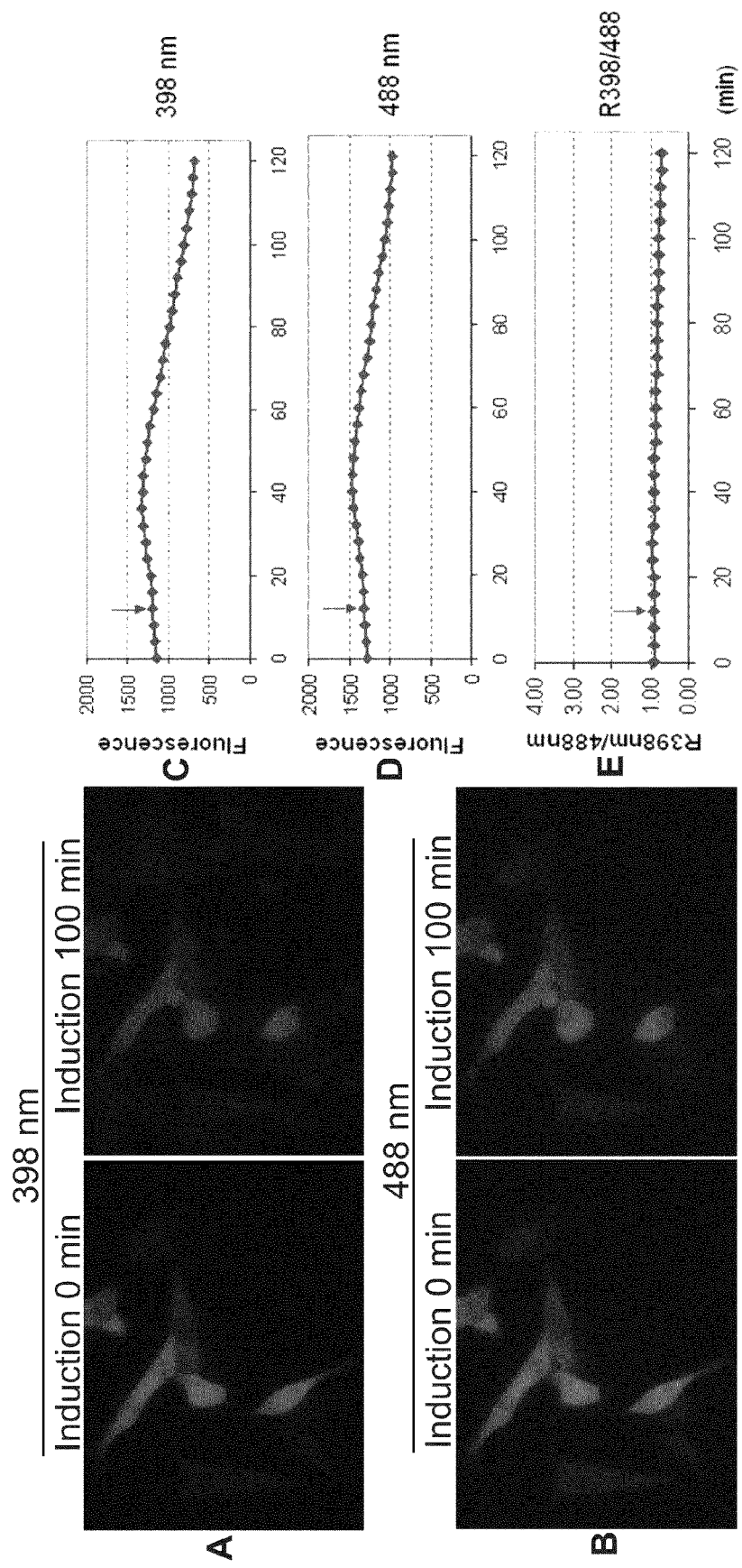
FIGS. 18A-18E illustrate fluorescence images and show graphs demonstrating the measured fluorescence intensity of Hela cells with caspase-3 transfection incubated with caspase-3 inhibitor DEVD-CHO, emitted at 510 nm with excitation of 398 nm (FIG. 18A) and 488 nm (FIG. 18B) before and after incubation with 1 μM staurosporine (STS). The fluorescence emission intensity at 510 nm of Hela cells transfected caspase-3 sensor with the incubation of caspase-3 inhibitor with excitation at 398 nm (FIG. 18C) and 488 nm (FIG. 18D) upon activation using STS induction exhibits a slight increase; the emission ratio (FIG. 18E) at 510 nm with excitation of 398/488 nm exhibits no change.
Figure 19:
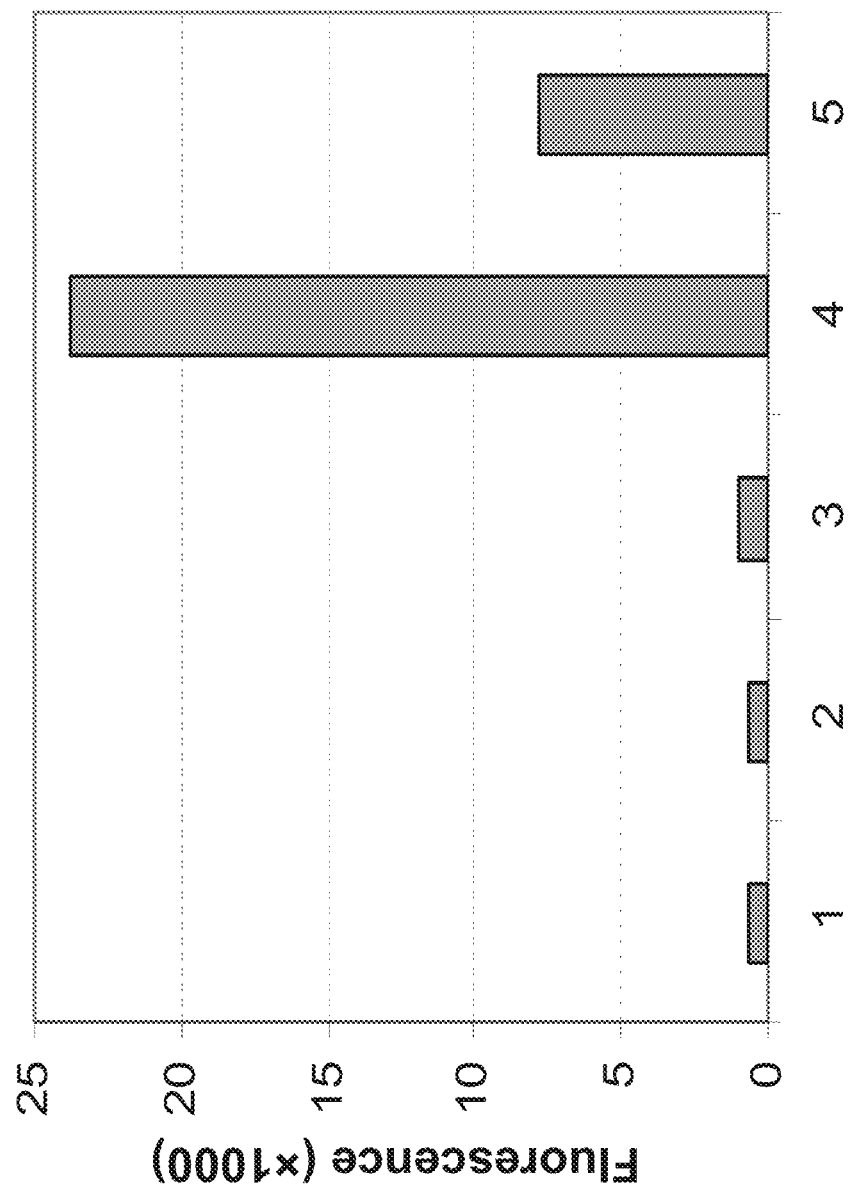
FIG. 19 is a graph that illustrates the caspase-3 activity determination using the caspase-3 fluorogenic kits after STS induction in Hela cells. Sample 1, 2 and 3 are the negative controls of buffer, buffer with caspase-3 substrate and buffer with cell lysates without induction. Sample 4 is the cell lysates with STS induction and caspase-3 substrate in buffer. Sample 5 is the 0.029 μg active caspase-3 with caspase-3 substrate in buffer.

In order to detect caspase-3 activation and inhibition in living cells, EGFP-cas3-1e was transfected into Hela cells. Both EGFP-T/C1 and the control (EGFP-wt) expressed in Hela cells exhibit strong fluorescence intensity after 24 to 48 hours. Upon caspase-3 activation with 1 uM staurosporine (STS), the fluorescence emission signal at 510 nm of cells with transfected EGFP-cas3-1e exhibited a significant increase with excitation at 398 nm and a significant decrease with excitation at 488 nm after the 1 µM STS induction (FIG. 16). The ratio (R398/488) of fluorescence signal change was obviously enhanced. However, the negative control, EGFP-wt, resulted in changes in both wavelengths possibly due to photobleaching or cell shrinkage, while producing no apparent ratiometric change (FIG. 17). On the other hand, After EGFP-cas3-1e was transfected and expressed in Hela cells, the caspase-3 inhibitor, DEVD-CHO, was incubated with transfected cells for overnight before the cell imaging. Results indicated that fluorescence of Hela cells at both wavelengths excitation revealed slight increase possibly due to the cell slight shrink after STS induction, and the ratio (R398/488) of fluorescence has no change (FIG. 19). Therefore, the caspase-3 activation in Hela cells with STS induction also can be effectively inhibited through caspase-3 inhibitor. The fluorescence increase of EGFP-cas3-1e with excitation of 398 nm and the fluorescence decrease of EGFP-cas3-1e with excitation of 488 nm are consistent with the results of EGFP-cas3-1e digestion with active caspase-3 in vitro. During the monitoring of fluorescence change in living cells with the time-course model, the cell status was compared before and after STS induction. Although the caspase-3 activity was activated during the first 1 hour induction, the cells are still alive and the cell shape has slightly change in becoming round due to the cell concentrated and beginning of apoptosis. Similar results were obtained from MIA PaCa-2 cells. Therefore, EGFP-cas3-1e is a sensitive caspase-3 sensor, which can be used for detecting caspase-3 activity in living cells in real time and also can be used for detecting the caspase-3 activity in the early stage of apoptosis.

Discussions

Criteria of Idea Caspase Sensors

In the design of ideal protease probes, several factors must be considered. First, the optical signal change must rapidly respond to the catalytic cleavage of the peptide bond instead of the binding process. Second, sensors should have high sensitivity with a large dynamic change. Ideally, the fluorescence emission or excitation wavelength of the chromophore will be shifted by the cleavage, which allows us to make ratiometric measurements to normalize the sensor concentrations in vivo. A large increase in chromophore signal, like Rhodamine-110, can also be used while a decrease in fluorescence signal upon cleavage is less desirable since many cellular factors may quench the fluorescence signal. Third, the designed sensor must have good selectivity for the enzymatic action. Current caspase kits derived from short peptides are less desirable due to the lack of structural features for specific enzymatic action. Fourth, the protease sensor must be stable enough for in vivo studies. Fifth, the protease sensor with capability to specifically report enzymatic action within the desired cellular compartments is highly desired. Currently-available detection methods simply relay on passive diffusion through the membrane and do not have the capability to detect the action at proper cellular locations and only permit short snapshots of the enzymatic action.

Our Novel Design of Caspase-3 Sensor

The compact 13 barrel structure with buried chromophore of GFP or related fluorescent proteins contributes to the overall protein stability, temperature and denaturant resistance, and strong resistance to various proteases such as trypsin, chymotrypsin, papain, subtilisin, thermolysin and pancreatin (Shimomura 1979; Ward and Bokman 1982; Ward, Prentice et al. 1982; Cody, Prasher et al. 1993). On the other hand, our lab and others have shown that GFP become much more proteolytically-sensitive upon mutations at several folding sensitive spots and fluorescence is lost. Chiang et al reported that GFP subject to proteases and factor Xa cleavage after inserting the protease cleavage linker in loops at sensitive positions (Chiang, Okou et al. 2001).

Due to the ability of EGFP-wt to resist proteases and the cleavage potential of the inserted cleavable linker, a grafting approach was used to develop the EGFP-based protease sensors. According to previous investigations, the cleavable linker for trypsin was inserted at location 172 of the single EGFP to obtain the sensitive trypsin sensor. Therefore, the specific cleavable linker for caspase-3 was grafted to the single EGFP, which resulted in the specific and sensitive caspase-3 sensor capable of detecting caspase-3 activity in cells or in vivo in real time, and monitoring the apoptosis in real time.

For investigating the optimal conditions for caspase-3 digestion of EGFP-EF172cas, different cleavage buffers for caspase-3 were investigated. When 10 µM EGFP-EF172cas was digested in 10 mM Tris, 100 mM NaCl, 1 mM EDTA, and 10 mM DTT, at pH 7.4 by adding 5 µl of 0.000032 unit/pi caspase-3 at room temperature, the absorbance at 397 nm reported during a time course model analysis exhibited no obvious change, and the addition of caspase-3 had in the presence of both the protonated and deprotonated forms of the chromophore had no distinguishable effect (data not shown). According to some investigators' experimental designs, glycerol was replaced by sucrose in the caspase-3 buffers, up to 10% of the final concentration. In order to investigate suitable buffers for fast caspase-3 digestion of EGFP-EF172cas, the substitution of 10% glycerol with 10% sucrose was investigated. The caspase-3 digestion of 10 µM EGFP-EF172cas was conducted in 50 mM HEPES, 10% sucrose, 100 mM NaCl, 1 mM EDTA, and 10 mM DTT, at pH 7.4 with 5 µl of 0.000032 unit/pi caspase-3 at room temperature. However, the cleavage effect was very weak and the cleavage reaction slow. This result indicated that 10% sucrose fails to produce the same effect as 10% glycerol, as in our studies. Moreover, according to the literature, 0.1% CHAPS can improve the binding of two subunits of caspase-3 for higher activity. The caspase-3 digestion of 10 µM EGFP-EF172cas was carried out in 50 mM HEPES, 10% glycerol, 100 mM NaCl, 1 mM EDTA, and 10 mM DTT, 0.1% CHAPS, at pH 7.4 with 5 µl of 0.000032 unit/µl caspase-3 added at room temperature. The cleavage of EGFP-EF172cas was evaluated under these conditions, and the observed rate constant was calculated at 0.029±0.00027. However, this result failed to indicate any significant difference between the presence or absence of CHAPS during the reaction. These experiments require additional confirmation regarding the effect of CHAPS, comparison of the buffer conditions, and determining the optimal caspase-3 digestion buffer conditions.

When performing the investigation in HeLa cells with STS induction for caspase-3 activation, the fluorescence was not significantly changed before induction in HeLa cells. After induction, there was obvious increase in fluorescence of EGFP-EF172cas2 at 398 nm excitation and significant decrease in fluorescence at 488 nm excitation in real time, which results in an increased fluorescence ratio change between 398 and 488 nm, and a corresponding increase in sensitivity for determining the caspase-3 activity in living cells, and an increase in the dynamic range up to 4 for the caspase-3 activity determination. Although there was a slight increase and then decrease in fluorescence of EGFP-wt at both wavelengths after STS induction, the relative fluorescence ratio change was negligible. A possible reason for this would be a change in the cell shape to which increases the fluorescence slightly during the apoptosis. Comparing the results of the HeLa cells to another cell line from pancreatic carcinoma, MIA PaCa-2 cells, the fluorescence change of EGFP-EF172cas2 in MIA PaCa-2 cells revealed similar results, with the ratio change increasing during the first 20 min and then stabilizing to a constant signal. However, the ratio change for EGFP-wt maintains a gradient increase, possibly as a result of the cell changing shape during apoptosis. Apoptosis is observed in MIA PaCa-2 is a little earlier and stronger than in HeLa cells. There is a huge fluorescence change with excitation at 398 nm in MIA PaCa-2 cells transfected with EGFP-EF172cas2. The cause of this is reasoned to be due to intrinsic high-level caspase-3 activity in MIA PaCa-2 cells and its activity is enhanced by STS induction.

The absorbance or fluorescence signal change is small during the caspase-3 digestion of EGFP-EF172cas and the cleavage is slow during the in vitro study. However, the fluorescence change is more rapid and pronounced in HeLa cells or MIA PaCa-2 cells under STS induction. It is believed that this is due to the higher concentration of caspase-3 in cells under STS induction compared to the in vitro study. Another possible reason for this is that the buffer conditions for the in vitro study, were not optimal for cleavage of the EGFP-based caspase-3 sensor. Through cell lysate analysis with fluorogenic caspase-3 substrate kits, the cell lysates have high-level caspase-3 activity, which is much higher than that of 0.029 µg of active caspase-3. However, the amount of caspase-3 using for EGFP-EF172cas digestion in vitro study was only 0.0029 µg. Meanwhile, this further confirmed that high-level caspase-3 can be activated by STS induction, and that the inversely-correlated fluorescence change of EGFP-based caspase-3 sensor at both wavelengths is a consequence of cleavage by active caspase-3.

Conclusions

An EGFP-based caspase-3 sensor, EGFP-EF172cas, was produced through a grafting approach, resulting in a sensor capable of exhibiting significant optical property changes upon addition of active caspase-3 in vitro, or the activation of caspase-3 in living cells. Due to the sensitivity of location 172 for inserting the cleavage linker, a ratiometric change in absorbance or fluorescence of EGFP-EF172cas at 398 and 488 nm can be analyzed quantitatively to detect caspase-3 activity. The fluorescence signal change of EGFP-EF172cas is also sensitive in HeLa cells and MIACapa2 cells, which is useful for probing the mechanisms of some diseases and also to track the pathological processes of some diseases related to caspase-3 activity in vivo. In addition, a specific signal peptide is also useful for investigating mechanisms of diseases related to proteases activities in various cell compartments in vivo, which will open new areas of research in biotechnology, cell biology, disease diagnosis, drug development and protease inhibitor screening.

REFERENCES FOR EXAMPLE 9, EACH OF WHICH ARE INCORPORATED BY REFERENCE

Alenzi, F. Q. (2005). "Apoptosis and diseases: regulation and clinical relevance." *Saudi Med J* 26(11): 1679-90.

Chiang, C. F., D. T. Okou, et al. (2001). "Green fluorescent protein rendered susceptible to proteolysis: positions for protease-sensitive insertions." *Arch Biochem Biophys* 394 (2): 229-35.

Cody, C. W., D. C. Prasher, et al. (1993). "Chemical structure of the hexapeptide chromophore of the *Aequorea* green-fluorescent protein." *Biochemistry* 32(5): 1212-8.

Fadeel, B. and S. Orrenius (2005). "Apoptosis: a basic biological phenomenon with wide-ranging implications in human disease." *J Intern Med* 258(6): 479-517.

Fan, T. J., L. H. Han, et al. (2005). "Caspase family proteases and apoptosis." *Acta Biochim Biophys Sin (Shanghai)* 37(11): 719-27.

Gurtu, V., S. R. Kain, et al. (1997). "Fluorometric and colorimetric detection of caspase activity associated with apoptosis." *Anal Biochem* 251(1): 98-102.

Han, A., T. Sonoda, et al. (2006). "Development of a fluorescence peptide chip for the detection of caspase activity." *Comb Chem High Throughput Screen* 9(1): 21-5.

Harpur, A. G., F. S. Wouters, et al. (2001). "Imaging FRET between spectrally similar GFP molecules in single cells." *Nat Biotechnol* 19(2): 167-9.

Kawai, H., T. Suzuki, et al. (2004). "Simultaneous imaging of initiator/effector caspase activity and mitochondrial membrane potential during cell death in living HeLa cells." *Biochim Biophys Acta* 1693(2): 101-10.

Kawai, H., T. Suzuki, et al. (2005). "Simultaneous real-time detection of initiator- and effector-caspase activation by double fluorescence resonance energy transfer analysis." *J Pharmacol Sci* 97(3): 361-8.

Kohler, C., S. Orrenius, et al. (2002). "Evaluation of caspase activity in apoptotic cells." *J Immunol Methods* 265(1-2): 97-110.

Lee, D., S. A. Long, et al. (2000). "Potent and selective nonpeptide inhibitors of caspases 3 and 7 inhibit apoptosis and maintain cell functionality." *J Biol Chem* 275(21): 16007-14.

Liu, J., M. Bhalgat, et al. (1999). "Fluorescent molecular probes V: a sensitive caspase-3 substrate for fluorometric assays." *Bioorg Med Chem Lett* 9(22): 3231-6.

Luo, K. Q., V. C. Yu, et al. (2001). "Application of the fluorescence resonance energy transfer method for studying the dynamics of caspase-3 activation during UV-induced apoptosis in living HeLa cells." *Biochem Biophys Res Commun* 283(5): 1054-60.

Luo, K. Q., V. C. Yu, et al. (2003). "Measuring dynamics of caspase-8 activation in a single living HeLa cell during TNFalpha-induced apoptosis." *Biochem Biophys Res Commun* 304(2): 217-22.

Shimomura, O. (1979). "Structure of the chromophore of *Aequorea* green fluorescent protein." *FEBS Letters* 104: 220-222.

Tawa, P., J. Tam, et al. (2001). "Quantitative analysis of fluorescent caspase substrate cleavage in intact cells and identification of novel inhibitors of apoptosis." *Cell Death Differ* 8(1): 30-7.

Ward, W. W. and S. H. Bokman (1982). "Reversible denaturation of *Aequorea* green-fluorescent protein: physical separation and characterization of the renatured protein." *Biochemistry* 21(19): 4535-40.

Ward, W. W., H. Prentice, et al. (1982). "Spectral perturbation of the *Aequorea* green fluorescent protein." *Photochem Photobiol* 35: 803-808.

Zhang, Y., C. Haskins, et al. (2004). "Detection of mitochondrial caspase activity in real time in situ in live cells." *Microsc Microanal* 10(4): 442-8.

Example 10

Thrombin, one of the most important members in serine protease family, plays a pivotal role in a wide range of physiological and pathological biological processes, including: hemostasis, thrombosis, tumor invasion, cell differentiation, angiogenesis, tissue injury, platelet aggregation and blood coagulation. Its proteolytic activity is highly related to these physiological and pathological processes, and is responsible for the conversion of fibrinogen to fibrin and the activation of blood coagulation and plasma factors such as factor V, factor VIII, factor XIII, and protein C. Although detection of thrombin activity in vitro studies, such as small molecular chromogenic or fluorogenic substrates, fluorescence resonance energy transfer (FRET) measurement, western blotting assay and DNA aptamer probes, has been made great progress, determination of the dynamic thrombin activity or tracking of thrombin activation process in living cells, within normal or abnormal tissues is still less information available, which is also dampered the development of thrombin inhibitors or agonists and antagonists of thrombin activated receptors for treatments of diseases related to thrombin activity. In our this paper, a series of sensitive EGFP-based thrombin sensors with high specificity, fast response to thrombin and large dynamic range are designed and developed, which will be helpful for resolving these problems as a promising thrombin sensor in living cells or in vivo in real-time determination.

Introduction

Thrombin, one of the most important members in serine protease family, plays a crucial role in a wide range of physiological and pathological biological processes, which is involved in hemostasis, thrombosis, tumor invasion, cell differentiation, angiogenesis, tissue injury, platelet aggregation and blood coagulation. Its proteolytic activity is highly related to these physiological and pathological processes, and responsible for the conversion of fibrinogen to fibrin and the activation of blood coagulation and plasma factors such as factor V, factor VIII, factor XIII, and protein C. Thrombin has been widely investigated due to its multiple functions since it was discovered, named and sequenced after the 19$^{th}$ century (Goldsack, Chambers et al. 1998). Thrombin is generated from its precursor prothrombin after tissue injury, which is involved in converting fibrinogen to fibrin during clotting cascade and mediating cellular functions through proteolytically activating protease activated receptors (PAR1, PAR3 and PAR4) on the cell surface (Coughlin 1999; Anderluh and Dolenc 2002). Following the activation of these receptors, numerous cellular effects such as chemotaxis, proliferation, extracellular matrix turnover and release of cytokines are initiated. Therefore, a series of tissue repair processes, the inflammatory pathogenesis and fibroproliferative disorder including pulmonary fibrosis and atherosclerosis are related to these receptor activation. On the other hand, many research reports revealed that some neurodegenerative diseases such as Alzheimer's disease, and a number of tumors due to fibrin formation and deposition, could be resulted from the disorder of thrombin activation. Due to these multiple functions of thrombin, physiological and pathological mechanisms of some diseases related to thrombin, factors or pathways of thrombin activation and its receptors on the cell surface, determination of thrombin activity in living cells or in vivo, investigation of thrombin triggers or inhibitors, development of agonists and antagonists for thrombin receptors are involved in extensive investigation and become a current heated medical field. In order to probe these physiological or pathological processes, thrombin activity determination is necessary.

Currently, although thrombin activation or inhibition can be monitored with real time PCR and western blotting, the measurement of thrombin activity and its inhibition is in situ rather than in vivo. The most common thrombin determination is still focused on cell lysate assays using chromogenic or fluorogenic small molecule dyes conjugated to a short peptide to monitor fixed cell imaging. The most common chromophores linked to short peptide fragments of 3-6 amino acids mimic the sequence encompassing the P1 to Pn cleavage sites (usually up to P3) are p-nitroaniline, 7-amino-4-methylcoumarin or fluorescein isothiocyanate-labeled casein. Although newly-developed peptide probes are able to penetrate cells, these probes are not ideal for the continuous dynamic imaging of enzyme actions due to limited lifetime, specificity and stability resulting from a lack of defined structure in solution due to their short sequences. Moreover, P1' to P3' sequence is still difficult to be optimized in these peptide probes and fast degradation of these short also hinders the delivery to specific sub-cellular locations. Fluorescent proteins with self-encoded chromophores are capable of monitoring numerous cellular events in living cells or organisms via live cell imaging. Many GFP-pair probes were developed to monitor thrombin activity through the change of fluorescence resonance energy transfer (FRET) (Zhang 2004). Although this method shows the advantage of being able to monitor the dynamic processes of protease activation in vitro and targeting of specific locations in vivo, the application of this class of thrombin sensors for in vivo imaging is limited by problems in translocation in vivo due to large size of fluorescent proteins, poor FRET efficiency from insuitable distance or unoptimal orientation between donor and acceptor. DNA aptamer or nano-particle probes for thrombin activity determination are also reported (Xiao, Lubin et al. 2005). Although they have high sensitivity to thrombin determination, their determination mechanism is still associated with the binding ability from negative charged DNA and positive charged probes. Therefore, it is not a real thrombin activity and also has long way to application in living cell imaging.

In this paper, we have successfully designed a series of thrombin sensors for the determination of thrombin activity in vitro or in vivo. Their optical change upon the action of thrombin was systematically investigated and steady state kinetic studies were conducted to obtain their kinetic parameters, Michaelis constants ($K_m$), turnover numbers ($k_{cat}$) and specificity constants ($k_{cat}/K_m$) for optimizing the cleavage linker in our designed thrombin sensors.

Materials and Methods

Design EGFP-Based Thrombin Sensors

Pet28a plasmid encoding EGFP was subjected to insertion of nucleotide sequence encoding a cleavable linker for thrombin at the location (Glu172) of EGFP using polymerase chain reaction (PCR) technique to obtain a thrombin sensor. The new-synthesized DNA was ligated with T4 DNA ligase, transformed into DH5α competent cells grown in LB-kanamycin medium, and then purified with a Qiagen Miniprep Kit. The constructed plasmid DNA was verified through automated DNA sequencing at the GSU core facility.

Expression and Purification of EGFP-Based Thrombin Sensors

To express EGFP-based thrombin sensors, a single colony was inoculated into 20 ml of LB media with 30 μg/ml kanamycin at 37° C. The cell culture was then agitated at 200 rpm overnight and transferred to 1 L of LB media with 30 μg/ml fresh kanamycin. Cell culture was further induced with 0.2 mM isopropyl-β-D-thiogalactopyranoside (IPTG) after optical density (OD) at 600 nm reached 0.6 and allowed to grow at 30° C. for another 16 to 20 h. The cells were harvested by centrifugation at 7000×g for 20 min. The cell pellets were then resuspended in 10 ml of lysis buffer (20 mM Tris, 10 mM NaCl, 0.1% Triton X-100, pH 8.8) and sonicated to disrupt the cell membrane. The solution was centrifuged at 20000×g for 20 min. The resulting supernatant was filtered and injected into a nickel-chelating column connected on FPLC loaded 0.1 M nickel sulfate solution. After washing with buffer A (50 mM phosphate, 250 mM NaCl, pH 7.4), the bound protein was eluted with a gradient of imidazole from 0 to 0.5 M in phosphate buffer. The purity of fractions was monitored by SDS-PAGE. The protein collected from FPLC was dialyzed into 10 mM Tris buffer with 1 mM DTT at pH 7.4 to remove imidazole. The concentration of purified protein was determined using a UV-1601 spectrophotometer (Shimadzu Scientific Instruments Inc.) at 280 nm to measure absorbance, and then calculated using an extinction coefficient of 21,890 $M^{-1}cm^{-1}$ for EGFP.

Kinetic Studies of EGFP-Based Thrombin Sensors

In order to investigate the kinetic change and to determine the steady-state kinetic parameters, Michaelis constants ($K_m$), turnover numbers ($k_{cat}$) and specificity constants ($k_{cat}/K_m$) for hydrolysis of EGFP-based thrombin sensors upon the action of thrombin, initial rates were measured at various EGFP-based thrombin sensor concentrations. The change of absorbance was monitored at 490 nm for 10 min using UV-1700 spectrometer (Shimadzu, Japan) in time-course model and the slope of absorbance increase was determined as the initial rate data. The data were fitted to Michaelis-Menten equation by nonlinear regression using Kaleida-Graph 3.5 software (Synergy software) to obtain $k_{cat}$, $K_m$, and $k_{cat}/K_m$.

Extinction Coefficient Constants of Thrombin Sensors

In order to determine the concentration of the product after thrombin digestion, the thrombin sensor samples after 10 min time course were added 5 µl of 40 µM thrombin for digestion overnight to completely cleave thrombin sensors. The absorbance at 490 nm of thrombin sensors was measured and then extinction coefficient constants were calculated through Beer-Lambert law. Based on the calculated extinction coefficient constants and absorbance change, the product concentration can be determined for initial rate calculation.

Calculation of Dynamic Range

In order to evaluate designed thrombin sensors, the dynamic range calculation for absorbance change upon thrombin digestion is determined through the following equation:

$$R_D = \frac{\frac{A_{490a}}{A_{398a}}}{\frac{A_{490b}}{A_{398b}}}$$

Where $A_{490a}$ and $A_{398a}$ are the absorbance at 490 nm and 398 nm after cleavage, respectively; $A_{490b}$ and $A_{398b}$ are the absorbance at 490 nm and 398 nm before cleavage, respectively.

Results

Design of EGFP-Based Thrombin Sensors

In order to develop sensitive thrombin sensors with optimal cleavage linkers for thrombin digestion for in vitro studies and in living cell imaging, a series of specific cleavage linkers for thrombin were designed and inserted the position 172 in EGFP and obtained different variants of thrombin sensors. A ratiometric signal change in absorbance or fluorescence was occurred upon the cleavage of the thrombin linker. Based on previous design of sensitive EGFP-based trypsin sensors and caspase-3 sensors, our novel thrombin sensors are still constructed the thrombin cleavage site in calmodulin EF-hand motif to insert into the position 172 of EGFP due to the high flexibility of the EF-hand, which can improve the accessibility of cleavage site for thrombin. On the other hand, amino acid residues from P1 to P4 and P1' to P2' were designed to examine their specificity to thrombin and compare the exposure degree of cleavage site for testing thrombin accessibility. In order to design the amino acid residues from P1 to P4 and P1' to P2' for improving substrate specificity, five cleavage linkers with residues, Gly-Arg-Gly, Phe-Asn-Pro-Arg-Gly-Phe, Phe-Thr-Pro-Arg-Gly-Phe, Phe-Asn-Pro-Arg-Ser-Phe and Phe-Thr-Pro-Arg-Gly-Phe, are based on the sequences of thrombin activation receptors (PAR1, PAR3 and PAR4) and some natural thrombin cleavable protein substrates. Different variants of thrombin sensor and their cleavage linkers for thrombin were shown in Table 7:

TABLE 7 designed thrombin sensors and their cleavage linkers

| Thrombin sensor name | The cleavage linker sequences (SEQ ID NO: 140-144) |
|---|---|
| EGFP-Thr1 | EEEIREAFRVFDKDGRGYISAAELRHVMTNL |
| EGFP-Thr1e | EEEIREAFRVFDKDGNGYISAFNPRGFMTNL |
| EGFP-Thr1f | EEEIREAFRVFDKDGNGYISAFNPRSFMTNL |
| EGFP-Thr1g | EEEIREAFRVFDKDGNGYISAFTPRGFMTNL |
| EGFP-Thr1h | EEEIREAFRVFDKDGNGYISAFTPRSFMTNL |

Optical Properties of EGFP-Based Thrombin Sensors

Figure 20:
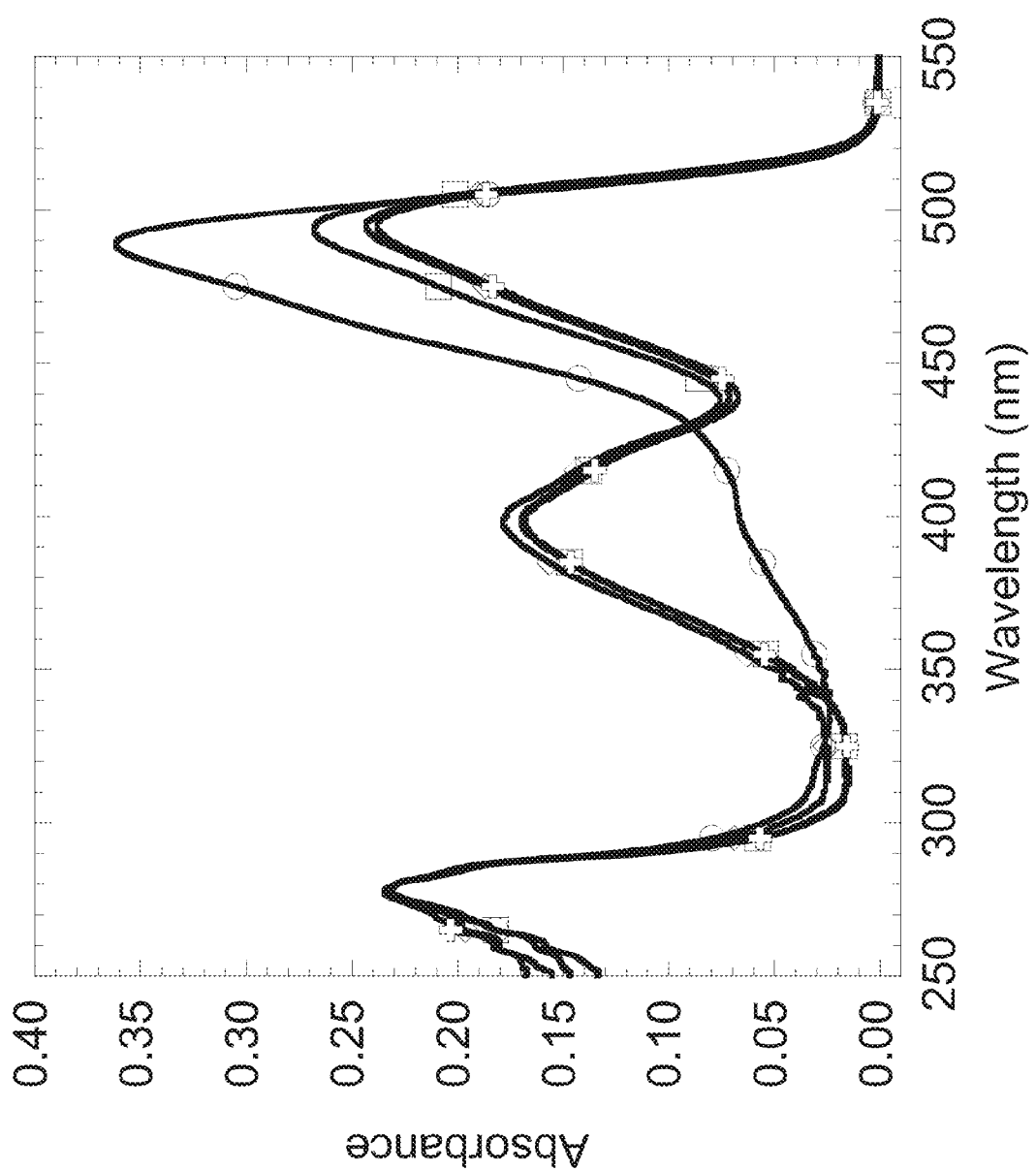
FIG. 20 is a graph that illustrates the UV-visible spectra of EGFP-wt (circle), EGFP-Thr1 (square), EGFP-Thr1e (diamond), and EGFP-Thr1f (+).

All variants of our designed EGFP-based thrombin sensors are successfully expressed in E. coli and exhibit strong fluorescence. Through nickel affinity column purification, purified EGFP-based thrombin sensors exhibit two strong absorption peaks, which are at 397 nm and 490 nm, as shown in FIG. 20. Two absorption peaks are resulted from both states of chromophore, ionic form and neutral form. However, different variants of these EGFP-based thrombin sensors have various components of ionic form and neutral form chromophore due to insertion of various cleavage linkers for thrombin. Due the cleavage sites in different locations between EGFP-Th1, EGFP-Thr1e and EGFP-Th3, EGFP-Thr1 has the slight high components of ionic chromophore form. EGFP-Thr1e and EGFP-Thr1e has no obvious difference due to cleavage site in the same location although the residue in the P2' position.

Kinetic Studies of EGFP-Based Thrombin Sensors

Figure 21:
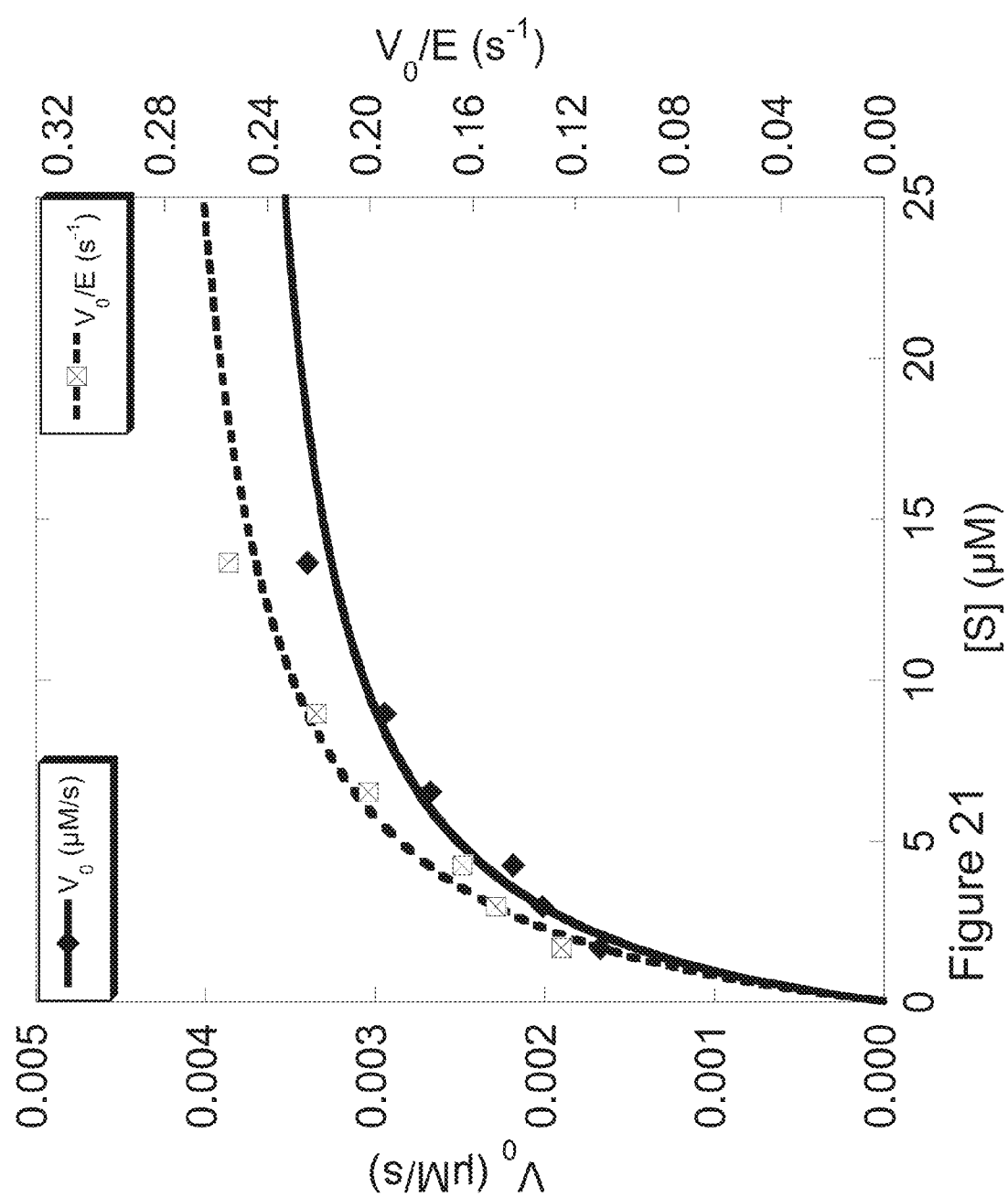
FIG. 21 is a graph that illustrates the kinetic parameters of EGFP-Thr1e with Michaelis-Menten equation fitting. The kcat, Km and kcat/Km are $0.29\pm0.02$ s-1, $2.81\pm0.69$ μM and $(10.49\pm1.46)\times10^4$ μM-1 s-1, respectively.

In order to investigate the optimal cleavage linkers for thrombin and to determine the steady-state kinetic parameters, $k_{cat}$, $K_m$, and $k_{cat}/K_m$ for hydrolysis of EGFP-based thrombin sensors upon the action of thrombin, initial rates were measured at various EGFP-based thrombin sensor concentrations in thrombin digestion buffer (50 mM Tris, 150 mM NaCl, 2.5 mM $CaCl_2$, pH 8.0). The kinetic parameters of EGFP-Thr1e were fitted through Michalis-menten equation, as shown in FIG. 21. The kinetic parameters, $k_{cat}$, $K_m$, and $k_{cat}/K_m$, are 0.29±0.02 $s^{-1}$, 2.81±0.69 µM, and (10.49±1.46)× $10^4$ $M^{-1}S^{-1}$.

In order to design a optimal cleavage linker for thrombin and improve thrombin specificity of EGFP-based thrombin sensors, the P1, P2, P3 and P4 position in P region and P1' and P2' position in P' region in thrombin sensor were systematically studied. Another four specific cleavage linkers (Phe-Asn-Pro-Arg-Gly-Phe, Phe-Asn-Pro-Arg-Ser-Phe, Phe-Thr-Pro-Arg-Gly-Phe and Phe-Thr-Pro-Arg-Ser-Phe) for thrombin were designed to obtain different thrombin sensor variants. The studies on kinetic parameters of these thrombin sensors were performed in thrombin digestion buffer (50 mM Tris, 150 mM NaCl, 2.5 mM CaCl$_2$, pH 8.0). Compared to the thrombin sensor with cleavage linker (Gly-Arg-Gly), The turnover number, k$_{cat}$, has significant increase with 5 folds and K$_m$ has great decrease with 10 folds. Therefore, substrate specificity (k$_{cat}$/K$_m$) of these four thrombin sensor variants is resulted in 50-fold increase. The kinetic parameters for all of these thrombin sensor variants are shown in Table 8.

TABLE 8 catalytic parameters for thrombin in 50 mM Tris, 150 mM, 2.5 mM CaCl$_2$, pH 8.0

| Sensor name | k$_{cat}$ (s$^{-1}$) | K$_m$ (μM) | k$_{cat}$/K$_m$ (M$^{-1}$ s$^{-1}$) | R$^2$ |
|---|---|---|---|---|
| EGFP-Thr1 | 0.057 ± 0.001 | 20.92 ± 0.96 | (2.77 ± 0.65) × 10$^3$ | 0.99892 |
| EGFP-Thr1e | 0.29 ± 0.02 | 2.81 ± 0.69 | (10.49 ± 1.46) × 10$^4$ | 0.9522 |
| EGFP-Thr1f | 0.23 ± 0.01 | 2.86 ± 0.28 | (8.02 ± 0.62) × 10$^4$ | 0.98313 |
| EGFP-Thr1g | ND (No detected) | | | |
| EGFP-Thr1h | ND | | | |

Extinction Coefficient Constants of Products after Thrombin Cleavage

After thrombin sensor samples were cleaved completely through thrombin digestion overnight, the absorbance of products at 490 nm was measured and then extinction coefficient constants were calculated through Beer-Lambert law. The extinction coefficient constants of the variants of these thrombin sensors have slightly different due to the various cleavage linkers. Their extinction coefficient constants of these cleavage products were shown in Table 9.

TABLE 9 extinction coefficient constants of cleavage products from thrombin sensors

| Thrombin sensor | Extinction coefficient constants (ε) (μM$^{-1}$cm$^{-1}$) |
|---|---|
| EGFP-Thr1 | 0.037 ± 0.005 |
| EGFP-Thr1e | 0.031 ± 0.004 |
| EGFP-Thr1f | 0.030 ± 0.003 |
| EGFP-Thr1g | ND |
| EGFP-Thr1h | ND |

Calculation of Dynamic Range of Thrombin Sensors

In order to evaluate the response of thrombin sensors to thrombin, the absorbance change (dynamic range) between before thrombin cleavage and after thrombin cleavage was measured. EGFP-Thr1, a cleavage site in loop-III region, revealed a large dynamic range. However, EGFP-Thr1e and EGFP-Thr1f, cleavage sites in F-helix, showed no significant difference in dynamic range. The difference in dynamic range of these thrombin sensors are possibly due to slight difference in conformation of cleaved products, which is still not clear. The dynamic range of thrombin sensor variants is shown in Table 10.

TABLE 10 the dynamic range of thrombin sensor variants

| Thrombin sensor | Dynamic range (D$_R$) |
|---|---|
| EGFP-Thr1 | 2.64 ± 0.10 |
| EGFP-Thr1e | 1.94 ± 0.23 |
| EGFP-Thr1f | 1.76 ± 0.18 |
| EGFP-Thr1g | ND |
| EGFP-Thr1h | ND |

Discussion

In our lab, EGFP-based calcium sensors were successfully designed and developed through the insertion of calcium binding motif, EF-hand, from calmodulin, which can be expressed in mammalian cells and can be used for tracking calcium signaling in vitro and in living cell studies (Zou, Ye et al. 2005). According to this grafting strategy, the specific cleavable linker for thrombin can be inserted in EGFP to develop sensitive thrombin sensors. On the other hand, EGFP can be easily expressed in bacteria and mammalian cells, which offers EGFP-based thrombin sensors for exploiting thrombin activity in vitro and investigating real-time thrombin activation or thrombin inhibition in living cells. In addition, EGFP-based thrombin sensors have characteristics of double wavelengths change in opposite directions for absorbance and excitation, which also provides the ratiometric measurement to determine thrombin activity.

As well known, loop-III has strong binding affinity for calcium and helices connected to loop-III can improve the flexibility of EF-hand (Ye, Shealy et al. 2003; Ye, Lee et al. 2005). The cleavage sites for thrombin were located in the modified EF-hand motif, which was grafted into EGFP to develop the sensitive thrombin sensors. According to our kinetic studies of thrombin sensors, the cleavage site in loop-III revealed the slow enzymatic reaction and lower substrate specificity to thrombin possibly due to the less accessibility to thrombin at this cleavage site, which is consistent with our previous result that the trypsin sensor with a cleavage site in loop-III can not be cleaved by trypsin. With the addition of flexible helices on both sides of the loop-III, the accessibility to thrombin and the cleavage rate on F-helix are significantly increased. A dynamic range of these thrombin sensors with specific cleavage site at F-helix is provided.

Due to our designed thrombin sensor variants based on EGFP, they have great potential to determine thrombin activity, thrombin activation or thrombin pathway in living cells in real time. Meanwhile, compared the kinetic parameters of commercially available thrombin kit, the binding affinity and specificity of our EGFP-based thrombin sensor variants to thrombin are significantly increased due to the lack of P' region residue design in thrombin detection kits containing small molecular dye. Therefore, some investigators are conducting the thrombin specificity studies with chromogenic or fluorogenic substrates. From literature reports, the substrate P1 residue should be in agreement with the known primary specificity of thrombin for basic residue and P1 position always prefer to positive charged residue Arg. Through the study on synthetic substrate library, thrombin has a strong preference for aliphatic amino acids at the P4 position, little preference at P3, and strict preference for proline at the P2 position (Sadasivan and Yee 2000). The substrates with arginine in the P1 position, proline or a proline homolog in the P2 position, and an apolar amino acid in the P3 position were identified to be better substrates for thromin (Harris, Backes et al. 2000). Extensive analysis of natural substrates, such as PAR1, PAR4, Factor XIII, Factor VIII, prothrombin, are highly conserved to be proline, arginine and glycine or serine at the P2, P1 and P1' position (Harris, Backes et al. 2000). Taking consideration of substrate specificity to thrombin, the kinetic parameter, $k_{cat}/K_m$, of these substrates conjugated to preferable amino acid residues and dyes, are ranged from $10^3$ to $10^7 M^{-1} S^{-1}$. The kinetic parameters of our designed thrombin sensors obviously reach or overpass these substrates. However, the significant advantages of our engineered thrombin sensors are focused on real-time tracking thrombin activity or activation processes in living cells or organs with ratiometric measurement, which can avoid to the influence from environment, such as expression level, background. Signal peptides for Endoplasmic reticulum (ER) or mitochondria can assist our thrombin sensors to track thrombin activity or investigate thrombin activation pathway in these subcellular compartments for understanding the mechanisms of diseases.

Conclusions

We have successfully developed EGFP-based thrombin sensors with optimal cleavage linkers that exhibit fast response, high sensitivity and specificity, large dynamic range with thrombin cleavage. Our thrombin sensor variants can be easily expressed in living cells for tracking thrombin activation and inhibition processes in real time and reveal ratiometric optical signal change during the determination for eliminating affect from background, expression level or orientation limitation. These thrombin sensors will be greatly benefited for probing physiological process and pathological mechanisms of diseases corresponding to the imbalance of thrombin activation and inhibition. Moreover, this method for protease sensor development will be promising to investigate other diseases related to protease activity.

REFERENCES FOR EXAMPLE 10, EACH OF WHICH ARE INCORPORATED BY REFERENCE

Anderluh, M. and Dolenc, M. S. (2002). "Thrombin receptor antagonists; recent advances in PAR-1 antagonist development." Curr Med Chem 9(13): 1229-50.

Coughlin, S. R. (1999). "How the protease thrombin talks to cells." Proc Natl Acad Sci USA 96(20): 11023-7.

Goldsack, N. R., Chambers, R. C., et al. (1998). "Thrombin." Int J Biochem Cell Biol 30(6): 641-6.

Harris, J. L., Backes, B. J., et al. (2000). "Rapid and general profiling of protease specificity by using combinatorial fluorogenic substrate libraries." Proc Natl Acad Sci USA 97(14): 7754-9.

Sadasivan, C. and Yee, V. C. (2000). "Interaction of the factor XIII activation peptide with alpha-thrombin. Crystal structure of its enzyme-substrate analog complex." J Biol Chem 275(47): 36942-8.

Xiao, Y., Lubin, A. A., et al. (2005). "Label-free electronic detection of thrombin in blood serum by using an aptamer-based sensor." Angew Chem Int Ed Engl 44(34): 5456-9.

Ye, Y., Lee, H. W., et al. (2005). "Probing site-specific calmodulin calcium and lanthanide affinity by grafting." J Am Chem Soc 127(11): 3743-50.

Ye, Y., Shealy, S., et al. (2003). "A grafting approach to obtain site-specific metal-binding properties of EF-hand proteins." Protein Eng 16(6): 429-34.

Zhang, B. (2004). "Design of FRET-based GFP probes for detection of protease inhibitors." Biochem Biophys Res Commun 323(2): 674-8.

Zou, J., Ye, Y., et al. (2005). "Expression and optical properties of green fluorescent protein expressed in different cellular environments." J Biotechnol 119(4): 368-78.

Sequence Listing (for sequences having underlined portions, the underlined portions may correspond to an analyte binding sequence, which are sequences on there own)

```
Sequence ID. No. 1-EGFP-T/C1 (EGFP-E-III-F-172)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EEEIREAFRVFDKDGNGY

ISAAELRHVMTNLDGSVQLADHYQQNTPIGDGPVLLPDNHYLSTQSALS

KDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 2-EGFP-T/C1-37
(EGFP-E-III-F-172-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EEEIREAFRVFDKDGNGY

ISAAELRHVMTNLDGSVQLADHYQQNTPIGDGPVLLPDNHYLSTQSALS

KDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 3-EGFP-T/C1b (EGFP-III-F-172)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)DKDGNGYISAAELRHVMT

NLDGSVQLADHYQQNTPIGDGPVLLPDNHYLSTQSALSKDPNEKRDHIV

LLEFVTAAGITLGMDELYK
```

The underlined portion is the inserted protease cleavage site for trypsin and chymotrypsin and the TYG portion in bold is the chromophore.

```
Sequence ID. No. 4-EGFP-T/C1b-37
(EGFP-III-F-172-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)DKDGNGYISAAELRHVMT

NLDGSVQLADHYQQNTPIGDGPVLLPDNHYLSTQSALSKDPNEKRDHIV

LLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 5-EGFP-T/C1c (EGFP-E-III-172)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIREAFRVFDKDGNGY
ISAAEDGSVQLADHYQQNTPIGDGPVLLPDNHYLSTQSALSKDPNEKRD
HIVLLEFVTAAGITLGMDELYK
```

The underlined portion is the inserted protease cleavage site for trypsin and chymotrypsin and the TYG portion in bold is the chromophore.

```
Sequence ID. No. 6-EGFP-T/C1c-37
(EGFP-E-III-172-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGNGY
ISAAEDGSVQLADHYQQNTPIGDGPVLLPDNHYLSTQSALSKDPNEKRD
HIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 7-EGFP-T/C1d (EGFP-III-172)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)DKDGNGYISAAEDGSVQL
ADHYQQNTPIGDGPVLLPDNHYLSTQSALSKDPNEKRDHIVLLEFVTAA
GITLGMDELYK
```

The underlined portion is the inserted protease cleavage site for trypsin and chymotrypsin and the TYG portion in bold is the chromophore.

```
Sequence ID. No. 8-EGFP-T/C1d-37 (EGFP-III-172-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)DKDGNGYISAAEDGSVQL
ADHYQQNTPIGDGPVLLPDNHYLSTQSALSKDPNEKRDHIVLLEFVTAA
GITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 9-EGFP-T/C1e (EGFP-E-III-F-R197)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIAEAFAVFDADGNGY
ISAAELRHVMTNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 10-EGFP-T/C1e-37
(EGFP-E-III-F-R197-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGNGY
ISAAELRHVMTNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 11-EGFP-T/C1f
(EGFP-E-III-F-172-GPRL)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIREAFRVFDKDGNGY
ISAAGPRLVMTNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 12-EGFP-T/C1f-37
(EGFP-E-III-F-172-GPRL-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGNGY
ISAAGPRLVMTNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 13-EGFP-T/C1g
(EGFP-III-F-172-GPRL)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)DKDGNGYISAAGPRLVMT
NLDGSVQLADHYQQNTPIGDGPVLLPDNHYLSTQSALSKDPNEKRDHIV
LLEFVTAAGITLGMDELYK
```

The underlined portion is the inserted protease cleavage site for trypsin and chymotrypsin and the TYG portion in bold is the chromophore.

```
Sequence ID. No. 14EGFP-T/C1g-37
(EGFP-III-F-172-GPRL-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)DKDGNGYISAAGPRLVMT
NLDGSVQLADHYQQNTPIGDGPVLLPDNHYLSTQSALSKDPNEKRDHIV
LLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 15-EGFP-T/C1h
(EGFP-E-III-F-R197-GPRL)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIAEAFAVFDADGNGY
ISAAGPRLVMTNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 16-EGFP-T/C1h-37
(EGFP-E-III-F-R197-GPRL-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIAEAFAVFDADGNGY
ISAAGPRLVMTNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 17-EGFP-T/C1i
(EGFP-E-III-F-172-GPARL)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIREAFRVFDKDGNGY
ISAAGPARLVMTNLDGSVQLADHYQQNTPIGDGPVLLPDNHYLSTQSAL
SKDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 18-EGFP-T/C1i-37
(EGFP-E-III-F-172-GPARL-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGNGY
ISAAGPARLVMTNLDGSVQLADHYQQNTPIGDGPVLLPDNHYLSTQSAL
SKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 19-EGFP-T/C1j
(EGFP-E-III-F-172-GPARLAI)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIREAFRVFDKDGNGY
ISAAGPRLAITNLDGSVQLADHYQQNTPIGDGPVLLPDNHYLSTQSALS
KDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 20-EGFP-T/C1j-37
(EGFP-E-III-F-172-GPARLAI-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGNGY
ISAAGPARLAITNLDGSVQLADHYQQNTPIGDGPVLLPDNHYLSTQSAL
SKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 21-EGFP-T/C1k
(EGFP-III-F-172-GPARLAI)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)DKDGNGYISAAGPARLAI

TNLDGSVQLADHYQQNTPIGDGPVLLPDNHYLSTQSALSKDPNEKRDHI

VLLEFVTAAGITLGMDELYK
```

The underlined portion is the inserted protease cleavage site for trypsin and chymotrypsin and the TYG portion in bold is the chromophore.

```
Sequence ID. No. 22-EGFP-T/C1k-37
(EGFP-III-F-172-GPARLAI-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)DKDGNGYISAAGPARLAI

TNLDGSVQLADHYQQNTPIGDGPVLLPDNHYLSTQSALSKDPNEKRDHI

VLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 23-EGFP-T/C1l
(EGFP-E-III-F-R197-GPARLAI)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EEEIAEAFAVFDADGNGY

ISAAGPARLAITNLDGSVQLADHYQQNTPIGDGPVLLPDNHYLSTQSAL

SKDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 24-EGFP-T/C1l-37
(EGFP-E-III-F-R197-GPARLAI-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EEEIAEAFAVFDADGNGY

ISAAGPARLAITNLDGSVQLADHYQQNTPIGDGPVLLPDNHYLSTQSAL

SKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 25-EGFP-T/C1m (EGFP-E-I-F-172)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EFKEAFSLFDKDGDGTIT

TKELGTVMRSLDGSVQLADHYQQNTPIGDGPVLLPDNHYLSTQSALSKD

PNEKRDHIVLLEFVTAAGITLGMDELYK
```

The underlined portion is the inserted protease cleavage site for trypsin and chymotrypsin and the TYG portion in bold is the chromophore.

```
Sequence ID. No. 26-EGFP-T/C1m-37
(EGFP-E-I-F-172-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EFKEAFSLFDKDGDGTIT

TKELGTVMRSLDGSVQLADHYQQNTPIGDGPVLLPDNHYLSTQSALSKD

PNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 27-EGFP-T/C1n
(EGFP-E-I-F-172-GPARLAI)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EFKEAFSLFDKDGDGTIT

TKELGPARLAIDGSVQLADHYQQNTPIGDGPVLLPDNHYLSTQSALSKD

PNEKRDHIVLLEFVTAAGITLGMDELYK
```

The underlined portion is the inserted protease cleavage site for trypsin and chymotrypsin and the TYG portion in bold is the chromophore.

```
Sequence ID. No. 28-EGFP-T/C1n-37
(EGFP-E-I-F-172-GPARLAI-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EFKEAFSLFDKDGDGTIT

TKELGPARLAIDGSVQLADHYQQNTPIGDGPVLLPDNHYLSTQSALSKD

PNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 29-EGFP-T/C1o (EGFP-E-II-F-172)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)ELQDMINEVDADGNGTID

FPEFLTMMARKDGSVQLADHYQQNTPIGDGPVLLPDNHYLSTQSALSKD

PNEKRDHIVLLEFVTAAGITLGMDELYK
```

The underlined portion is the inserted protease cleavage site for trypsin and chymotrypsin and the TYG portion in bold is the chromophore.

```
Sequence ID. No. 30-EGFP-T/C1o-37
(EGFP-E-II-F-172-37)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYITADKQKNGIKANFKIRHNIE(172)ELQDMINEVDADGNG

TIDFPEFLTMMARKDGSVQLADHYQQNTPIGDGPVLLPDNHYLSTQSA

LSKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 31-EGFP-T/C1p
(EGFP-E-II-F-172-GPARLAI)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYIMADKQKNGIKVNFKIRHNIE(172)ELQDMINEVDADGNG

TIDFPEFLGPARLAIDGSVQLADHYQQNTPIGDGPVLLPDNHYLSTQS

ALSKDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 32-EGFP-T/C1p-37
(EGFP-E-II-F-172-GPARLAI-37)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYITADKQKNGIKANFKIRHNIE(172)ELQDMINEVDADGNG

TIDFPEFLGPARLAIDGSVQLADHYQQNTPIGDGPVLLPDNHYLSTQS

ALSKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 33-EGFP-T/C1q
(EGFP-E-IV-F-172)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYIMADKQKNGIKVNFKIRHNIE(172)EEVDENAIREADIDG

DGQVNYEEFVQMMTAKDGSVQLADHYQQNTPIGDGPVLLPDNHYLSTQ

SALSKDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 34-EGFP-T/C1q-37
(EGFP-E-IV-F-172-37)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYITADKQKNGIKANFKIRHNIE(172)EEVDEMIREADIDGD

GQVNYEEFVQMMTAKDGSVQLADHYQQNTPIGDGPVLLPDNHYLSTQS

ALSKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 35-EGFP-T/C1r
(EGFP-E-IV-F-172-GPARLAI)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYIMADKQKNGIKVNFKIRHNIE(172)EEVGPARLAIDIDGD

GQVNYEEFVQMMTADGSVQLADHYQQNTPIGDGPVLLPDNHYLSTQSA

LSKDPNEKRDHIVLLEFVTAAGITLGMDELYK
```

The underlined portion is the inserted protease cleavage site for trypsin and chymotrypsin and the TYG portion in bold is the chromophore.

```
Sequence ID. No. 36-EGFP-T/C1r-37
(EGFP-E-IV-F-172-GPARLAI-37)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYITADKQKNGIKANFKIRHNIE(172)EEVGPARLAIDIDGD

GQVNYEEFVQMMTADGSVQLADHYQQNTPIGDGPVLLPDNHYLSTQSA

LSKDPNEKRDHIVLLEFVTAAGITLGMDELYK
```

The underlined portion is the inserted protease cleavage site for trypsin and chymotrypsin and the TYG portion in bold is the chromophore. (The mutant M153T and V163A were added for 37° C. expression).

```
Sequence ID. No. 37-YFP-T/C1 (YFP-E-III-F-172)
Yellow Flourescent Protein variants,
(YFP: S65G, V68L, S72A, T203Y)
MVSKGEELFTGWPILVELDGDLNGHKFSVSGEGEGDATYGKLTLKFIC

TTGKLPVPWPTLVTTLGYGVQCFSRYPDHMKQHDFFKSAMPEGYVQER

TIFFKDDGNYKTRAEVKFEGDTLVNRIELKGIDFKEDGNILGHKLEYN

YNSHNVYIMADKQKNGIKVNFKIRHNIE(172)EEEIREAFRVFDKDG

NGYISAAELRHVMTNLDGSVQLADHYQQNTPIGDGPVLLPDNHYLSYQ

SALSKDPNEKRDHIVLLEFVTAAGITLGMDELYK
```

The underlined portion is the inserted protease cleavage site for trypsin and chymotrypsin, and the GYG portion in bold is the chromophore.

```
Sequence ID. No. 38-Venus-T/C1 (Venus-E-III-F-172)
Enhanced Yellow Flourescent Protein variants,
(Venus: F46L, F64L, S65G, V68L, S72A,
V163A, S175G, T203Y)
MVSKGEELFTGWPILVELDGDLNGHKFSVSGEGEGDATYGKLTLKLICTT

GKLPVPWPTLVTTLGYGLQCFARYPDHMKQHDFFKSAMPEGYVQERTIFF

KDDGNYKTRAEVKFEGDTLVNRIELKGIDFKEDGNILGHKLEYNYNSHNV

YIMADKQKNGIKANFKIRHNIE(172)EEEIREAFRVFDKDGNGYISAAE

LRHVMTNLDGGVQLADHYQQNTPIGDGPVLLPDNHYLSYQSALSKDPNEK

RDHIVLLEFVTAAGITLGMDELYK
```

The underlined portion is the inserted protease cleavage site for trypsin and chymotrypsin, and the GYG portion in bold is the chromophore.

```
Sequence ID. No. 39-CFP-T/C1 (CFP-E-III-F-172),
Cyanide Fluorescent Protein variant,
(CFP: Y66W, N146I, M152T, V163A, N212K)
MVSKGEELFTGWPILVELDGDLNGHKFSVSGEGEGDATYGKLTLKFICT

TGKLPVPWPTLVTTLSWGVQCFSRYPDHMKQHDFFKSAMPEGYVQERTI

FFKDDGNYKTRAEVKFEGDTLVNRIELKGIDFKEDGNILGHKLEYIYNS

HNVYITADKQKNGIKANFKIRHNIE(172)EEEIREAFRVFDKDGNGYI

SAAEVDEVDSVMTNLDGSVQLADHYQQNTPIGDGPVLLPDNHYLSTQSA

LSKDPKEKRDHIVLLEFVTAAGITLGMDELYK
```

The underlined portion is the inserted protease cleavage site for trypsin and chymotrypsin, and the SWG portion in bold is the chromophore.

```
Sequence ID. No. 40-BFP-T/C1 (BFP-E-III-F-172)
Blue Flourescent Protein variant,
(BFP: Y66H, Y145F)
MVSKGEELFTGWPILVELDGDLNGHKFSVSGEGEGDATYGKLTLKFIC

TTGKLPVPWPTLVTTLSHGVQCFSRYPDHMKQHDFFKSAMPEGYVQER

TIFFKDDGNYKTRAEVKFEGDTLVNRIELKGIDFKEDGNILGHKLEFN

YNSHNVYIMADKQKNGIKVNFKIRHNIE(172)EEEIREAFRVFDKDG

NGYISAAELRHVMTNLDGSVQLADHYQQNTPIGDGPVLLPDNHYLSTQ

SALSKDPNEKRDHIVLLEFVTAAGITLGMDELYK
```

The underlined portion is the inserted protease cleavage site for trypsin and chromophore, and the SHG portion in bold is the chromophore.

```
Sequence ID. No. 41-mCherry-T/C1 (mCherry-
E-III-F-172), Red Fluorescent Protein
variant
MVSKGEEDNMAIIKEFMRFKVHMEGSVNGHEFEIEGEGEGRPYEGTQTA

KLKVTKGGPLPFAWDILSPQFMYGSKAYVKHPADIPDYLKLSFPEGFKW

ERVMNFEDGGWTVTQDSSLQDGEFIYKVKLRGTNFPSDGPVMQKKTMGW

EASSERMYPEDGALKGEIKMRLKLK(172)EEEIREAFRVFDKDGNGYI

SAAELRHVMTNLDGGHYDAEVKTTYKAKKPVQLPGAYNVNIKLDITSHN

EDYTIVEQYERAEGRHSTGGMDELYK
```

The underlined portion is the inserted protease cleavage site for trypsin and chymotrypsin, and the MYG portion in bold is the chromophore.

```
Sequence ID. No. 42-mStrawberry-T/C1
(mStrawberry-E-III-F-172), Red Flourescent
Protein variant
MVSKGEENNMAIIKEFMRFKVRMEGSVNGHEFEIEGEGEGRPYEGTQT

AKLKVTKGGPLPFAWDILTPNFTYGSKAYVKHPADIPDYLKLSFPEGF

KWERVMNFEDGGWTVTQDSSLQDGEFIYKVKLRGTNFPSDGPVMQKKT

MGWEASSERMYPEDGALKGEIKMRLKLK(172)EEEIREAFRVFDKDG

NGYISAAELRHVMTNLDGGHYDAEVKTTYKAKKPVQLPGAYIVGIKLD

ITSHNEDYTIVELYERAEGRHSTGGMDELYK
```

The underlined portion is the inserted protease cleavage site for trypsin and chromophore, and the TYG portion in bold is the chromophore.

```
Sequence ID. No. 43-EGFP-T/C1-ER
(EGFP-E-III-F-172-GPRL-ER)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYIMADKQKNGIKVNFKIRHNIE(172)EEEIREAFRVFDKDG

NGYISAAGPRLVMTNLDGSVQLADHYQQNTPIGDGPVLLPDNHYLSTQ

SALSKDPNEKRDHIVLLEFVTAAGITLGMDELYKKDEL
```

The underlined portion is the inserted protease cleavage site for trypsin and chymotrypsin and the TYG portion in bold is the chromophore. KEDL is the signal peptide for endoplasmic reticulum.

```
Sequence ID. No. 44-EGFP-T/C1-mito
(EGFP-E-III-F-172-GPRL-mito)
MLLSVPLLLGLLGLAAADMVSKGEELFTGWPILVELDGDLNGHKFSVSG

EGEGDATYGKLTLKFICTTGKLPVPWPTLVTTLTYGVQCFSRYPDHMKQ

HDFFKSAMPEGYVQERTIFFKDDGNYKTRAEVKFEGDTLVNRIELKGID
```

FKEDGNILGHKLEYNYNSHNVYIMADKQKNGIKVNFKIRHNIE(172)E
EEIREAFRVFDKDGNGYISAAGPRLVMTNLDGSVQLADHYQQNTPIGDG
PVLLPDNHYLSTQSALSKDPNEKRDHIVLLEFVTAAGITLGMDELYK

The underlined portion is the inserted protease cleavage site for trypsin and chymotrypsin and the TYG portion in bold is the chromophore. MLLSVPLLLGLLGLAAAD is the signal peptide for mitochondrial matrix.

Sequence ID. No. 45-EGFP-Thr1
(EGFP-E-III-F-N188R)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)EEEIREAFRVFDKDGRGY
ISAAELRHVMTNLDGSVQLADHYQQNTPIGDGPVLLPDNHYLSTQSALS
KDPNEKRDHIVLLEFVTAAGITLGMDELYK The underlined portion is the inserted protease cleavage site for thrombin and the TYG portion in bold is the chromophore.

Sequence ID. No. 46-EGFP-Thr1-37
(EGFP-E-III-F-N188R-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGRGY
ISAAELRHVMTNLDGSVQLADHYQQNTPIGDGPVLLPDNHYLSTQSALS
KDPNEKRDHIVLLEFVTAAGITLGMDELYK The underlined portion is the inserted protease cleavage site for thrombin and the TYG portion in bold is the chromophore. (The mutant M153T and V163A were added for 37° C. expression).

Sequence ID. No. 47-EGFP-Thr1b
(EGFP-III-F-N188R)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIE(172)DKDGRGYISAAELRHVMT
NLDGSVQLADHYQQNTPIGDGPVLLPDNHYLSTQSALSKDPNEKRDHIV
LLEFVTAAGITLGMDELYK The underlined portion is the inserted protease cleavage site for thrombin and the TYG portion in bold is the chromophore.

Sequence ID. No. 48-EGFP-Thr1b-37
(EGFP-III-F-N188R-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)DKDGRGYISAAELRHVMT
NLDGSVQLADHYQQNTPIGDGPVLLPDNHYLSTQSALSKDPNEKRDHIV
LLEFVTAAGITLGMDELYK The underlined portion is the inserted protease cleavage site for thrombin and the TYG portion in bold is the chromophore. (The mutant M153T and V163A were added for 37° C. expression).

Sequence ID. No. 49-EGFP-Thr1c
(EGFP-E-III-N188R)
MVSKGEELFTGVVPILVELDGDLNGHKFSVSGEGEGDATYGKLTLKFI
CTTGKLPVPWPTLVTTLTYGVQCFSRYPDHMKQHDFFKSAMPEGYVQE
RTIFFKDDGNYKTRAEVKFEGDTLVNRIELKGIDFKEDGNILGHKLEY
NYNSHNVYIMADKQKNGIKVNFKIRHNIE(172)EEEIREAFRVFDKD
GRGYISAAEDGSVQLADHYQQNTPIGDGPVLLPDNHYLSTQSALSKDP
NEKRDHIVLLEFVTAAGITLGMDELYK The underlined portion is the inserted protease cleavage site for thrombin and the TYG portion in bold is the chromophore.

Sequence ID. No. 50-EGFP-Thr1c-37
(EGFP-E-III-N188R-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)EEEIREAFRVFDKDGRGY
ISAAEDGSVQLADHYQQNTPIGDGPVLLPDNHYLSTQSALSKDPNEKRD
HIVLLEFVTAAGITLGMDELYK The underlined portion is the inserted protease cleavage site for thrombin and the TYG portion in bold is the chromophore. (The mutant M153T and V163A were added for 37° C. expression).

Sequence ID. No. 51-EGFP-Thr1d (EGFP-III-N188R)
MVSKGEELFTGVVPILVELDGDLNGHKFSVSGEGEGDATYGKLTLKF
ICTTGKLPVPWPTLVTTLTYGVQCFSRYPDHMKQHDFFKSAMPEGYV
QERTIFFKDDGNYKTRAEVKFEGDTLVNRIELKGIDFKEDGNILGHK
LEYNYNSHNVYIMADKQKNGIKVNFKIRHNIE(172)DKDGRGYISA
AEDGSVQLADHYQQNTPIGDGPVLLPDNHYLSTQSALSKDPNEKRDH
IVLLEFVTAAGITLGMDELYK The underlined portion is the inserted protease cleavage site for thrombin and the TYG portion in bold is the chromophore.

Sequence ID. No. 52-EGFP-Thr1d-37
(EGFP-III-N188R-37)
MVSKGEELFTGVVPILVELDGDLNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYITADKQKNGIKANFKIRHNIE(172)DKDGRGYISAAEDGSVQL -continued
ADHYQQNTPIGDGPVLLPDNHYLSTQSALSKDPNEKRDHIVLLEFVTAA

GITLGMDELYK

The underlined portion is the inserted protease cleavage site for thrombin and the TYG portion in bold is the chromophore. (The mutant M153T and V163A were added for 37° C. expression).

```
Sequence ID. No. 53-EGFP-Thr1e
(EGFP-E-III-F-FNPRGF)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EEEIREAFRVFDKDGRGY

ISAFNPRGFMTNLDGSVQLAHYQQNTPIGDGPVLLPDNHYLSTQSALSK

DPNEKRDHIVLLEFVTAAGITLGMDELYK
```

The underlined portion is the inserted protease cleavage site for thrombin and the TYG portion in bold is the chromophore.

```
Sequence ID. No. 54-EGFP-Thr1e-37
(EGFP-E-III-F-FNPRGF-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EEEIREAFRVFDKDGRGY

ISAFNPRGFMTNLDGSVQLADYQQNTPIGDGPVLLPDNHYLSTQSALSK

DPNEKRDHIVLLEFVTAAGITLGMDELYK
```

The underlined portion is the inserted protease cleavage site for thrombin and the TYG portion in bold is the chromophore. (The mutant M153T and V163A were added for 37° C. expression).

```
Sequence ID. No. 55-EGFP-Thr1f
(EGFP-E-III-F-FNPRSF)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EEEIREAFRVFDKDGRGY

ISAFNPRSFMTNLDGSVQLADHYQQNTPIGDGPVLLPDNHYLSTQSALS

KDPNEKRDHIVLLEFVTAAGITLGMDELYK
```

The underlined portion is the inserted protease cleavage site for thrombin and the TYG portion in bold is the chromophore.

```
Sequence ID. No. 56-EGFP-Thr1f-37
(EGFP-E-III-F-FNPRSF-37)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EEEIREAFRVFDKDGRGY
```

-continued
ISAFNPRGFMTNLDGSVQLADHYQQNTPIGDGPVLLPDNHYLSTQSALS

KDPNEKRDHIVLLEFVTAAGITLGMDELYK

The underlined portion is the inserted protease cleavage site for thrombin and the TYG portion in bold is the chromophore. (The mutant M153T and V163A were added for 37° C. expression).

```
Sequence ID. No. 57-EGFP-Thr1g
(EGFP-E-III-F-FTPRGF)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EEEIREAFRVFDKDGRGY

ISAFTPRGFMTNLDGSVQLADHYQQNTPIGDGPVLLPDNHYLSTQSALS

KDPNEKRDHIVLLEFVTAAGITLGMDELYK
```

The underlined portion is the inserted protease cleavage site for thrombin and the TYG portion in bold is the chromophore.

```
Sequence ID. No. 58-EGFP-Thr1g-37
(EGFP-E-III-F-FTPRGF-37)
MVSKGEELFTGVVPILVELDGDLNGHKFSVSGEGEGDATYGKLTLKFIC

PTTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIE(172)EEEIREAFRVFDKDGRGY

ISAFTPRGFMTNLDGSVQLADHYQQNTPIGDGPVLLPDNHYLSTQSALS

KDPNEKRDHIVLLEFVTAAGITLGMDELYK
```

The underlined portion is the inserted protease cleavage site for thrombin and the TYG portion in bold is the chromophore. (The mutant M153T and V163A were added for 37° C. expression).

```
Sequence ID. No. 59-EGFP-Thr1h
(EGFP-E-III-F-FTPRSF)
MVSKGEELFTGVVPILVELDGDLNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIE(172)EEEIREAFRVFDKDGRGY

ISAFTPRSFMTNLDGSVQLADHYQQNTPIGDGPVLLPDNHYLSTQSALS

KDPNEKRDHIVLLEFVTAAGITLGMDELYK
```

The underlined portion is the inserted protease cleavage site for thrombin and the TYG portion in bold is the chromophore.

```
Sequence ID. No. 60-EGFP-Thr1h-37
(EGFP-E-III-F-FTPRSF-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)EEEIREAFRVFDKDGRGYI
```

-continued

SAFTPRSFMTNLDGSVQLADHYQQNTPIGDGPVLLPDNHYLSTQSALSK

DPNEKRDHIVLLEFVTAAGITLGMDELYK

The underlined portion is the inserted protease cleavage site for thrombin and the TYG portion in bold is the chromophore. (The mutant M153T and V163A were added for 37° C. expression).

Sequence ID. No. 61-EGFP-cas3-1 (EGFP-172cas)
MVSKGEELFTGVVPILVELDGDLNGHKFSVSGEGEGDATYGKLTLKFI

CTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEY

NYNSHNVYIMADKQKNGIKVNFKIRHNIE(172)DEVDDGSVQLADHY

QQNTPIGDGPVLLPDNHYLSTQSALSKDPNEKRDHIVLLEFVTAAGIT

LGMDELYK

The underlined portion is the inserted protease cleavage site for caspase-3 and the TYG portion in bold is the chromophore.

Sequence ID. No. 62-EGFP-cas3-1-37
(EGFP-172cas-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)DEVDDGSVQLADHYQQNTP

IGDGPVLLPDNHYLSTQSALSKDPNEKRDHIVLLEFVTAAGITLGMDEL

YK

The underlined portion is the inserted protease cleavage site for caspase-3 and the TYG portion in bold is the chromophore. (The mutant M153T and V163A were added for 37° C. expression).

Sequence ID. No. 63-EGFP-cas3-1b
(EGFP-GGSGG-DEVD-GGSGG-172)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)GGSGGDEVDGGSGGDGSVQLAD

HYQQNTPIGDGPVLLPDNHYLSTQSALSKDPNEKRDHIVLLEFVTAAGIT

LGMDELYK

The underlined portion is the inserted protease cleavage site for caspase-3 and the TYG portion in bold is the chromophore.

Sequence ID. No. 64-EGFP-cas3-1b-37
(EGFP-GGSGG-DEVD-GGSGG-172-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)GGSGGDEVDGGSGGDGSVQ

LADHYQQNTPIGDGPVLLPDNHYLSTQSALSKDPNEKRDHIVLLEFVTA

AGITLGMDELYK

The underlined portion is the inserted protease cleavage site for caspase-3 and the TYG portion in bold is the chromophore. (The mutant M153T and V163A were added for 37° C. expression).

Sequence ID. No. 65-EGFP-cas3-1c (EGFP-III-172cas)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)DKDGRGYISAAEDEVDGSVQLA

DHYQQNTPIGDGPVLLPDNHYLSTQSALSKDPNEKRDHIVLLEFVTAAGI

TLGMDELYK

The underlined portion is the inserted protease cleavage site for caspase-3 and the TYG portion in bold is the chromophore.

Sequence ID. No. 66-EGFP-cas3-1c-37
(EGFP-III-172cas-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)DKDGRGYISAAEDEVDGSV

QLADHYQQNTPIGDGPVLLPDNHYLSTQSALSKDPNEKRDHIVLLEFVT

AAGITLGMDELYK

The underlined portion is the inserted protease cleavage site for caspase-3 and the TYG portion in bold is the chromophore. (The mutant M153T and V163A were added for 37° C. expression).

Sequence ID. No. 67-EGFP-cas3-1d (EGFP-EF-172cas)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)EEEIREAFRVFDEVDLRHV

MTNLDGSVQLADHYQQNTPIGDGPVLLPDNHYLSTQSALSKDPNEKRDH

IVLLEFVTAAGITLGMDELYK

The underlined portion is the inserted protease cleavage site for caspase-3 and the TYG portion in bold is the chromophore.

Sequence ID. No. 68-EGFP-cas3-1d-37
(EGFP-EF-172cas-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)<u>EEEIREAFRVFDEVDLRHV</u>

<u>MTNL</u>DGSVQLADHYQQNTPIGDGPVLLPDNHYLSTQSALSKDPNEKRDH

IVLLEFVTAAGITLGMDELYK

The underlined portion is the inserted protease cleavage site for caspase-3 and the TYG portion in bold is the chromophore. (The mutant M153T and V163A were added for 37° C. expression).

```
Sequence ID. No. 69-EGFP-cas3-1e
(EGFP-E-DEVD-GG-DEVD-F-172)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)<u>EEEIREAFRVFDEVDGGDE</u>

<u>VDLRHV</u>MTNLDGSVQLADHYQQNTPIGDGPVLLPDNHYLSTQSALSKDP

NEKRDHIVLLEFVTAAGITLGMDELYK

The underlined portion is the inserted protease cleavage site for caspase-3 and the TYG portion in bold is the chromophore.

```
Sequence ID. No. 70-EGFP-cas3-1e-37
(EGFP-E-DEVD-GG-DEVD-F-172-37)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)<u>EEEIREAFRVFDEVDGGDE</u>

<u>VDLRHV</u>MTNLDGSVQLADHYQQNTPIGDGPVLLPDNHYLSTQSALSKDP

NEKRDHIVLLEFVTAAGITLGMDELYK

The underlined portion is the inserted protease cleavage site for caspase-3 and the TYG portion in bold is the chromophore. (The mutant M153T and V163A were added for 37° C. expression).

```
Sequence ID. No. 71-EGFP-cas3-1f
(EGFP-E-III-F-172-LDEVDG)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)<u>EEEIREAFRVFDKDGNGYI</u>

<u>SAAELDEVDG</u>VMTNLDGSVQLADHYQQNTPIGDGPVLLPDNHYLSTQSA

LSKDPNEKRDHIVLLEFVTAAGITLGMDELYK

The underlined portion is the inserted protease cleavage site for caspase-3 and the TYG portion in bold is the chromophore.

```
Sequence ID. No. 72-EGFP-cas3-1f-37
(EGFP-E-III-F-172-LDEVDG-37)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)<u>EEEIREAFRVFDKDGNGYI</u>

<u>SAAELDEVDG</u>VMTNLDGSVQLADHYQQNTPIGDGPVLLPDNHYLSTQSA

LSKDPNEKRDHIVLLEFVTAAGITLGMDELYK

The underlined portion is the inserted protease cleavage site for caspase-3 and the TYG portion in bold is the chromophore. (The mutant M153T and V163A were added for 37° C. expression).

```
Sequence ID. No. 73-EGFP-cas3-1g
(EGFP-E-III-F-172-LDEVDS)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)<u>EEEIREAFRVFDKDGNGYI</u>

<u>SAAELDEVDS</u>VMTNLDGSVQLADHYQQNTPIGDGPVLLPDNHYLSTQSA

LSKDPNEKRDHIVLLEFVTAAGITLGMDELYK

The underlined portion is the inserted protease cleavage site for caspase-3 and the TYG portion in bold is the chromophore.

```
Sequence ID. No. 74-EGFP-cas3-1g-37
(EGFP-E-III-F-172-LDEVDS-37)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)<u>EEEIREAFRVFDKDGNGYI</u>

<u>SAAELDEVDS</u>VMTNLDGSVQLADHYQQNTPIGDGPVLLPDNHYLSTQSA

LSKDPNEKRDHIVLLEFVTAAGITLGMDELYK

The underlined portion is the inserted protease cleavage site for caspase-3 and the TYG portion in bold is the chromophore. (The mutant M153T and V163A were added for 37° C. expression).

```
Sequence ID. No. 75-EGFP-cas3-1h
(EGFP-E-III-F-172-VDEVDG)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)<u>EEEIREAFRVFDKDGNGYI</u>

<u>SAAEVDEVDG</u>VMTNLDGSVQLADHYQQNTPIGDGPVLLPDNHYLSTQSA

LSKDPNEKRDHIVLLEFVTAAGITLGMDELYK

The underlined portion is the inserted protease cleavage site for caspase-3 and the TYG portion in bold is the chromophore.

```
Sequence ID. No. 76-EGFP-cas3-1h-37
(EGFP-E-III-F-172-VDEVDG-37)
MVSKGEELFTGWPILVELDGDLNGHKFSVSGEGEGDATYGKLTLKFICT
```

TGKLPVPWPTLVTTLTYGVQCFSRYPDHMKQHDFFKSAMPEGYVQERTI

```
FFKDDGNYKTRAEVKFEGDTLVNRIELKGIDFKEDGNILGHKLEYNYNS

HNVYITADKQKNGIKANFKIRHNIE(172)EEEIREAFRVFDKDGNYI

SAAEVDEVDGVMTNLDGSVQLADHYQQNTPIGDGPVLLPDNHYLSTQSA

LSKDPNEKRDHIVLLEFVTAAGITLGMDELYK
```

The underlined portion is the inserted protease cleavage site for caspase-3 and the TYG portion in bold is the chromophore. (The mutant M153T and V163A were added for 37° C. expression).

```
Sequence ID. No. 77-EGFP-cas3-1i
(EGFP-E-III-F-172-VDEVDS)
MVSKGEELFTGWPILVELDGDLNGHKFSVSGEGEGDATYGKLTLKFIC

TTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

YNSHNVYIMADKQKNGIKVNFKIRHNIE(172)EEEIREAFRVFDKDG

NGYISAAEVDEVDSVMTNLDGSVQLADHYQQNTPIGDGPVLLPDNHYL

STQSALSKDPNEKRDHIVLLEFVTAAGITLGMDELYK
```

The underlined portion is the inserted protease cleavage site for caspase-3 and the TYG portion in bold is the chromophore.

```
Sequence ID. No. 78-EGFP-cas3-1i-37
(EGFP-E-III-F-172-VDEVDS-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)EEEIREAFRVFDKDGNYI

SAAEVDEVDSVMTNLDGSVQLADHYQQNTPIGDGPVLLPDNHYLSTQSA

LSKDPNEKRDHIVLLEFVTAAGITLGMDELYK
```

The underlined portion is the inserted protease cleavage site for caspase-3 and the TYG portion in bold is the chromophore. (The mutant M153T and V163A were added for 37° C. expression).

```
Sequence ID. No. 79-mCherry-cas3 (mCherry-EFcas3),
Red Fluorescent Protein variant
MVSKGEEDNMAIIKEFMRFKVHMEGSVNGHEFEIEGEGEGRPYEGTQTA

KLKVTKGGPLPFAWDILSPQFMYGSKAYVKHPADIPDYLKLSFPEGFKW

ERVMNFEDGGWTVTQDSSLQDGEFIYKVKLRGTNFPSDGPVMQKKTMGW

EASSERMYPEDGALKGEIKMRLKLK(172)EEEIREAFRVFVDEVDGLR

HVMTNLDGGHYDAEVKTTYKAKKPVQLPGAYNVNIKLDITSHNEDYTIV

EQYERAEGRHSTGGMDELYK
```

The underlined portion is the inserted protease cleavage site for trypsin and chymotrypsin, and the MYG portion in bold is the chromophore.

```
Sequence ID. No. 80-mStrawberry-cas3 (mStrawberry-
EF172cas3), Red Flourescent Protein variant
MVSKGEENNMAIIKEFMRFKVRMEGSVNGHEFEIEGEGEGRPYEGTQTA

KLKVTKGGPLPFAWDILTPNFTYGSKAYVKHPADIPDYLKLSFPEGFKW

ERVMNFEDGGWTVTQDSSLQDGEFIYKVKLRGTNFPSDGPVMQKKTMGW

EASSERMYPEDGALKGEIKMRLKLK(172)EEEIREAFRVFVDEVDGLR

HVMTNLDGGHYDAEVKTTYKAKKPVQLPGAYIVGIKLDITSHNEDYTIV

ELYERAEGRHSTGGMDELYK
```

The underlined portion is the inserted protease cleavage site for trypsin and chromophore, and the TYG portion in bold is the chromophore.

```
Sequence ID. No. 81-EGFP-cas8-1 (EGFP-172cas8)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)LETDDGSVQLADHYQQNTPIGD

GPVLLPDNHYLSTQSALSKDPNEKRDHIVLLEFVTAAGITLGMDELYK
```

The underlined portion is the inserted protease cleavage site for caspase-8 and the TYG portion in bold is the chromophore.

```
Sequence ID. No. 82-EGFP-cas8-1-37
(EGFP-172cas8-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)LETDDGSVQLADHYQQNTP

IGDGPVLLPDNHYLSTQSALSKDPNEKRDHIVLLEFVTAAGITLGMDEL

YK
```

The underlined portion is the inserted protease cleavage site for caspase-8 and the TYG portion in bold is the chromophore. (The mutant M153T and V163A were added for 37° C. expression).

```
Sequence ID. No. 83-EGFP-cas8-1b
(EGFP-GGSGG-LETD-GGSGG-172)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)GGSGGLETDGGSGGDGSVQ

LADHYQQNTPIGDGPVLLPDNHYLSTQSALSKDPNEKRDHIVLLEFVTA

AGITLGMDELYK
```

The underlined portion is the inserted protease cleavage site for caspase-8 and the TYG portion in bold is the chromophore.

```
Sequence ID. No. 84-EGFP-cas8-1b-37
(EGFP-GGSGG-LETD-GGSGG-172-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI
```

```
FFKDDGNYKTRAEVKFEGDTLVNRIELKGIDFKEDGNILGHKLEYNYNS

HNVYITADKQKNGIKANFKIRHNIE(172)GGSGGLETDGGSGGDGSVQ

LADHYQQNTPIGDGPVLLPDNHYLSTQSALSKDPNEKRDHIVLLEFVTA

AGITLGMDELYK
```

The underlined portion is the inserted protease cleavage site for caspase-8 and the TYG portion in bold is the chromophore. (The mutant M153T and V163A were added for 37° C. expression).

```
Sequence ID. No. 85-EGFP-cas8-1c (EGFP-III-172cas8)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)DKDGRGYISAAELETDGSVQLA

DHYQQNTPIGDGPVLLPDNHYLSTQSALSKDPNEKRDHIVLLEFVTAAGI

TLGMDELYK
```

The underlined portion is the inserted protease cleavage site for caspase-8 and the TYG portion in bold is the chromophore.

```
Sequence ID. No. 86-EGFP-cas8-1c-37
(EGFP-III-172cas8-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYITADKQKNGIKANFKIRHNIE(172)DKDGRGYISAAELETDGSV

QLADHYQQNTPIGDGPVLLPDNHYLSTQSALSKDPNEKRDHIVLLEFVT

AAGITLGMDELYK
```

The underlined portion is the inserted protease cleavage site for caspase-8 and the TYG portion in bold is the chromophore. (The mutant M153T and V163A were added for 37° C. expression).

```
Sequence ID. No. 87-EGFP-cas8-1d (EGFP-EF-172cas8)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)EEEIREAFRVFLETDLRHV

MTNLDGSVQLADHYQQNTPIGDGPVLLPDNHYLSTQSALSKDPNEKRDH

IVLLEFVTAAGITLGMDELYK
```

The underlined portion is the inserted protease cleavage site for caspase-8 and the TYG portion in bold is the chromophore.

```
Sequence ID. No. 88-EGFP-cas8-1d-37
(EGFP-EF-172cas8-37)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI
```

```
FFKDDGNYKTRAEVKFEGDTLVNRIELKGIDFKEDGNILGHKLEYNYNS

HNVYITADKQKNGIKANFKIRHNIE(172)EEEIREAFRVFLETDLRHV

MTNLDGSVQLADHYQQNTPIGDGPVLLPDNHYLSTQSALSKDPNEKRDH

IVLLEFVTAAGITLGMDELYK
```

The underlined portion is the inserted protease cleavage site for caspase-8 and the TYG portion in bold is the chromophore. (The mutant M153T and V163A were added for 37° C. expression).

```
Sequence ID. No. 89-EGFP-cas8-1e
(EGFP-E-LETD-GG-LETD-F-172)
MVSKGEELFTGWPILVELDGDLNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIE(172)EEEIREAFRVFLETDGGLE

TDLRHVMTNLDGSVQLADHYQQNTPIGDGPVLLPDNHYLSTQSALSKDP

NEKRDHIVLLEFVTAAGITLGMDELYK
```

The underlined portion is the inserted protease cleavage site for caspase-8 and the TYG portion in bold is the chromophore.

```
Sequence ID. No. 90-EGFP-cas8-1e-37
(EGFP-E-LETD-GG-LETD-F-172-37)
MVSKGEELFTGVVPILVELDGDLNGHKFSVSGEGEGDATYGKLTLKF

ICTTGKLPVPWPTLVTTLTYGVQCFSRYPDHMKQHDFFKSAMPEGYV

QERTIFFKDDGNYKTRAEVKFEGDTLVNRIELKGIDFKEDGNILGHK

LEYNYNSHNVYITADKQKNGIKANFKIRHNIE(172)EEEIREAFRV

FLETDGGLETDLRHVMTNLDGSVQLADHYQQNTPIGDGPVLLPDNHY

LSTQSALSKDPNEKRDHIVLLEFVTAAGITLGMDELYK
```

The underlined portion is the inserted protease cleavage site for caspase-8 and the TYG portion in bold is the chromophore. (The mutant M153T and V163A were added for 37° C. expression).

```
Sequence ID. No. 91-EGFP-cas8-1f
(EGFP-E-III-F-172-LLETDG)
MVSKGEELFTGVVPILVELDGDLNGHKFSVSGEGEGDATYGKLTLKF

ICTTGKLPVPWPTLVTTLTYGVQCFSRYPDHMKQHDFFKSAMPEGYV

QERTIFFKDDGNYKTRAEVKFEGDTLVNRIELKGIDFKEDGNILGHK

LEYNYNSHNVYIMADKQKNGIKVNFKIRHNIE(172)EEEIREAFRV

FDKDGNGYISAAELLETDGVMTNLDGSVQLADHYQQNTPIGDGPVLL

PDNHYLSTQSALSKDPNEKRDHIVLLEFVTAAGITLGMDELYK
```

The underlined portion is the inserted protease cleavage site for caspase-8 and the TYG portion in bold is the chromophore.

```
Sequence ID. No. 92-EGFP-cas8-1f-37
(EGFP-E-III-F-172-LLETDG-37)
MVSKGEELFTGVVPILVELDGDLNGHKFSVSGEGEGDATYGKLTLKF

ICTTGKLPVPWPTLVTTLTYGVQCFSRYPDHMKQHDFFKSAMPEGYV
```

-continued
QERTIFFKDDGNYKTRAEVKFEGDTLVNRIELKGIDFKEDGNILGHK

LEYNYNSHNVYITADKQKNGIKANFKIRHNIE(172)EEIREAFRV

FDKDGNGYISAAELLETDGVMTNLDGSVQLADHYQQNTPIGDGPVLL

PDNHYLSTQSALSKDPNEKRDHIVLLEFVTAAGITLGMDELYK

The underlined portion is the inserted protease cleavage site for caspase-8 and the TYG portion in bold is the chromophore. (The mutant M153T and V163A were added for 37° C. expression).

```
Sequence ID. No. 93-EGFP-cas8-1g
(EGFP-E-III-F-172-LLETDS)
MVSKGEELFTGVVPILVELDGDLNGHKFSVSGEGEGDATYGKLTLKF
```
ICTTGKLPVPWPTLVTTLTYGVQCFSRYPDHMKQHDFFKSAMPEGYV

QERTIFFKDDGNYKTRAEVKFEGDTLVNRIELKGIDFKEDGNILGHK

LEYNYNSHNVYIMADKQKNGIKVNFKIRHNIE(172)EEIREAFRV

FDKDGNGYISAAELLETDSVMTNLDGSVQLADHYQQNTPIGDGPVLL

PDNHYLSTQSALSKDPNEKRDHIVLLEFVTAAGITLGMDELYK

The underlined portion is the inserted protease cleavage site for caspase-8 and the TYG portion in bold is the chromophore.

```
Sequence ID. No. 94-EGFP-cas8-1g-37
(EGFP-E-III-F-172-LLETDS-37)
MVSKGEELFTGVVPILVELDGDLNGHKFSVSGEGEGDATYGKLTLKF
```
ICTTGKLPVPWPTLVTTLTYGVQCFSRYPDHMKQHDFFKSAMPEGYV

QERTIFFKDDGNYKTRAEVKFEGDTLVNRIELKGIDFKEDGNILGHK

LEYNYNSHNVYITADKQKNGIKANFKIRHNIE(172)EEIREAFRV

FDKDGNGYISAAELLETDSVMTNLDGSVQLADHYQQNTPIGDGPVLL

PDNHYLSTQSALSKDPNEKRDHIVLLEFVTAAGITLGMDELYK

The underlined portion is the inserted protease cleavage site for caspase-8 and the TYG portion in bold is the chromophore. (The mutant M153T and V163A were added for 37° C. expression).

```
Sequence ID. No. 95-EGFP-cas8-1h
(EGFP-E-III-F-172-VLETDG)
MVSKGEELFTGVVPILVELDGDLNGHKFSVSGEGEGDATYGKLTLK
```
FICTTGKLPVPWPTLVTTLTYGVQCFSRYPDHMKQHDFFKSAMPEG

YVQERTIFFKDDGNYKTRAEVKFEGDTLVNRIELKGIDFKEDGNIL

GHKLEYNYNSHNVYIMADKQKNGIKVNFKIRHNIE(172)EEIRE

AFRVFDKDGNGYISAAEVLETDGVMTNLDGSVQLADHYQQNTPIGD

GPVLLPDNHYLSTQSALSKDPNEKRDHIVLLEFVTAAGITLGMDEL

YK

The underlined portion is the inserted protease cleavage site for caspase-8 and the TYG portion in bold is the chromophore.

```
Sequence ID. No. 96-EGFP-cas8-1h-37
(EGFP-E-III-F-172-VLETDG-37)
MVSKGEELFTGVVPILVELDGDLNGHKFSVSGEGEGDATYGKLTL
```
KFICTTGKLPVPWPTLVTTLTYGVQCFSRYPDHMKQHDFFKSAMP

EGYVQERTIFFKDDGNYKTRAEVKFEGDTLVNRIELKGIDFKEDG

NILGHKLEYNYNSHNVYITADKQKNGIKANFKIRHNIE(172)EE

EIREAFRVFDKDGNGYISAAEVLETDGVMTNLDGSVQLADHYQQN

TPIGDGPVLLPDNHYLSTQSALSKDPNEKRDHIVLLEFVTAAGIT

LGMDELYK

The underlined portion is the inserted protease cleavage site for caspase-3 and the TYG portion in bold is the chromophore. (The mutant M153T and V163A were added for 37° C. expression).

```
Sequence ID. No. 97-EGFP-cas8-1i
(EGFP-E-III-F-172-VLETDS)
MVSKGEELFTGVVPILVELDGDLNGHKFSVSGEGEGDATYGKLTL
```
KFICTTGKLPVPWPTLVTTLTYGVQCFSRYPDHMKQHDFFKSAMP

EGYVQERTIFFKDDGNYKTRAEVKFEGDTLVNRIELKGIDFKEDG

NILGHKLEYNYNSHNVYIMADKQKNGIKVNFKIRHNIE(172)EE

EIREAFRVFDKDGNGYISAAEVLETDSVMTNLDGSVQLADHYQQN

TPIGDGPVLLPDNHYLSTQSALSKDPNEKRDHIVLLEFVTAAGIT

GLMDELYK

The underlined portion is the inserted protease cleavage site for caspase-8 and the TYG portion in bold is the chromophore.

```
Sequence ID. No. 98-EGFP-cas8-1i-37
(EGFP-E-III-F-172-VLETDS-37)
MVSKGEELFTGVVPILVELDGDLNGHKFSVSGEGEGDATYGKLTL
```
KFICTTGKLPVPWPTLVTTLTYGVQCFSRYPDHMKQHDFFKSAMP

EGYVQERTIFFKDDGNYKTRAEVKFEGDTLVNRIELKGIDFKEDG

INLGHKLEYNYNSHNVYITADKQKNGIKANFKIRHNIE(172)EE

EIREAFRVFDKDGNGYISAAEVLETDSVMTNLDGSVQLADHYQQN

TPIGDGPVLLPDNHYLSTQSALSKDPNEKRDHIVLLEFVTAAGIT

LGMDELYK

The underlined portion is the inserted protease cleavage site for caspase-8 and the TYG portion in bold is the chromophore. (The mutant M153T and V163A were added for 37° C. expression).

```
Sequence ID. No. 99-mCherry-cas8 (mCherry-
EFcas8), Red Fluorescent Protein variant
MVSKGEEDNMAIIKEFMRFKVHMEGSVNGHEFEIEGEGEGRPYE
```
GTQTAKLKVTKGGPLPFAWDILSPQFMYGSKAYVKHPADIPDYL

KLSFPEGFKWERVMNFEDGGVVTVTQDSSLQDGEFIYKVKLRGT

NFPSDGPVMQKKTMGVVEASSERMYPEDGALKGEIKMRLKLK(172)

EEEIREAFRVFVLETDGLRHVMTNLDGGHYDAEVKTTYKAKKPV

QLPGAYNVNIKLDITSHNEDYTIVEQYERAEGRHSTGGMDELYK

The underlined portion is the inserted protease cleavage site for trypsin and chymotrypsin, and the MYG portion in bold is the chromophore.

```
Sequence ID. No. 100-mStrawberry-cas8
(mStrawberry-EF172cas8), Red Flourescent
Protein variant
MVSKGEENNMAIIKEFMRFKVRMEGSVNGHEFEIEGEGEGRPYEG

TQTAKLKVTKGGPLPFAWDILTPNFTYGSKAYVKHPADIPDYLKL

SFPEGFKWERVMNFEDGGVVTVTQDSSLQDGEFIYKVKLRGTNFP

SDGPVMQKKTMGWEASSERMYPEDGALKGEIKMRLKLK(172)EE

EIREAFRVFVLETDGLRHVMTNLDGGHYDAEVKTTYKAKKPVQLP

GAYIVGIKLDITSHNEDYTIVELYERAEGRHSTGGMDELYK
```

The underlined portion is the inserted protease cleavage site for trypsin and chromophore, and the TYG portion in bold is the chromophore.

```
Sequence ID. No. 101-EGFP-cas9-1
(EGFP-172cas9)
MVSKGEELFTGVVPILVELDGDLNGHKFSVSGEGEGDATYGKLTLKFI

PCTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEY

NYNSHNVYIMADKQKNGIKVNFKIRHNIE(172)LEHDDGSVQLADHY

QQNTPIGDGPVLLPDNHYLSTQSALSKDPNEKRDHIVLLEFVTAAGIT

LGMDELYK
```

The underlined portion is the inserted protease cleavage site for caspase-9 and the TYG portion in bold is the chromophore.

```
Sequence ID. No. 102-EGFP-cas9-1-37
(EGFP-172cas9-37)
MVSKGEELFTGVVPILVELDGDLNGHKFSVSGEGEGDATYGKLTLKFI

CTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEY

NYNSHNVYITADKQKNGIKANFKIRHNIE(172)LEHDDGSVQLADHY

QQNTPIGDGPVLLPDNHYLSTQSALSKDPNEKRDHIVLLEFVTAAGIT

LGMDELYK
```

The underlined portion is the inserted protease cleavage site for caspase-9 and the TYG portion in bold is the chromophore. (The mutant M153T and V163A were added for 37° C. expression).

```
Sequence ID. No. 103-EGFP-cas9-1b
(EGFP-GGSGG-LEHD-GGSGG-172)
MVSKGEELFTGVVPILVELDGDLNGHKFSVSGEGEGDATYGKLTLKFI

CTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEY

NYNSHNVYIMADKQKNGIKVNFKIRHNIE(172)GGSGGLEHDGGSGG

DGSVQLADHYQQNTPIGDGPVLLPDNHYLSTQSALSKDPNEKRDHIVL

LEFVTAAGITLGMDELYK
```

The underlined portion is the inserted protease cleavage site for caspase-9 and the TYG portion in bold is the chromophore.

```
Sequence ID. No. 104-EGFP-cas9-1b-37
(EGFP-GGSGG-LEHD-GGSGG-172-37)
MVSKGEELFTGVVPILVELDGDLNGHKFSVSGEGEGDATYGKLTLKF

ICTTGKLPVPWPTLVTTLTYGVQCFSRYPDHMKQHDFFKSAMPEGYV

QERTIFFKDDGNYKTRAEVKFEGDTLVNRIELKGIDFKEDGNILGHK

LEYNYNSHNVYITADKQKNGIKANFKIRHNIE(172)GGSGGLEHDG

GSGGDGSVQLADHYQQNTPIGDGPVLLPDNHYLSTQSALSKDPNEKR

DHIVLLEFVTAAGITLGMDELYK
```

The underlined portion is the inserted protease cleavage site for caspase-9 and the TYG portion in bold is the chromophore. (The mutant M153T and V163A were added for 37° C. expression).

```
Sequence ID. No. 105-EGFP-cas9-1c
(EGFP-III-172cas9)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)DKDGRGYISAAELEHDGSVQLA

DHYQQNTPIGDGPVLLPDNHYLSTQSALSKDPNEKRDHIVLLEFVTAAGI

TLGMDELYK
```

The underlined portion is the inserted protease cleavage site for caspase-9 and the TYG portion in bold is the chromophore.

```
Sequence ID. No. 106-EGFP-cas9-1c-37
(EGFP-III-172cas9-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYITADKQKNGIKANFKIRHNIE(172)DKDGRGYISAAELEHDGSVQLA

DHYQQNTPIGDGPVLLPDNHYLSTQSALSKDPNEKRDHIVLLEFVTAAGI

TLGMDELYK
```

The underlined portion is the inserted protease cleavage site for caspase-9 and the TYG portion in bold is the chromophore. (The mutant M153T and V163A were added for 37° C. expression).

```
Sequence ID. No. 107-EGFP-cas9-1d
(EGFP-EF-172cas9)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF
```

Sequence ID. No. 108-EGFP-cas9-1d-37
(EGFP-EF-172cas9-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYITADKQKNGIKANFKIRHNIE(172)<u>EEEIREAFRVFLEHDLRHVMTN</u>

<u>LDGSVQLADHYQQNTPIGDGPVLLPDNHYLSTQSALSKDPNEKRDHIVLL</u>

EFVTAAGITLGMDELYK

The underlined portion is the inserted protease cleavage site for caspase-9 and the TYG portion in bold is the chromophore. (The mutant M153T and V163A were added for 37° C. expression).

Sequence ID. No. 109-EGFP-cas9-1e
(EGFP-E-LEHD-GG-LEHD-F-172)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)<u>EEEIREAFRVFLETDGGLEHDL</u>

<u>RHVMTNLDGSVQLADHYQQNTPIGDGPVLLPDNHYLSTQSALSKDPNEKR</u>

<u>DHIVLLEFVTAAGITLGMDELYK</u>

The underlined portion is the inserted protease cleavage site for caspase-9 and the TYG portion in bold is the chromophore.

Sequence ID. No. 110-EGFP-cas9-1e-37
(EGFP-E-LEHD-GG-LEHD-F-172-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYITADKQKNGIKANFKIRHNIE(172)<u>EEEIREAFRVFLETDGGLEHDL</u>

<u>RHVMTNLDGSVQLADHYQQNTPIGDGPVLLPDNHYLSTQSALSKDPNEKR</u>

<u>DHIVLLEFVTAAGITLGMDELYK</u>

The underlined portion is the inserted protease cleavage site for caspase-9 and the TYG portion in bold is the chromophore. (The mutant M153T and V163A were added for 37° C. expression).

Sequence ID. No. 111-EGFP-cas9-1f
(EGFP-E-III-F-172-LLEHDG)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)<u>EEEIREAFRVFDKDGNGYISAA</u>

<u>ELLEHDGVMTNLDGSVQLADHYQQNTPIGDGPVLLPDNHYLSTQSALSKD</u>

<u>PNEKRDHIVLLEFVTAAGITLGMDELYK</u>

The underlined portion is the inserted protease cleavage site for caspase-9 and the TYG portion in bold is the chromophore.

Sequence ID. No. 112-EGFP-cas9-1f-37
(EGFP-E-III-F-172-LLEHDG-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYITADKQKNGIKANFKIRHNIE(172)<u>EEEIREAFRVFDKDGNGYISAA</u>

<u>ELLEHDGVMTNLDGSVQLADHYQQNTPIGDGPVLLPDNHYLSTQSALSKD</u>

<u>PNEKRDHIVLLEFVTAAGITLGMDELYK</u>

The underlined portion is the inserted protease cleavage site for caspase-9 and the TYG portion in bold is the chromophore. (The mutant M153T and V163A were added for 37° C. expression).

Sequence ID. No. 113-EGFP-cas9-1g
(EGFP-E-III-F-172-LLEHDS)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIE(172)<u>EEEIREAFRVFDKDGNGYISAA</u>

<u>ELLEHDSVMTNLDGSVQLADHYQQNTPIGDGPVLLPDNHYLSTQSALSKD</u>

<u>PNEKRDHIVLLEFVTAAGITLGMDELYK</u>

The underlined portion is the inserted protease cleavage site for caspase-9 and the TYG portion in bold is the chromophore.

Sequence ID. No. 114-EGFP-cas8-1g-37
(EGFP-E-III-F-172-LLEHDS-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYITADKQKNGIKANFKIRHNIE(172)<u>EEEIREAFRVFDKDGNGYISAA</u>

<u>ELLEHDSVMTNLDGSVQLADHYQQNTPIGDGPVLLPDNHYLSTQSALSKD</u>

<u>PNEKRDHIVLLEFVTAAGITLGMDELYK</u>

The underlined portion is the inserted protease cleavage site for caspase-9 and the TYG portion in bold is the chromophore. (The mutant M153T and V163A were added for 37° C. expression).

Sequence ID. No. 115-EGFP-cas9-1h
(EGFP-E-III-F-172-VLEHDG)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

-continued

FKDDGNYKTRAEVKFEGDTLVNRIELKGIDFKEDGNILGHKLEYNYNSHN

VYIMADKQKNGIKVNFKIRHNIE(172)<u>EEEIREAFRVFDKDGNGYISAA</u>

<u>EVLEHDGVMTNL</u>DGSVQLADHYQQNTPIGDGPVLLPDNHYLSTQSALSKD

PNEKRDHIVLLEFVTAAGITLGMDELYK

The underlined portion is the inserted protease cleavage site for caspase-9 and the TYG portion in bold is the chromophore.

Sequence ID. No. 116-EGFP-cas9-1h-37
(EGFP-E-III-F-172-VLEHDG-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYI<u>T</u>ADKQKNGIK<u>A</u>NFKIRHNIE(172)<u>EEEIREAFRVFDKDGNGYISAA</u>

<u>EVLEHDG</u>VMTNLDGSVQLADHYQQNTPIGDGPVLLPDNHYLSTQSALSKD

PNEKRDHIVLLEFVTAAGITLGMDELYK

The underlined portion is the inserted protease cleavage site for caspase-3 and the TYG portion in bold is the chromophore. (The mutant M153T and V163A were added for 37° C. expression).

Sequence ID. No. 117-EGFP-cas9-1i
(EGFP-E-III-F-172-VLEHDS)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHNV

YIMADKQKNGIKVNFKIRHNIE(172)<u>EEEIREAFRVFDKDGNGYISAAEV</u>

<u>LEHDS</u>VMTNLDGSVQLADHYQQNTPIGDGPVLLPDNHYLSTQSALSKDPNE

KRDHIVLLEFVTAAGITLGMDELYK

The underlined portion is the inserted protease cleavage site for caspase-9 and the TYG portion in bold is the chromophore.

Sequence ID. No. 118-EGFP-cas9-1i-37
(EGFP-E-III-F-172-VLEHDS-37)
MVSKGEELFTGVVPILVELDGDLNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYI<u>T</u>ADKQKNGIK<u>A</u>NFKIRHNIE(172)<u>EEEIREAFRVFDKDGNGYISAA</u>

<u>EVLEHDS</u>VMTNLDGSVQLADHYQQNTPIGDGPVLLPDNHYLSTQSALSKD

PNEKRDHIVLLEFVTAAGITLGMDELYK

The underlined portion is the inserted protease cleavage site for caspase-9 and the TYG portion in bold is the chromophore. (The mutant M153T and V163A were added for 37° C. expression).

| Sequence no | Name | Also called | Cleavage sequence | enzyme |
|---|---|---|---|---|
| 8a | | | | |
| 8b | | | | |
| 9a | EGFP-cas-1a | | | |
| 9b | EGFP-cas-1a-37 | EGFP-172cas | DEVD | |
| 10a | EGFP-cas-1b | EGFP-GGSGG-172 | GGSGG-DEVD-GGSGG | |
| 10b | EGFP-cas-1b-37 | EGFP-DEVD-GGSGG-172 | | |
| 11a | EGFP-cas-1c | | | |
| 11b | EGFP-cas-1c-37 | EGFP-III-172casIII-DEVD | | |
| 12a | EGFP-cas-1d | EGFP-EF-172cas | E helix-DEVD-F helix | |
| 12b | EGFP-cas-1d-37 | | | |
| 13a | EGFP-cas-1e | EGFP-E-DEVD-GG-DEVD-F-172 | E helix-DEVD-GG-DEVD-F helix | |
| 13b | EGFP-cas-1e-37 | | | |

Sequence ID. No. 119, EGFP
MVSKGEELFTGVVPILVELDGDLNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDGPVLLPDNH
YLSTQSALSKDPNEKRDHIVLLEFVTAAGITLGMDELYK
TYG portion in bold is the chromophore.

Sequence ID. No. 120, YFP
MVSKGEELFTGVVPILVELDGDLNGHKFSVSGEGEGDATYGKLTLKFICT
TGKLPVPWPTLVTTLGYGLQCFARYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDGPVLLPDNH
YLSTQSALSKDPNEKRDHIVLLEFVTAAGITLGMDELYK
GYG portion in bold is the chromophore.

Sequence ID. No. 121, Venus
MVSKGEELFTGVVPILVELDGDLNGHKFSVSGEGEGDATYGKLTLK<u>L</u>ICT
TGKLPVPWPTLVTTLGYGLQCF<u>A</u>RYPDHMKQHDFFKSAMPEGYVQERTIF
FKDDGNYKTRAEVKFEGDTLVNRIELKGIDFKEDGNILGHKLEYNYNSHN
VYIMADKQKNGIK<u>A</u>NFKIRHNIEDG<u>G</u>VQLADHYQQNTPIGDGPVLLPDNH
YLS<u>Y</u>QSALSKDPNEKRDHIVLLEFVTAAGITLGMDELYK
GYG portion in bold is the chromophore.

Sequence ID. No. 122, CFP
MVSKGEELFTGVVPILVELDGDLNGHKFSVSGEGEGDATYGKLTLKFICT
TGKLPVPWPTLVTTLSWGVQCFSRYPDHMKQHDFFKSAMPEGYVQERTIF
FKDDGNYKTRAEVKFEGDTLVNRIELKGIDFKEDGNILGHKLEY<u>I</u>YNSHN
VYI<u>T</u>ADKQKNGIK<u>A</u>NFKIRHNIEDGSVQLADHYQQNTPIGDGPVLLPDNH
YLSTQSALSKDP<u>K</u>EKRDHIVLLEFVTAAGITLGMDELYK
SWG portion in bold is the chromophore.

Sequence ID. No. 123, BFP
MVSKGEELFTGVVPILVELDGDLNGHKFSVSGEGEGDATYGKLTLKFICT
TGKLPVPWPTLVTTLSHGVQCFSRYPDHMKQHDFFKSAMPEGYVQERTIF
FKDDGNYKTRAEVKFEGDTLVNRIELKGIDFKEDGNILGHKLE<u>F</u>NYNSHN
VYIMADKQKNGIKVNFKIRHNIEDGSVQLADHYQQNTPIGDGPVLLPDNH
YLSTQSALSKDPNEKRDHIVLLEFVTAAGITLGMDELYK
SHG portion in bold is the chromophore.

Sequence ID. No. 124, mCherry
MVSKGEEDNMAIIKEFMRFKVHMEGSVNGHEFEIEGEGEGRPYEGTQTAK
LKVTKGGPLPFAWDILSPQFMYGSKAYVKHPADIPDYLKLSFPEGFKWER
VMNFEDGGVVTVTQDSSLQDGEFIYKVKLRGTNFPSDGPVMQKKTMGWEA
SSERMYPEDGALKGEIKMRLKLKDGGHYDAEVKTTYKAKKPVQLPGAYNV
NIKLDITSHNEDYTIVEQYERAEGRHSTGGMDELYK
MYG portion in bold is the chromophore.

Sequence ID. No. 125, mStrawberry
MVSKGEENNMAIIKEFMRFKVRMEGSVNGHEFEIEGEGEGRPYEGTQTAK
LKVTKGGPLPFAWDILTPNFTYGSKAYVKHPADIPDYLKLSFPEGFKWER
VMNFEDGGVVTVTQDSSLQDGEFIYKVKLRGTNFPSDGPVMQKKTMGWEA
SSERMYPEDGALKGEIKMRLKLKDGGHYDAEVKTTYKAKKPVQLPGAYIV
GIKLDITSHNEDYTIVELYERAEGRHSTGGMDELYK
TYG portion in bold is the chromophore.

Sequence ID. No. 126
EEEIREAFRVFDKDGNGYISAAELRHVMTNL

Sequence ID. No. 127
EEEIREAFRVFDKDGNGYISAAE

Sequence ID. No. 128
DKDGNGYISAAELRHVMTNL

Sequence ID. No. 129
EEEIAEAFAVFDADGNGYISAAELRHVMTNL

Sequence ID. No. 130
DKDGNGYISAAE

Sequence ID. No. 131
EEEIREAFRVFDKDGNGYISAAGPRLVMTNL

Sequence ID. No. 132
DKDGNGYISAAGPRLVMTNL

Sequence ID. No. 133
EEEIAEAFAVFDADGNGYISAAGPRLVMTNL

Sequence ID. No. 134
EEEIREAFRVFDKDGNGYISAAGPARLVMTNL

Sequence ID. No. 135
DKDGNGYISAAGPARLVMTNL

Sequence ID. No. 136
EEEIAEAFAVFDADGNGYISAAGPARLVMTNL

Sequence ID. No. 137
EEEIREAFRVFDKDGNGYISAAGPARLAITNL

Sequence ID. No. 138
DKDGNGYISAAGPARLAITNL

Sequence ID. No. 139
EEEIAEAFAVFDADGNGYISAAGPARLAITNL

Sequence ID. No. 140
EEEIREAFRVFDKDGRGYISAAELRHVMTNL

Sequence ID. No. 141
EEEIREAFRVFDKDGNGYISAFNPRGFMTNL

Sequence ID. No. 142
EEEIREAFRVFDKDGNGYISAFNPRSFMTNL

Sequence ID. No. 143
EEEIREAFRVFDKDGNGYISAFTPRGFMTNL

Sequence ID. No. 144
EEEIREAFRVFDKDGNGYISAFTPRSFMTNL

---

We claim the following:

1. An enzyme sensor comprising:
   a fluorescent protein; and
   a molecular recognition motif having an amino acid sequence, the molecular recognition motif comprising:
   an analyte binding site, where the analyte binding site comprises an enzyme cleavage site and a binding site, where the binding site has an amino acid sequence according to SEQ ID NO: 130, and where the cleavage site is fused to the C-terminus of the binding domain,
   where the molecular recognition motif amino acid sequence is operatively linked to or integrated within the fluorescent protein,
   where an interaction of an analyte with the molecular recognition motif produces an optically detectable change in the fluorescent protein.

2. The enzyme sensor of claim 1, wherein the interaction of the analyte and the molecular recognition motif is the binding of the analyte to analyte binding site.

3. The enzyme sensor of claim 1, wherein the interaction of the analyte and the molecular recognition motif is the cleavage of the analyte binding site at the cleavage site.

4. The enzyme sensor of claim 1, wherein the analyte is a protease.

5. The enzyme sensor of claim 1, wherein the fluorescent protein further comprises a helical motif fused to the N-terminus of the binding site.

6. The enzyme sensor of claim 1, wherein the fluorescent protein further comprises a helical motif fused to the C-terminus of the enzyme cleavage site.

7. The enzyme sensor of claim 1, wherein the enzyme cleavage site and binding site are different amino acid sequences within the molecular recognition motif amino acid sequence.

8. The enzyme sensor of claim 1, wherein the enzyme cleavage site and binding site are the same amino acid sequence within the molecular recognition motif amino acid sequence.

9. An enzyme sensor comprising:
   a fluorescent protein; and
   a molecular recognition motif having an amino acid sequence, the molecular recognition motif comprising:
   an analyte binding site, where the analyte binding site comprises an enzyme cleavage site and a binding site, where the binding site has an amino acid sequence according to a modified SEQ ID NO: 130, where the modified SEQ ID NO: 130 is identical to SEQ ID NO: 130 except the lysine in SEQ ID NO: 130 is substituted with alanine, and where the cleavage site is fused to the C-terminus of the binding domain,
   where the molecular recognition motif amino acid sequence is operatively linked to or integrated within the fluorescent protein,
   where an interaction of an analyte with the molecular recognition motif produces an optically detectable change in the fluorescent protein.

10. An enzyme sensor comprising:
    a fluorescent protein; and
    a molecular recognition motif having an amino acid sequence, the molecular recognition motif comprising:
    an analyte binding site, where the analyte binding site comprises an enzyme cleavage site and a binding site, where the binding site has an amino acid sequence according to a modified SEQ ID NO: 130, where the modified SEQ ID NO: 130 is identical to SEQ ID NO: 130 except the lysine in SEQ ID NO: 130 is substituted with alanine and the glutamate in SEQ ID NO: 130 is deleted, and where the cleavage site is fused to the C-terminus of the binding domain,
    where the molecular recognition motif amino acid sequence is operatively linked to or integrated within the fluorescent protein,
    where an interaction of an analyte with the molecular recognition motif produces an optically detectable change in the fluorescent protein.

11. The enzyme sensor of claim 9, wherein the enzyme cleavage site is a cleavage site for an enzyme selected from the group consisting of trypsin, chymotrypsin, or granzyme.

12. An enzyme sensor comprising:
    a fluorescent protein; and
    a molecular recognition motif having an amino acid sequence, the molecular recognition motif comprising:
    an analyte binding site, where the analyte binding site comprises an enzyme cleavage site and a binding site, where the binding site has an amino acid sequence according to a modified SEQ ID NO: 130, where the modified SEQ ID NO: 130 is identical to SEQ ID NO: 130 except the glutamate in SEQ ID NO: 130 is deleted, and where the cleavage site is fused to the C-terminus of the binding domain,
    where the molecular recognition motif amino acid sequence is operatively linked to or integrated within the fluorescent protein,
    where an interaction of an analyte with the molecular recognition motif produces an optically detectable change in the fluorescent protein.

13. The enzyme sensor of claim 12, wherein the enzyme cleavage site is a cleavage site for an enzyme selected from the group consisting of trypsin, chymotrypsin, or granzyme.

14. An enzyme sensor comprising:
    a fluorescent protein; and
    a molecular recognition motif having an amino acid sequence, the molecular recognition motif comprising:
    an analyte binding site, where the analyte binding site comprises an enzyme cleavage site and a binding site, where the binding site has an amino acid sequence according to a modified SEQ ID NO: 130, where the modified SEQ ID NO: 130 is identical to SEQ ID NO: 130 except the asparagine in SEQ ID NO: 130 is substituted with arginine, and where the cleavage site is fused to the C-terminus of the binding domain,
    where the molecular recognition motif amino acid sequence is operatively linked to or integrated within the fluorescent protein,
    where an interaction of an analyte with the molecular recognition motif produces an optically detectable change in the fluorescent protein.

15. The enzyme sensor of claim 14, wherein the enzyme cleavage site is a cleavage site for an enzyme selected from the group consisting of thrombin, caspase-3, caspase-8, and caspase 9.

16. An enzyme sensor comprising:
    a fluorescent protein; and
    a molecular recognition motif having an amino acid sequence, the molecular recognition motif comprising:
    an analyte binding site, where the analyte binding site comprises an enzyme cleavage site and a binding site, where the binding site has an amino acid sequence according to a modified SEQ ID NO: 130, where the modified SEQ ID NO: 130 is identical to SEQ ID NO: 130 except the alanine$_{11}$ of SEQ ID NO: 130 and the glutamate of SEQ ID NO: 130 are deleted from SEQ ID NO: 130, and where the cleavage site is fused to the C-terminus of the binding domain, where the molecular recognition motif amino acid sequence is operatively linked to or integrated within the fluorescent protein, where an interaction of an analyte with the molecular recognition motif produces an optically detectable change in the fluorescent protein.

17. The enzyme sensor of claim 16, wherein the enzyme cleavage site is a cleavage site for thrombin.

18. The enzyme sensor of claim 1, wherein the fluorescent protein is a green fluorescent protein.

* * * * *